(12) United States Patent
Kouji et al.

(10) Patent No.: US 8,691,819 B2
(45) Date of Patent: Apr. 8, 2014

(54) ALPHA HELIX MIMETIC COMPOSITIONS FOR TREATING CANCER AND OTHER CBP/CATENIN-MEDIATED DISEASES AND CONDITIONS

(75) Inventors: Hiroyuki Kouji, Yokohama (JP); Yuji Kogami, Yokohama (JP); Takenao Odagami, Yokohama (JP)

(73) Assignee: PRISM BioLab Corporation (JP)

( * ) Notice: Subject to any disclaimer, the term of this patent is extended or adjusted under 35 U.S.C. 154(b) by 15 days.

(21) Appl. No.: 13/124,104

(22) PCT Filed: Oct. 14, 2009

(86) PCT No.: PCT/JP2009/068085
§ 371 (c)(1),
(2), (4) Date: May 20, 2011

(87) PCT Pub. No.: WO2010/044485
PCT Pub. Date: Apr. 22, 2010

(65) Prior Publication Data
US 2011/0263607 A1    Oct. 27, 2011

Related U.S. Application Data

(60) Provisional application No. 61/105,088, filed on Oct. 14, 2008.

(51) Int. Cl.
*A01N 43/58*   (2006.01)
*A01N 43/60*   (2006.01)
*A61K 31/50*   (2006.01)
*A61K 31/495*  (2006.01)
*C07D 487/00*  (2006.01)

(52) U.S. Cl.
USPC ....................................................... 514/249

(58) Field of Classification Search
None
See application file for complete search history.

(56) References Cited

U.S. PATENT DOCUMENTS

| | | | |
|---|---|---|---|
| 5,440,013 | A | 8/1995 | Kahn |
| 5,929,237 | A | 7/1999 | Kahn |
| 6,013,458 | A | 1/2000 | Kahn |
| 6,762,185 | B1 | 7/2004 | Kahn |
| 2005/0004131 | A1 | 1/2005 | Flohr |
| 2005/0209256 | A1 | 9/2005 | Andres |

FOREIGN PATENT DOCUMENTS

| WO | WO 94/03494 | 2/1994 |
|---|---|---|
| WO | WO09849168 | * 11/1998 |
| WO | WO 01/00210 | 1/2001 |
| WO | WO 01/16135 | 3/2001 |
| WO | WO 03/031448 | 4/2003 |
| WO | WO 2004/035587 | 4/2004 |
| WO | WO 2004/072077 | 8/2004 |
| WO | WO 2004/093828 | 11/2004 |
| WO | WO 2005/021025 | 3/2005 |
| WO | WO 2005/116032 | 12/2005 |
| WO | WO 2007/056513 | 5/2007 |
| WO | WO 2007/056593 | 5/2007 |
| WO | WO 2009/051397 | 4/2009 |
| WO | WO 2009/148192 | 12/2009 |
| WO | WO 2010/044485 | 4/2010 |

OTHER PUBLICATIONS

Eguchi et al., "Design, Synthesis, and Evaluation of Opioid Analogues with Non-Peptidic β-Turn Scaffold: Enkephalin and Endomorphin Mimetics," Journal of Medicinal Chemistry, 2002, pp. 1395-1398, vol. 45.
Eguchi et al., "Solid-phase synthesis and solution structure of bicyclic β-turn peptidomimetics: diversity at the i position," Tetrahedron Letters, 2001, pp. 1237-1239, vol. 42.
Eguchi et al., "Solid-Phase Synthesis and Structural Analysis of Bicyclic β-Turn Mimetics Incorporating Functionality at the i to i +3 Positions," Journal of the American Chemical Society, 1999, pp. 12204-12205, vol. 121.
Piergentili et al., "Solution-phase synthesis of ICG-001, a β-turn peptidomimetic molecule inhibitor of β-catenin-Tcf-mediated transcription," Tetrahedron, 2007, pp. 12912-12916, vol. 63.
International Search Report of PCT/JP2009/068085, mailed May 2, 2010 (6 pages).
U.S. Appl. No. 61/105,088, filed Oct. 14, 2008.
Written Opinion of the International Search Authority of PCT/JP2009/068085 (7 pages).
Adnot, 2005, The Journal of Clinical Investigation, 115(6): 1461-1463.
Albranches et al., 2003, Biotechnology Letters, 25: 725-730.
Bao et al., 2000, Gynecologic Oncology, 78: 373-9.
Behrens et al., 1996, Nature, 382: 638-642.
Bellusci et al., 1997, Development, 124: 4867-4878.
Bienz et al., 2000, Cell, 103: 311-20.
Bitar et al., 1999, Cell and Tissue Research, 298: 233-242.
Blanc-Brude et al., 2002, Nature Medicine, 8: 987-994.

(Continued)

*Primary Examiner* — Jeffrey Murray
(74) *Attorney, Agent, or Firm* — Barry L. Davison; Davis Wright Tremaine LLP

(57) ABSTRACT

Alpha-helix mimetic structures and compounds represented by the formula (I) wherein the general formula and the definition of each symbol are as defined in the specification, a compound relating thereto, and methods relating thereto, are disclosed. Applications of these compounds in the treatment of medical conditions, e.g., cancer diseases, fibrotic diseases, and pharmaceutical compositions comprising the mimetics are further disclosed.

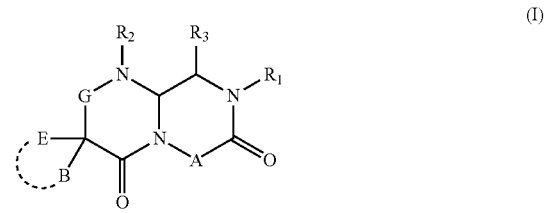

(I)

26 Claims, 3 Drawing Sheets

(56) References Cited

OTHER PUBLICATIONS

Borok et al., 1995, American Journal of Respiratory Cell and Molecular Biology, 12: 50-55.
Bouvet et al., 2002, Cancer Research, 62: 1534-1540.
Brown et al., 2000, Digestive Diseases and Sciences, 45: 1578-84.
Caca et al., 1999, Cell Growth & Differentiation, 10: 369-376.
Cadigan et al., 1997, Genes & Development, 11: 3286-3305.
Cao et al., 1999, Clinical Cancer Research, 5: 267-274.
Carri et al., 1994, International Journal of Developmental Neuroscience, 12: 567-578.
Chauvet et al., 1996, Glia, 18: 211-223.
Chen et al., 2001, The Journal of Cell Biology, 152: 87-96.
Chilosi et al., 2003, American Journal of Pathology, 162: 1495-1502.
Cho et al., 1999, Plant Molecular Biology, 40: 419-429.
Chrivia et al., 1993, Nature, 365: 855-859.
Chu et al., 2003, Neuroscience Letters, 343: 129-133.
Clark et al., 2001, American Journal of Physiology—Lung Cellular and Molecular, 280: L705-L715.
Collingwood et al., 1999, Journal of Molecular Endocrinology, 23: 255-275.
Crawford et al., 1999, Oncogene, 18: 2883-2891.
Crispino, et al., 1999, Molecular Cell, 3: 219-228.
Daniels et al., 2001, Trends in Biochemical Sciences, 26: 672-678.
Danto et al., 1995, American Journal of Respiratory Cell and Molecular Biology, 12: 497-502.
DasGupta et al., 1999, Development 126: 4557-4568.
Davis et al., 2002, Cancer Research, 62: 7247-7253.
Demidem et al., 2001, Cancer Research, 61: 2294-2300.
Deng et al., 2003, Experimental Neurology, 182: 373-382.
Dinsmore, 1999, Journal of the American Osteopathic Association, 99(9) Suppl.: 1S.
Dinsmore, 1999, Journal of the American Osteopathic Association, 99(9) Suppl.: 6S.
Eckner et al., 1994, Genes & Development, 8: 869-884.
Fleisher et al., 1996, Advanced Drug Delivery Reviews, 19: 115-130.
Fox et al., 1999, Revue Neurologique (Paris), 155 Suppl. 4: S33-7.
Fraser et al., 2001, Biochemical Society Symposia, 67: 89-100.
Fuchs, 1999, the Harvey Lectures, 94: 47-78.
Fujimuro et al., 2003, Nature Medicine, 9: 300-306.
Fukunaga et al., 1999, Cell Transplantation, 8: 435-441.
Gallop et al., 1994, Journal of Medicinal Chemistry, 37: 1233-1251.
Gat et al., 1998, Cell, 95: 605-614.
Goff et al., 1991, Genes & Development, 5: 298-309.
Gomez, 1995, Brain and Development, vol. 17, Supplement 1, 55-57.
Gong et al., 1999, Plant Molecular Biology, 41: 33-44.
Graminski et al., 1994, Biotechnology, 12: 1008-1011.
Grube et al., 2004, Herz, 29: 162-166.
Guo et al., 2002, Cancer Research, 62: 4678-4684.
Gurwitz, 2000, Trends in Neurosciences, 23: 386.
Hanai et al., 2002, The Journal of Cell Biology, 158: 529-539.
Hayashi et al., 1997, Proceedings of the National Academy of Sciences of USA, 94: 242-247.
He et al., 1998, Science, 281: 1509-1512.
He et al., 1999, Cell, 99: 335-345.
Hecht et al., 2000, EMBO Journal, 19: 1839-1850.
Hirata et al., 1997, Journal of Neurobiology, 32: 415-25.
Hobo et al., 1999, Proceedings of the National Academy of Sciences of USA, 96: 15348-15353.
Hollenberg et al., 1995, Molecular and Cellular Biology, 15: 3813-3822.
Hsu et al., 1998, Molecular and Cellular Biology, 18: 4807-4818.
Hunter, 2006, Advanced Drug Delivery Reviews, 58: 347-349.
Janknecht et al., 1996, Nature, 383: 22-23.
Jue et al., 1992, Molecular and Cellular Biology, 12: 321-328.
Kapanci et al., 1995, American Journal of Respiratory and Critical Care Medicine, 152: 2163-2169.
Kasper et al., 1996, Histology and Histopathology, 11: 463-483.
Kato et al., 1983, Developmental Brain Research, 11: 143-147.
Kawamorita et al., 2002, Human Cell, 15: 178-182.
Kawanami et al., 1982, Laboratory Investigation, 46: 39-53.
Khalil et al., 1991, American Journal of Respiratory Cell and Molecular Biology, 5: 155-162.
Kinzler et al., 1996, Cell, 87: 159-170.
Kispert et al., 1996, Development, 122: 3627-3637.
Kolligs et al., 1999, Molecular and Cellular Biology, 19: 5696-5706.
Koo et al., 1993, Proceedings of the National Academy of Sciences of USA, 90: 4748-4752.
Koutsourakis et al., 2001, Mechanisms of Development, 105: 105-114.
Kril et al., 2001, International Review of Neurobiology, 48: 167-217.
Kudo et al., 2003, Biochemical Pharmacology, 66: 289-295.
Kurz et al., 2002, Journal of neural transmission. Supplementum, 62: 127-33.
Labonte et al., 2000, Hepatology Research, 18: 72-85.
Lacza et al., 2003, Brain Research Protocols, 11: 145-154.
Lam et al., 1991 Nature 354: 82-84.
Landesman-Bollag et al., 2001, Oncogene, 20: 3247-3257.
Lemere et al., 2003, Neurochemical Research, 28: 1017-1027.
Lemon et al., 1999, Current Opinion in Genetics & Development, 9: 499-504.
Leo et al., 2000, Gene, 245: 1-11.
Li et al., 2000, Developmental Biology, 248: 68-81.
Lin et al., 2001, Developmental Dynamics, 222: 26-39.
Litingtung et al., 1998, Nature Genetics, 20: 58-61.
Lu et al., 1999, Breast Cancer Research and Treatment, 57: 183-92.
Mak, et al., 2003, The Journal of Biological Chemistry, 278: 5947-5951.
Malik et al., 2000, Trends in Biochemical Sciences, 25: 277-283.
Manteuffel-Cymborowska, 1999, Acta Biochimica Polonica, 46: 77-89.
Marin et al., Geriatrics, 57: 36-40, 2002.
McGregor et al., 1993, Diseases of the Colon & Rectum, 36: 834-839.
McKenna et al., 1999, The Journal of Steroid Biochemistry and Molecular Biology, 69: 3-12.
McMurtry et al., 2005, The Journal of Clinical Investigation, 115(6): 1479-1491.
Miller et al., 1999, Oncogene, 18: 7860-7872.
Miloloza et al., 2000, Human Molecular Genetics, 9: 1721-1727.
Min et al., 1998, Genes & Development, 12: 3156-3161.
Molenaar et al., 1996, Cell, 86: 391-399.
Monkley et al., 1996, Development, 122: 3343-3353.
Moon et al., 1997, Trends in Genetics, 13: 157-162.
Morin et al., 1996, Proceedings of the National Academy of Sciences of USA, 93, 7950-7954.
Morin et al., 1997, Science, 275: 1787-1790.
Moss et. al., 2001, American Journal of Respiratory and Critical Care Medicine, 163: 669-671.
Motoyama et al., 1998, Nature Genetics, 20: 54-57.
Muller-Spahn et al., 1999, European Archives of Psychiatry and Clinical Neuroscience, 249 Suppl. 3: 37-42.
Munoz-Elias et al., 2003, Stem Cells, 21: 437-448.
Nicolaou et al., 1994, Angewandte Chemie International Edition in English, 33: 183-186.
Nilsson et al., 2002, Cancer Chemotherapy and Pharmacology, 49: 93-100.
Nusse et al., 1992, Cell, 69: 1073-1087.
Ogawa et al., 2000, Gene, 245: 21-29.
Okanami et al., 1996, Genes to Cells, 1 :87-99.
Orford et al., 1999, The Journal of Cell Biology, 146: 855-867.
O'Shea et al., 1991, Neuron, 7: 231-7.
Pachernik et al., 2002, Reproduction Nutrition Development, 42: 317-326.
Parr et al., 1994, Current Opinion in Genetics & Development, 4: 523-528.
Parr et al., 2001, Developmental Biology, 237: 324-332.
Peifer et al., 2000, Science, 287: 1606-1609.
Pellitteri et al., 2001, European Journal of Histochemistry, 45: 367-376.
Pepicelli et al., 1998, Current Biology, 8: 1083-1086.
Polakis, 2000, Genes & Development, 14: 1837-1851.

(56) References Cited

OTHER PUBLICATIONS

Polakis et al., 2000, Colon Cancer Prevention: Dietary Modulation of Cellular and Molecular Mechanisms (Advances in Experimental Medicine and Biology), 470: 23-32.
Randolph et al., 1995, Journal of the American Chemical Society, 117: 5712-19.
Robyr et al., 2000, Molecular Endocrinology, 14: 329-347.
Rocchi et al., 2003, Brain Research Bulletin, 61: 1-24.
Rodova et al., 2002, The Journal of Biological Chemistry, 277: 29577-29583.
Roose et al., 1999, Science, 285: 1923-1926.
Rowan et al., 2003, Philosophical Transactions of the Royal Society B: Biological Sciences, 358: 821-828.
Rubinfeld et al., 1996, Science, 272: 1023-1026.
Rubinfeld et al., 1997, Science, 275: 1790-1792.
Rydel et al., 1988, Proceedings of the National Academy of Sciences of USA, 85: 1257-1261.
Sakanaka et al., 1998, Proceedings of the National Academy of Sciences of USA, 95: 3020-3023.
Sakanaka et al., 1999, The Journal of Biological Chemistry, 274: 14090-14093.
Sant'Angelo et al., 2003, Neurochemical Research, 28: 1009-1015.
Sata, 2003, Trends in Cardiovascular Medicine, 13: 249-253.
Sata et al., 2002, Nature Medicine, 8: 403-409.
Satoh et al., 1999, Biochemical and Biophysical Research Communications, 258: 50-53.
Selman et al., 2000, American Journal of Physiology—Lung Cellular and Molecular Physiology, 279: L562-L574.
Shawler et al., 1995, Journal of Immunotherapy with Emphasis on Tumor Immunology, 17: 201-8.
Shih et al., 1996, Proceedings of the National Academy of Sciences of USA, 93: 13896-13901.
Shikama et al., 1997, Trends in Cell Biology, 7: 230-236.
Shtutman et al., 1999, Proceedings of the National Academy of Sciences of USA, 96: 5522-5527.
Shu et al., 2002, Development, 129: 4831-4842.
Simonet et al., 1995, Proceedings of the National Academy of Sciences of USA, 92: 12461-12465.
Simosa et al., 2005, Journal of Vascular Surgery, 41: 682-690.
Skubitz et al., 1991, The Journal of Cell Biology, 115: 1137-1148.
Smalley et al., 1999, Cancer and Metastasis Reviews, 18: 215-230.
Song et al., 2000, The Journal of Biological Chemistry, 275: 23790-23797.
Sprenger-Haussels et al., 2000, Plant Journal, 22: 1-8.
Stavridis et al., 2003, Biochemical Society Transactions, 31: 45-49.
Stein et al., 1990, Journal of Virology, 64: 4421-4427.
Storey et al., 2002, Frontiers in Bioscience 7: e155-184.
Strovel et al., 1999, Experimental Cell Research, 253: 637-648.
Su et al., 1993, Science, 262: 1734-1737.
Takahashi et al., 2000, International Journal of Cancer, 85: 243-247.
Takemaru et al., 2000, The Journal of Cell Biology, 149: 249-254.
Tapia et al., 2006, Proceedings of the National Academy of Sciences of USA, 103: 15079-15084.
Tebar et al., 2001, Mechanisms of Development, 109: 437-440.
Tetsu et al., 1999, Nature, 398: 422-426.
Tsukamoto et al., 1988, Cell, 55: 619-625.
Tsunoda et al., 1999, Anticancer Research, 19: 1149-52.
Uhal et al., 1995, American Journal of Physiology—Lung Cellular and Molecular Physiology, 269: L819-L828.
Uhal et al., 1998, American Journal of Physiology—Lung Cellular and Molecular Physiology, 275: L1192-L1199.
Ulmasov et al., 1999, Proceedings of the National Academy of Sciences of USA, 96: 5844-5849.
Vanhems et al., 1990, European Journal of Neuroscience, 2: 776-782.
Verstijnen et al., 1988, Anticancer Research, 8: 1193-1200.
Vetter et al., 1995, Current Biology, 5: 168-178.
Wan et al., 2003, Chinese Medical Journal, 116: 428-431.
Wang et al., 2005, Arteriosclerosis, Thrombosis, and Vascular Biology, 25: 2081-2087.
Warburton et al., 2000, Mechanisms of Development, 92: 55-81.
Weaver et al., 1999, Development, 126: 4005-4015.
Weeraratna et al., 2002, Cancer Cell, 1: 279-288.
Weidenfeld et al., 2002, The Journal of Biological Chemistry, 277: 21061-21070.
Weiner, 1997, Harvard Review of Psychiatry, 4: 306-316.
Willert et al., 1998, Current Opinion in Genetics & Development, 8: 95-102.
Xia et al., 2001, Proceedings of the National Academy of Sciences of USA, 98: 10863-10868.
Yamaguchi et al., 1999, Development, 126: 1211-1223.
Yost et al., 1996, Genes & Development, 10: 1443-1454.
Zaloom et al., 1981, The Journal of Organic Chemistry, 46: 5173-76.
Zhang et al., 2001, Cancer Research, 61: 8664-8667.
Zhou et al., 1997, Developmental Dynamics, 210: 305-314.

\* cited by examiner

ALPHA HELIX MIMETIC COMPOSITIONS FOR TREATING CANCER AND OTHER CBP/CATENIN-MEDIATED DISEASES AND CONDITIONS

CROSS REFERENCES TO RELATED APPLICATIONS

This application is the United States national phase of PCT/JP2009/06085, filed Oct. 14, 2009, which claims the benefit of Provisional U.S. Patent Application No. 60/105,088, filed Oct. 14, 2008.

TECHNICAL FIELD

The present invention relates generally to alpha-helix mimetic structures and to a compound relating thereto. The invention also relates to applications in the treatment of medical conditions, e.g., cancer diseases, fibrotic diseases, and pharmaceutical compositions comprising the mimetics.

BACKGROUND ART

Recently, non-peptide compounds have been developed which more closely mimic the secondary structure of reverse-turns found in biologically active proteins or peptides. For example, U.S. Pat. No. 5,440,013 to Kahn and published PCT applications nos. WO94/03494, WO01/00210A1, and WO01/16135A2 to Kahn each disclose conformationally constrained, non-peptidic compounds, which mimic the three-dimensional structure of reverse-turns. In addition, U.S. Pat. No. 5,929,237 and its continuation-in-part U.S. Pat. No. 6,013,458, both to Kahn, disclose conformationally constrained compounds which mimic the secondary structure of reverse-turn regions of biologically active peptides and proteins. In relation to reverse-turn mimetics, Kahn disclosed new conformationally constrained compounds which mimic the secondary structure of alpha-helix regions of biologically active peptide and proteins in WO2007/056513 and WO2007/056593.

While significant advances have been made in the synthesis and identification of conformationally constrained, reverse-turn and alpha-helix mimetics, there remains a need in the art for small molecules which mimic the secondary structure of peptides. There is also a need in the art for libraries containing such members, as well as techniques for synthesizing and screening the library members against targets of interest, particularly biological targets, to identify bioactive library members.

The present invention also fulfills these needs, and provides further related advantages by providing conformationally constrained compounds which mimic the secondary structure of alpha-helix regions of biologically active peptides and proteins.

Wnt signaling pathway regulates a variety of processes including cell growth, oncogenesis, and development (Moon et al., 1997, Trends Genet. 13, 157-162; Miller et al., 1999, Oncogene 18, 7860-7872; Nusse and Varmus, 1992, Cell 69, 1073-1087; Cadigan and Nusse, 1997, Genes Dev. 11, 3286-3305; Peifer and Polakis, 2000 Science 287, 1606-1609; Polakis 2000, Genes Dev. 14, 1837-1851). Wnt signaling pathway has been intensely studied in a variety of organisms. The activation of TCF4/β-catenin mediated transcription by Wnt signal transduction has been found to play a key role in its biological functions (Molenaar et al., 1996, Cell 86:391-399; Gat et al., 1998 Cell 95:605-614; Orford et al., 1999 J. Cell. Biol. 146:855-868; Bienz and Clevers, 2000, Cell 103: 311-20).

In the absence of Wnt signals, tumor suppressor gene adenomatous polyposis coli (APC) simultaneously interacts with the serine kinase glycogen synthase kinase (GSK)-3β and β-catenin (Su et al., 1993, Science 262, 1734-1737: Yost et al., 1996 Genes Dev. 10, 1443-1454: Hayashi et al., 1997, Proc. Natl. Acad. Sci. USA, 94, 242-247: Sakanaka et al., 1998, Proc. Natl. Acad. Sci. USA, 95, 3020-3023: Sakanaka and William, 1999, J. Biol. Chem 274, 14090-14093). Phosphorylation of APC by GSK-3β regulates the interaction of APC with β-catenin, which in turn may regulate the signaling function of β-catenin (B. Rubinfeld et al., Science 272, 1023, 1996). Wnt signaling stabilizes β-catenin allowing its translocation to the nucleus where it interacts with members of the lymphoid enhancer factor (LEF1)/T-cell factor (TCF4) family of transcription factors (Behrens et al., 1996 Nature 382, 638-642: Hsu et al., 1998, Mol. Cell. Biol. 18, 4807-4818: Roose et al., 1999 Science 285, 1923-1926).

Recently c-myc, a known oncogene, was shown to be a target gene for β-catenin/TCF4-mediated transcription (He et al., 1998 Science 281 1509-1512: Kolligs et al., 1999 Mol. Cell. Biol. 19, 5696-5706). Many other important genes, including cyclin D1, and metalloproteinase, which are also involved in oncogenesis, have been identified to be regulated by TCF4/β-catenin transcriptional pathway (Crawford et al., 1999, Oncogene 18, 2883-2891: Shtutman et al., 1999, Proc. Natl. Acad. Sci. USA., 11, 5522-5527: Tetsu and McCormick, 1999 Nature, 398, 422-426). Moreover, overexpression of several downstream mediators of Wnt signaling has been found to regulate apoptosis (Morin et al., 1996, Proc. Natl. Acad. Sci. USA, 93, 7950-7954: He et al., 1999, Cell 99, 335-345: Orford et al, 1999 J. Cell. Biol., 146, 855-868: Strovel and Sussman, 1999, Exp. Cell. Res., 253, 637-648). Overexpression of APC in human colorectal cancer cells induced apoptosis (Morin et al., 1996, Proc. Natl. Acad. Sci. USA., 93, 7950-7954), ectopic expression of β-catenin inhibited apoptosis associated with loss of attachment to extracellular matrix (Orford et al, 1999, J. Cell Biol.146, 855-868). Inhibition of TCF4/β-catenin transcription by expression of dominant-negative mutant of TCF4 blocked Wnt-1-mediated cell survival and rendered cells sensitive to apoptotic stimuli such as anti-cancer agent (Shaoqiong Chen et al., 2001, J. Cell. Biol., 152, 1, 87-96) and APC mutation inhibits apoptosis by allowing constitutive survivin expression, a well-known anti-apoptotic protein (Tao Zhang et al., 2001, Cancer Research, 62, 8664-8667).

Although mutations in the Wnt gene have not been found in human cancer, a mutation in APC or β-catenin, as is the case in the majority of colorectal tumors, results in inappropriate activation of TCF4, overexpression of c-myc and production of neoplastic growth (Rubinfel et al, 1997, Science, 275, 1790-1792: Morin et al, 1997, Science, 275, 1787-1790: Caca et al, 1999, Cell. Growth. Differ. 10, 369-376). The tumor suppressor gene (APC) is lost or inactivated in 85% of colorectal cancers and in a variety of other cancers as well (Kinzler and Vogelstein, 1996, Cell 87, 159-170). APCs principal role is that of a negative regulator of the Wnt signal transduction cascade. A center feature of this pathway involves the modulation of the stability and localization of a cytosolic pool of β-catenin by interaction with a large Axin-based complex that includes APC. This interaction results in phosphorylation of β-catenin thereby targeting it for degradation.

CREB binding proteins (CBP)/p300 were identified initially in protein interaction assays, first through its association with the transcription factor CREB (Chrivia et al, 1993, Nature, 365, 855-859) and later through its interaction with the adenoviral-transforming protein E1A (Stein et al., 1990, J. Viol., 64, 4421-4427: Eckner et al., 1994, Genes. Dev., 8, 869-884). CBP had a potential to participate in variety of cellular functions including transcriptional coactivator function (Shikama et al., 1997, Trends. Cell. Biol., 7, 230-236: Janknecht and Hunter, 1996, Nature, 383, 22-23). CBP/p300 potentiates β-catenin-mediated activation of the siamois promoter, a known Wnt target (Hecht et al, 2000, EMBO J. 19, 8, 1839-1850). β-catenin interacts directly with the CREB-binding domain of CBP and β-catenin synergizes with CBP to stimulate the transcriptional activation of TCF4/β-catenin (Ken-Ichi Takemaru and Randall T. Moon, 2000 J. Cell. Biol., 149, 2, 249-254).

SUMMARY OF THE INVENTION

The present invention relates generally to alpha-helix mimetic structures and to a compound relating thereto. The invention also relates to applications in the treatment of medical conditions, e.g., cancer diseases, fibrotic diseases, and pharmaceutical compositions comprising the mimetics.

From the above background discussions, it is seen that TCF4/β-catenin and CBP complex of Wnt pathway can be taken as target molecules for the regulation of cell growth, oncogenesis and apoptosis of cells, etc. Accordingly, the present invention also addresses a need for compounds that block TCF4/β-catenin transcriptional pathway by inhibiting CBP, and therefore can be used for treatment of cancer, especially colorectal cancer, and fibrotic diseases. In aspects thereof, the present invention is directed to a new type of conformationally constrained compounds, which mimic the secondary structure of alpha-helix regions of biologically active peptides and proteins. This invention also discloses libraries containing such compounds, as well as the synthesis and screening thereof.

Accordingly, the present invention includes the following embodiments.

(1) A compound having the following general formula (I):

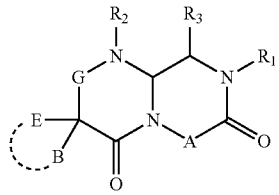

wherein
A is —(CHR$^7$)—;
  wherein
    R$^7$ is hydrogen, optionally substituted alkyl, optionally substituted alkenyl, optionally substituted alkynyl, optionally substituted aryl, optionally substituted heteroaryl, optionally substituted cycloalkyl, optionally substituted heterocycloalkyl, optionally substituted arylalkyl, optionally substituted heteroarylalkyl, optionally substituted cycloalkylalkyl, or optionally substituted heterocycloalkylalkyl;
B and E are the same or different and independently selected from hydrogen, optionally substituted alkyl, optionally substituted alkenyl, and optionally substituted alkynyl
or form an optionally substituted spiro ring indicated by dashed lines;

G is —NH—, —NR$^6$—, —O—, —CH$_2$—, —CHR$^6$— or —C(R$^6$)$_2$—;
  wherein
    each R$^6$ is the same or different and independently selected from optionally substituted alkyl, optionally substituted alkenyl, and optionally substituted alkynyl;
R$^1$ is optionally substituted alkyl, optionally substituted alkenyl, optionally substituted alkynyl, optionally substituted arylalkyl, optionally substituted heteroarylalkyl, optionally substituted cycloalkylalkyl, or optionally substituted heterocycloalkylalkyl;
R$^2$ is —W$^{21}$—W$^{22}$—Rb—R$^{20}$;
  wherein
    W$^{21}$ is —(CO)— or —(SO$_2$)—;
    W$^{22}$ is bond, —O—, —NH— or optionally substituted lower alkylene;
    Rb is bond or optionally substituted lower alkylene; and
    R$^{20}$ is optionally substituted alkyl, optionally substituted alkenyl, optionally substituted alkynyl, optionally substituted aryl, optionally substituted heteroaryl, optionally substituted cycloalkyl, or optionally substituted heterocycloalkyl; and
R$^3$ is hydrogen, optionally substituted alkyl, optionally substituted alkenyl, or optionally substituted alkynyl;
with the proviso that
1) when Rb is optionally substituted lower alkylene, then W$^{22}$ should be —O— or —NH—,
2) when E and B are hydrogen, then R$^3$ should be hydrogen,
3) when G is —NH—, —CH$_2$—, —CHR$^6$— or —NR$^6$—, then B and E should not be hydrogen, and
4) when G is —O—, B and E are hydrogen and R$^3$ is hydrogen, then R$^1$ should not be 8-quinolylmethyl;
or a pharmaceutically acceptable salt thereof.

(2) The compound according to (1) mentioned above, wherein, in the formula (I),
B and E are the same or different and independently selected from hydrogen, optionally substituted alkyl, optionally substituted alkenyl, and optionally substituted alkynyl
or form an optionally substituted 3-, 4-, 5-, 6- or 7 membered unsaturated monocyclic ring, when the formed spiro ring is heterocyclic ring, the hetero atom is selected from S, N and O and a number of hetero atom is 1.

(3) The compound according to (1) mentioned above, wherein, in the formula (I),
B and E are the same or different and independently selected from hydrogen, and optionally substituted alkyl or form an optionally substituted 3-, 4-, 5-, 6- or 7 membered unsaturated monocyclic ring, when the formed spiro ring is heterocyclic ring, the hetero atom is selected from S, N and O and a number of hetero atom is 1.

(4) The compound according to (1) mentioned above, wherein, in the formula (I),
G is —NR$^6$—, —O—, —CH$_2$— or —C(R$^6$)$_2$—;
  wherein
    each R$^6$ is the same or different and independently selected from optionally substituted alkyl, optionally substituted alkenyl, and optionally substituted alkynyl.

(5) The compound according to (1) mentioned above, wherein, in the formula (I),
G is —O—.

(6) The compound according to (1) mentioned above, wherein, in the formula (I),
G is —O—, and
B and E are hydrogen.

(7) The compound according to (1) mentioned above, wherein, in the formula (I),
R$^3$ is hydrogen.

(8) The compound according to (1) mentioned above, wherein, in the formula (I),
A is —(CHR$^7$)—;
wherein
R$^7$ is optionally substituted alkyl, optionally substituted aryl, or optionally substituted arylalkyl.

(9) The compound according to (1) mentioned above, wherein, in the formula (I),
R$^1$ is optionally substituted alkyl, optionally substituted arylalkyl, optionally substituted heteroarylalkyl, or optionally substituted cycloalkylalkyl.

(10) The compound according to (1) mentioned above, wherein, in the formula (I),
R$^2$ is —W$^{21}$—W$^{22}$—Rb—R$^{20}$;
wherein
W$^{21}$ is —(CO)— or —(SO$_2$)—;
W$^{22}$ is bond, —O—, —NH— or optionally substituted lower alkylene;
Rb is bond or optionally substituted lower alkylene; and
R$^{20}$ is optionally substituted alkyl, optionally substituted aryl, or optionally substituted heteroaryl.

(11) The compound according to (1) mentioned above, wherein, in the formula (I),
A is —(CHR$^7$)—;
wherein
R$^7$ is optionally substituted alkyl, or optionally substituted arylalkyl; and
R$^1$ is optionally substituted alkyl, optionally substituted arylalkyl, optionally substituted heteroarylalkyl, or optionally substituted cycloalkylalkyl; and
R$^2$ is —W$^{21}$—W$^{22}$—Rb—R$^{20}$;
wherein
W$^{21}$ is —(CO)— or —(SO$_2$)—;
W$^{22}$ is bond, —O—, —NH— or optionally substituted lower alkylene;
Rb is bond or optionally substituted lower alkylene; and
R$^{20}$ is optionally substituted alkyl, optionally substituted aryl, optionally substituted heteroaryl.

(12) The compound according to (1) mentioned above, wherein, in the formula (I),
R$^1$ is —Ra—R$^{10}$;
wherein
Ra is optionally substituted lower alkylene and
R$^{10}$ is optionally substituted aryl or optionally substituted heteroaryl.

(13) The compound according to (12) mentioned above, wherein, in the formula (I),
R$^{10}$ is optionally substituted biphenyl, optionally substituted phenyl, optionally substituted pyridyl, optionally substituted pyrimidyl, optionally substituted pyridazinyl, optionally substituted pyrazinyl, optionally substituted triazinyl, optionally substituted pyrrolyl, optionally substituted thienyl, optionally substituted furyl, optionally substituted thiazolyl, optionally substituted oxazolyl, optionally substituted imidazolyl, optionally substituted naphthyl, optionally substituted tetrahydronaphthyl, optionally substituted quinolinyl, optionally substituted isoquinolinyl, optionally substituted quinazolinyl, optionally substituted quinoxalinyl, optionally substituted cinnolinyl, optionally substituted naphthyridinyl, optionally substituted benzotriazinyl, optionally substituted pyridopyrimidinyl, optionally substituted pyridopyrazinyl, optionally substituted pyridopyridazinyl, optionally substituted pyridotriazinyl, optionally substituted indenyl, optionally substituted benzofuryl, optionally substituted benzothienyl, optionally substituted indolyl, optionally substituted indazolyl, optionally substituted benzoxazolyl, optionally substituted benzimidazolyl, optionally substituted benzothiazolyl, optionally substituted benzothiadiazolyl, optionally substituted furopyridinyl, optionally substituted thienopyridinyl, optionally substituted pyrrolopyridinyl, optionally substituted oxazolopyridinyl, optionally substituted thiazolopyridinyl or optionally substituted imidazopyridinyl.

(14) The compound according to (1) mentioned above, wherein, in the formula (I),
R$^2$ is —W$^{21}$—W$^{22}$—Rb—R$^{20}$;
wherein
W$^{21}$ is —(CO)— or —(SO$_2$)—;
W$^{22}$ is bond, —O—, —NH— or optionally substituted lower alkylene;
Rb is bond or optionally substituted lower alkylene; and
R$^{20}$ is optionally substituted aryl or optionally substituted heteroaryl.

(15) The compound according to (14) mentioned above, wherein, in the formula (I),
R$^{20}$ is optionally substituted biphenyl, optionally substituted phenyl, optionally substituted pyridyl, optionally substituted pyrimidyl, optionally substituted pyridazinyl, optionally substituted pyrazinyl, optionally substituted triazinyl, optionally substituted pyrrolyl, optionally substituted thienyl, optionally substituted furyl, optionally substituted thiazolyl, optionally substituted oxazolyl, optionally substituted imidazolyl, optionally substituted naphthyl, optionally substituted tetrahydronaphthyl, optionally substituted quinolinyl, optionally substituted isoquinolinyl, optionally substituted quinazolinyl, optionally substituted quinoxalinyl, optionally substituted cinnolinyl, optionally substituted naphthyridinyl, optionally substituted benzotriazinyl, optionally substituted pyridopyrimidinyl, optionally substituted pyridopyrazinyl, optionally substituted pyridopyridazinyl, optionally substituted pyridotriazinyl, optionally substituted indenyl, optionally substituted benzofuryl, optionally substituted benzothienyl, optionally substituted indolyl, optionally substituted indazolyl, optionally substituted benzoxazolyl, optionally substituted benzimidazolyl, optionally substituted benzothiazolyl, optionally substituted benzothiadiazolyl, optionally substituted furopyridinyl, optionally substituted thienopyridinyl, optionally substituted pyrrolopyridinyl, optionally substituted oxazolopyridinyl, optionally substituted thiazolopyridinyl or optionally substituted imidazopyridinyl.

(16) The compound according to (1) mentioned above, wherein, in the formula (I),
R$^3$ is selected from hydrogen and C$_{1-4}$ lower alkyl group.

(17) The compound according to (1) mentioned above, wherein, in the formula (I),
R$^7$ of A is -Rc-R$^{70}$
wherein
Rc is bond or optionally substituted lower alkylene, and
R$^{70}$ is optionally substituted aryl or optionally substituted heteroaryl.

(18) The compound according to (17) mentioned above, wherein, in the formula (I),
R$^{70}$ is optionally substituted biphenyl, optionally substituted phenyl, optionally substituted pyridyl, optionally substituted pyrimidyl, optionally substituted pyridazinyl, optionally substituted pyrazinyl, optionally substituted triazinyl, optionally substituted pyrrolyl, optionally substituted thienyl, optionally substituted furyl, optionally substituted thiazolyl, optionally substituted oxazolyl, optionally substituted imidazolyl, optionally substituted naphthyl, optionally substituted tetrahydronaphthyl, optionally substituted quinolinyl, optionally substituted isoquinolinyl, optionally substituted quinazolinyl, optionally substituted quinoxalinyl, optionally substituted cinnolinyl, optionally substituted naphthyridinyl, optionally substituted benzotriazinyl, optionally substituted pyridopyrimidinyl, optionally substituted pyridopyrazinyl, optionally substituted pyridopyridazinyl, optionally substituted pyridotriazinyl, optionally substituted indenyl, optionally substituted benzofuryl, optionally substituted benzothienyl, optionally substituted indolyl, optionally substituted indazolyl, optionally substituted benzoxazolyl, optionally substituted benzimidazolyl, optionally substituted benzothiazolyl, optionally substituted benzothiadiazolyl, optionally substituted furopyridinyl, optionally substituted thienopyridinyl, optionally substituted pyrrolopyridinyl, optionally substituted oxazolopyridinyl, optionally substituted thiazolopyridinyl or optionally substituted imidazopyridinyl.

(19) The compound according to (2) mentioned above, in which, in the formula (I),
$R^1$ is —Ra—$R^{10}$;
wherein
Ra is optionally substituted lower alkylene, and
$R^{10}$ is optionally substituted aryl, or optionally substituted heteroaryl, and
$R^3$ is selected from hydrogen and $C_{1-4}$ lower alkyl group.

(20) The compound according to (2) mentioned above, wherein, in the formula (I),
$R^2$ is —$W^{21}$—$W^{22}$—Rb—$R^{20}$;
wherein
$W^{21}$ is —(CO)— or —(SO$_2$)—;
$W^{22}$ is bond, —O—, —NH— or optionally substituted lower alkylene;
Rb is bond or optionally substituted lower alkylene; and
$R^{20}$ is optionally substituted aryl or optionally substituted heteroaryl; and
$R^3$ is selected from hydrogen and $C_{1-4}$ lower alkyl group.

(21) The compound according to (2) mentioned above, wherein, in the formula (I),
$R^7$ of A is -Rc-$R^{70}$
wherein
Rc is bond or optionally substituted lower alkylene, and
$R^{70}$ is optionally substituted aryl or optionally substituted heteroaryl; and
$R^3$ is selected from hydrogen and $C_{1-4}$ lower alkyl group.

(22) The compound according to (2) mentioned above, wherein, in the formula (I),
G is —$NR^6$—, —O—, —$CH_2$— or —$C(R^6)_2$—;
wherein
each $R^6$ is the same or different and independently selected from optionally substituted alkyl, optionally substituted alkenyl, and optionally substituted alkynyl; and
$R^3$ is selected from hydrogen and $C_{1-4}$ lower alkyl group.

(23) The compound according to (2) mentioned above, wherein, in the formula (I),
G is —$NR^6$—, —O—, —$CH_2$— or —$C(R^6)_2$—;
wherein
each $R^6$ is the same or different and independently selected from optionally substituted alkyl, optionally substituted alkenyl, and optionally substituted alkynyl; and
$R^3$ is hydrogen.

(24) The compound according to (3) mentioned above, wherein, in the formula (I),
$R^1$ is —Ra—$R^{10}$;
wherein
Ra is optionally substituted lower alkylene, and
$R^{10}$ is optionally substituted allyl and
$R^3$ is selected from hydrogen and $C_{1-4}$ lower alkyl group.

(25) The compound according to (3) mentioned above, wherein, in the formula (I),
$R^2$ is —$W^{21}$—$W^{22}$—Rb—$R^{20}$;
wherein
$W^{21}$ is —(CO)— or —(SO$_2$)—;
$W^{22}$ is bond, —O—, —NH— or optionally substituted lower alkylene;
Rb is bond or optionally substituted lower alkylene; and
$R^{20}$ is optionally substituted aryl or optionally substituted heteroaryl, and
$R^3$ is selected from hydrogen and $C_{1-4}$ lower alkyl group.

(26) The compound according to (3) mentioned above, wherein, in the formula (I),
$R^7$ of A is -Rc-$R^{70}$
wherein
Rc is bond or optionally substituted lower alkylene, and
$R^{70}$ is optionally substituted aryl or optionally substituted heteroaryl; and
$R^3$ is selected from hydrogen and $C_{1-4}$ lower alkyl group.

(27) The compound according to (3) mentioned above, wherein, in the formula (I),
G is —$NR^6$—, —O—, —$CH_2$— or —$C(R^6)_2$—;
wherein
each $R^6$ is the same or different and independently selected from optionally substituted alkyl, optionally substituted alkenyl, and optionally substituted alkynyl; and
$R^3$ is selected from hydrogen and $C_{1-4}$ lower alkyl group.

(28) The compound according to (3) mentioned above, wherein, in the formula (I),
G is —$NR^6$—, —O—, —$CH_2$— or —$C(R^6)_2$—;
wherein
each $R^6$ is the same or different and independently selected from optionally substituted alkyl, optionally substituted alkenyl, and optionally substituted alkynyl; and
$R^3$ is hydrogen.

(29) The compound according to (5) mentioned above, wherein, in the formula (I),
$R^1$ is —Ra—$R^{10}$;
wherein
Ra is optionally substituted lower alkylene, and
$R^{10}$ is optionally substituted allyl and
$R^3$ is selected from hydrogen or $C_{1-4}$ lower alkyl group.

(30) The compound according to (5) mentioned above, wherein, in the formula (I),
$R^2$ is —$W^{21}$—$W^{22}$—Rb—$R^{20}$;
wherein
$W^{21}$ is —(CO)— or —(SO$_2$)—;
$W^{22}$ is bond, —O—, —NH— or optionally substituted lower alkylene;
Rb is bond or optionally substituted lower alkylene; and
$R^{20}$ is optionally substituted aryl or optionally substituted heteroaryl, and
$R^3$ is selected from hydrogen and $C_{1-4}$ lower alkyl group:

(31) The compound according to (5) mentioned above, wherein, in the formula (I),
$R^7$ of A is -Rc-$R^{70}$
wherein
Rc is bond or optionally substituted lower alkylene, and
$R^{70}$ is optionally substituted aryl or optionally substituted heteroaryl; and
$R^3$ is selected from hydrogen and $C_{1-4}$ lower alkyl group.

(32) The compound according to (5) mentioned above, wherein, in the formula (I),
$R^3$ is hydrogen.

(33) The compound according to (6) mentioned above, wherein, in the formula (I),
$R^1$ is —Ra—$R^{10}$;

wherein
  Ra is optionally substituted lower alkylene, and
  $R^{10}$ is optionally substituted allyl and
  $R^3$ is selected from hydrogen and $C_{1-4}$ lower alkyl group.
(34) The compound according to (6) mentioned above, wherein, in the formula (I),
  $R^2$ is —$W^{21}$—$W^{22}$—Rb—$R^{20}$;
  wherein
    $W^{21}$ is —(CO)— or —($SO_2$)—;
    $W^{22}$ is bond, —O—, —NH— or optionally substituted lower alkylene;
    Rb is bond or optionally substituted lower alkylene; and
    $R^{20}$ is optionally substituted aryl or optionally substituted heteroaryl, and
  $R^3$ is selected from hydrogen and $C_{1-4}$ lower alkyl group.
(35) The compound according to (6) mentioned above, wherein, in the formula (I),
  $R^7$ of A is -Rc-$R^{70}$
  wherein
    Rc is bond or optionally substituted lower alkylene, and
    $R^{70}$ is optionally substituted aryl or optionally substituted heteroaryl; and
  $R^3$ is selected from hydrogen and $C_{1-4}$ lower alkyl group.
(36) The compound according to (6) mentioned above, wherein, in the formula (I),
  $R^3$ is hydrogen.
(37) The compound according to any of (2), (3) and (5) mentioned above, wherein, in the formula (I),
  $R^1$ is —Ra—$R^{10}$;
  wherein
    Ra is optionally substituted lower alkylene, and
    $R^{10}$ is optionally substituted aryl, or optionally substituted heteroaryl,
  $R^2$ is —$W^{21}$—$W^{22}$—Rb—$R^{20}$;
  wherein
    $W^{21}$ is —(CO)— or —($SO_2$)—;
    $W^{22}$ is bond, —O—, —NH— or optionally substituted lower alkylene;
    Rb is bond or optionally substituted lower alkylene;
    $R^{20}$ is optionally substituted aryl or optionally substituted heteroaryl;
  $R^3$ is selected from hydrogen and $C_{1-4}$ lower alkyl group;
  $R^7$ of A is -Rc-$R^{70}$
  wherein
    Rc is bond or optionally substituted lower alkylene, and
    $R^{70}$ is optionally substituted aryl or optionally substituted heteroaryl.
(38) The compound according to any of (2), (3) mentioned above, wherein, in the formula (I),
  G is —$NR^6$—, —O—, —$CH_2$— or —$C(R^6)_2$—;
  wherein
    each $R^6$ is the same or different and independently selected from optionally substituted alkyl, optionally substituted alkenyl, and optionally substituted alkynyl;
  $R^1$ is —Ra—$R^{10}$;
  wherein
    Ra is optionally substituted lower alkylene, and
    $R^{10}$ is optionally substituted aryl, or optionally substituted heteroaryl,
  $R^2$ is —$W^{21}$—$W^{22}$—Rb—$R^{20}$;
  wherein
    $W^{21}$ is —(CO)— or —($SO_2$)—;
    $W^{22}$ is bond, —O—, —NH— or optionally substituted lower alkylene;
    Rb is bond or optionally substituted lower alkylene; and
    $R^{20}$ is optionally substituted aryl or optionally substituted heteroaryl;
  $R^3$ is hydrogen; and
  $R^7$ of A is -Rc-$R^{70}$
  wherein
    Rc is bond or optionally substituted lower alkylene, and
    $R^{70}$ is optionally substituted aryl or optionally substituted heteroaryl.
(39) The compound according to any of (19), (24) and (38) mentioned above, wherein, in the formula (I),
  $R^{10}$ is optionally substituted biphenyl, optionally substituted phenyl, optionally substituted pyridyl, optionally substituted pyrimidyl, optionally, substituted pyridazinyl, optionally substituted pyrazinyl, optionally substituted triazinyl, optionally substituted pyrrolyl, optionally substituted thienyl, optionally substituted furyl, optionally substituted thiazolyl, optionally substituted oxazolyl, optionally substituted imidazolyl, optionally substituted naphthyl, optionally substituted tetrahydronaphthyl, optionally substituted quinolinyl, optionally substituted isoquinolinyl, optionally substituted quinazolinyl, optionally substituted quinoxalinyl, optionally substituted cinnolinyl, optionally substituted naphthyridinyl, optionally substituted benzotriazinyl, optionally substituted pyridopyrimidinyl, optionally substituted pyridopyrazinyl, optionally substituted pyridopyridazinyl, optionally substituted pyridotriazinyl, optionally substituted indenyl, optionally substituted benzofuryl, optionally substituted benzothienyl, optionally substituted indolyl, optionally substituted indazolyl, optionally substituted benzoxazolyl, optionally substituted benzimidazolyl, optionally substituted benzothiazolyl, optionally substituted benzothiadiazolyl, optionally substituted furopyridinyl, optionally substituted thienopyridinyl, optionally substituted pyrrolopyridinyl, optionally substituted oxazolopyridinyl, optionally substituted thiazolopyridinyl or optionally substituted imidazopyridinyl.
(40) The compound according to any of (20), (25) and (38) mentioned above, in which, in the formula (I),
  $R^{20}$ is optionally substituted biphenyl, optionally substituted phenyl, optionally substituted pyridyl, optionally substituted pyrimidyl, optionally substituted pyridazinyl, optionally substituted pyrazinyl, optionally substituted triazinyl, optionally substituted pyrrolyl, optionally substituted thienyl, optionally substituted furyl, optionally substituted thiazolyl, optionally substituted oxazolyl, optionally substituted imidazolyl, optionally substituted naphthyl, optionally substituted tetrahydronaphthyl, optionally substituted quinolinyl, optionally substituted isoquinolinyl, optionally substituted quinazolinyl, optionally substituted quinoxalinyl, optionally substituted cinnolinyl, optionally substituted naphthyridinyl, optionally substituted benzotriazinyl, optionally substituted pyridopyrimidinyl, optionally substituted pyridopyrazinyl, optionally substituted pyridopyridazinyl, optionally substituted pyridotriazinyl, optionally substituted indenyl, optionally substituted benzofuryl, optionally substituted benzothienyl, optionally substituted indolyl, optionally substituted indazolyl, optionally substituted benzoxazolyl, optionally substituted benzimidazolyl, optionally substituted benzothiazolyl, optionally substituted benzothiadiazolyl, optionally substituted furopyridinyl, optionally substituted thienopyridinyl, optionally substituted pyrrolopyridinyl, optionally substituted oxazolopyridinyl, optionally substituted thiazolopyridinyl or optionally substituted imidazopyridinyl.
(41) The compound according to any of (21), (26) and (38) mentioned above, in which, in the formula (I),
  $R^{70}$ is optionally substituted biphenyl, optionally substituted phenyl, optionally substituted pyridyl, optionally substituted pyrimidyl, optionally substituted pyridazinyl, optionally substituted pyrazinyl, optionally substituted triazinyl, optionally substituted pyrrolyl, optionally substituted thienyl, optionally substituted furyl, optionally substituted thiazolyl, optionally substituted oxazolyl, optionally substituted imidazolyl, optionally substituted naphthyl, optionally substituted tetrahydronaphthyl, optionally substituted quinolinyl, optionally substituted isoquinolinyl, optionally substituted quinazolinyl, optionally substituted quinoxalinyl, optionally substituted cinnolinyl, optionally substituted naphthyridinyl, optionally substituted benzotriazinyl, optionally substituted pyridopyrimidinyl, optionally substituted pyridopyrazinyl, optionally substituted pyridopyridazinyl, optionally substituted pyridotriazinyl, optionally substituted indenyl, optionally substituted benzofuryl, optionally substituted benzothienyl, optionally substituted indolyl, optionally substituted indazolyl, optionally substituted benzoxazolyl, optionally substituted benzimidazolyl, optionally substituted benzothiazolyl, optionally substituted benzothiadiazolyl, optionally substituted furopyridinyl, optionally substituted thienopyridinyl, optionally substituted pyrrolopyridinyl, optionally substituted oxazolopyridinyl, optionally substituted thiazolopyridinyl or optionally substituted imidazopyridinyl.

(42) The compound according to any of (37) and (38) mentioned above, in which, in the formula (I), $R^{10}$ is optionally substituted biphenyl, optionally substituted phenyl, optionally substituted pyridyl, optionally substituted pyrimidyl, optionally substituted pyridazinyl, optionally substituted pyrazinyl, optionally substituted triazinyl, optionally substituted pyrrolyl, optionally substituted thienyl, optionally substituted furyl, optionally substituted thiazolyl, optionally substituted oxazolyl, optionally substituted imidazolyl, optionally substituted naphthyl, optionally substituted tetrahydronaphthyl, optionally substituted quinolinyl, optionally substituted isoquinolinyl, optionally substituted quinazolinyl, optionally substituted quinoxalinyl, optionally substituted cinnolinyl, optionally substituted naphthyridinyl, optionally substituted benzotriazinyl, optionally substituted pyridopyrimidinyl, optionally substituted pyridopyrazinyl, optionally substituted pyridopyridazinyl, optionally substituted pyridotriazinyl, optionally substituted indenyl, optionally substituted benzofuryl, optionally substituted benzothienyl, optionally substituted indolyl, optionally substituted indazolyl, optionally substituted benzoxazolyl, optionally substituted benzimidazolyl, optionally substituted benzothiazolyl, optionally substituted benzothiadiazolyl, optionally substituted furopyridinyl, optionally substituted thienopyridinyl, optionally substituted pyrrolopyridinyl, optionally substituted oxazolopyridinyl, optionally substituted thiazolopyridinyl or optionally substituted imidazopyridinyl;

$R^{20}$ is optionally substituted biphenyl, optionally substituted phenyl, optionally substituted pyridyl, optionally substituted pyrimidyl, optionally substituted pyridazinyl, optionally substituted pyrazinyl, optionally substituted triazinyl, optionally substituted pyrrolyl, optionally substituted thienyl, optionally substituted furyl, optionally substituted thiazolyl, optionally substituted oxazolyl, optionally substituted imidazolyl, optionally substituted naphthyl, optionally substituted tetrahydronaphthyl, optionally substituted quinolinyl, optionally substituted isoquinolinyl, optionally substituted quinazolinyl, optionally substituted quinoxalinyl, optionally substituted cinnolinyl, optionally substituted naphthyridinyl, optionally substituted benzotriazinyl, optionally substituted pyridopyrimidinyl, optionally substituted pyridopyrazinyl, optionally substituted pyridopyridazinyl, optionally substituted pyridotriazinyl, optionally substituted indenyl, optionally substituted benzofuryl, optionally substituted benzothienyl, optionally substituted indolyl, optionally substituted indazolyl, optionally substituted benzoxazolyl, optionally substituted benzimidazolyl, optionally substituted benzothiazolyl, optionally substituted benzothiadiazolyl, optionally substituted furopyridinyl, optionally substituted thienopyridinyl, optionally substituted pyrrolopyridinyl, optionally substituted oxazolopyridinyl, optionally substituted thiazolopyridinyl or optionally substituted imidazopyridinyl; and $R^{70}$ is optionally substituted biphenyl, optionally substituted phenyl, optionally substituted pyridyl, optionally substituted pyrimidyl, optionally substituted pyridazinyl, optionally substituted pyrazinyl, optionally substituted triazinyl, optionally substituted pyrrolyl, optionally substituted thienyl, optionally substituted furyl, optionally substituted thiazolyl, optionally substituted oxazolyl, optionally substituted imidazolyl, optionally substituted naphthyl, optionally substituted tetrahydronaphthyl, optionally substituted quinolinyl, optionally substituted isoquinolinyl, optionally substituted quinazolinyl, optionally substituted quinoxalinyl, optionally substituted cinnolinyl, optionally substituted naphthyridinyl, optionally substituted benzotriazinyl, optionally substituted pyridopyrimidinyl, optionally substituted pyridopyrazinyl, optionally substituted pyridopyridazinyl, optionally substituted pyridotriazinyl, optionally substituted indenyl, optionally substituted benzofuryl, optionally substituted benzothienyl, optionally substituted indolyl, optionally substituted indazolyl, optionally substituted benzoxazolyl, optionally substituted benzimidazolyl, optionally substituted benzothiazolyl, optionally substituted benzothiadiazolyl, optionally substituted furopyridinyl, optionally substituted thienopyridinyl, optionally substituted pyrrolopyridinyl, optionally substituted oxazolopyridinyl, optionally substituted thiazolopyridinyl or optionally substituted imidazopyridinyl.

(43) A compound having the following general formula (II):

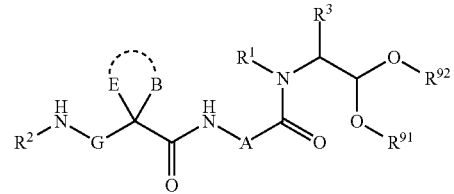

wherein

A is —(CHR$^7$)—;

wherein $R^7$ is hydrogen, optionally substituted alkyl, optionally substituted alkenyl, optionally substituted alkynyl, optionally substituted aryl, optionally substituted heteroaryl, optionally substituted cycloalkyl, optionally substituted heterocycloalkyl, optionally substituted arylalkyl, optionally substituted heteroarylalkyl, optionally substituted cycloalkylalkyl, or optionally substituted heterocycloalkylalkyl;

B and E are the same or different and independently selected from hydrogen, optionally substituted alkyl, optionally substituted alkenyl, and optionally substituted alkynyl or form an optionally substituted spiro ring indicated by dashed lines;

G is —NH—, —NR$^6$—, —O—, —CH$_2$—, —CHR$^6$— or —C(R$^6$)$_2$—;
wherein
each R$^6$ is the same or different and independently selected from optionally substituted alkyl, optionally substituted alkenyl, and optionally substituted alkynyl;
R$^1$ is optionally substituted alkyl, optionally substituted alkenyl, optionally substituted alkynyl, optionally substituted arylalkyl, optionally substituted heteroarylalkyl, optionally substituted cycloalkylalkyl, or optionally substituted heterocycloalkylalkyl;
R$^2$ is —W$^{21}$—W$^{22}$—Rb—R$^{20}$;
wherein
W$^{21}$ is —(CO)— or —(SO$_2$)—;
W$^{22}$ is bond, —O—, —NH— or optionally substituted lower alkylene;
Rb is bond or optionally substituted lower alkylene; and
R$^{20}$ is optionally substituted alkyl, optionally substituted alkenyl, optionally substituted alkynyl, optionally substituted aryl, optionally substituted heteroaryl, optionally substituted cycloalkyl, or optionally substituted heterocycloalkyl;
R$^3$ is hydrogen, optionally substituted alkyl, optionally substituted alkenyl, or optionally substituted alkynyl;
R$^{91}$ is selected from optionally substituted alkyl, linker and solid support; and
R$^{92}$ is selected from optionally substituted alkyl, linker and solid support;
with the proviso that
(1) when Rb is optionally substituted lower alkylene, then W$^{22}$ should be —O— or —NH—,
(2) when E and B are hydrogen, then R$^3$ should be hydrogen,
(3) when G is —NH—, —CH$_2$—, —CHR$^6$— or —NR$^6$—, then B and E should not be hydrogen, and
(4) when G is —O—, B and E are hydrogen and R$^3$ is hydrogen, then R$^1$ should not be 8-quinolylmethyl; or a salt thereof.

(44) The compound according to (43) mentioned above, wherein, in the formula (II),
B and E are the same or different and independently selected from hydrogen, optionally substituted alkyl, optionally substituted alkenyl, and optionally substituted alkynyl
or form an optionally substituted 3-, 4-, 5-, 6- or 7 membered unsaturated monocyclic ring, when the formed spiro ring is heterocyclic ring, the hetero atom is selected from S, N and O and a number of hetero atom is 1.

(45) The compound according to (43) mentioned above, wherein, in the formula (II),
B and E are the same or different and independently selected from hydrogen, and optionally substituted alkyl or form an optionally substituted 3-, 4-, 5-, 6- or 7 membered unsaturated monocyclic ring, when the formed spiro ring is heterocyclic ring, the hetero atom is selected from S, N and O and a number of hetero atom is 1.

(46) The compound according to (43) mentioned above, wherein, in the formula (II),
G is —NR$^6$—, —O—, —CH$_2$— or —C(R$^6$)$_2$—;
wherein
each R$^6$ is the same or different and independently selected from optionally substituted alkyl, optionally substituted alkenyl, and optionally substituted alkynyl,

(47) The compound according to (43) mentioned above, wherein, in the formula (II),
G is —O—.

(48) The compound according to (43) mentioned above, wherein, in the formula (II),
G is —O—, and
B and E are hydrogen.

(49) The compound according to (43) mentioned above, wherein, in the formula (II),
R$^3$ is hydrogen.

(50) The compound according to (43) mentioned above, wherein, in the formula (II),
A is —(CHR$^7$)—;
wherein
R$^7$ is optionally substituted alkyl, optionally substituted aryl, or optionally substituted arylalkyl.

(51) The compound according to (43) mentioned above, wherein, in the formula (II),
R$^1$ is optionally substituted alkyl, optionally substituted arylalkyl, optionally substituted heteroarylalkyl, or optionally substituted cycloalkylalkyl.

(52) The compound according to (43) mentioned above, wherein, in the formula (II),
R$^2$ is —W$^{21}$—W$^{22}$—Rb—R$^{20}$,
wherein
W$^{21}$ is —(CO)— or —(SO$_2$)—;
W$^{22}$ is bond, —O—, —NH— or optionally substituted lower alkylene;
Rb is bond or optionally substituted lower alkylene; and
R$^{20}$ is optionally substituted alkyl, optionally substituted aryl, or optionally substituted heteroaryl.

(53) The compound according to (43) mentioned above, wherein, in the formula (II),
A is —(CHR$^7$)—;
wherein
R$^7$ is optionally substituted alkyl, or optionally substituted arylalkyl;
R$^1$ is optionally substituted alkyl, optionally substituted arylalkyl, optionally substituted heteroarylalkyl, or optionally substituted cycloalkylalkyl; and
R$^2$ is —W$^{21}$—W$^{22}$—Rb—R$^{20}$;
wherein
W$^{21}$ is —(CO)— or —(SO$_2$)—;
W$^{22}$ is bond, —O—, —NH— or optionally substituted lower alkylene;
Rb is bond or optionally substituted lower alkylene; and
R$^{20}$ is optionally substituted alkyl, optionally substituted aryl, optionally substituted heteroaryl.

(54) The compound according to (43) mentioned above, wherein, in the formula (II),
R$^1$ is —Ra—R$^{10}$;
wherein
Ra is optionally substituted lower alkylene and
R$^{10}$ is optionally substituted aryl or optionally substituted heteroaryl.

(55) The compound according to (54) mentioned above, wherein, in the formula (II),
R$^{10}$ is optionally substituted biphenyl, optionally substituted phenyl, optionally substituted pyridyl, optionally substituted pyrimidyl, optionally substituted pyridazinyl, optionally substituted pyrazinyl, optionally substituted triazinyl, optionally substituted pyrrolyl, optionally substituted thienyl, optionally substituted furyl, optionally substituted thiazolyl, optionally substituted oxazolyl, optionally substituted imidazolyl, optionally substituted naphthyl, optionally substituted tetrahydronaphthyl, optionally substituted quinolinyl, optionally substituted isoquinolinyl, optionally substituted quinazolinyl, optionally substituted quinoxalinyl, optionally substituted cinnolinyl, optionally substituted naphthyridinyl, optionally substituted benzotriazinyl, optionally substituted pyridopyrimidinyl, optionally substituted pyridopyrazinyl, optionally substituted pyridopyridazinyl, optionally substituted pyridotriazinyl, optionally substituted indenyl, optionally substituted benzofuryl, optionally substituted benzothienyl, optionally substituted indolyl, optionally substituted indazolyl, optionally substituted benzoxazolyl, optionally substituted benzimidazolyl, optionally substituted benzothiazolyl, optionally substituted benzothiadiazolyl, optionally substituted furopyridinyl, optionally substituted thienopyridinyl, optionally substituted pyrrolopyridinyl, optionally substituted oxazolopyridinyl, optionally substituted thiazolopyridinyl or optionally substituted imidazopyridinyl.

(56) The compound according to (43) mentioned above, wherein, in the formula (II),
$R^2$ is —$W^{21}$—$W^{22}$—Rb—$R^{20}$;
wherein
$W^{21}$ is —(CO)— or —($SO_2$)—;
$W^{22}$ is bond, —O—, —NH— or optionally substituted lower alkylene;
Rb is bond or optionally substituted lower alkylene; and
$R^{20}$ is optionally substituted aryl or optionally substituted heteroaryl.

(57) The compound according to (56) mentioned above, wherein, in the formula (II),
$R^{20}$ is optionally substituted biphenyl, optionally substituted phenyl, optionally substituted pyridyl, optionally substituted pyrimidyl, optionally substituted pyridazinyl, optionally substituted pyrazinyl, optionally substituted triazinyl, optionally substituted pyrrolyl, optionally substituted thienyl, optionally substituted furyl, optionally substituted thiazolyl, optionally substituted oxazolyl, optionally substituted imidazolyl, optionally substituted naphthyl, optionally substituted tetrahydronaphthyl, optionally substituted quinolinyl, optionally substituted isoquinolinyl, optionally substituted quinazolinyl, optionally substituted quinoxalinyl, optionally substituted cinnolinyl, optionally substituted naphthyridinyl, optionally substituted benzotriazinyl, optionally substituted pyridopyrimidinyl, optionally substituted pyridopyrazinyl, optionally substituted pyridopyridazinyl, optionally substituted pyridotriazinyl, optionally substituted indenyl, optionally substituted benzofuryl, optionally substituted benzothienyl, optionally substituted indolyl, optionally substituted indazolyl, optionally sdbstitUted benzoxazolyl, optionally substituted benzimidazolyl, optionally substituted benzothiazolyl, optionally substituted benzothiadiazolyl, optionally substituted furopyridinyl, optionally substituted thienopyridinyl, optionally substituted pyrrolopyridinyl, optionally substituted oxazolopyridinyl, optionally substituted thiazolopyridinyl or optionally substituted imidazopyridinyl.

(58) The compound according to (43) mentioned above, wherein, in the formula (II),
$R^3$ is selected from hydrogen and $C_{1-4}$ lower alkyl group.

(59) The compound according to (43) mentioned above, wherein, in the formula (II),
$R^7$ of A is -Rc-$R^{70}$
wherein
Rc is bond or optionally substituted lower alkylene, and
$R^{70}$ is optionally substituted aryl or optionally substituted heteroaryl.

(60) The compound according to (59) mentioned above, wherein, in the formula (II),
$R^{70}$ is optionally substituted biphenyl, optionally substituted phenyl, optionally substituted pyridyl, optionally substituted pyrimidyl, optionally substituted pyridazinyl, optionally substituted pyrazinyl, optionally substituted triazinyl, optionally substituted pyrrolyl, optionally substituted thienyl, optionally substituted furyl, optionally substituted thiazolyl, optionally substituted oxazolyl, optionally substituted imidazolyl, optionally substituted naphthyl, optionally substituted tetrahydronaphthyl, optionally substituted quinolinyl, optionally substituted isoquinolinyl, optionally substituted quinazolinyl, optionally substituted quinoxalinyl, optionally substituted cinnolinyl, optionally substituted naphthyridinyl, optionally substituted benzotriazinyl, optionally substituted pyridopyrimidinyl, optionally substituted pyridopyrazinyl, optionally substituted pyridopyridazinyl, optionally substituted pyridotriazinyl, optionally substituted indenyl, optionally substituted benzofuryl, optionally substituted benzothienyl, optionally substituted indolyl, optionally substituted indazolyl, optionally substituted benzoxazolyl, optionally substituted benzimidazolyl, optionally substituted benzothiazolyl, optionally substituted benzothiadiazolyl, optionally substituted furopyridinyl, optionally substituted thienopyridinyl, optionally substituted pyrrolopyridinyl, optionally substituted oxazolopyridinyl, optionally substituted thiazolopyridinyl or optionally substituted imidazopyridinyl.

(61) The compound according to (44) mentioned above, in which, in the formula (II),
$R^1$ is —Ra—$R^{10}$;
wherein
Ra is optionally substituted lower alkylene, and
$R^{10}$ is optionally substituted aryl, or optionally substituted heteroaryl, and
$R^3$ is selected from hydrogen and $C_{1-4}$ lower alkyl group.

(62) The compound according to (44) mentioned above, wherein, in the formula (II),
$R^2$ is —$W^{21}$—$W^{22}$—Rb—$R^{20}$;
wherein
$W^{21}$ is —(CO)— or —($SO_2$)—;
$W^{22}$ is bond, —O—, —NH— or optionally substituted lower alkylene;
Rb is bond or optionally substituted lower alkylene; and
$R^{20}$ is optionally substituted aryl or optionally substituted heteroaryl; and
$R^3$ is selected from hydrogen and $C_{1-4}$ lower alkyl group.

(63) The compound according to (44) mentioned above, wherein, in the formula (II),
$R^7$ of A is -Rc-$R^{70}$
wherein
Rc is bond or optionally substituted lower alkylene, and
$R^{70}$ is optionally substituted aryl or optionally substituted heteroaryl; and
$R^3$ is selected from hydrogen and $C_{1-4}$ lower alkyl group.

(64) The compound according to (44) mentioned above, wherein, in the formula (II),
G is —$NR^6$—, —O—, —$CH_2$— or —$C(R^6)_2$—;
wherein
each $R^6$ is the same or different and independently selected from optionally substituted alkyl, optionally substituted alkenyl, and optionally substituted alkynyl; and
$R^3$ is selected from hydrogen and $C_{1-4}$ lower alkyl group.

(65) The compound according to (44) mentioned above, wherein, in the formula (II),
G is —$NR^6$—, —O—, —$CH_2$— or —$C(R^6)_2$—;
wherein
each $R^6$ is the same or different and independently selected from optionally substituted alkyl, optionally substituted alkenyl, and optionally substituted alkynyl; and
$R^3$ is hydrogen.

(66) The compound according to (45) mentioned above, wherein, in the formula (II),
$R^1$ is —Ra—$R^{10}$;
wherein
Ra is optionally substituted lower alkylene, and
$R^{10}$ is optionally substituted allyl and
$R^3$ is selected from hydrogen and $C_{1-4}$ lower alkyl group.

(67) The compound according to (45) mentioned above, wherein, in the formula (II),
$R^2$ is $—W^{21}—W^{22}—Rb—R^{20}$;
wherein
$W^{21}$ is $—(CO)—$ or $—(SO_2)—$;
$W^{22}$ is bond, $—O—$, $—NH—$ or optionally substituted lower alkylene;
Rb is bond or optionally substituted lower alkylene; and
$R^{20}$ is optionally substituted aryl or optionally substituted heteroaryl, and
$R^3$ is selected from hydrogen and $C_{1-4}$ lower alkyl group.

(68) The compound according to (45) mentioned above, wherein, in the formula (II),
$R^7$ of A is -Rc-$R^{70}$
wherein
Rc is bond or optionally substituted lower alkylene, and
$R^{70}$ is optionally substituted aryl or optionally substituted heteroaryl; and
$R^3$ is selected from hydrogen and $C_{1-4}$ lower alkyl group.

(69) The compound according to (45) mentioned above, wherein, in the formula (II),
G is $—NR^6—$, $—O—$, $—CH_2—$ or $—C(R^6)_2—$;
wherein
each $R^6$ is the same or different and independently selected from optionally substituted alkyl, optionally substituted alkenyl, and optionally substituted alkynyl; and
$R^3$ is selected from hydrogen and $C_{1-4}$ lower alkyl group.

(70) The compound according to (45) mentioned above, wherein, in the formula (II),
G is $—NR^6—$, $—O—$, $—CH_2—$ or $—C(R^6)_2—$;
wherein
each $R^6$ is the same or different and independently selected from optionally substituted alkyl, optionally substituted alkenyl, and optionally substituted alkynyl; and
$R^3$ is hydrogen.

(71) The compound according to (47) mentioned above, wherein, in the formula (II),
$R^1$ is $—Ra—R^{10}$;
wherein
Ra is optionally substituted lower alkylene, and
$R^{10}$ is optionally substituted allyl and
$R^3$ is selected from hydrogen or $C_{1-4}$ lower alkyl group.

(72) The compound according to (47) mentioned above, wherein, in the formula (II),
$R^2$ is $—W^{21}—W^{22}—Rb—R^{20}$;
wherein
$W^{21}$ is $—(CO)—$ or $—(SO_2)—$;
$W^{22}$ is bond, $—O—$, $—NH—$ or optionally substituted lower alkylene;
Rb is bond or optionally substituted lower alkylene; and
$R^{20}$ is optionally substituted aryl or optionally substituted heteroaryl, and
$R^3$ is selected from hydrogen and $C_{1-4}$ lower alkyl group.

(73) The compound according to (47) mentioned above, wherein, in the formula (II),
$R^7$ of A is -Rc-$R^{70}$
wherein
Rc is bond or optionally substituted lower alkylene, and
$R^{70}$ is optionally substituted aryl or optionally substituted heteroaryl; and
$R^3$ is selected from hydrogen and $C_{1-4}$ lower alkyl group.

(74) The compound according to (47) mentioned above, wherein, in the formula (II),
$R^3$ is hydrogen.

(75) The compound according to (48) mentioned above, wherein, in the formula (II),
$R^1$ is $—Ra—R^{10}$;
wherein
Ra is optionally substituted lower alkylene, and
$R^{10}$ is optionally substituted allyl and
$R^3$ is selected from hydrogen and $C_{1-4}$ lower alkyl group.

(76) The compound according to (48) mentioned above, wherein, in the formula (II),
$R^2$ is $—W^{21}—W^{22}—Rb—R^{20}$;
wherein
$W^{21}$ is $—(CO)—$ or $—(SO_2)—$;
$W^{22}$ is bond, $—O—$, $—NH—$ or optionally substituted lower alkylene;
Rb is bond or optionally substituted lower alkylene; and
$R^{20}$ is optionally substituted aryl or optionally substituted heteroaryl, and
$R^3$ is selected from hydrogen and $C_{1-4}$ lower alkyl group.

(77) The compound according to (48) mentioned above, wherein, in the formula (II),
$R^7$ of A is -Rc-$R^{70}$
wherein
Rc is bond or optionally substituted lower alkylene, and
$R^{70}$ is optionally substituted aryl or optionally substituted heteroaryl; and
$R^3$ is selected from hydrogen and $C_{1-4}$ lower alkyl group.

(78) The compound according to (48) mentioned above, wherein, in the formula (II),
$R^3$ is hydrogen.

(79) The compound according to any of (44), (45) and (47) mentioned above, wherein, in the formula (II),
$R^1$ is $—Ra—R^{10}$;
wherein
Ra is optionally substituted lower alkylene, and
$R^{10}$ is optionally substituted aryl, or optionally substituted heteroaryl,
$R^2$ is $—W^{21}—W^{22}—Rb—R^{20}$;
wherein
$W^{21}$ is $—(CO)—$ or $—(SO_2)—$;
$W^{22}$ is bond, $—O—$, $—NH—$ or optionally substituted lower alkylene;
Rb is bond or optionally substituted lower alkylene;
$R^{20}$ is optionally substituted aryl or optionally substituted heteroaryl;
$R^3$ is selected from hydrogen and $C_{1-4}$ lower alkyl group;
$R^7$ of A is -Rc-$R^{70}$
wherein
Rc is bond or optionally substituted lower alkylene, and
$R^{70}$ is optionally substituted aryl or optionally substituted heteroaryl.

(80) The compound according to any of (44) and (45) mentioned above, wherein, in the formula (I),
G is $—NR^6—$, $—O—$, $—CH_2—$ or $—C(R^6)_2—$;
wherein
each $R^6$ is the same or different and independently selected from optionally substituted alkyl, optionally substituted alkenyl, and optionally substituted alkynyl;
$R^1$ is $—Ra—R^{10}$;
wherein
Ra is optionally substituted lower alkylene, and
$R^{10}$ is optionally substituted aryl, or optionally substituted heteroaryl,
$R^2$ is $—W^{21}—W^{22}—Rb—R^{20}$;
wherein
$W^{21}$ is $—(CO)—$ or $—(SO_2)—$;
$W^{22}$ is bond, $—O—$, $—NH—$ or optionally substituted lower alkylene;
Rb is bond or optionally substituted lower alkylene; and
$R^{20}$ is optionally substituted aryl or optionally substituted heteroaryl;

R³ is hydrogen; and

R⁷ of A is -Rc-R⁷⁰
wherein
Rc is bond or optionally substituted lower alkylene, and
R⁷⁰ is optionally substituted aryl or optionally substituted heteroaryl.

(81) The compound according to any of (61), (66) and (80) mentioned above, wherein, in the formula (I), R¹⁰ is optionally substituted biphenyl, optionally substituted phenyl, optionally substituted pyridyl, optionally substituted pyrimidyl, optionally substituted ipyridazinyl, optionally substituted pyrazinyl, optionally substituted triazinyl, optionally substituted pyrrolyl, optionally substituted thienyl, optionally substituted furyl, optionally substituted thiazolyl, optionally substituted oxazolyl, optionally substituted imidazolyl, optionally substituted naphthyl, optionally substituted tetrahydronaphthyl, optionally substituted quinolinyl, optionally substituted isoquinolinyl, optionally substituted quinazolinyl, optionally substituted quinoxalinyl, optionally substituted cinnolinyl, optionally substituted naphthyridinyl, optionally substituted benzotriazinyl, optionally substituted pyridopyrimidinyl, optionally substituted pyridopyrazinyl, optionally substituted pyridopyridazinyl, optionally substituted pyridotriazinyl, optionally substituted indenyl, optionally substituted benzofuryl, optionally substituted benzothienyl, optionally substituted indolyl, optionally substituted indazolyl, optionally substituted benzoxazolyl, optionally substituted benzimidazolyl, optionally substituted benzothiazolyl, optionally substituted benzothiadiazolyl, optionally substituted furopyridinyl, optionally substituted thienopyridinyl, optionally substituted pyrrolopyridinyl, optionally substituted oxazolopyridinyl, optionally substituted thiazolopyridinyl or optionally substituted imidazopyridinyl.

(82) The compound according to any of (62), (67) and (80) mentioned above, in which, in the formula (I), R²⁰ is optionally substituted biphenyl, optionally substituted phenyl, optionally substituted pyridyl, optionally substituted pyrimidyl, optionally substituted pyridazinyl, optionally substituted pyrazinyl, optionally substituted triazinyl, optionally substituted pyrrolyl, optionally substituted thienyl, optionally substituted furyl, optionally substituted thiazolyl, optionally substituted oxazolyl, optionally substituted imidazolyl, optionally substituted naphthyl, optionally substituted tetrahydronaphthyl, optionally substituted quinolinyl, optionally substituted isoquinolinyl, optionally substituted quinazolinyl, optionally substituted quinoxalinyl, optionally substituted cinnolinyl, optionally substituted naphthyridinyl, optionally substituted benzotriazinyl, optionally substituted pyridopyrimidinyl, optionally substituted pyridopyrazinyl, optionally substituted pyridopyridazinyl, optionally substituted pyridotriazinyl, optionally substituted indenyl, optionally substituted benzofuryl, optionally substituted benzothienyl, optionally substituted indolyl, optionally substituted indazolyl, optionally substituted benzoxazolyl, optionally substituted benzimidazolyl, optionally substituted benzothiazolyl, optionally substituted benzothiadiazolyl, optionally substituted furopyridinyl, optionally substituted thienopyridinyl, optionally substituted pyrrolopyridinyl, optionally substituted oxazolopyridinyl, optionally substituted thiazolopyridinyl or optionally substituted imidazopyridinyl.

(83) The compound according to any of (63), (68) and (80) mentioned above, in which, in the formula (I), R⁷⁰ is optionally substituted biphenyl, optionally substituted phenyl, optionally substituted pyridyl, optionally substituted pyrimidyl, optionally substituted pyridazinyl, optionally substituted pyrazinyl, optionally substituted triazinyl, optionally substituted pyrrolyl, optionally substituted thienyl, optionally substituted furyl, optionally substituted thiazolyl, optionally substituted oxazolyl, optionally substituted imidazolyl, optionally substituted naphthyl, optionally substituted tetrahydronaphthyl, optionally substituted quinolinyl, optionally substituted isoquinolinyl, optionally substituted quinazolinyl, optionally substituted quinoxalinyl, optionally substituted cinnolinyl, optionally substituted naphthyridinyl, optionally substituted benzotriazinyl, optionally substituted pyridopyrimidinyl, optionally substituted pyridopyrazinyl, optionally substituted pyridopyridazinyl, optionally substituted pyridotriazinyl, optionally substituted indenyl, optionally substituted benzofuryl, optionally substituted benzothienyl, optionally substituted indolyl, optionally substituted indazolyl, optionally substituted benzoxazolyl, optionally substituted benzimidazolyl, optionally substituted benzothiazolyl, optionally substituted benzothiadiazolyl, optionally substituted furopyridinyl, optionally substituted thienopyridinyl, optionally substituted pyrrolopyridinyl, optionally substituted oxazolopyridinyl, optionally substituted thiazolopyridinyl or optionally substituted imidazopyridinyl.

(84) The compound according to any of (79) and (80) mentioned above, in which, in the formula (I), R¹⁰ is optionally substituted biphenyl, optionally substituted phenyl, optionally substituted pyridyl, optionally substituted pyrimidyl, optionally substituted pyridazinyl, optionally substituted pyrazinyl, optionally substituted triazinyl, optionally substituted pyrrolyl, optionally substituted thienyl, optionally substituted furyl, optionally substituted thiazolyl, optionally substituted oxazolyl, optionally substituted imidazolyl, optionally substituted naphthyl, optionally substituted tetrahydronaphthyl, optionally substituted quinolinyl, optionally substituted isoquinolinyl, optionally substituted quinazolinyl, optionally substituted quinoxalinyl, optionally substituted cinnolinyl, optionally substituted naphthyridinyl, optionally substituted benzotriazinyl, optionally substituted pyridopyrimidinyl, optionally substituted pyridopyrazinyl, optionally substituted pyridopyridazinyl, optionally substituted pyridotriazinyl, optionally substituted indenyl, optionally substituted benzofuryl, optionally substituted benzothienyl, optionally substituted indolyl, optionally substituted indazolyl, optionally substituted benzoxazolyl, optionally substituted benzimidazolyl, optionally substituted benzothiazolyl, optionally substituted benzothiadiazolyl, optionally substituted furopyridinyl, optionally substituted thienopyridinyl, optionally substituted pyrrolopyridinyl, optionally substituted oxazolopyridinyl, optionally substituted thiazolopyridinyl or optionally substituted imidazopyridinyl;

R²⁰ is optionally substituted biphenyl, optionally substituted phenyl, optionally substituted pyridyl, optionally substituted pyrimidyl, optionally substituted pyridazinyl, optionally substituted pyrazinyl, optionally substituted triazinyl, optionally substituted pyrrolyl, optionally substituted thienyl, optionally substituted furyl, optionally substituted thiazolyl, optionally substituted oxazolyl, optionally substituted imidazolyl, optionally substituted naphthyl, optionally substituted tetrahydronaphthyl, optionally substituted quinolinyl, optionally substituted isoquinolinyl, optionally substituted quinazolinyl, optionally substituted quinoxalinyl, optionally substituted cinnolinyl, optionally substituted naphthyridinyl, optionally substituted benzotriazinyl, optionally substituted pyridopyrimidinyl, optionally substituted pyridopyrazinyl, optionally substituted pyridopyridazinyl, optionally substituted pyridotriazinyl, optionally substituted indenyl, optionally substituted benzofuryl, optionally substituted benzothienyl, optionally substituted indolyl, optionally substituted indazolyl, optionally substituted benzoxazolyl, optionally substituted benzimidazolyl, optionally substituted benzothiazolyl, optionally substituted benzothiadiazolyl, optionally substituted furopyridinyl, optionally substituted thienopyridinyl, optionally substituted pyrrolopyridinyl, optionally substituted oxazolopyridinyl, optionally substituted thiazolopyridinyl or optionally substituted imidazopyridinyl; and $R^{70}$ is optionally substituted biphenyl, optionally substituted phenyl, optionally substituted pyridyl, optionally substituted pyrimidyl, optionally substituted pyridazinyl, optionally substituted pyrazinyl, optionally substituted triazinyl, optionally substituted pyrrolyl, optionally substituted thienyl, optionally substituted furyl, optionally substituted thiazolyl, optionally substituted oxazolyl, optionally substituted imidazolyl, optionally substituted naphthyl, optionally substituted tetrahydronaphthyl, optionally substituted quinolinyl, optionally substituted isoquinolinyl, optionally substituted quinazolinyl, optionally substituted quinoxalinyl, optionally substituted cinnolinyl, optionally substituted naphthyridinyl, optionally substituted benzotriazinyl, optionally substituted pyridopyrimidinyl, optionally substituted pyridopyrazinyl, optionally substituted pyridopyridazinyl, optionally is substituted pyridotriazinyl, optionally substituted indenyl, optionally substituted benzofuryl, optionally substituted benzothienyl, optionally substituted indolyl, optionally substituted indazolyl, optionally substituted benzoxazolyl, optionally substituted benzimidazolyl, optionally substituted benzothiazolyl, optionally substituted benzothiadiazolyl, optionally substituted furopyridinyl, optionally substituted thienopyridinyl, optionally substituted pyrrolopyridinyl, optionally substituted oxazolopyridinyl, optionally substituted thiazolopyridinyl or optionally substituted imidazopyridinyl.

The present invention is also directed to libraries containing one or more compounds of formula (I) above, as well as methods for synthesizing such libraries and methods for screening the same to identify biologically active compounds.

In another embodiment, a pharmaceutical composition comprises the compound of formula (I) or pharmaceutically acceptable salt thereof, and, if necessary, together with a pharmaceutical acceptable carrier or diluent. Compositions containing a compound of this invention in combination with a pharmaceutically acceptable carrier or diluent are also disclosed.

In another embodiment, there is a method of treating a cancerous condition or fibrosis by administering the compound of formula (I). The present invention also provides methods for preventing or treating disorders associated with Wnt signaling pathway. Disorders that may be treated or prevented using a compound or composition of the present invention include tumor or cancer (e.g., KSHV-associated tumor), fibrotic diseases, restenosis associated with angioplasty, polycystic kidney disease, aberrant angiogenesis disease, tuberous sclerosis complex, hair loss, and Alzheimer's disease. Such methods comprise administering to a subject in need thereof a compound or composition of the present invention in an amount effective to achieve the desired outcome.

These and other aspects of this invention will be apparent upon reference to the attached figure and following detailed description. To this end, various references are set forth herein, which describe in more detail certain procedures, compounds and/or compositions, and are incorporated by reference in their entirety.

DETAILED DESCRIPTION OF THE INVENTION

Figure 1:
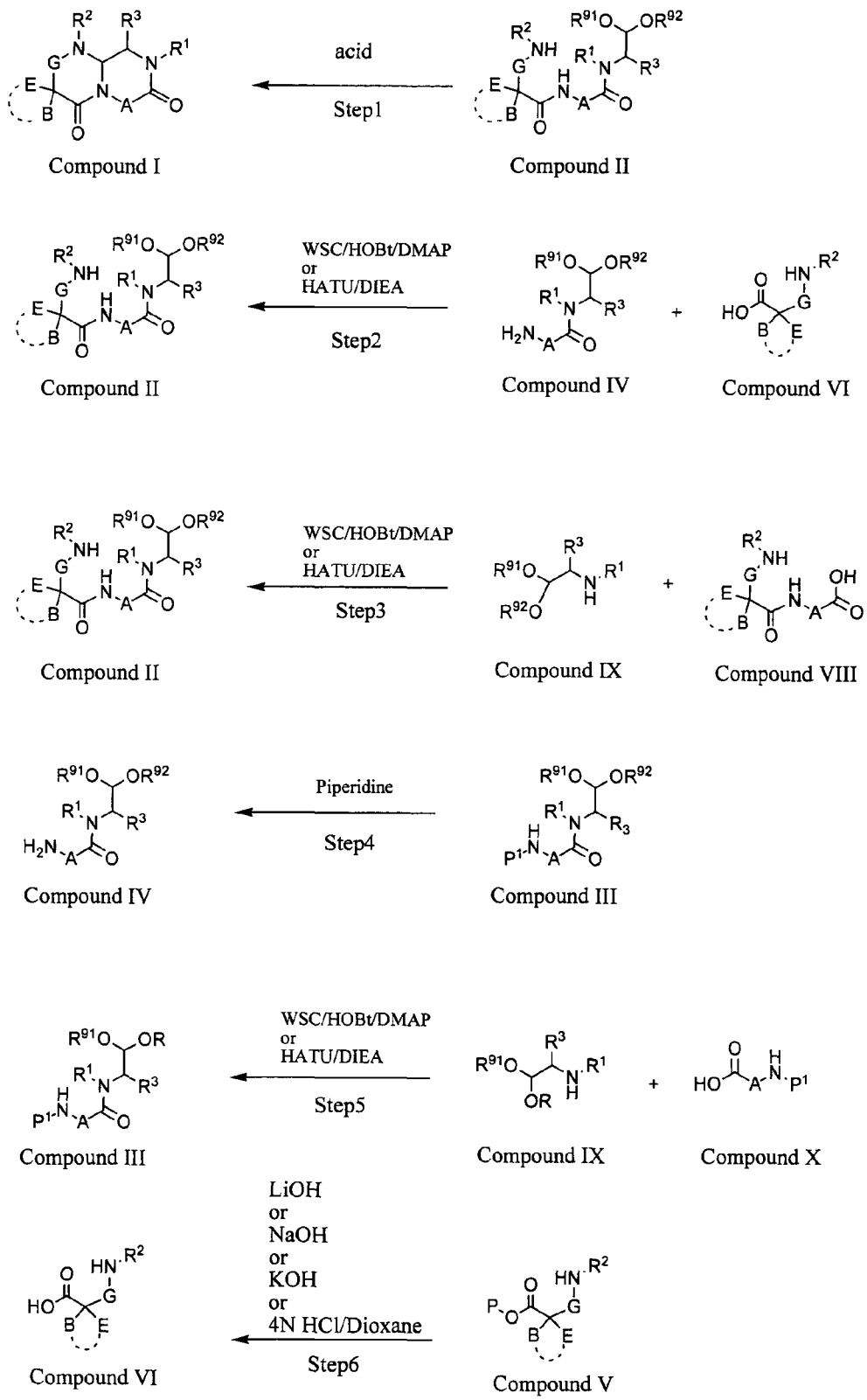
FIGS. 1 to 3 provide a general retrosynthesis for preparing alpha-helix mimetics of the present invention.

The present invention relates generally to alpha-helix mimetic structures and to a compound relating thereto. The present invention is also directed to conformationally constrained compounds that mimic the secondary structure of alpha-helix regions of biological peptide and proteins (also referred to herein as "alpha-helix mimetics"), and is also directed to chemical libraries relating thereto. The compound of the present invention is useful as bioactive agents, including (but not limited to) use as diagnostic, prophylactic and/or therapeutic agents. The alpha-helix mimetic structure libraries of this invention are useful in the identification of bioactive agents having such uses. In the practice of the present invention, the libraries may contain from tens to hundreds to thousands (or greater) of individual alpha-helix structures (also referred to herein as "members").

Definitions

Unless otherwise stated, the following terms used in the specification and claims shall have the following meanings for the purposes of this application.

"Lower", unless indicated otherwise, means that the number of the carbon atoms constituting the given radicals is between one and six.

"Optionally substituted", unless otherwise stated, means that a given radical may consist of only hydrogen substituents through available valencies or may further comprise one or more non-hydrogen substituents through available valencies. In general, a non-hydrogen substituent may be any substituent that may be bound to an atom of the given radical that is specified to be substituted. Examples of substituents include, but are not limited to, —$R^8$, —OH, —$OR^8$, —COOH, —$COOR^8$, —$CONH_2$, —$CONHR^8$, $CONR^8R^4$, —$NH_2$, —$NHR^8$, —$NR^8R^4$, —SH, —$SR^8$, —$SOR^8$, —$SO_2R^8$, —$SO_2NH_2$, $SO_2NHR^8$, —$SO_2NR^8R^4$, —$SO_3H$, —$SO_3R^8$, —$NHC(NH_2)NH$, —$NHC(NHR^8)$ $NR^4$, —$NHC(NH_2)NR^4$, —$OPO(OH)_2$, —$OPO(ONa)_2$, and halogen, wherein $R^8$ and $R^4$ is independently selected from linear or branched chain, cyclic or noncyclic, optionally substituted alkyl chain, aryl, heteroaryl, arylalkyl and heteroarylalkyl moieties. In addition, the substituents may be protected by a protecting group, or may itself be a protecting group. Examples of the protecting group include benzyl group, t-butyl group, 1-ethoxyethyl group, 3,4,5,6-tetrahydro-2H-pyran-2-yl group, triphenylmethyl group, 1-methoxy-1-methylethyl group, methoxymethyl group, ethoxymethyl group, triethylsilyl group, tri-n-butylsilyl group, t-butyldimethylsilyl group and the like.

"Halogen" means fluorine, chlorine, bromine or iodine.

"Halo" means fluoro, chloro, bromo or iodo.

"Alkyl" means a linear or branched, saturated, aliphatic radical having a chain of carbon atoms. $C_{X-Y}$ alkyl is typically used where X and Y indicate the number of carbon atoms in the chain. The number of carbon atoms in the chain is preferably 1 to 10, more preferably 1 to 6, further preferably 1 to 4. Non-exclusive examples of alkyl include methyl, ethyl, propyl, isopropyl, butyl, sec-butyl, isobutyl, tert-butyl, pentyl, isopentyl, neopentyl, tert-pentyl, hexyl, isohexyl, and the like. "Noncyclic alkyl" equals to "alkyl" as used here.

"Alkenyl" means a linear or branched, carbon chain that contains at least one carbon-carbon double bond. $C_{X-Y}$ alkenyl is typically used where X and Y indicate the number of carbon atoms in the chain. The number of carbon atoms in the chain is preferably 2 to 10, more preferably 2 to 6. Non-exclusive examples of alkenyl include ethenyl(vinyl), allyl, isopropenyl, 2-methylallyl, 1-pentenyl, hexenyl, heptenyl, 1-propenyl, 2-butenyl, 2-methyl-2-butenyl, and the like.

"Alkynyl" means a linear or branched, carbon chain that contains at least one carbon-carbon triple bond. $C_{X-Y}$ alkynyl is typically used where X and Y indicate the number of carbon atoms in the chain. The number of carbon atoms in the chain is preferably 2 to 10, more preferably 2 to 6. Non-exclusive examples of alkynyl include ethynyl, propargyl, 3-methyl-1-pentynyl, 2-heptynyl and the like.

"Alkylene", unless indicated otherwise, means a linear or branched, saturated, aliphatic, polyvalent carbon chain. $C_{X-Y}$ alkylene is typically used where X and Y indicate the number of carbon atoms in the chain. The number of carbon atoms in the chain is preferably 1 to 10, more preferably 1 to 6. Non-exclusive examples of alkylene include methylene ($-CH_2-$), ethylene ($-CH_2CH_2-$), methylmethylene ($-CH(CH_3)-$), 1,2-propylene ($-CH_2CH(CH_3)-$), 1,3-propylene ($-CH_2CH_2CH_2-$), 1,2-butylene ($-CH_2CH(CH_2CH_3)-$), 1,3-butylene ($-CH_2CH_2CH(CH_3)-$), 1,4-butylene ($-CH_2CH_2CH_2CH_2-$), 2-methyltetramethylene ($-CH_2CH(CH_3)CH_2CH_2-$) pentamethylene ($-CH_2CH_2CH_2CH_2CH_2-$), 1,2,3-propanetriyl, 1,3,3-propanetriyl and the like.

"Oxy" means the radical $-O-$. It is noted that the oxy radical may be further substituted with a variety of substituents to form different oxy groups including hydroxy, alkoxy, aryloxy, heteroaryloxy and the like.

"Thio" means the radical $-S-$. It is noted that the thio radical may be further substituted with a variety of substituents to form different thio groups including mercapto, alkylthio, arylthio, heteroarylthio and the like.

"Sulfinyl" means the radical $-SO-$. It is noted that the sulfinyl radical may be further substituted with a variety of substituents to form different sulfinyl groups including alkylsulfinyl, aryl sulfinyl, heteroarylsulfinyl and the like.

"Sulfonyl" means the radical $-SO_2-$. It is noted that the sulfonyl radical may be further substituted with a variety of substituents to form different sulfonyl groups including alkylsulfonyl, arysulfonyl, heteroarylsulfonyl and the like.

"Alkoxy" means an oxygen moiety having a further alkyl substituent. $C_{x-y}$ alkoxy is typically used where X and Y indicate the number of carbon atoms in the chain. The number of carbon atoms in the chain is preferably 1 to 10, more preferably 1 to 6. Non-exclusive examples of C alkoxy include methoxy, ethoxy, propoxy, isopropoxy, butoxy, sec-butoxy, isobutoxy, tert-butoxy, pentoxy, isopentoxy, neopentoxy, tert-pentoxy, hexyloxy, isohexyloxy, and the like.

"Heteroatom" refers to an atom that is not a carbon atom and hydrogen atom. Particular examples of heteroatoms include, but are not limited to nitrogen, oxygen, and sulfur.

"Aryl" means a monocyclic or polycyclic radical wherein each ring is aromatic or when fused with one or more rings forms an aromatic ring. $C_{X-Y}$ aryl is typically used where X and Y indicate the number of carbon atoms in the ring assembly. The number of carbon atoms in the ring is preferably 6 to 14, more preferably 6 to 10. Non-exclusive examples of aryl include phenyl, naphthyl, indenyl, azulenyl, biphenyl, fluorenyl, anthracenyl, phenalenyl and the like. "Aryl" may partially be hydrogenated. Non-exclusive examples of partially hydrogenated aryl include tetrahydronaphthyl, indanyl and the like.

"Heteroaryl" means a monocyclic or polycyclic aromatic radical wherein at least one ring atom is a heteroatom and the remaining ring atoms are carbon. "X-Y membered heteroaryl" is typically used where X and Y indicate the number of carbon atoms and heteroatoms in the ring assembly. The number of carbon atoms and heteroatoms in the ring is preferably 5 to 14, more preferably 5 to 10. Monocyclic heteroaryl groups include, but are not limited to, cyclic aromatic groups having five or six ring atoms, wherein at least one ring atom is a heteroatom and the remaining ring atoms are carbon. The nitrogen atoms can be optionally quaternerized and the sulfur atoms can be optionally oxidized. Non-exclusive examples of monocyclic heteroaryl group of this invention include, but are not limited to, those derived from furan, thiophene, pyrrole, imidazole, isothiazole, isoxazole, oxadiazole, oxazole, 1,2,3-oxadiazole, pyrazine, pyrazole, pyridazine, pyridine, pyrimidine, triazine, pyrrole, thiazole, 1,3,4-thiadiazole, triazole and tetrazole. "Heteroaryl" also includes, but is not limited to, bicyclic or tricyclic rings, wherein the heteroaryl ring is fused to one or two rings independently selected from the group consisting of an aryl ring, a cycloalkyl ring, and another monocyclic heteroaryl or heterocycloalkyl ring. Non-exclusive examples of bicyclic or tricyclic heteroaryl include, but are not limited to, those derived from benzofuran (ex. benzo[b]furan), benzothiophene (ex. benzo[b]thiophene), benzimidazole, benzotriazine (ex. benzo[e] [1,2,4]triazine, benzo[d] [1,2,3]triazine), pyridopyrimidine (ex. pyrido[4,3-d]pyrimidine, pyrido [3,4-d]pyrimidine, pyrido[3,2-d]pyrimidine, pyrido[2,3-d] pyrimidine), pyridopyrazine (ex. pyrido[3,4-b]pyrazine, pyrido[2,3-b]pyrazine), pyridopyridazine (ex. pyrido[2,3-c] pyridazine, pyrido[3,4-c]pyridazine, pyrido[4,3-c]pyridazine, pyrido[3,2-c]pyridazine), pyridotriazine (ex. pyrido [2,3-d][1,2,3]triazine, pyrido[3,4-d][1,2,3]triazine, pyrido[4, 3-d] [1,2,3]triazine, pyrido[3,2-d][1,2,3]triazine, pyrido[3,4-e] [1,2,4]triazine, pyrido[3,2-e][1,2,4]triazine), benzothiadiazole(ex. benzo[c][1,2,5]thiadiazole), furopyridine (ex. furo[3,2-b]pyridine, furo[3,2-c]pyridine, furo[2,3-c]pyridine, furo[2,3-b]pyridine), oxazolopyridine (ex. oxazolo[4,5-b]pyridine, oxazolo[4,5-c]pyridine, oxazolo[5, 4-c]pyridine, oxazolo[5,4-b]pyridine), thiazolopyridine (ex. thiazolo[4,5-b]pyridine, thiazolo[4,5-c]pyridine, thiazolo[5, 4-c]pyridine, thiazolo[5,4-b]pyridine), imidazopyridine (ex. imidazo[1,2a]pyridine, imidazo[4,5-c]pyridine, imidazo[1, 5-a]pyridine), quinazoline, thienopyridine (ex. thieno[2,3-c] pyridine, thieno[3,2-b]pyridine, thieno[2,3-b]pyridine), indolizine, quinoline, isoquinoline, phthalazine, quinoxaline, cinnoline, naphthyridine, quinolizine, indole, isoindole, indazole, indoline, benzoxazole, benzopyrazole, benzothiazole, pyrazolopyridine(ex. pyrazolo[1,5-a]pyridine), imidazopyrimidine (ex. imidazo[1,2-a]pyrimidine, imidazo[1,2-c]pyrimidine, imidazo[1,5-a]pyrimidine, imidazo[1,5-c]pyrimidine), pyrrolopyridine (ex. pyrrolo[2,3-b]pyridine, pyrrolo[2, 3-c]pyridine, pyrrolo[3,2-c]pyridine, pyrrolo[3,2-b] pyridine), pyrrolopyrimidine (ex. pyrrolo[2,3-d]pyrimidine, pyrrolo[3,2-d ]pyrimidine, pyrrolo[1,2-c]pyrimidine, pyrrolo [1,2-a]pyrimidine), pyrrolopyrazine (ex. pyrrolo[2,3-b]pyrazine pyrrolo[1,2-a ]pyrazine), pyrrolopyridazine (ex. pyrrolo [1,2-b]pyridazine), triazopyridine (ex. triazo[1,5-a]pyridine), pteridine, purine, carbazole, acridine, permidine, 1,10-phenanthroline, phenoxathiin, phenoxazine, phenothiazine, phenazine and the like. The bicyclic or tricyclic heteroaryl rings can be attached to the parent molecule through either the heteroaryl group itself or the aryl, cycloalkyl, or heterocycloalkyl group to which it is fused.

"Cycloalkyl" means a non-aromatic, saturated or partially unsaturated, monocyclic, fused bicyclic or bridged polycyclic ring radical. $C_{X-Y}$ cycloalkyl is typically used where X and Y indicate the number of carbon atoms in the ring assembly. The number of carbon atoms in the ring is preferably 3 to 10, more preferably 3 to 8. Non-exclusive examples of cycloalkyl include cyclopropyl, cyclobutyl, cyclopentyl, cyclohexyl, cyclohexenyl, 2,5-cyclohexadienyl, bicyclo [2.2.2]octyl, adamantan-1-yl, decahydronaphthyl, bicyclo [2.2.1]hept-1-yl, and the like. "Cyclic alkyl" equals to "cycloalkyl" as used here.

"Heterocycloalkyl" means cycloalkyl, as defined in this application, provided that one or more of the atoms forming the ring is a heteroatom selected, independently from N, O, and S. $C_{X-Y}$ heterocycloalkyl is typically used where X and Y indicate the number of carbon atoms and heteroatoms in the ring assembly. The number of carbon atoms and heteroatoms in the ring is preferably 3 to 10, more preferably 3 to 8. Non-exclusive examples of heterocycloalkyl include piperidyl, 4-morpholyl, 4-piperazinyl, pyrrolidinyl, perhydropyrrolidinyl, 1,4-diazaperhydroepinyl, 1,3-dioxanyl, 1,4-dioxanyl and the like.

Moreover, the above-mentioned definitions can apply to groups wherein the above-mentioned substituents are connected. For example, "arylalkyl" means linear or branched alkyl group which is substituted by one or more aryl groups, such as benzyl, 1-phenylethyl, 2-phenylethyl, 3-phenylpropyl, 1-naphthylmethyl, 2-naphthylmethyl, benzhydryl, 2,2-diphenylethyl, trityl and the like.

"Spiro ring" as used herein refers to saturated or unsaturated cycloalkane or saturated or unsaturated heterocycloalkane.

"Cycloalkane" means a non-aromatic, saturated or partially unsaturated, monocyclic, fused bicyclic or bridged polycyclic ring. $C_{X-Y}$ cycloalkane is typically used where X and Y indicate the number of carbon atoms in the ring assembly. The number of carbon atoms in the ring is preferably 3 to 10, more preferably 3 to 8. Non-exclusive examples of cycloalkane include cyclopropane, cyclobutane, cyclopentane, cyclohexane, cycloheptane, cyclooctane, cyclopropene, cyclobutene, cyclopentene, cyclohexene, cycloheptene, cyclooctene and the like.

"Heterocycloalkane" means cycloalkane, as defined in this Application, provided that one or more of the atoms forming the ring is a heteroatom selected, independently from N, O, and S. $C_{X-Y}$ heterocycloalkane is typically used where X and Y indicate the number of carbon atoms and heteroatoms in the ring assembly. The number of carbon atoms and heteroatoms in the ring is preferably 3 to 10, more preferably 3 to 8. Non-exclusive examples of heterocycloalkane include piperidine, morpholine, homomorpholine, thiomorpholine, homothiomorpholine, piperazine, homopiperazine, pyrrolidine, perhydropyrrolizine, tetrahydrofuran, tetrahydrothiophene, tetrahydropyran, tetrahydro-2H-thiopyran, azepane, 1,3-dioxane, 1,4-dioxane and the like.

"Fused ring" as used herein refers to a ring that is bonded to another ring to form a compound having a bicyclic structure when the ring atoms that are common to both rings are directly bound to each other. Non-exclusive examples of common fused rings include decalin, naphthalene, anthracene, phenanthrene, indole, furan, benzofuran, quinoline, and the like. Compounds having fused ring systems may be saturated, partially saturated or aromatic.

"Bridging ring" as used herein refers to a ring that is bonded to another ring to form a compound having a bicyclic structure where two ring atoms that are common to both rings are not directly bound to each other. Non-exclusive examples of common compounds having a bridging ring include adamantine, borneol, norbornane, 7-oxabicyclo[2.2.1]heptane, and the like.

"Protected derivatives" means derivatives of compound in which a reactive site or sites are blocked with protecting groups. A comprehensive list of suitable protecting groups can be found in T. W. Greene, *Protecting Groups in Organic Synthesis*, 3rd edition, John Wiley & Sons, Inc. 1999.

"Isomers" mean any compound having an identical molecular formulae but differing in the nature or sequence of bonding of their atoms or in the arrangement of their atoms in space. Isomers that differ in the arrangement of their atoms in space are termed "stereoisomers". Stereoisomers that are not mirror images of one another are termed "diastereomers" and stereoisomers that are nonsuperimposable mirror images are termed "enantiomers" or sometimes "optical isomers". A carbon atom bonded to four nonidentical substituents is termed a "chiral center". A compound with one chiral center has two enantiomeric forms of opposite chirality. A mixture of the two enantiomeric forms is termed a "racemic mixture". A compound that has more than one chiral center has $2^{n-1}$ enantiomeric pairs, where n is the number of chiral centers. Compounds with more than one chiral center may exist as either an individual diastereomer or as a mixture of diastereomers, termed a "diastereomeric mixture". When one chiral center is present a stereoisomer may be characterized by the absolute configuration of that chiral center. Absolute configuration refers to the arrangement in space of the substituents attached to the chiral center. Enantiomers are characterized by the absolute configuration of their chiral centers and described by the R- and S-sequencing rules of Cahn, Ingold and Prelog. Conventions for stereochemical nomenclature, methods for the determination of stereochemistry and the separation of stereoisomers are well known in the art (e.g., see "Advanced Organic Chemistry", 4th edition, March, Jerry, John Wiley & Sons, New York, 1992).

"Animal" includes humans, non-human mammals (e.g., mice, rats, dogs, cats, rabbits, cattle, horses, sheep, goats, swine, deer, and the like) and non-mammals (e.g., birds, and the like).

"Disease" specifically includes any unhealthy condition of an animal or part thereof and includes an unhealthy condition that may be caused by, or incident to, medical or veterinary therapy applied to that animal, i.e., the "side effects" of such therapy.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salt" or "salt" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo [2.2.2]oct-2-ene-1-carboxylic acid, glucoheptonic acid, 4,4'- methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like.

Pharmaceutically acceptable salt or salt also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

"Amount effective to treat" or means that amount which, when administered to an animal for treating a disease, is sufficient to effect such treatment for the disease.

"Amount effective to prevent" means that amount which, when administered to an animal for prevent a disease, is sufficient to effect such prophylaxis for the disease.

"Effective amount" equals to "amount effective to treat" and "amount effective to prevent".

"Treatment" or "treat" means any administration of a compound of the present invention and includes:

(1) preventing the disease from occurring in an animal which may be predisposed to the disease but does not yet experience or display the pathology or symptomatology of the disease, (2) inhibiting the disease in an animal that is experiencing or displaying the pathology or symptomatology of the disease (i.e., arresting further development of the pathology and/or symptomatology), or (3) ameliorating the disease in an animal that is experiencing or displaying the pathology or symptomatology of the disease (i.e., reversing the pathology and/or symptomatology).

It is noted in regard to all of the definitions provided herein that the definitions should be interpreted as being open ended in the sense that further substituents beyond those specified may be included.

Alpha-Helix Mimetic

In one aspect of the present invention, a compound having an alpha-helix mimetic structure is disclosed having the following formula (I):

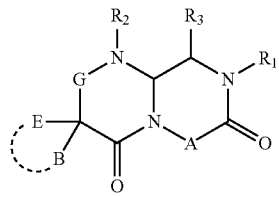

wherein
A is —(CHR$^7$)—,
  wherein
  R$^7$ is hydrogen, optionally substituted alkyl, optionally substituted alkenyl, optionally substituted alkynyl, optionally substituted aryl, optionally substituted heteroaryl, optionally substituted cycloalkyl, optionally substituted heterocycloalkyl, optionally substituted arylalkyl, optionally substituted heteroarylalkyl, optionally substituted cycloalkylalkyl, or optionally substituted heterocycloalkylalkyl;
B and E are the same or different and independently selected from hydrogen, optionally substituted alkyl, optionally substituted alkenyl, and optionally substituted alkynyl or form an optionally substituted spiro ring indicated by dashed lines;
G is —NH—, —NR$^6$—, —O—, —CH$_2$—, —CHR$^6$— or —C(R$^6$)$_2$—.
  wherein
  each R$^6$ is the same or different and independently selected from optionally substituted alkyl, optionally substituted alkenyl, and optionally substituted alkynyl;
R$^1$ is optionally substituted alkyl, optionally substituted alkenyl, optionally substituted alkynyl, optionally substituted arylalkyl, optionally substituted heteroarylalkyl, optionally substituted cycloalkylalkyl, or optionally substituted heterocycloalkylalkyl;
R$^2$ is —W$^{21}$—W$^{22}$—Rb—R$^{20}$,
  wherein
  W$^{21}$ is —(CO)— or —(SO$_2$)—;
  W$^{22}$ is bond, —O—, —NH— or optionally substituted lower alkylene;
  Rb is bond or optionally substituted lower alkylene; and
  R$^{20}$ is optionally substituted alkyl, optionally substituted alkenyl, optionally substituted alkynyl, optionally substituted aryl, optionally substituted heteroaryl, optionally substituted cycloalkyl, or optionally substituted heterocycloalkyl; and
R$^3$ is hydrogen, optionally substituted alkyl, optionally substituted alkenyl, or optionally substituted alkynyl;
with the proviso that
1) when Rb is optionally substituted lower alkylene, then W$^{22}$ should be —O— or —NH—,
2) when E and B are hydrogen, then R$^3$ should be hydrogen,
3) when G is —NH—, —CH$_2$—, —CHR$^6$— or —NR$^6$—, then B and E should not be hydrogen, and
4) when G is —O—, B and E are hydrogen and R$^3$ is hydrogen, then R$^1$ should not be 8-quinolylmethyl;
or a pharmaceutically acceptable salt thereof.

In one embodiment, A is —(CHR$^7$)—, wherein R$^7$ is hydrogen, optionally substituted alkyl, optionally substituted alkenyl, optionally substituted alkynyl, optionally substituted aryl, optionally substituted heteroaryl, optionally substituted cycloalkyl, optionally substituted heterocycloalkyl, optionally substituted arylalkyl, optionally substituted heteroarylalkyl, optionally substituted cycloalkylalkyl or optionally substituted heterocycloalkylalkyl.

Examples of optionally substituted alkyl group include methyl, ethyl, propyl, isopropyl, butyl, isobutyl, sec-butyl, tert-butyl, pentyl, isopentyl, aminoethyl, aminopropyl, aminobutyl, carboxymethyl, carboxyethyl, carboxypropyl, carboxybutyl, carbamoylmethyl, carbamoylethyl, carbamoylpropyl, carbamoylbutyl, methoxyethyl, methoxypropyl, methoxybutyl, methylthiomethyl, methylthioethyl, methylthiopropyl, methylthiobutyl, hydroxymethyl, hydroxyethyl, hydroxypropyl, hydroxybutyl, ethoxycarbonylmethyl, ethoxycarbonylethyl, aminomethyl, aminomethyl, aminopropyl, aminobutyl, and the like.

Examples of alkenyl group include ethenyl, allyl, 1-propenyl, 2-methylallyl and the like.

Examples of alkynyl group include 1-propynyl, ethynyl and the like.

Examples of aryl and heteroaryl include biphenyl, phenyl, pyridyl, pyrimidyl, pyridazinyl, pyrazinyl, triazinyl, pyrrolyl, thienyl, furyl, thiazolyl, oxazolyl, imidazolyl, tetrahydronaphthyl, naphthyl, quinolinyl, isoquinolinyl, quinazolinyl, quinoxalinyl, cinnolinyl, naphthyridinyl, benzotriazinyl, indenyl, pyridopyrimidinyl, pyridopyrazinyl, pyridopyridazinyl, pyridotriazinyl, benzofuryl, benzothienyl, indolyl, indazolyl, benzoxazolyl, benzimidazolyl, benzothiazolyl, benzothiadiazolyl, furopyridinyl, thienopyridinyl, pyrropyridinyl, oxazolopyridinyl, thiazolopyridinyl, imidazopyridinyl and the like.

Examples of cycloalkyl and heterocycloalkyl include cyclopropyl, cyclobutyl, cyclopentyl, cyclohexyl, cycloheptyl, adamantyl and the like.

In another embodiment, A is —(CHR$^7$)—, wherein R$^7$ is optionally substituted aryl, optionally substituted heteroaryl, optionally substituted cycloalkyl, optionally substituted heterocycloalkyl, optionally substituted arylalkyl, optionally substituted heteroarylalkyl, optionally substituted cycloalkylalkyl or optionally substituted heterocycloalkylalkyl, each of which is represented by -Rc-R$^{70}$ wherein Rc is bond or optionally substituted lower alkylene, and R$^{70}$ is optionally substituted aryl, optionally substituted heteroaryl, optionally substituted cycloalkyl or optionally substituted heterocycloalkyl.

Examples of lower alkylene group include methylene, ethylene, methylmethylene, 1,2-propylene, 1,3-propylene, 1,2-butylene, 1,3-butylene, 1,4-butylene, 1,2,3-propanetriyl, 1,3,3-propanetriyl and the like.

Examples of aryl group and heteroaryl group include biphenyl, phenyl, pyridyl, pyrimidyl, pyridazinyl, pyrazinyl, triazinyl, pyrrolyl, thienyl, furyl, thiazolyl, oxazolyl, imidazolyl, tetrahydronaphthyl, naphthyl, quinolinyl, isoquinolinyl, quinazolinyl, quinoxalinyl, cinnolinyl, naphthyridinyl, benzotriazinyl, indenyl, pyridopyrimidinyl, pyridopyrazinyl, pyridopyridazinyl, pyridotriazinyl, benzofuryl, benzothienyl, indolyl, indazolyl, benzoxazolyl, benzimidazolyl, benzothiazolyl, benzothiadiazolyl, furopyridinyl, thienopyridinyl, pyrrolopyridinyl, oxazolopyridinyl, thiazolopyridinyl, imidazopyridinyl and the like.

Examples of cycloalkyl group and heterocycloalkyl group include cyclopropyl, cyclobutyl, cyclopentyl, cyclohexyl, cycloheptyl, adamantly and the like.

In a particular embodiment of formula (I), in the above-mentioned embodiments R$^{70}$ is optionally substituted aryl or optionally substituted heteroaryl.

Examples of aryl group and heteroaryl group include biphenyl, phenyl, pyridyl, pyrimidyl, pyridazinyl, pyrazinyl, triazinyl, pyrrolyl, thienyl, furyl, thiazolyl, oxazolyl, imidazolyl, tetrahydronaphthyl, naphthyl, quinolinyl, isoquinolinyl, quinazolinyl, quinoxalinyl, cinnolinyl, naphthyridinyl, benzotriazinyl, indenyl, pyridopyrimidinyl, pyridopyrazinyl, pyridopyridazinyl, pyridotriazinyl, benzofuryl, benzothienyl, indolyl, indazolyl, benzoxazolyl, benzimidazolyl, benzothiazolyl, benzothiadiazolyl, furopyridinyl, thienopyridinyl, pyrrolopyridinyl, oxazolopyridinyl, thiazolopyridinyl, imidazopyridinyl and the like.

Preferred examples of aryl group and heteroaryl group include phenyl, pyridyl, pyrimidyl, pyridazinyl, pyrazinyl, triazinyl, pyrrolyl, thienyl, furyl, thiazolyl, oxazolyl, imidazolyl, benzothienyl and the like.

Most preferred example of ary group include phenyl, naphthyl and the like.

Examples of substituents for R$^7$ include —R$^8$, —OH, —OR$^8$, —OC(O)R$^8$, —OC(O)OR$^8$, —COOH, —COOR$^8$, —CONH$_2$, —CONHR$^8$, —CONR$^8$R$^4$, —NH$_2$, —NHR$^8$, —NR$^8$R$^4$, —SH, —SR$^8$, —SO$_2$R$^8$, —SO$_2$NH$_2$, —SO$_2$NHR$^8$, —SO$_2$NR$^8$R$^4$, —SO$_3$H, —SOR$^8$, —NHC(NH$_2$)(=NH), —NHC(NHR$^8$)(=NR$^4$), —OP(=O)(OH)$_2$, —OP(=O)(ONa)$_2$, —OP(=O)(OR$^8$)$_2$, —OP(=O)(OR$^8$)(OH), —OP(=O)(OH)—O—P(=O)(OH)$_2$, —OP(=O)(ONa)—O—OP(=O)(ONa)$_2$, —CN, —NO$_2$ and halogen, wherein R$^8$ and R$^4$ is independently selected from linear or branched chain, cyclic or noncyclic, substituted or unsubstituted, alkyl chain, aryl and arylalkyl moieties.

Preferred examples of the substituents include —OH, —COOH, —OC(O)R$^8$, —OC(O)OR$^8$, —NH$_2$, —SH, —SO$_3$H, —SOR$^8$, —OP(=O)(OH)$_2$, —OP(=O)(OR$^8$)$_2$, —OP(=O)(OR$^8$)(OH), —OP(=O)(ONa)$_2$, —OP(=O)(OH)—O—P(=O)(OH)$_2$, —OP(=O)(ONa)—O—OP(=O)(ONa)$_2$, and halogen.

Most preferred examples of the substituents include —OH, —OP(=O)(OH)$_2$, —OP(=O)(ONa)$_2$, and halogen.

In a particular embodiment of formula (I), in the above-mentioned embodiments R$^7$ is phenyl, benzyl, phenethyl, 1-naphthyl, 2-naphthyl, 4-hydroxybenzyl, 4-benzyloxybenzyl or imidazolyl-5-methyl, methyl, n-butyl, isobutyl, isopropyl, hydroxymethyl, benzyloxymethyl, 4-aminobutyl, carboxymethyl, 2-carboxyethyl, carbamoylmethyl, 2-carbamoylethyl, ethoxycarbonylmethyl, 2-ethoxycarbonylethyl.

In one embodiment, B and E are the same or different and independently selected from hydrogen, optionally substituted alkyl, optionally substituted alkenyl, and optionally substituted alkynyl, or form an optionally substituted spiro ring indicated by dashed lines.

Examples of optionally substituted alkyl group include methyl, ethyl, propyl, isopropyl, butyl, isobutyl, sec-butyl, tert-butyl, pentyl, isopentyl, aminoethyl, aminopropyl, aminobutyl, carboxymethyl, carboxyethyl, carboxypropyl, carboxybutyl, carbamoylmethyl, carbamoylethyl, carbamoylpropyl, carbamoylbutyl, methoxyethyl, methoxypropyl, methoxybutyl, methylthiomethyl, methylthioethyl, methylthiopropyl, methylthiobutyl, hydroxyethyl, hydroxypropyl, hydroxybutyl and the like.

Examples of alkenyl group include ethenyl, allyl, 2-methylallyl and the like.

Examples of alkynyl group include 1-propynyl, ethynyl and the like.

Examples of spiro ring group include cyclopropane, cyclobutane, cyclopentane, cyclohexane, cycloheptane, pyrrolidine, tetrahydrofuran, tetrahydrothiophene, piperidine, tetrahydropyran, tetrahydro-2H-thiopyran, azepane, cyclopentene and the like.

In a particular embodiment of formula (I), in the above-mentioned embodiments Q designates a structural sector of the compound;

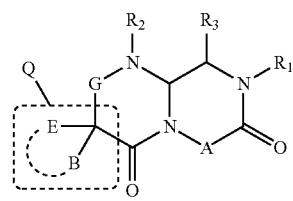

wherein spiro ring of Q selected from one of the following group:

EB-1

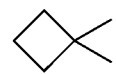

EB-2

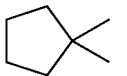
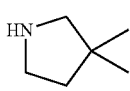
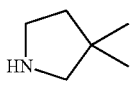
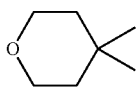
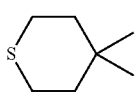
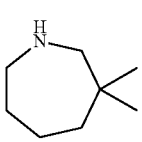
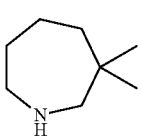

and the like.

EB-3
EB-4
EB-5
EB-6
EB-7
EB-8
EB-9
EB-10
EB-11
EB-12
EB-13
EB-14
EB-15
EB-16
EB-17

In one embodiment, G is —NH—, —NR$^6$—, —O—, —CH$_2$—, —CHR$^6$— or —C(R$^6$)$_2$—, wherein R$^6$ is the same or different and independently selected from optionally substituted alkyl, optionally substituted alkenyl and optionally substituted alkynyl.

G is preferably —NR$^6$—, —O—, —CH$_2$— or —C(R$^6$)$_2$— more preferably —NR$^6$— or —O—.

Examples of alkyl group include C$_{1-4}$ alkyl such as methyl, ethyl, propyl, isopropyl, butyl, isobutyl, sec-butyl, tert-butyl and the like.

Examples of alkenyl group include ethenyl, allyl, 1-propenyl, 2-methylallyl and the like.

Examples of alkynyl group include 1-propynyl, ethynyl and the like.

R$^6$ is preferably optionally substituted alkyl or optionally substituted alkenyl, more preferably lower alkyl (ex. methyl) or lower alkenyl (ex. allyl).

In one embodiment of formula (I), R$^1$ is optionally substituted alkyl, optionally substituted alkenyl, optionally substituted alkynyl, optionally substituted arylalkyl, optionally substituted heteroarylalkyl, optionally substituted cycloalkylalkyl or optionally substituted heterocycloalkylalkyl.

Examples of optionally substituted alkyl group include methyl, ethyl, propyl, isopropyl, butyl, isobutyl, sec-butyl, tert-butyl, pentyl, isopentyl, aminoethyl, aminopropyl, aminobutyl, dimethylaminoethyl, carboxymethyl, carboxyethyl, carboxypropyl, carboxybutyl, carbamoylmethyl, carbamoylethyl, carbamoylpropyl, carbamoylbutyl, methoxyethyl, methoxypropyl, methoxybutyl, methylthiomethyl, methylthioethyl, methylthiopropyl, methylthiobutyl, ethoxycarbonylmethyl, hydroxyethyl, hydroxypropyl, hydroxybutyl and the like.

Examples of alkenyl group include ethenyl, allyl, 2-methylallyl and the like.

Examples of alkynyl group include 1-propynyl, ethynyl, and the like.

In another embodiment of formula (I), R$^1$ is optionally substituted arylalkyl, optionally substituted heteroarylalkyl, optionally substituted cycloalkylalkyl or optionally substituted heterocycloalkylalkyl, each of which is represented by —Ra—R$^{10}$; wherein Ra is optionally substituted lower alkylene and R$^{10}$ is optionally substituted aryl, optionally substituted heteroaryl, optionally substituted cycloalkyl or optionally substituted heterocycloalkyl.

Examples of lower alkylene group include methylene, ethylene, methylmethylene, 1,2-propylene, 1,3-propylene, 1,2-butylene, 1,3-butylene, 1,4-butylene, 1,2,3-propanetriyl, 1,3,3-propanetriyl and the like.

Examples of aryl group and heteroaryl group include biphenyl, phenyl, pyridyl, pyrimidyl, pyridazinyl, pyrazinyl, triazinyl, pyrrolyl, thienyl, furyl, thiazolyl, oxazolyl, imidazolyl, tetrahydronaphthyl, naphthyl, quinolinyl, isoquinolinyl, quinazolinyl, quinoxalinyl, cinnolinyl, naphthyridinyl, benzotriazinyl, indenyl, pyridopyrimidinyl, pyridopyrazinyl, pyridopyridazinyl, pyridotriazinyl, benzofuryl, benzothienyl, indolyl, indazolyl, benzoxazolyl, benzimidazolyl, benzothiazolyl, benzothiadiazolyl, furopyridinyl, thienopyridinyl, pyrrolopyridinyl, oxazolopyridinyl, thiazolopyridinyl, imidazopyridinyl and the like.

Examples of cycloalkyl group and heterocycloalkyl group include cyclopropyl, cyclobutyl, cyclopentyl, cyclohexyl, cycloheptyl, adamantly and the like.

In a particular embodiment of formula (I), in the above-mentioned embodiments Ra is optionally substituted lower alkylene and R$^{10}$ is optionally substituted aryl or optionally substituted heteroaryl.

Examples of lower alkylene group include methylene, ethylene, methylmethylene, 1,2-propylene, 1,3-propylene, 1,2-butylene, 1,3-butylene, 1,4-butylene, 1,2,3-propanetriyl, 1,3,3-propanetriyl and the like.

Examples of aryl group and heteroaryl group include biphenyl, phenyl, pyridyl, pyrimidyl, pyridazinyl, pyrazinyl, triazinyl, pyrrolyl, thienyl, furyl, thiazolyl, oxazolyl, imidazolyl, tetrahydronaphthyl, naphthyl, quinolinyl, isoquinolinyl, quinazolinyl, quinoxalinyl, cinnolinyl, naphthyridinyl, benzotriazinyl, indenyl, pyridopyrimidinyl, pyridopyrazinyl, pyridopyridazinyl, pyridotriazinyl, benzofuryl, benzothienyl, indolyl, indazolyl, benzoxazolyl, benzimidazolyl, benzothiazolyl, benzothiadiazolyl, furopyridinyl, thienopyridinyl, pyrrolopyridinyl, oxazolopyridinyl, thiazolopyridinyl, imidazopyridinyl and the like.

Preferred examples of lower alkylene group include methylene, ethylene, 1,3-propylene and the like.

Preferred examples of aryl group and heteroaryl group include bicyclic fused aryl group and bicyclic fused heteroaryl group such as naphthyl, quinolinyl, isoquinolinyl, quinazolinyl, quinoxalinyl, cinnolinyl, naphthyridinyl, benzotriazinyl, indenyl, pyridopyrimidinyl, pyridopyrazinyl, pyridopyridazinyl, pyridotriazinyl, benzofuryl, benzothienyl, indolyl, indazolyl, benzoxazolyl, benzimidazolyl, benzothiazolyl, benzothiadiazolyl, furopyridinyl, thienopyridinyl, pyrropyridinyl, oxazolopyridinyl, thiazolopyridinyl, imidazopyridinyl and the like.

Examples of substituents for $R^1$ include —$R^8$, —OH, —$OR^8$, —COOH, —$COOR^8$, —$CONH_2$, —$CONHR^8$, —$CONR^8R^4$, —$NH_2$, —$NHR^8$, —$NR^8R^4$, —SH, —$SR^8$, —$SOR^8$, —$SO_2R^8$, —$SO_2NH_2$, —$SO_2NHR^8$, —$SO_2NR^8R^4$, —$SO_3H$, —$SO_3R^8$, —NHC($NH_2$)NH, —NHC($NHR^8$)$NR^4$, —NHC($NH_2$)$NR^4$, —OP(=O)(OH)$_2$, —OP(=O)(ONa)$_2$, and halogen, wherein $R^8$ and $R^4$ is independently selected from linear or branched chain, cyclic or noncyclic, optionally substituted alkyl chain, aryl, heteroaryl, arylalkyl and heteroarylalkyl.

Preferred examples of the substituents include —$NH_2$, —OH, —$OR^8$, —COOH, —$COOR^8$, —$CONH_2$, —$CONHR^8$, —$CONR^8R^4$, —$NHR^8$, —$NR^8R^4$, halogen.

More prefered examples of the substituents include —$NH_2$, —OH, —COOH, —COOMe, —$CONH_2$, halogen.

In a particular embodiment of formula (I), in the above-mentioned embodiments $R^1$ is isopentyl, 2-hydroxyethyl, 2-carboxyethyl, 2-methoxycarbonyletyl, benzyl, 2,4-difluorobenzyl, 4-hydroxybenzyl, 1-phenylethyl, 2-phenylethyl, 3-phenylpropyl, 3,3-diphenylpropyl, cyclohexylmethyl, pyridyl-4-methyl, pyridyl-2-methyl, thienyl-1-methyl, thienyl-2-methyl, imidazolyl-5-methyl, 1-naphthylmethyl, 2-naphthylmethyl, 4-quinolinylmethyl, 8-quinolinylmethyl, 5-chloroquinolin-8-ylmethyl, 5-isoquinolynylmethyl, 8-isoquinolynylmethyl, 5-chloroisoquinolin-8-ylmethyl, indazolyl-7-ylmethyl, benzothiazol-4-ylmethyl, benzothiazol-7-ylmethyl, 7-fluorobenzothiazol-4-ylmethyl, 4-fluorobenzothiazol-7-ylmethyl, 2-aminobenzothiazol-4-ylmethyl, 2-aminobenzothiazol-7-ylmethyl, 2-amino-7-fluorobenzothiazol-4-ylmethyl, 2-amino-4-fluorobenzothiazol-7-ylmethyl, benzooxazol-4-ylmethyl, benzooxazol-7-ylmethyl, 7-fluorobenzooxazol-4-ylmethyl, 4-fluorobenzooxazol-7-ylmethyl, 2-aminobenzooxazol-4-ylmethyl, 2-aminobenzooxazol-7-ylmethyl, 2-amino-7-fluorobenzooxazol-4-ylmethyl, 2-amino-4-fluorobenzooxazol-7-ylmethyl, benzothiophen-3-ylmethyl, 7-fluorobenzothiophen-3-ylmethyl, benzothiophen-4-ylmethyl, benzothiophen-7-ylmethyl, benzothiophen-7-ylmethyl, 7-fluorobenzothiophen-4-ylmethyl, 4-fluorobenzothiophen-7-ylmethyl, benzothiadiazol-4-ylmethyl, benzofuran-3-ylmethyl, 7-fluorobenzofuran-3-ylmethyl, benzofuran-4-ylmethyl, benzofuran-7-ylmethyl, 7-fluorobenzofuran-4-ylmethyl or 4-fluorobenzofuran-7-ylmethyl.

In one embodiment of formula (I), $R^2$ is —$W^{21}$—$W^{22}$—Rb—$R^{20}$, wherein $W^{21}$ is —(CO)— or —($SO_2$)—; $W^{22}$ is bond, —O—, —NH— or optionally substituted lower alkylene; Rb is bond or optionally substituted lower alkylene; and $R^{20}$ is, optionally substituted alkyl, optionally substituted alkenyl, optionally substituted alkynyl, optionally substituted aryl, optionally substituted heteroaryl, optionally substituted cycloalkyl or optionally substituted heterocycloalkyl.

Examples of lower alkylene group for $W^{22}$ include methylene, ethylene, propylene, butylene and the like.

Examples of lower alkylene group for Rb include methylene, ethylene, methylmethylene, 1,2-propylene, 1,3-propylene, 1,2-butylene, 1,3-butylene, 1,4-butylene, 1,2,3-propanetriyl, 1,3,3-propanetriyl and the like.

Examples of optionally substituted alkyl group for $R^{20}$ include methyl, ethyl, propyl, isopropyl, butyl, isobutyl, sec-butyl, tert-butyl, pentyl, isopentyl, aminomethyl, aminoethyl, dimethylaminoethyl, aminopropyl, aminobutyl, carboxymethyl, carboxyethyl, carboxypropyl, carboxybutyl, carbamoylmethyl, carbamoylethyl, carbamoylpropyl, carbamoylbutyl, methoxymethyl, methoxyethyl, methoxypropyl, methoxybutyl, methylthiomethyl, methylthioethyl, methylthiopropyl, methylthiobutyl, hydroxymethyl, hydroxyethyl, hydroxypropyl, hydroxybutyl and the like.

Examples of alkenyl group for $R^{20}$ include ethenyl, allyl, 1-propenyl, 2-methylallyl and the like.

Examples of alkynyl group for $R^{20}$ include 1-propynyl, ethynyl and the like.

Examples of aryl group and heteroaryl group for $R^{20}$ include biphenyl, phenyl, pyridyl, pyrimidyl, pyridazinyl, pyrazinyl, triazinyl, pyrrolyl, thienyl, furyl, thiazolyl, oxazolyl, imidazolyl, tetrahydronaphthyl, naphthyl, quinolinyl, isoquinolinyl, quinazolinyl, quinoxalinyl, cinnolinyl, naphthyridinyl, benzotriazinyl, indenyl, pyridopyrimidinyl, pyridopyrazinyl, pyridopyridazinyl, pyridotriazinyl, benzofuryl, benzothienyl, indolyl, indazolyl, benzoxazolyl, benzimidazolyl, benzothiazolyl, benzothiadiazolyl, furopyridinyl, thienopyridinyl, pyrrolopyridinyl, oxazolopyridinyl, thiazolopyridinyl, imidazopyridinyl and the like.

Examples of cycloalkyl group and heterocycloalkyl group for $R^{20}$ include cyclopropyl, cyclobutyl, cyclopentyl, cyclohexyl, cycloheptyl, adamantyl and the like.

In a particular embodiment of formula (I), in the above-mentioned embodiments $R^2$ is —$W^{21}$—$W^{22}$—Rb—$R^{20}$; $W^{21}$ is —(CO)— or —($SO_2$)—; $W^{22}$ is bond, —O= or —NH—; Rb is bond or optionally substituted lower alkylene; $R^{20}$ is optionally substituted alkyl, optionally substituted aryl or optionally substituted heteroaryl.

Examples of lower alkylene group for Rb include methylene, ethylene, methylmethylene, 1,2-propylene, 1,3-propylene, 1,2-butylene, 1,3-butylene, 1,4-butylene, 1,2,3-propanetriyl, 1,3,3-propanetriyl and the like.

Examples of optionally substituted alkyl group for $R^{20}$ include methyl, ethyl, propyl, isopropyl, butyl, isobutyl, sec-butyl, tert-butyl, pentyl, isopentyl, aminomethyl, aminoethyl, dimethylaminoethyl, aminopropyl, aminobutyl, carboxymethyl, carboxyethyl, carboxypropyl, carboxybutyl, carbamoylmethyl, carbamoylethyl, carbamoylpropyl, carbamoylbutyl, methoxymethyl, methoxyethyl, methoxypropyl, methoxybutyl, methylthiomethyl, methylthioethyl, methylthiopropyl, methylthiobutyl, hydroxymethyl, hydroxyethyl, hydroxypropyl, hydroxybutyl and the like.

Examples of aryl group and heteroaryl group include biphenyl, phenyl, pyridyl, pyrimidyl, pyridazinyl, pyrazinyl, triazinyl, pyrrolyl, thienyl, furyl, thiazolyl, oxazolyl, imidazolyl, tetrahydronaphthyl, naphthyl, quinolinyl, isoquinolinyl, quinazolinyl, quinoxalinyl, cinnolinyl, naphthyridinyl, benzotriazinyl, indenyl, pyridopyrimidinyl, pyridopyrazinyl, pyridopyridazinyl, pyridotriazinyl, benzofuryl, benzothienyl, indolyl, indazolyl, benzoxazolyl, benzimidazolyl, benzothiazolyl, benzothiadiazolyl, furopyridinyl, thienopyridinyl, pyrrolopyridinyl, oxazolopyridinyl, thiazolopyridinyl, imidazopyridinyl and the like.

In a further embodiment of formula (I), in the above-mentioned embodiments $R^2$ is —$W^{21}$—$W^{22}$—Rb—$R^{20}$, wherein $W^{21}$ is —(CO)— or —(SO$_2$)—; $W^{22}$ is bond, —O—, —NH—, methylene, ethylene, propylene or butylene; Rb is bond, methylene, ethylene, methylmethylene, 1,2-propylene, 1,3-propylene, 1,2-butylene, 1,3-butylene, 1,4-butylene, 1,2,3-propanetriyl or 1,3,3-propanetriyl; and $R^{20}$ is methyl, ethyl, propyl, isopropyl, butyl, isobutyl, sec-butyl, tert-butyl, aminoethyl, dimethylaminoethyl, aminopropyl, aminobutyl, carboxymethyl, carboxyethyl, carboxypropyl, carboxybutyl, carbamoylmethyl, carbamoylethyl, carbamoylpropyl, carbamoylbutyl, methoxyethyl, methoxypropyl, methoxybutyl, methylthiomethyl, methylthioethyl, methylthiopropyl, methylthiobutyl, hydroxyethyl, hydroxypropyl, hydroxybutyl, ethenyl, ethynyl, allyl, 1-propynyl, 2-methylallyl, 1-propynyl, optionally substituted cyclopropyl, optionally substituted cyclobutyl, optionally substituted cyclopentyl, optionally substituted cyclohexyl, optionally substituted cycloheptyl, optionally substituted adamantly, optionally substituted biphenyl, optionally substituted phenyl, optionally substituted pyridyl, optionally substituted pyrimidyl, optionally substituted pyridazinyl, optionally substituted pyrazinyl, optionally substituted triazinyl, optionally substituted pyrrolyl, optionally substituted thienyl, optionally substituted furyl, optionally substituted thiazolyl, optionally substituted oxazolyl, optionally substituted imidazolyl, optionally substituted naphthyl, optionally substituted quinolinyl, optionally substituted isoquinolinyl, optionally substituted quinazolinyl, optionally substituted quinoxalinyl, optionally substituted cinnolinyl, optionally substituted naphthyridinyl, optionally substituted benzotriazinyl, optionally substituted pyridopyrimidinyl, optionally substituted pyridopyrazinyl, optionally substituted pyridopyridazinyl, optionally substituted pyridotriazinyl, optionally substituted benzofuryl, optionally substituted benzothiopenyl, optionally substituted indolyl, optionally substituted indenyl, optionally substituted benzooxazolyl, optionally substituted benzimidazolyl, optionally substituted benzothiazolyl, optionally substituted furopyridinyl, optionally substituted thienopyridinyl, optionally substituted pyrropyridinyl, optionally substituted oxazolopyridinyl, optionally substituted thiazolopyridinyl, optionally substituted imidazopyridinyl.

In particular embodiment of formula (I), in the above-mentioned embodiments $R^2$ is —$W^{21}$—$W^{22}$—Rb—$R^{20}$, wherein $W^{21}$ is —(CO)—; $W^{22}$ is —NH—; Rb is bond, methylene or ethylene; and $R^{20}$ is optionally substituted biphenyl, optionally substituted phenyl, optionally substituted pyridyl, optionally substituted pyrimidyl, optionally substituted pyridazinyl, optionally substituted pyrazinyl, optionally substituted triazinyl, optionally substituted pyrrolyl, optionally substituted thienyl, optionally substituted furyl, optionally substituted thiazolyl, optionally substituted oxazolyl, optionally substituted imidazolyl or optionally substituted naphthyl.

Preferred examples of aryl group and heteroaryl group include monocyclic aryl group or monocyclic heteroaryl group such as phenyl, naphthyl, pyridyl, pyrimidyl, pyridazinyl, pyrazinyl, triazinyl, pyrrolyl, thienyl, furyl, thiazolyl, oxazolyl, imidazolyl and the like.

Examples of substituents for $R^{20}$ include —$R^8$, —OH, —$OR^8$, —COOH, —$COOR^8$, —$CONH_2$, —$CONHR^8$, —$CONR^8R^4$, —$NH_2$, —$NHR^8$, —$NR^8R^4$, —SH, —$SR^8$, —$SO_2R^8$, —$SO_2NH_2$, —$SO_2NHR^8$, —$SO_2NR^8R^4$—$SO_3H$, —$SOR^8$, —$NHC(NH_2)(=NH)$, —$NHC(NHR^8)NR^4$, —OP(=O)(OH)$_2$, —OP(=O)(ONa)$_2$, —CN, —$NO_2$ and halogen, wherein $R^8$ and $R^4$ is independently selected from linear or branched chain, cyclic or noncyclic, substituted or unsubstituted, alkyl chain, aryl and arylalkyl moieties.

Preferred examples of the substituents include —$NH_2$, —OH, —$OR^8$, —COOH, —$CONH_2$, —$CONHR^8$, —$CONR^8R^4$, —$NHR^8$, —$NR^8R^4$, or halogen.

In one embodiment of formula (I), $R^3$ is hydrogen, optionally substituted alkyl, optionally substituted alkenyl or, optionally substituted alkynyl.

Preferable examples of alkyl group include $C_{1-4}$ alkyl group such as methyl, ethyl, propyl, isopropyl, butyl, isobutyl, sec-butyl, tert-butyl and the like.

Examples of alkenyl group include ethenyl, allyl, 2-methylallyl and the like.

Examples of alkynyl group include 1-propynyl, ethynyl and the like.

$R^3$ is preferably hydrogen or $C_{1-4}$ alkyl such as methyl, ethyl, propyl, isopropyl, butyl, isobutyl, sec-butyl or tert-butyl, more preferably methyl or ethyl.

In particular embodiment of formula (I), in the above-mentioned embodiments $R^3$ is hydrogen or methyl.

In order to avoid an accidental anticipation, the following provisos (1) to (4) are added to the formula (I);
(1) when Rb is optionally substituted lower alkylene, then $W^{22}$ should be —O— or —NH—,
(2) when E and B are hydrogen, then $R^3$ should be hydrogen,
(3) when G is —NH—, —$CH_2$—, —$CHR^6$— or —$NR^6$—, then B and E should not be hydrogen, and
4) when G is —O—, B and E are hydrogen and $R^3$ is hydrogen, then $R^1$ should not be 8-quinolylmethyl.

Figure 2:
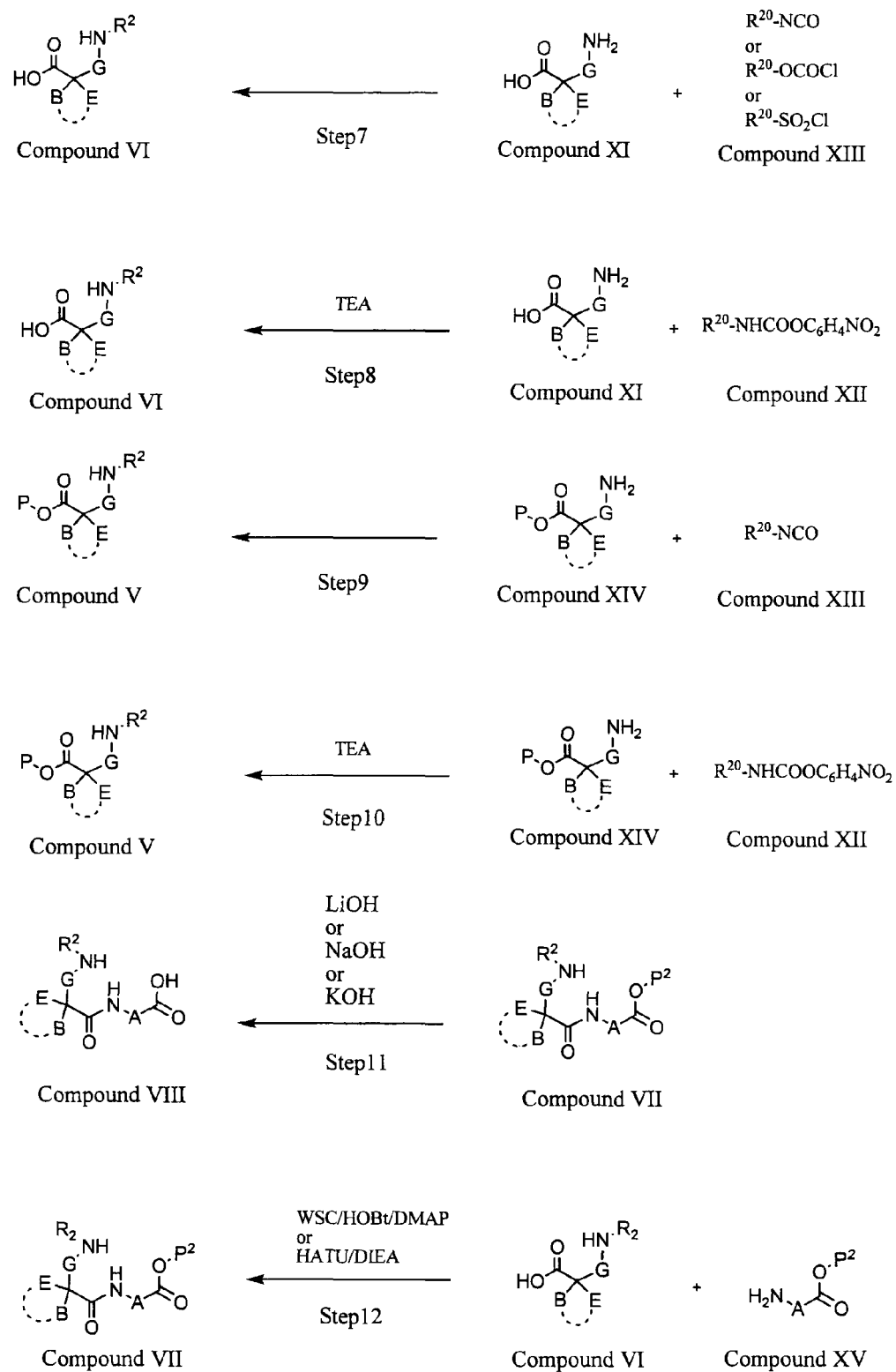
Figure 3:
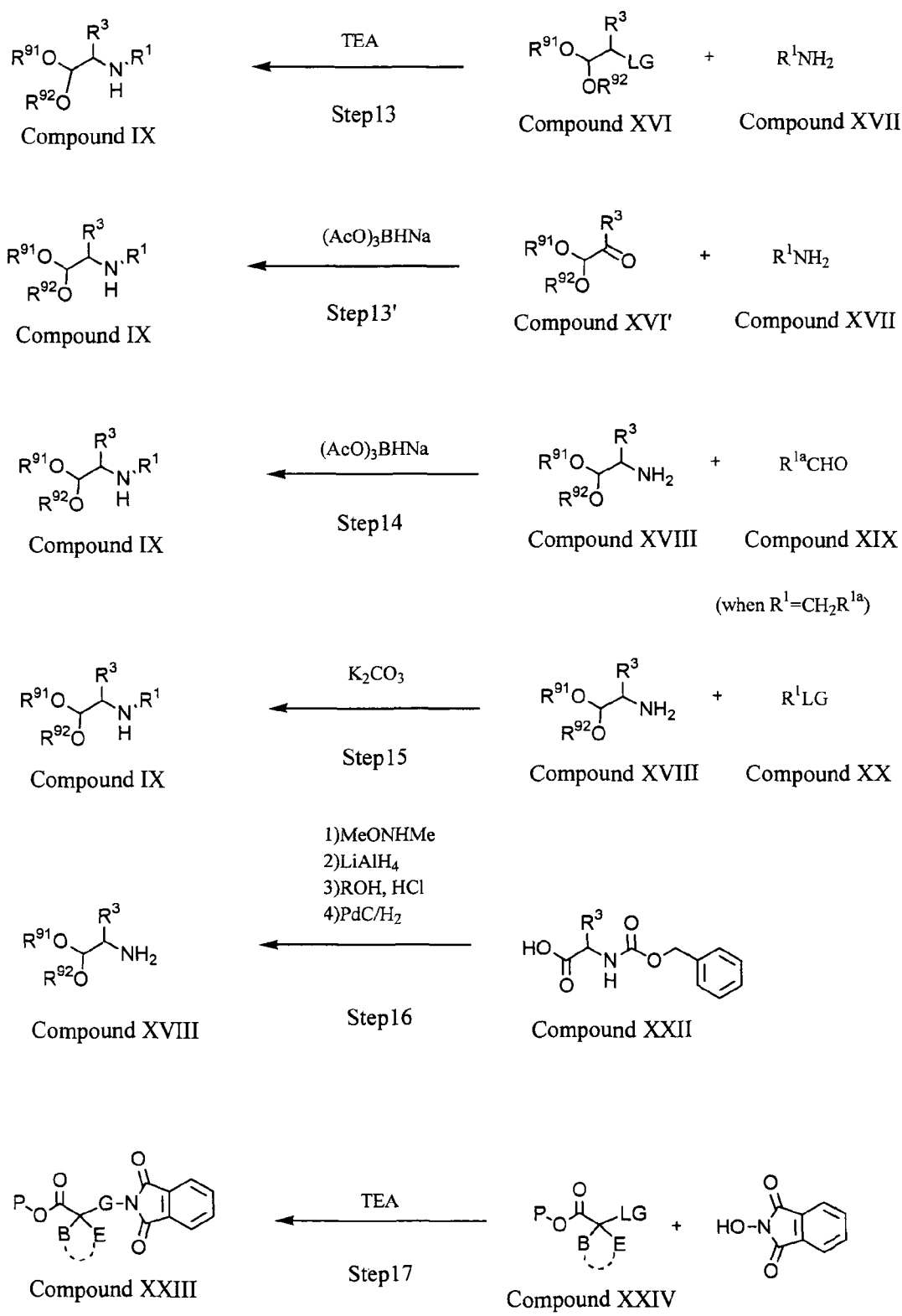

The general retrosynthesis of the compounds in this invention may be synthesized by the technique illustrated in FIGS. 1 to 3.

Referring to FIG. 3, for example, a Compound IX may have the indicated structure wherein $R^1$ and $R^3$ are as defined above, and $R^{91}$ and $R^{92}$ are a protective group suitable for use in synthesis, where this protection group may be joined to a polymeric solid support or linker to enable solid-phase synthesis. Suitable $R^{91}$ and $R^{92}$ groups include optionally substituted alkyl groups and, in a preferred embodiment, both of $R^{91}$ and $R^{92}$ are a methyl or ethyl group. Such Compound IX may be readily synthesized by reductive amination of $H_2N$—$R^1$ with $CH(OR^{91})(OR^{92})$—$CR^3O$, by reductive amination of $R^{1a}$—CHO (when $R^1$=$CH_2R^{1a}$) with $CH(OR^{91})(OR^{92})$—$CHR^3NH_2$, by a displacement reaction between $H_2N$—$R^1$ and $CH(OR^{91})(OR^{92})$—$CHR^3$-LG (wherein LG refers to a leaving group, e.g., a halogen (Hal) group) or by a displacement reaction between LG-$R^1$ and $CH(OR^{91})(OR^{92})$—$CHR^3$—$NH_2$ (wherein LG refers to a leaving group, e.g., a halogen (Hal) group).

Referring to FIG. 1, a Compound III may have the indicated structure wherein $P^1$ is an amino protection group suitable for use in peptide synthesis, and the other symbols are as defined above. Preferred protection groups include 9H-fluorenylmethyloxycarbonyl (Fmoc), t-butyl dimethylsilyl (TB-DMS), t-butyloxycarbonyl (BOC), methyloxycarbonyl (MOC), and allyloxycarbonyl (Alloc). N-Protected amino acids are commercially available; for example, Fmoc amino acids are available from a variety of sources. In the case of the azido derivative of an amino acid serving as the Compound III, such compounds may be prepared from the corresponding amino acid by the reaction disclosed by Zaloom et al. (J. Org. Chem. 46:5173-76, 1981).

Referring to FIG. 2, a Compounds VII and XV may have the indicated structure wherein $P^2$ is a carboxy protection group suitable for use in peptide synthesis, and other symbols are as defined above. Preferred protection groups include alkyl groups and, in a preferred embodiment, $P^2$ is a methyl or ethyl group.

A Compound VI of this invention may have the indicated structure wherein G, E, B, and $R^2$ are as defined above. Other suitable Compounds VI are commercially available from a variety of sources or can be prepared by methods well known in organic chemistry.

Compound X, XI, XII, XIII, XIV, XV, XVI, XVII, XVIII, XIX, XX, XXII, XXIII and XXIV are commercially available from a variety of sources or can be prepared by methods well known in organic chemistry.

As illustrated in FIG. 1, the alpha-helix mimetic compounds of formula (I) may be synthesized by reacting a Compound IX with a Compound X to yield a combined Compound III, followed by treating the combined Compound III with piperidine to provide Compound IV, reacting the Compound IV with Compound VI sequentially to provide a combined Compound II, and then cyclizing this intermediate to yield an alpha-helix mimetic structure of formula (I). Or, as illustrated in FIG. 2, the alpha-helix mimetic compounds of formula (I) may be synthesized by reacting a Compound VI with a Compound XV to yield a combined Compound VII, followed by treating the Compound VII with lithium hydroxide, sodium hydroxide or potassium hydroxide to provide Compound VIII. As illustrated in FIG. 1, the Compound VIII reacts with Compound IX sequentially to provide a combined Compound II, followed by cyclizing this intermediate to yield an alpha-helix mimetic structure of formula (I).

The preparation method of Compound (I) is not limited in the methods described herein. For example, the compounds of the present invention can be produced by modifying or converting a substituent of a compound serving as a precursor of the compounds according to method or combination of methods described in ordinary publications in the field of chemistry.

The syntheses of representative Compounds of this invention are described in working Examples.

A compound having the following general formula (II) is a novel intermediate compound for preparing the compound of the formula (I).

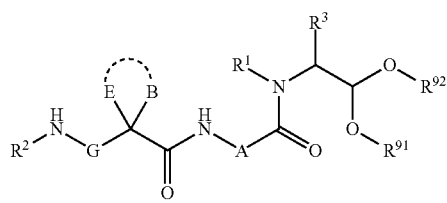

wherein
A is —(CHR$^7$)—;
wherein
R$^7$ is hydrogen, optionally substituted alkyl, optionally substituted alkenyl, optionally substituted alkynyl, optionally substituted aryl, optionally substituted heteroaryl, optionally substituted cycloalkyl, optionally substituted heterocycloalkyl, optionally substituted arylalkyl, optionally substituted heteroarylalkyl, optionally substituted cycloalkylalkyl, or optionally substituted heterocycloalkylalkyl;
B and E are the same or different and independently selected from hydrogen, optionally substituted alkyl, optionally substituted alkenyl, and optionally substituted alkynyl or form an optionally substituted spiro ring indicated by dashed lines;
G is —NH—, —NR$^6$—, —O—, —CH$_2$—, —CHR$^6$— or —C(R$^6$)$_2$—;
wherein
each R$^6$ is the same or different and independently selected from optionally substituted alkyl, optionally substituted alkenyl, and optionally substituted alkynyl;
R$^1$ is optionally substituted alkyl, optionally substituted alkenyl, optionally substituted alkynyl, optionally substituted arylalkyl, optionally substituted heteroarylalkyl, optionally substituted cycloalkylalkyl, or optionally substituted heterocycloalkylalkyl;
R$^2$ is —W$^{21}$—W$^{22}$—Rb—R$^{20}$;
wherein
W$^{21}$ is —(CO)— or —(SO$_2$)—;
W$^{22}$ is bond, —O—, —NH— or optionally substituted lower alkylene;
Rb is bond or optionally substituted lower alkylene; and
R$^{20}$ is optionally substituted alkyl, optionally substituted alkenyl, optionally substituted alkynyl, optionally substituted aryl, optionally substituted heteroaryl, optionally substituted cycloalkyl, or optionally substituted heterocycloalkyl;
R$^3$ is hydrogen, optionally substituted alkyl, optionally substituted alkenyl, or optionally substituted alkynyl;
R$^{91}$ is selected from optionally substituted alkyl, linker and solid support; and
R$^{92}$ is selected from optionally substituted alkyl, linker and solid support.

In order to avoid an accidental anticipation, the following provisos (1) to (4) are added to the formula (II);
(1) when Rb is optionally substituted lower alkylene, then W$^{22}$ should be —O— or —NH—,
(2) when E and B are hydrogen, then R$^3$ should be hydrogen,
(3) when G is —NH—, —CH$_2$—, —CHR$^6$— or —NR$^6$—, then B and E should not be hydrogen, and
(4) when G is —O—, B and E are hydrogen and R$^3$ is hydrogen, then R$^1$ should not be 8-quinolylmethyl.

Examples and preferable embodiments of A, G, E, B, R$^1$, R$^2$, and R$^3$ in the formula (II) are the same as those for the formula (I).

Examples of optionally substituted alkyl for R$^{91}$ and R$^{92}$ include those as defined for R$^7$ and the like.

Examples of linker and solid support for R$^{91}$ and R$^{92}$ include those for preparing the libraries as explained below.

The cyclization reaction of Compound (II) for preparing Compound (I) is explained in detail in the following.

This cyclization reaction can be carried out by reacting the Compound II with an acid.

The order of addition of the reagents is not particularly limited, and, for example, an acid may be added to Compound II or vice versa.

The acid to be used in the cyclization reaction is not particularly limited, and examples thereof include inorganic acids such as hydrochloric acid, nitric acid, sulfuric acid, phosphoric acid and the like; organic acids such as formic acid, acetic acid, trifluoroacetic acid, propionic acid, methanesulfonic acid, p-toluenesulfonic acid, trifluoromethanesulfonic acid; hydrogen chloride solution; hydrogen bromide solution; hydrogen fluoride and the like.

In addition, water, anisole, m-cresol, ethanedithiol, thioanisole or triisopropylsilane can be used with along the acid.

The amount of the acid to be used in the cyclization reaction is generally 0.001 mol to 1000 mol, preferably 1 mol to 100 mol, more preferably 5 mol to 50 mol, relative to 1 mol of Compound II.

The cyclization reaction may be performed with or without solvent. The solvent to be used in the cyclization reaction may be any as long as it does not inhibit the reaction. Examples thereof include ethers such as tetrahydrofuran (THF), methyl tert-butyl ether, 1,4-dioxane, diethylene glycol dimethyl ether (diglyme), ethylene glycol dimethyl ether, 1,3-dioxolane, 2-methyltetrahydrofuran and the like; aprotic polar solvents such as N,N-dimethylformamide (DMF), N,N-dimethylacetamide (DMAc), dimethyl sulfoxide (DMSO), sulfolane, N-methyl-2-pyrrolidinone (NMP), 1,3-dimethyl-2-imidazolidinone (DMI), hexamethyl phosphoramide (HMPA), acetonitrile, propionitrile and the like; halogenated solvents such as methylene chloride, 1,2-dichloroethane, carbon tetrachloride, monochlorobenzene and the like; aromatic hydrocarbon such as benzene, toluene, xylene and the like; water and the like, and a mixed solvent thereof. When a mixed solvent is used, the solvents may be mixed at optional ratios.

While the reaction temperature in the cyclization reaction depends on the reagent to be used and the like, it is generally from −40° C. to 120° C., preferably from −20° C. to 60° C., more preferably from −10° C. to 40° C. The reaction time is generally 0.5 hr to 96 hr, preferably 1 hr to 48 hr.

The compound (I) to be obtained in the cyclization reaction can be isolated and purified by a conventional method such as extraction, water-washing, acid washing, alkali washing, crystallization, recrystallization, silica gel column chromatography.

Furthermore continuing the explanation, the compounds of the present invention, salts thereof and derivatives thereof useful as prodrugs are excellent in pharmacological action selectivity, safety (various toxicities and safety pharmacology), pharmacokinetic performance, physicochemical property and the like, and therefore the usefulness as active ingredients of medicaments can be confirmed.

Examples of tests concerning pharmacological action selectivity include, but not be limited to, the following list including inhibition or activation assays on various pharmacological target receptors, inhibition assays on various pharmacological target enzymes, ion channels or transporters, cell tests to be used for the evaluation for various pharmacological action, and the like.

Examples of tests concerning safety include, but not be limited to, the following list including cytotoxic tests (e.g., tests using HL60 cells, hepatocytes, etc., and the like), genotoxicity tests (e.g., Ames test, mouse lymphoma TK test, chromosomal aberration test, micronucleus test and the like), skin sensitization tests (e.g., Buehler method, GPMT method, APT method, LLNA test and the like), skin photosensitization tests (e.g., Adjuvant and Strip method and the like), eye irritation tests (e.g., single instillation, short-term continuation instillation, repetitive instillation and the like), safety pharmacology tests for the cardiovascular system (e.g., telemetry method, APD method, hERG inhibition assay and the like), safety pharmacology tests for the central nervous system (e.g., FOB method, modified version of Irwin method and the like), safety pharmacology tests for the respiratory system (e.g., measurement method using a respiratory function measuring apparatus, measurement method using a blood gas analyzer and the like), general toxicity tests, and the like.

Examples of tests concerning pharmacokinetic performance include, but not be limited to, the following list including cytochrome P450 enzyme inhibition or induction tests, cell permeability tests (e.g., tests using CaCO-2 cells, MDCK cells etc., and the like), drug transporter ATPase assay, oral absorption tests, blood concentration transition measurement tests, metabolism tests (e.g., stability test, metabolite molecular species test, reactivity test and the like), solubility tests (e.g., solubility test based on turbidity method and the like), and the like.

Examples of tests concerning physicochemical property include, but not be limited to, the following list including chemical stability test (e.g., stability test using HPLC etc., and the like), partition coefficient (e.g., partition test using octanol phase/water phase and the like), ionization constant test, crystallization test, and the like.

The compound of the present invention is useful as bioactive agents, such as diagnostic, prophylactic, and therapeutic agents. For example, the compound of the present invention may be used for modulating a cell signaling transcription factor related peptides in a warm-blooded animal, by a method comprising administering to the animal an effective amount of the compound of formula (I).

In another embodiment, there is a method of treating a cancerous condition or fibrosis by administering the compound of formula (I). The compounds of the formula (I) can be used for inhibiting or treating disorders modulated by Wnt-signaling pathway, such as cancer, such as colorectal cancer, and so forth.

In another embodiment, a pharmaceutical composition comprises the compound of formula (I) or a pharmaceutically acceptable salt thereof, and, if desired or necessary, together with a pharmaceutical acceptable carrier. In another aspect, it is an object of the present invention to provide a pharmaceutical composition comprising an effective amount of the compound having general formula (I) and pharmaceutically acceptable carrier, which can be used for treatment of disorders modulated by Wnt signaling pathway, especially by TCF4-β-catenin-CBP complex.

Further, the present invention is to provide a method for inhibiting the growth of tumor cells by using the above-described composition of the present invention; a method for inducing apoptosis of tumor cells by using the above-described composition of the present invention; a method for treating a disorder modulated by TCF4-β-catenin-CBP complex by using the above-described composition of the present invention; and a method of treating cancer such as colorectal cancer by administering the composition of the present invention together with other anti-cancer agent such as 5-fluorouracil (5-FU), taxol, cisplatin, mitomycin C, tegafur, raltitrexed, capecitabine, and irinotecan, etc.

In another aspect of this invention, libraries containing compound of the present invention is disclosed. Once assembled, the libraries of the present invention may be screened to identify individual members having bioactivity. Such screening of the libraries for bioactive members may involve; for example, evaluating the binding activity of the members of the library or evaluating the effect the library members have on a functional assay. Screening is normally accomplished by contacting the library members (or a subset of library members) with a target of interest, such as, for example, an antibody, enzyme, receptor or cell line. Library members which are capable of interacting with the target of interest, are referred to herein as "bioactive library members" or "bioactive mimetics". For example, a bioactive mimetic may be a library member which is capable of binding to an antibody or receptor, or which is capable of inhibiting an enzyme, or which is capable of eliciting or antagonizing a functional response associated, for example, with a cell line. In other words, the screening of the libraries of the present invention determines which library members are capable of interacting with one or more biological targets of interest. Furthermore, when interaction does occur, the bioactive mimetic (or mimetics) may then be identified from the library members. The identification of a single (or limited number) of bioactive mimetic(s) from the library yields alpha-helix mimetic structures which are themselves biologically active, and thus are useful as diagnostic, prophylactic or therapeutic agents, and may further be used to significantly advance identification of lead compounds in these fields.

Synthesis of the peptide mimetics of the library of the present invention may be accomplished using known peptide synthesis techniques, in combination with the first, second and third component pieces of this invention. More specifically, any amino acid sequence may be added to the N-terminal and/or C-terminal of the conformationally constrained alpha-helix mimetic. To this end, the mimetics may be synthesized on a solid support (such as PAM resin) by known techniques (see, e.g., John M. Stewart and Janis D. Young, Solid Phase Peptide Synthesis, 1984, Pierce Chemical Comp., Rockford, Ill.) or on a silyl-linked resin by alcohol attachment (see Randolph et al., J. Am Chem. Soc. 117:5712-19, 1995).

In addition, a combination of both solution and solid phase synthesis techniques may be utilized to synthesize the peptide mimetics of this invention. For example, a solid support may be utilized to synthesize the linear peptide sequence up to the point that the conformationally constrained alpha-helix is added to the sequence. A suitable conformationally constrained alpha-helix mimetic structure which has been previously synthesized by solution synthesis techniques may then be added as the next "amino acid" to the solid phase synthesis (i.e., the conformationally constrained alpha-helix mimetic, which has both an N-terminus and a C-terminus, may be utilized as the next amino acid to be added to the linear peptide). Upon incorporation of the conformationally constrained alpha-helix mimetic structures into the sequence, additional amino acids may then be added to complete the peptide bound to the solid support. Alternatively, the linear N-terminus and C-terminus protected peptide sequences may be synthesized on a solid support, removed from the support, and then coupled to the conformationally constrained alpha-helix mimetic structures in solution using known solution coupling techniques.

As to methods for constructing the libraries, traditional combinatorial chemistry techniques (see, e.g., Gallop et al., J. Med. Chem. 37:1233-1251, 1994) permit a vast number of compounds to be rapidly prepared by the sequential combination of reagents to a basic molecular scaffold. Combinatorial techniques can be used to construct peptide libraries derived from the naturally occurring amino acids. For example, by taking 20 mixtures of 20 suitably protected and different amino acids and coupling each with one of the 20 amino acids, a library of 400 (i.e., $20^2$) dipeptides is created. Repeating the procedure seven times results in the preparation of a peptide library comprised of about 26 billion (i.e., $20^8$) octapeptides.

Specifically, synthesis of the peptide mimetics of the library of the present invention may be accomplished using known peptide synthesis techniques, such as those disclosed, for example, in WO 2005/116032, which is incorporated herein by reference.

In a further aspect of this invention, the present invention provides methods for screening the libraries for bioactivity and isolating bioactive library members.

In one embodiment, data of biological activity is determined in the following manner. All of compounds are assayed by using a method of the following reporter gene assay.

Reporter Gene Assay

Screening for inhibitory action of the Wnt signaling pathway can be carried out according to the following procedure using the stably transfected cell line Hek-293, STF1.1.

Growth Medium: DMEM, 10% FBS, Pen-Strep, supplemented with 400 μg/mL G418 to maintain selection of SuperTOPFLASH driven Luciferase gene 1. On the day prior to assay, split cells into a white opaque 96-well plate at 20,000 cells per well in 200 microliters of complete growth medium
2. Incubate the plate overnight at 37° C., 5% $CO_2$ and allow the cells to attach
3. Next day, prepare the inhibitors to be tested in complete growth medium, without G418, at 2× the desired final concentration (all conditions are done in duplicates)
4. Carefully remove the old medium from each well using a multiple pipettor
5. Add 50 microliters of fresh growth medium (without G148) containing the inhibitor to each well
6. Be sure to include 2 wells containing medium only, 2 wells for stimulation control, 2 wells for DMSO control, and wells for the positive control ICG-001 (2, 5, and 10 micromolar)
7. Once all inhibitors and controls are added, incubate the plate for 1 hour at 37° C., 5% $CO_2$
8. While plate is incubating, prepare fresh 20 mM LiCl in complete growth medium (without G418)
9. After 1 hour, remove plate from incubator and add 50 microliters of the medium containing 20 mM LiCl to each well, except for the two wells of the unstimulated control (add 50 microliters of just complete medium)
10. Incubate the plate for 24 hours at 37° C., 5% $CO_2$
11. After 24 hours, add 100 microliters of BrightGlo (Promega, Cat. #: G7573) to each well
12. Shake plate for 5 minutes to ensure complete lysis
13. Read plate on the Packard TopCount The libraries of the present invention also can be screened for bioactivity by other various techniques and methods. For example, the screening assay may be performed by (1) contacting the mimetics of a library with a biological target of interest, such as a receptor, to allow binding between the mimetics of the library and the target to occur, and (2) detecting the binding event by an appropriate assay, such as the calorimetric assay disclosed by Lam et al. (Nature 354:82-84, 1991) or Graminski et al. (Biotechnology 12:1008-1011, 1994) (both of which are incorporated herein by reference). In a preferred embodiment, the library members are in solution and the target is immobilized on a solid phase. Alternatively, the library may be immobilized on a solid phase and may be probed by contacting it with the target in solution.

A method for carrying out a binding assay also can be applied as follows. The method can include providing a composition that includes a first co-activator, an interacting protein, and a test compound. The amino acid structure of the first co-activator includes a binding motif of LXXLL, LXXLI or FxxFF wherein X is any amino acid. The method further includes detecting an alteration in binding between the first co-activator and the interacting protein due to the presence of the compound, and then characterizing the test compound in terms of its effect on the binding. The assay may be carried out by any means that can measure the effect of a test compound on the binding between two proteins. Many such assays are known in the art and can be utilized in the method of the present invention, including the so-called Two-Hybrid and Split-Hybrid systems. The Two-Hybrid system, and various means to carry out an assay using this system, are described in, e.g., U.S. Pat. No. 6,410,245. The Split-Hybrid system has been described by, e.g., Hsiu-Ming Shih et al. Proc. Natl. Acad. Sci. USA, 93:13896-13901, Nov. 1996; and John D. Crispino, et al. Molecular Cell, 3:1-20, Feb. 1999. In the Split-Hybrid system, a fusion protein is utilized where protein X is fused to the lexA DNA binding domains (pLexA) and protein Y is fused to the transcription activator VP16 (pSHM.1LacZ). Interaction between lexA-X and VP16-Y leads to the expression of the Tetracycline repressor protein (TetR). TetR prevents transcription of the HIS3 reporter gene, making the cells unable to grow on media lacking histidine. Disruption of protein-protein interaction will restore the ability of the cells to grow on such media by shutting down expression of the tetracycline repressor. Accordingly, compounds of the present invention may be added to the growing cells, and if the addition of the compound restores the ability of the cells to grow on the media, the compound may be seen as an effective disruptor of the protein- protein interaction. The yeast strains required to make the Split-Hybrid system work can be employed with two hybrid LexA/VP16 constructs such as those described by Stanley M. Hollenberg, et al. Molecular and Cellular Biology 15(7):3813-3822, Jul. 1995. A useful modification of the Split-Hybrid system was utilized by Takemaru, K. I. and Moon, R. T. J. of Cell Biol. 149:249-254, 2000.

Other assay formats can also be suitable. For example, reporter gene assays for AP-1, ELISA, for example, blocking the production of IL-2 by a T-cell line after stimulation with CD3 and CD28 to look for inhibitors of IL-2 transcription. Direct binding assays (between coactivators and their partners) can be performed by surface plasmon resonance spectroscopy (Biacore, Sweden, manufactures suitable instruments) or ELISA.

Exemplary transcriptional regulators include, without limitation, VP16, VP64, p300, CBP, PCAF.SRC1 PvALF, AtHD2A and ERF-2. See, for example, Robyr et al. (2000) Mol. Endocrinol. 14:329-347; Collingwood et al. (1999) J. Mol. Endocrinol. 23:255-275; Leo et al. (2000) Gene 245:1-11; Manteuffel-Cymborowska (1999) Acta Biochim. Pol. 46:77-89; McKenna et al. (1999) J. Steroid Biochem. Mol. Biol. 69:3-12; Malik et al. (2000) Trends Biochem. Sci. 25:277-283; and Lemon et al. (1999) Curr. Opin. Genet. Dev. 9:499-504. Other exemplary transcription factors include, without limitation, OsGAI, HALF-1, C1, AP1, ARF-5, -6, -7, and -8, CPRF1, CPRF4, MYC-RP/GP, and TRAB1. See, for example, Ogawa et al. (2000) Gene 245:21 -29; 5 Okanami et al. (1996) Genes Cells 1 :87-99; Goff et al. (1991) Genes Dev. 5:298 -309; Cho et al. (1999) Plant Mol. Biol. 40:419-429; Ulmason et al. (1999) Proc. Natl. Acad. Sci. USA 96:5844-5849; Sprenger-Haussels et al. (2000) Plant J. 22:1-8; Gong et al. (1999) Plant Mol. Biol. 41:33-44; and Hobo et al. (1999) Proc. Natl. Acad. Sci. USA 96:15,348-15,353.

The transcriptional coactivator can be a human transcriptional coactivator. In another embodiment, the transcriptional coactivator is a member of the p300/CBP family of co-activators which have histone acetyltransferase activity. P300 is described for example by Eckner et al, 1994 and CBP by Bannister and Kouzarides, 1996. For the 5 purposes of the present invention, reference to p300/CBP refers to human allelic and synthetic variants of p300, and to other mammalian variants and allelic and synthetic variants thereof, as well as fragments of said human and mammalian forms of p300. In one aspect of the assay, the interacting protein is a transcription factor or a second co-activator. In one aspect of the assay, the interacting protein is any one of RIP140; SRC-1 (NCoA-1); TIF2 (GRIP-1; SRC-2); p (CIP; RAC3; ACTR; AIB-1; TRAM-1; SRC-3); CBP (p300); TRAPs (DRIPS); PGC-1; CARM-1; PRIP (ASC-2; AIB3; RAP250; NRC); GT-198; and SHARP (CoAA; p68; p72). In another aspect of the assay, the interacting protein is any one of TAL 1; p73; MDm2; TBP; HIF-1; Ets-1; RXR; p65; AP-1; Pit-1; HNF-4; Stat2; HPV E2; BRCA1; p45 (NF-E2); c-Jun; c-myb; Tax; Sap 1; YYi; SREBP; ATF-1; ATF-4; Cubitus; Interruptus; Gli3; MRF; AFT-2; JMY; dMad; PyLT: HPV E6; CITTA; Tat; SF-1; E2F; junB; RNA helicase A; C/EBP β; GATA-1; Neuro D; Microphthalimia; E1A; TFIIB; p53; P/CAF; Twist; Myo D; pp9O RSK; c-Fos; and SV40 Large T. In another aspect of the assay, the interacting protein is any one of ERAP140; RIP140; RIP160; Trip1; SWI1 (SNF); ARA70; RAP46; TIF1; TIF2; GRIP1; and TRAP. In another aspect of the invention, the interacting protein is any one of VP16; VP64; p300; CBP; PCAF; SRC1 PvALF; AtHD2A; ERF-2; OsGAI; HALF-1; C1; AP-1; ARF-5; ARF-6; ARF-7; ARF-8; CPRF1; CPRF4; MYC-RP/GP; and TRAB1. In another aspect of the invention, the first co-activator is CBP or p300.

The test compound is selected from compounds as described herein. For example, compounds having the formula (I). Typically, a test compound can be evaluated at several different concentrations, where these concentrations will be selected, in part, based on the conditions of the assay, e.g., the concentrations of the first co-activator and the interacting protein. Concentrations in the range of about 0.1 to 10 µM may be used. In one aspect, the assay evaluates the relative efficacy of two compounds to affect the binding interaction between two proteins, where at least one of those two compounds is a compound of the present invention. The more effective compound can than serve as a reference compound in a study of the relationship between compound structure and compound activity.

Compounds of general formula (I) may inhibit CBP-mediated transcriptional activation in cancer cells due to their specific binding to CBP. The compounds of the present invention may also inhibit the survivin expression in SW480 cells, and therefore, inhibit the oncogenic activity in cancer to cells.

The compounds of the present invention can be used for inhibiting cancer cells, and thus, would be useful for the regulation of cell growth. The compounds of the present invention can be also advantageously used for inducing apoptosis in cells.

The present invention is also related to prodrugs using the libraries containing one or more compounds of formula (I). A prodrug is typically designed to release the active drug in the body during or after absorption by enzymatic and/or chemical hydrolysis. The prodrug approach is an effective means of improving the oral bioavailability or i.v. administration of poorly water-soluble drugs by chemical derivatization to more water-soluble compounds. The most commonly used prodrug approach for increasing aqueous solubility of drugs containing a hydroxyl group is to produce esters containing an ionizable group; e.g., phosphate group, carboxylate group, alkylamino group (Fleisher et al., Advanced Drug Delivery Reviews, 115-130, 1996; Davis et al., Cancer Res., 7247-7253).

In other aspects, the present invention provides pharmaceutical compositions containing a compound having the general formula (I). These compositions may be used in various methods (e.g., treating cancer, fibrosis or Alzheimer's disease) of the present invention as described in detail below.

The pharmaceutical composition of the present invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions (e.g., injection) used for parenteral (particularly, intravenous), intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. In addition, pH may be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound, e.g., a compound having general formula (I) in the required amount, in an appropriate solvent with one or a combination of ingredients enumerated above, as required, followed by filtered sterilization. Generally, dispersions are prepared by incorporating the active compound into a sterile vehicle that contains a dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof. Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules.

Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent I such as peppermint, methyl salicylate, or orange flavoring.

For administration by inhalation, the compounds are delivered in the form of an aerosol spray from pressured container or dispenser that contains a suitable propellant; e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It can be advantageous to formulate oral or parenteral compositions in dosage unit form for ease of administration and uniformity of dosage. Dosage unit form as used herein refers to physically discrete units suited as unitary dosages for the subject to be treated; each unit containing a 5 predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

For instance, in certain embodiments, a pharmaceutical composition of the present invention is one suitable for oral administration in unit dosage form such as a tablet or capsule that contains from about 1 mg to about 1 g of the compound of this invention. In some other embodiments, a pharmaceutical composition of the present invention is one suitable for intravenous, subcutaneous or intramuscular injection. A patient may receive, for example, an intravenous, subcutaneous or intramuscular dose of about 1 µg/kg to about 1 g/kg of the compound of the present invention. The intravenous, subcutaneous and intramuscular dose may be given by means of a bolus injection or by continuous infusion over a period of time. Alternatively a patient will receive a daily oral dose approximately equivalent to the daily parenteral dose, the composition being administered 1 to 4 times per day.

Preferably, the compound of the formula (I) of the present invention can be administered intravenously (particularly preferably, by continuous drip infusion or rapid intravenous administration) to mammals inclusive of human.

In the case, the dose is selected appropriately depending on various factors such as the body weight and/or age of patients, and/or the degree of the symptom and an administration route. For example, the dose of the compound of the formula (I) for intravenous administration is generally in the range of 1 to 10000 mg/day/m$^2$ human body surface area, preferably in the range of 1 to 5000 mg/day/m$^2$ human body surface area, and more preferably 10 to 5000 mg/day/m$^2$ human body surface area by continuous drip infusion administration.

The pharmaceutical composition containing the compound of general formulae (I) can be used for treatment of disorders modulated by Wnt signaling pathway, especially cancer, more especially colorectal cancer.

In one aspect, the present invention provides methods for inhibiting tumor growth. Such methods comprise the step of administering to a subject (e.g., a mammalian subject) having a tumor a compound with general formula (I) in an amount effective to inhibit tumor growth. A compound or composition inhibits tumor growth if the tumor sizes are statistically significantly smaller in subjects with the treatment of the compound or composition than those without the treatment.

The inhibitory effect of a particular compound or composition of the present invention on tumor growth may be characterized by any appropriate methods known in the art. For instance, the effect of the compound or composition on survivin expression may be measured. Compounds or compositions down-regulate survivin expression are likely to have inhibitory effects on tumor growth. In addition, assays using tumor cell lines (e.g., soft agar assays using SW480 cells) and animal models for tumor growth (e.g., nude mice grafted with tumor cells and Min mouse model) may also be used to evaluate the inhibitory effect on tumor growth of a given compound or composition as described in detail in the examples. Other exemplary animal models or xenografts for tumor growth include those for breast cancer (Guo et al, Cancer Res. 62: 4678-84, 2002; Lu et al, Breast Cancer Res. Treat. 57: 183-92, 1999), pancreatic cancer (Bouvet et al, Cancer Res. 62: 1534-40, 2002), ovarian tumor (Nilsson et al, Cancer Chemother. Pharmacol. 49: 93-100, 2002; Bao et al, Gynecol. Oncol. 78: 373-9, 2000), melanoma (Demidem et al, Cancer Res. 61: 2294-300, 2001), colorectal cancer (Brown et al, Dig. Dis. Sci. 45: 1578-84, 2000; Tsunoda et al, Anticancer Res. 19: 1149-52, 1999; Cao et al, Clin. Cancer Res. 5: 267-74, 1999; Shawler et al, J. Immunother. Emphasis Tumor Immunol. 17: 201-8, 1995; McGregor et al, Dis. Colon. Rectum. 36: 834-9, 1993; Verstijnen et al, Anticancer Res. 8: 1193-200, 1988), hepatocellular cancer (Labonte et al, Hepatol. Res. 18: 72-85, 2000), and gastric cancer (Takahashi et al, Int. J. Cancer 85: 243-7, 2000).

The compound or composition that inhibits tumor growth may be administrated into a subject with a tumor via an appropriate route depending on, for example, the tissue in which the tumor resides. The appropriate dosage may be determined using knowledge and techniques known in the art as described above. The effect of the treatment of the compound or composition on tumor growth may also be monitored using methods known in the art. For instance, various methods may be used for monitoring the progression and/or growth of colorectal cancer, including colonoscopy, sigmoidoscopy, biopsy, computed tomograph, ultrasound, magnetic resonance imaging, and positron emission tomography. Methods for monitoring the progression and/or growth of ovarian cancer include, for example, ultrasound, computed tomography, magnetic resonance imaging, chest X-ray, laparoscopy, and tissue sampling.

In a related aspect, the present invention provides a method for treating or preventing cancer or fibrosis. Such methods comprise the step of administering to a subject in need thereof a compound or composition having general formula (I) in an amount effective to treat or prevent cancer or fibrosis in the subject. Treating cancer (or fibrosis) is understood to encompass reducing or eliminating cancer progression, e.g., cancer growth and metastasis (or fibrosis, as applicable). Preventing cancer (or fibrosis) is understood to encompass preventing or delaying the onset of cancer (or fibrosis, as applicable). Various types of cancer may be treated or prevented by the present invention. They include, but are not limited to, lung cancer, breast cancer, colorectal cancer, stomach cancer, pancreatic cancer, liver cancer, uterus cancer, ovarian cancer, gliomas, melanoma, lymphoma, and leukemia. A subject in need of treatment may be a human or non-human primate or other animal with various types of cancer.

A subject in need of prevention may be a human or non-human primate or other animal that is at risk for developing cancer or fibrosis. Methods for diagnosing cancer (or fibrosis) and screening for individuals with high risk of cancer (or fibrosis) are known in the art and may be used in the present invention. For instance, colorectal cancer may be diagnosized by fecal occult blood test, sigmoidoscopy, colonoscopy, barium enema with air contrast, and virtual colonoscopy. An individual with high risk of colorectal cancer may have one or more colorectal cancer risk factors such as a strong family history of colorectal cancer or polyps, a known family history of hereditary colorectal cancer syndromes, a personal history of adenomatous polyps, and a personal history of chronic inflammatory bowel disease.

A compound with general formula (I) useful in cancer (or fibrosis) treatment or prevention may be identified by appropriate methods known in the art. Methods that may be used to select compounds for inhibitory effect on tumor growth as described above may also be used. The route of administration, the dosage of a given compound, the effectiveness of the treatment may be determined using knowledge and techniques known in the art. Factors that may be considered in making such a determination include, for example, type and stage of the cancer (or fibrosis) to be treated.

The compound with general formula (I) useful in cancer treatment and prevention may be administered in combination with an other anti-neoplastic agent. The anti-neoplastic agent refers to a compound that inhibits tumor growth.

Specific examples of the other anti-neoplastic agent include alkylating agents such as thiotepa and CYTOXAN (RTM) cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin;

callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (see, e.g., Agnew, Chem Intl. Ed. Engl. 33:183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRLAMYCIN (RTM) doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU), tegafur, raltitrexed; folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine; dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK (RTM) polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL (RTM) paclitaxel (Bristol-Myers Squibb Oncology, Princeton, N.J.), ABRAKANETM Cremophor-free, albumin-engineered nanoparticle formulation of paclitaxel (American Pharmaceutical Partners, Schaumberg, Ill.), and TAXOTERE (RTM) doxetaxel (Rhne-Poulenc Rorer, Antony, France); chloranbucil; GEMZAR (RTM) gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; NAVELBINE (RTM) vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids such as retinoic acid; capecitabine; and pharmaceutically acceptable salts, acids or derivatives of any of the above.

In addition, examples of the other anti-neoplastic agent also include anti-hormonal agents that act to regulate or inhibit -hormone action on tumors such as anti-estrogens and selective estrogen receptor modulators (SERMs), including, for example, tamoxifen (including NOLVADEX (RTM) tamoxifen), raloxifene, droloxifene, 4-hydroxytamoxifen, trioxifene, keoxifene, LY117018, onapristone, and FARESTON toremifene; aromatase inhibitors that inhibit the enzyme aromatase, which regulates estrogen production in the adrenal glands, such as, for example, 4(5)-imidazoles, aminoglutethimide, MEGASE (RTM) megestrol acetate, AROMASIN (RTM) exemestane, formestane, fadrozole, RIVISOR (RTM) vorozole, FEMARA (RTM) letrozole, and ARIMIDEX (RTM). anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Ralf and H-Ras; ribozymes such as a VEGF expression inhibitor (e.g., ANGIOZYME (RTM) ribozyme) and a HER2 expression inhibitor; vaccines such as gene therapy vaccines, for example, ALLOVECTIN (RTM) vaccine, LEUVECTIN (RTM) vaccine, and VAXID (RTM) vaccine; PROLEUKIN (RTM) rIL-2; LURTOTECAN (RTM) topoisomerase 1 inhibitor; ABARELIX (RTM) rmRH; and pharmaceutically acceptable salts, acids or derivatives of any of the above.

Moreover, examples of the other anti-neoplastic agent also include a "growth inhibitory agent" referring to a compound or composition which inhibits growth of a cell in vitro and/or in vivo. Thus, the growth inhibitory agent may be one which significantly reduces the percentage of cells in S phase. Examples of growth inhibitory agents include agents is that block cell cycle progression (at a place other than S phase), such as agents that induce G1 arrest and M-phase arrest. Classical M-phase blockers include the vincas (vincristine and vinblastine), TAXOL®, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C.

Furthermore, examples of the other anti-neoplastic agent also include a "molecular target drug" that blocks the proliferation and metastasis of cancer by interfering with specific molecules involved in carcinogenesis (the process by which normal cells become cancer cells), tumor growth, or tumor spread. Specific examples of the "molecular target drug" include kinase inhibitors that inhibit kinase activity on tumors, including, for example, imatinib, erlotinib, gefitinib, sunitinib, sorafenib, dasatinib, nilotinib; antibodies that bind to the cell surface molecule on tumor cells or to the growth factor and the like such as, for example, ibritumomab, cetuximab, trastuzumab, panitumumab, bevacizumab, rituximab; and proteasome inhibitors that inhibit the proteasome which regulates protein expression and function by degradation of ubiquitinylated proteins, such as bortezomib; and pharmaceutically acceptable salts, acids or derivatives of any of above.

Further information can be found in The Molecular Basis of Cancer, Mendelsohn and Israel, eds., Chapter 1, entitled "Cell cycle regulation, oncogenes, and antineoplastic drugs" by Murakami et al. (W B Saunders: Philadelphia, 1995), especially p. 13.

A compound with general formula (I) administered in combination with an anti-neoplastic agent does not necessarily require that the compound and the anti-neoplastic agent be administered concurrently. The compound and the agent may be administered separately as long as at a time point, they both have effects on same cancer cells.

For example, the administration mode may be exemplified by (1) administration of a single preparation obtained by simultaneously formulating the compound of formula (I) and the other anti-neoplastic agent, (2) simultaneous administration through the same administration route of two preparations obtained by separately formulating the compound of formula (I) and the other anti-neoplastic agent, (3) administration with a time interval through the same administration route of two preparations obtained by separately formulating the compound of formula (I) and the other anti-neoplastic agent, (4) simultaneous administration through different administration routes of two preparations obtained by separately formulating the compound of formula (I) and the other anti-neoplastic agent, (5) administration with a time interval through different administration routes of two preparations obtained by separately formulating the compound of formula (I) and the other anti-neoplastic agent (e.g., administration in order of the compound of formula (I) and then the other anti-neoplastic agent, or administration in the reverse order), or the like. The amount of the other anti-neoplastic agent to be administered can be appropriately selected with reference to the clinically used dosage. The mixing ratio of the compound of the compound of formula (I) and the other anti-neoplastic agent can be appropriately selected in accordance with the subject of administration, administration route, disease to be treated, symptoms, combination, and the like.

In addition, the compound of the present invention can be also used in combination with, for example, gene therapy involving VEGF, TNFa or the like, or therapeutic methods involving various antibody medicines or the like.

In a further related aspect, the present invention provides methods for promoting apoptosis in cancer cells. Such methods comprise the step of contacting cancer cells with a compound having general formula (I) in an amount effective to promote apoptosis in these cells. A compound promotes apoptosis if the number of cancer cells undergoing apoptosis is statistically significantly larger in the presence of the compound than that in the absence of the compound. Such compounds may be identified by methods known in the art (e.g., measuring caspase activities and/or cell death) using cultured cancer cell lines, xenografts, or animal cancer models. Preferably, the compound is more active in promoting apoptosis in cancer cells than in normal cells. Cancer cells treatable by the present method may be from various tissue origins.

In another aspect of the present invention, a method for treating a disorder modulated by Wnt signaling pathway in which the method comprises administering to a patient a safe and effective amount of the compounds having general formula (I) is disclosed. Pharmaceutical composition containing the compound of the present invention can be also used for this purpose. In this connection, it is found in the present invention that the compounds having general formula (I) or the pharmaceutical composition containing thereof can be useful for the treatment of disorder modulated by TCF4/β-catenin/CBP complex, which is believed to be responsible for initiating the overexpression of cancer cells related to Wnt signaling pathway. Thus, it is another aspect of the present invention to provide a method for the treatment of disorder modulated by TCF4/β-catenin/CBP complex, using the compounds having the general formula (I).

The present invention also provides compounds and methods for inhibiting survivin expression. Survivin is a target gene of the TCF/β-catenin pathway, and more specifically is a target gene of the TCF/β-catenin/CBP pathway. It is a member of the IAP (Inhibitor of Apoptosis Protein) family of proteins. Biological activity associated with survivin includes: highly expressed at G2/M, regulating cell cycle entry and exit; associated with microtubule, centrosomes, centromeres and midbody depending upon the phases of the cell cycle; and anti-apoptosis via interacting directly or indirectly with caspases (e.g., caspase 3, 7 and 9). In connection with cancer, survivin is widely and highly expressed in tumor cells, but expressed to little or no extent in normal tissue cells. Also, it has been observed that cancer patients whose tumors expressed survivin had a decreased overall survival. Furthermore, the degree of survivin expression has been correlated with other cancer markers, e.g., Ki67, PNCA, p53, APC, etc.

The effect of a particular compound of the present invention on survivin expression may be characterized by methods known in the art. Such methods include methods for characterizing survivin expression at the transcriptional or translational level. Exemplary methods for characterizing survivin expression at the transcriptional level are: cDNA microarry, reverse transcription-polymerase chain reaction (RT-PCR), chromatin immunoprecipitation (ChIP), and assays for reporter activities driven by survivin promoter. Exemplary methods for characterizing survivin expression at the translational level are: Western blot analysis, immunochemistry and caspase activities. Detailed descriptions of the above exemplary methods may be found in the examples below.

As described above, the present invention provides methods for inhibiting survivin expression. Such methods comprise the step of contacting a survivin-expressing cell with a compound of the present invention in an amount effective to inhibit survivin expression. A compound inhibits survivin expression if survivin expression in a cell is decreased in the presence of the compound compared to survivin expression in the absence of the compound. Survivin-expressing cells include tumor cells that express, such as cells in or from lung cancer, breast cancer, stomach cancer, pancreatic cancer, liver cancer, uterus cancer, ovarian cancer, gliomas, melanoma, colorectal cancer, lymphoma and leukemia. The step of contacting the survivin-expressing cells with the compound may be performed in vitro, ex vivo, or in vivo. A compound useful in inhibiting survivin expression may be identified, and the effects of a particular compound of the present invention may be characterized, by appropriate methods known in the art, as described in detail above.

Compounds of the present invention also may inhibit the expression of survivin. Blanc-Brude et al., Nat. Medicine 8:987 (2002), have shown that survivin is a critical regulator of smooth muscle cell apoptosis which is important in pathological vessel-wall remodeling. Accordingly, another aspect of the present invention provides a method of treating or preventing restenosis associated with angioplasty comprising administering to a subject in need thereof a safe and effective amount of an alpha-helix mimetic of the present invention. In one embodiment the invention treats the restenosis, i.e., administration of an alpha-helix mimetic of the present invention to a subject having restenosis achieves a reduction in the severity, extent, or degree, etc. of the restenosis. In another embodiment the invention prevents the restenosis, i.e., administration of an alpha-helix mimetic of the present invention to a subject that is anticipated to develop new or additional restenosis achieves a reduction in the anticipated severity, extent, or degree, etc. of the restenosis. Optionally, the subject is a mammalian subject.

Compounds of the present invention also may inhibit TCF/β-catenin transcription. Rodova et al., J. Biol. Chem. 277: 29577 (2002), have shown that PKD-1 promoter is a target of the TCF/β-catenin pathway. Accordingly, another aspect of the present invention provides a method of treating or preventing polycystic kidney disease comprising administering to a subject in need thereof a safe and effective amount of an alpha-helix mimetic of the present invention. In one embodiment the invention treats the polycystic kidney disease, i.e., administration of an alpha-helix mimetic of the present invention to a subject having polycystic kidney disease achieves a reduction in the severity, extent, or degree, etc. of the polycystic kidney disease. In another embodiment the invention prevents polycystic kidney disease, i.e., administration of an alpha-helix mimetic of the present invention to a subject that is anticipated to develop new or additional polycystic kidney disease achieves a reduction in the anticipated severity, extent, or degree, etc. of the polycystic kidney disease. Optionally, the subject is a mammalian subject.

Compounds of the present invention also may inhibit the expression of Wnt signaling. Hanai et al., J. Cell Bio. 158:529 (2002), have shown that endostatin, a known anti-angiogenic factor, inhibits Wnt signaling. Accordingly, another aspect of the present invention provides a method of treating or preventing aberrant angiogenesis disease comprising administering to a subject in need thereof a safe and effective amount of an alpha-helix mimetic of the present invention. In one embodiment the invention treats the aberrant angiogenesis disease, i.e., administration of an alpha-helix mimetic of the present invention to a subject having aberrant angiogenesis disease achieves a reduction in the severity, extent, or degree, etc. of the aberrant angiogenesis disease. In another embodiment the invention prevents aberrant angiogenesis disease, i.e., administration of an alpha-helix mimetic of the present invention to a subject that is anticipated to develop new or additional aberrant angiogenesis disease achieves a reduction in the anticipated severity, extent, or degree, etc. of the aberrant angiogenesis disease. Optionally, the subject is a mammalian subject.

Compounds of the present invention also may inhibit Wnt TCF/β-catenin signalling. Accordingly, another aspect of the invention provides a method of treating or preventing tuberous sclerosis complex (TSC) comprising administering to a subject in need thereof a safe and effective amount of an alpha-helix mimetic the present invention. Subjects having TSC typically develop multiple focal lesions in the brain, heart, kidney and other tissues (see, e.g., Gomez, M. R. Brain Dev. 17(suppl): 55-57 (1995)). Studies in mammalian cells have shown that overexpression of TSC1 (which expresses hamartin) and TSC2 (which expresses tuberin) negatively regulates cell proliferation and induces G1/S arrest (see, e.g., Miloloza, A. et al., Hum. Mol. Genet. 9: 1721-1727 (2000)). Other studies have shown that hamartin and tuberin function at the level of the β-catenin degradation complex, and more specifically that these proteins negatively regulate β-catenin stability and activity by participating in the β-catenin degradation complex (see, e.g., Mak, B.C., et al. J. Biol. Chem. 278(p8): 5947-5951, (2003)). β-catenin is a 95-kDa protein that participates in cell adhesion through its association with members of the membrane-bound cadherin family, and in cell proliferation and differentiation as a key component of the Wnt/Wingless pathway (see, e.g., Daniels, D.L., et al., Trends Biochem. Sci 26: 672-678 (2001)).

Misregulation of this pathway has been shown to be oncogenic in humans and rodents. The present invention provides compounds that modulate β-catenin activity, and particularly its interactions with other proteins, and accordingly may be used in the treatment of TSC. Thus, in one embodiment the invention treats TSC, i.e., administration of an alpha-helix mimetic of the present invention to a subject having TSC achieves a reduction in the severity, extent, or degree, etc. of the TSC. In another embodiment the invention prevents TSC, i.e., administration of an alpha-helix mimetic of the present invention to a subject that is anticipated to develop new or additional TSC achieves a reduction in the anticipated severity, extent, or degree, etc. of the TSC. Optionally, the subject is a mammalian subject.

Compounds of the present invention also may inhibit the expression of Wnt signalling. The Kaposi's sarcoma-associated herpesvirus (KSHV) latency-associated nuclear antigen (LANA) is expressed in all KSHV-associated tumors, including Kaposi's sarcoma (KS) and β-cell malignancies such as primary effusion lymphoma (PEL) and multicentric Castleman's disease. Fujimuro, M. et al., Nature Medicine 9(3): 300-306 (2003), have shown that LANA acts to stabilize β-catenin, apparently by redistribtution of the negative regular GSK-3β. The present invention provides compounds and methods for inhibiting β-catenin protein interactions, e.g., β-catenin/TCF complex formation. Thus, the compounds of the present invention thwart the LANA-induced accumulation of β-catenin/TCF complex and, at least in part, the consequences of KSHV infection. Accordingly, another aspect of the present invention provides a method of treating or preventing conditions due to infection by Karposi's sarcoma-associated herpesvirus (KSHV). Such conditions include KSHV-associated tumors, including Kaposi's sarcoma (KS) and primary effusion lymphoma (PEL). The method comprises administering to a subject in need thereof a safe and effective amount of an alpha-helix mimetic the present invention. In one embodiment the invention treats the KSHV-associated tumor, i.e., administration of an alpha-helix mimetic of the present invention to a subject having a KSHV-associated tumor achieves a reduction in the severity, extent, or degree, etc. of the tumor. In another embodiment the invention prevents a KSHV-associated tumor, i.e., administration of an alpha-helix mimetic of the present invention to a subject that is anticipated to develop new or additional KSHV-associated tumors achieves a reduction in the anticipated severity, extent, or degree, etc. of the tumor. Optionally, the subject is a mammalian subject.

LEF/TCF DNA-binding proteins act in concert with activated β-catenin (the product of Wnt signaling) to transactivate downstream target genes. DasGupta, R. and Fuchs, E. Development 126(20):4557-68 (1999) demonstrated the importance of activated LEF/TCF complexes at distinct times in hair development and cycling when changes in cell fate and differentiation commitments take place. Furthermore, in skin morphogenesis, β-catenin has been shown to be essential for hair follicle formation, its overexpression causing the "furry" phenotype in mice (Gat, U., et al. Cell 95:605-614 (1998) and Fuchs, E. Harvey Lect. 94:47-48 (1999). See also Xia, X. et al. Proc. Natl. Aad. Sci. USA 98:10863-10868 (2001). Compounds of the present invention have been shown to inhibit the expression of Wnt signaling, and interfere with formation of β-catenin complexes. Accordingly, the present invention provides a method for modulating hair growth comprising administering to a subject in need thereof a safe and effective amount of an alpha-helix mimetic the present invention, where the amount is effective to modulate hair growth in the subject. Optionally, the subject is a mammalian subject.

The present invention also provides compounds that may be useful in treating or preventing Alzheimer's disease.

Alzheimer's disease (AD) is a neurodegenerative disease with progressive dementia. This disease is accompanied by three main structural changes in the brain, namely, i) intracellular protein deposits (also known as neurofibrillary tangles, or NFT), ii) extracellular protein deposits termed amyloid plaques that are surrounded by dystrophic neuritis, and iii) diffuse loss of neurons.

The compounds or compositions of the present invention may rescue defects in neuronal differentiation caused by a presenilin-1 mutation and may decrease the number, or rate at which neuronal precursor populations differentiate to neurons in Alzheimer's brains. Presenilins are transmembrane proteins whose functions are related to trafficking, turnover and cleavage of Notch and Amyloid Precursor Protein. Missense mutations in presenilin 1 (PS-1) are associated with early-onset familial Alzheimer's disease (Fraser et al, Biochem. Soc. Symp. 67, 89 (2001)). The compounds of the present invention may be applicable not only to individuals with PS-1 familial Alzheimer's mutations, but also to general Alzheimer's patients.

In addition, the present invention can provide a method for treating or preventing Alzheimer's disease comprising administering to a subject in need thereof a safe and effective amount of an alpha-helix mimetic of the present invention, where the amount is effective to treat or prevent Alzheimer's disease in the subject. Treating Alzheimer's disease is understood to encompass reducing or eliminating the manifestation of symptoms characteristic of Alzheimer's disease, or delaying the progression of this disease. Preventing Alzheimer's disease is understood to encompass preventing or delaying the onset of this disease.

A subject in need of treatment may be a human or non-human primate or other animal that is at various stages of Alzheimer's disease. Methods for diagnosing Alzheimer's disease are known in the art (see, e.g., Dinsmore, J. Am. Osteopath. Assoc. 99.9, Suppl. p:S1-6, 1999; Kurz et al., J. Neural Transm. Suppl. 62: 127-33, 2002; Storey et al., Front Viosci. 7: e155-84, 2002; Marin etal., Geriatrics 57: 36-40, 2002; Kril and Halliday, Int. Rev. Neurobiol. 48: 167-217, 2001; Gurwitz, Trends Neurosci. 23: 386, 2000; Muller-Spahn and Hock, Eur. Arch. Psychiatry Clin. Neurosci. 249 Suppl. 3: 37-42; Fox and Rossor, Rev. Neuro. (Paris) 155 Suppl. 4: S33-7, 1999), including the use of neuropsychological measures, functional imaging measures, biological markers, and autopsy of brain tissue. A subject in need of prevention may be a human or non-human primate or other animal that is at risk for developing Alzheimer's disease, such as an individual having a mutation of certain genes responsible for this disease (e.g., genes encoding amyloid precursor protein, presenilin 1, and presenilin 2), and/or a gene involved in the pathogenesis of this disease (e.g., apolipoprotein E gene) (Rocchi etal., Brain Res. Bull. 61: 1-24, 2003).

Compounds with structures as set forth in formula (I) may be screened for their activities in treating or preventing Alzheimer's disease by any appropriate methods known in the art. Such screening may be initially performed using in vitro cultured cells (e.g, PC-12 cells). Compounds capable of rescuing defects in neuronal differentiation caused by a presenilin 1 mutation may be further screened using various animal models for Alzheimer's disease. Alternatively, compounds with structures as set forth in formula (I) may be directedly tested in animal models for Alzheimer's disease. Many model systems are known in the art and may be used in the present invention (see, e.g., Rowan et al., Philos. Trans. R. Soc. Lond. B. Biol. Sci. 358: 821-8, 2003; Lemere et al., Neurochem. Res. 28: 1017-27, 2003; Sant'Angelo et al., Neurochem. Res. 28: 1009-15, 2003; Weiner Harv. Rev. Psychiatry 4: 306-16, 1997). The effects of the selected compounds on treating or preventing Alzheimer's disease may be characterized or monitored by methods known in the art for evaluating the progress of Alzheimer's disease, including those described above for diagnosing this disease.

The present invention also provides methods for promoting neurite outgrowth. Such methods comprise the step of contacting a neuron with a compound according to formula (I) in an amount effective to promote neurite outgrowth. These methods are useful in treating neurodegenerative diseases (e.g., glaucoma, macular degeneration, Parkinson's Disease, and Alzheimer's disease) and injuries to nervous system. A compound promotes neurite outgrowth if the neurite lengths of neurons are statistically significantly longer in the presence of the compound than those in the absence of the compound. Such a compound may be identified using in vitro cultured cells (e.g, PC-12 cells, neuroblastoma B104 cell) (Bitar et al., Cell Tissue Res. 298: 233-42, 1999; Pellitteri et al., Eur. J. Histochem. 45: 367-76, 2001; Satoh et al., Biochem. Biophys. Res. Commun. 258: 50-3, 1999; Hirata and Fujisawa, J. Neurobiol. 32:415-25, 1997; Chauvet etal., Glia 18: 211-23, 1996; Vetter and Bishop, Curr. Biol. 5: 168-78, 1994; Koo et al., Proc. Natl. Acad. Sci. USA 90: 4748-52, 1993; Skubitz et al., J. Cell Biol. 115: 1137-48, 1991; O'Shea et al., Neuron 7: 231-7, 1991; Rydel and Greene, Proc. Natl. Acad. Sci. USA 85: 1257-61, 1988) or using explants (Kato et al., Brain Res. 31: 143-7, 1983, Vanhems etal., Eur. J. Neurosci. 2: 776-82, 1990; Carri et al., Int. J. Dev. Neurosci. 12: 567-78, 1994). Contacting a neuron with a compound according to the present invention may be carried out in vitro or in vivo. The resulting treated neuron, if generated in vitro, may be transplanted into a tissue in need thereof (Lacza et al., Brain Res. Brain Res. Protoc. 11: 145-54, 2003; Chu et al., Neurosci. Lett 343: 129-33, 2003; Fukunaga et al., Cell Transplant 8: 435-41, 1999).

The present invention also provides methods for promoting differentiation of a neural stem cell comprising contacting a neural stem cell with a compound according to formula (I) in an amount effective to promote differentiation of a neural stem cell. Such methods are also useful in treating neurodegenerative diseases (e.g., glaucoma, macular degeneration, Parkinson's disease, and Alzheimer's disease) and injuries to nervous system. "Neural stem cell" refers to a clonogenic, undifferentiated, multipotent cell capable of differentiating into a neuron, an astrocyte or an oligodendrocyte under appropriate conditions. A compound promotes differentiation of neural stem cells if neural stem cells exhibit a statistically significantly higher degree of differentiation in the presence of the compound than in the absence of the compound. Such a compound may be identified using assays involving in vitro cultured stem cells or animal models (Albranches et al., Biotechnol. Lett. 25: 725-30, 2003; Deng et al., Exp. Neurol. 182: 373-82, 2003; Munoz-Elias et al., Stem Cells 21: 437-48, 2003; Kudo et al, Biochem. Pharmacol. 66: 289-95, 2003; Wan et al., Chin. Med. J. 116: 428-31, 2003; Kawamorita et al., Hum. Cell 15: 178-82, 2002; Stavridis and Smith, Biochem. Soc. Trans. 31: 45-9, 2003; Pachernik et al., Reprod. Nutr. Dev. 42: 317-26, 2002; Fukunaga et al., supra). The neural stem cell may be a cultured stem cell, a stem cell freshly isolated from its source tissue, or a stem cell within its source organism. Thus, contacting the neural stem cell with a compound according to the present invention may be carried out either in vitro (for a cultured or freshly isolated stem cell) or in vivo (for a stem cell within its source organism). The resulting differentiated neural cell, if generated in vitro, may be transplanted into a tissue in need thereof (Lacza et al., supra; Chu et al., supra; Fukunaga et al., supra). Such a tissue includes a brain tissue or other nervous tissue that suffers from a trauma or a neurodegenerative disease.

In an embodiment of the present invention, the compound(s) of the present invention or pharmaceutical formulations containing one or more compounds of the present invention are useful in the treatment and/or prevention of fibrosis in general. Below is a further description of examples of various types/forms of fibrosis that are treatable with the compounds of the present invention.

Transforming growth factor β (TGF-β), a key mediator in the development of fibrosis, is important in cell proliferation and differentiation, apoptosis, and deposition of extracellular matrix (ECM). TGF-β signaling activates both the Smad and AP-1 transcription pathways. TGF-β in the airways of patients with pulmonary fibrosis (PF) may function initially as a "healing molecule" involved in the diminution of initial airway inflammation and in tissue repair. However, with continued inflammatory response such as may occur in PF, the balance may be shifted, to excessive ECM deposition and development of airway fibrosis.

Fibroproliferative diseases are generally caused by the activation of resident stellate cells which are found in most organs. This activation of stellate cells leads to their conversion to myofibroblasts which display characteristics of muscle and non-muscle cells. Activated stellate cells initiate inflammatory signals, principally mediated through TGF-β. Inflammatory cytokines and mediators in addition to TGF-β, lead to proliferation of myofibroblasts. Stellate-derived myofibroblasts proliferate and replace healthy, functional organ cells with extra-cellular matrix that exhibit muscle and connective tissue traits. Ultimately, organ failure results when the nonfunctional fibrotic honeycomb matrix replaces a critical number of healthy cells.

The initial cause of fibrosis is believed to be the result of injury or insult to organ tissues. This cellular injury to organ tissues can often be traced to toxic or infectious agents. Pulmonary fibrosis, or interstitial lung disease, is often the result of smoking, chronic asthma, chronic obstructive pulmonary disease (COPD) or pneumonia. Fibrosis affects nearly all tissues and organ systems. Non-limiting examples of disorders in which fibrosis is a major cause of morbidity and mortality are listed below.

Major-Organ Fibrosis

Interstitial lung disease (ILD) includes a wide range of distinct disorders in which pulmonary inflammation and fibrosis are the final common pathway of pathology. There are more than 150 causes of ILD, including sarcoidosis, silicosis, adverse drug reactions, infections and collagen vascular diseases and systemic sclerosis (scleroderma).

Idiopathic pulmonary fibrosis (IPFi) is the most common type of ILD. Liver cirrhosis has similar causes to ILD, with viral hepatitis, schistosomiasis and chronic alcoholism being the major causes worldwide.

Kidney disease including diabetes can damage and scar the kidneys, which leads to progressive loss of function. Untreated hypertension can also contribute to the fibroproliferation of the kidneys.

Heart disease associated with scar tissue can impair the heart's pumping ability.

Eye disease includes macular degeneration and retinal and vitreal retinopathy can impair vision.

Chronic pancreatitis is an irreversible disease of the pancreas characterized by chronic inflammation and fibrosis which leads to the loss of endocrine and exocrine function.

Fibroproliferative disorders include systemic and local scleroderma. Scleroderma is a chronic connective tissue disease that may be localized or systemic, and may have an affect in many organs and tissues of the body.

Keloids and hypertrophic scars, which can occur after surgery, traumatic wounds, burns, or even scratches. They manifest as an overgrowth of scar tissue at the site of injury.

Atherosclerosis and restenosis. Restenosis refers to the re-narrowing of a coronary artery after angioplasty to treat atherosclerosis. Scarring associated with trauma can be associated with overgrowth of scar tissue at the site of the trauma-related injury. Surgical complications can lead to fibrosis in any organ in which scar tissue and fibroproliferation result from the surgical procedures.

Chemotherapy induced fibrosis can occur in, for example, the lungs following chemotherapy, manifests as pulmonary fibrosis, and can be severe enough to require lung transplant, even in cases where the underlying malignancy did not affect the lungs.

Radiation-induced fibrosis (RIF) is a serious and common complication of radiation therapy that may cause chronic pain, neuropathy, limited movement of joints, and swelling of the lymph nodes. It occurs most often in breast, head, neck, and connective tissues. RIF may develop from 4-6 months to 1-2 years following exposure to radiation therapy, and it becomes more severe over time. Risk factors for developing RIF include high radiation dose, large volumes of tissue exposed to radiation, and radiation combined with surgery, chemotherapy, or both.

Burns can lead to fibrosis when there is an overproduction of ECM proteins. Excessive ECM deposition causes the tissue to become fibrotic.

Pulmonary Fibrosis

Pulmonary fibrosis destroys the lung's ability to transport oxygen and other gases into or out of the blood. This disease modifies the delicate and elastic tissues of the lung, changing these tissues into thicker, stiff fibrous tissue. This change or replacement of the original tissue is similar to the permanent scarring that can occur to other damaged tissues. Scarring of the lung reduces the lung's ability to allow gases (i.e. oxygen, carbon dioxide) to pass into or out of the blood. Gradually, the air sacs of the lungs become replaced by fibrotic tissue. When the scar forms, the tissue becomes thicker causing an irreversible loss of the tissue's ability to transfer oxygen into the bloodstream. Symptoms include shortness of breath, particularly with exertion; chronic dry, hacking cough; fatigue and weakness; discomfort in the chest; loss of appetite; and rapid weight loss.

Several causes of pulmonary fibrosis are known and they include occupational and environmental exposures. Many jobs, particularly those that involve mining or that expose workers to asbestos or metal dusts, can cause pulmonary fibrosis. Workers doing these kinds of jobs may inhale small particles (like silica dusts or asbestos fibers) that can damage the lungs, especially the small airways and air sacs, and cause the scarring associated with fibrosis. Agricultural workers also can be affected. Some organic substances, such as moldy hay, cause an allergic reaction in the lung. This reaction is called Farmer's Lung and can cause pulmonary fibrosis. Other fumes found on farms are directly toxic to the lungs.

Another cause is Sarcoidosis, a disease characterized by the formation of granulomas (areas of inflammatory cells), which can attack any area of the body but most frequently affects the lungs.

Certain medicines may have the undesirable side effect of causing pulmonary fibrosis, as can radiation, such as treatment for breast cancer. Connective tissue or collagen diseases such as systemic sclerosis are also associated with pulmonary fibrosis. Although genetic and familial factors may be involved, this cause is not as common as the other causes listed above.

In Chronic Obstructive Pulmonary Disease (COPD), connective tissue proliferation and fibrosis can characterize severe COPD. COPD can develop as a result of smoking or chronic asthma.

Idiopathic Pulmonary, Fibrosis (IPF)

When all known causes of interstitial lung disease have been ruled out, the condition is called "idiopathic" (of unknown origin) pulmonary fibrosis (IPF). Over 83,000 Americans are living with IPF, and more than 31,000 new cases develop each year. This debilitating condition involves scarring of the lungs. The lungs' air sacs develop scar, or fibrotic tissue, which gradually. interferes with the body's ability to transfer the oxygen into the bloodstream, preventing vital organs and tissue from obtaining enough oxygen to function normally.

There are several theories as to what may cause IPF, including viral illness and allergic or environmental exposure (including tobacco smoke). These theories are still being researched. Bacteria and other microorganisms are not thought to be the cause of IPF. There is also a familial form of the disease, known as familial idiopathic pulmonary fibrosis. Additional research is being done to determine whether there is a genetic tendency to develop the disease, as well as to determine other causes of IPF.

Patients with IPF suffer similar symptoms to those with pulmonary fibrosis when their lungs lose the ability to transfer oxygen into the bloodstream. The symptoms include shortness of breath, particularly during or after physical activity; spasmodic, dry cough; gradual, unintended weight loss; fatigue and weakness; chest discomfort; clubbing, or enlargement of the ends of the fingers (or sometimes the toes) due to a buildup of tissue. These symptoms can greatly reduce IPF patients' quality of life. Pulmonary rehabilitation, and oxygen therapy can reduce the lifestyle-altering effects of IPF, but do not provide a cure.

In order to develop a treatment for fibrotic disease, it is important to focus on the common pathway to the ultimate pathology that is shared by the disease states, regardless of cause or of tissue in which it is manifested. Several components of the causative pathway are discussed below, particularly in relation to the role of β-catenin.

Other Pathological Conditions

Survivin, an inhibitor of apoptosis, is implicated in pulmonary hypertension. CK2 kinase activity has been shown to promote cell survival by increasing survivin expression via β-catenin Tef/Lef-mediated transcription. Tapia, J. C. et al., Proc. Nat. Acad. Sci. U.S.A. 103: 15079-84 (2006). This pathway therefore provides another opportunity to utilize the present compounds to alter the β-catenin-mediated gene transcription processes.

McMurtry, M.S. et al., J. Clin. Invest. 115:1461-1463 (2005) reported that survivin was expressed in the pulmonary arteries of patients with pulmonary arterial hypertension, but not in the pulmonary arteries of patients without pulmonary arterial hypertension. Comparable results were found in rats treated with monocrotaline to induce pulmonary arterial hypertension. In the rats, survival was prolonged and the pulmonary arterial hypertension was reversed by gene therapy with inhalation of an adenovirus carrying a survivin mutant with dominant-negative properties.

Survivin expression is upregulated in hyperproliferative neovasculature (Simosa, et al., J. Vase. Surg. 41:682-690, 2005). Survivin was specifically expressed in human atherosclerotic plaque and stenotic vein grafts. In a rabbit model of hyperplasia after balloon injury of iliofemoral arteries, treatment with a phosphorylation-defective survivin mutant vector reduced the neointimal area. The correlation between survinin expression and regulation of a smooth muscle cell phenotype after vascular injury points to survivin as a target for therapy in treating vascular disease.

Survivin is amenable to targeting by administration of a compound disclosed herein via one or more of the routes as described herein. Without being bound by a particular mode of action, the compounds disclosed herein can be administered in the form of coated stents, for example in connection with angioplasty. The methods for preparing coated stents are described in the art and would be modified as needed for use with the compounds of the invention. For example, U.S. Pat. No. 7,097,850 discloses and teaches methods of coating a stent with a variety of bioactive compounds. U.S. Pat. No. 7,087,078 discloses methods of preparing a stent with at least one active ingredient. Both coronary and peripheral stents are amenable to incorporating one or more compounds disclosed herein. Further teachings regarding drug-coated stents is available in Grube, E. et al., Herz 29:162-6 (2004) and W. L. Hunter, Adv. Drug Deliv. Rev. 58:347-9 (2006).

Bone marrow cells contribute to transplant-associated atherosclerosis (Sata, M., Trends Cardiovasc. Med. 13:249-253, 2003). Bone marrow cells also contribute to the pathogenesis of lesion formation after n'lechanical vascular injury (Sata, M. et al., Nat. Med. 8:403-409, 2002). Thus, by treating atherosclerosis and vascular damage with one of more compounds of the invention, reduction in vascular lesion formation can be accomplished.

Survivin also plays a role in vein graft hyperplasia (Wang, G.J. et al., Arterioscler. Thromb. Vasc. Biol. 25:2081-2087, 2005). Bypass grafts often develop intimal hyperplasia, a fibroproliferative lesion characterized by intimal thickening. Rabbit vein grafts were treated with adenoviral survivin constructs. Transgene expression was demonstrated in all the adenovirus-treated grafts. Treatment with a dominant negative mutant adenovirus decreased cellular proliferation in the early phase of graft remodeling. The data provide evidence for an important role of survivin in the regulation of vein graft remodeling in this system as well, and further support a role for the compounds of the invention in conjunction with bypass grafts.

Lymphangioleiomyomatosis (LAM) is a disease that occurs in some patients with tuberous sclerosis complex (Moss, J. et al., Am. J. Respir. Crit. Care Med. 163:669-671, 2001).

Cystic lung disease in LAM is characterized by abnormal smooth muscle cell proliferation. Compounds disclosed herein are expected to find use in regulating and alleviating the cell proliferation, thus moderating the clinical symptoms.

The Role of TGF-β

In pulmonary fibrosis, the normally thin lung tissue is replaced with thick, coarse scar tissue that impairs the flow of oxygen into the blood and leads to a loss of lung function.

A growing body of research suggests that excess TGF-β is the immediate cause of the fibrosis. This over-expression of TGF-β has been shown to cause pulmonary fibrosis in mice. An abnormally high TGF-β signal causes healthy epithelial cells in the lung to die via apoptosis. Cell death leads to the replacement of healthy lung tissue by thick, poor functioning scar tissue. Apoptosis of healthy epithelial cells is required prior to the development of pulmonary fibrosis (Elias et al). One form of treatment of fibrotic lung disorders involves administering drugs that specifically inhibit TGF-β, which in turn blocks apoptosis, preventing the formation of fibrotic tissue in the lung. However, for reasons discussed below, TGF-β itself may not be an ideal therapeutic target.

TGF-β is a member of the transforming growth factor-superfamily which consists of secreted polypeptide signaling molecules involved in cell proliferation and differentiation, apoptosis, deposition of extracellular matrix (ECM) and cell adhesion. TGF-β is a potent inhibitor of cell growth, and has immunosuppressive properties. However, TGF-β also causes the deposition of ECM components leading to fibrosis. A role for TGF-β as a key mediator in the development of fibrosis relates to its ability to act as a chemoattractant for fibroblasts, stimulate fibroblast procollagen gene expression/collagen protein synthesis, and inhibit collagen breakdown. TGF-β further stabilizes the ECM by inhibiting the expression of ECM proteases and stimulating the expression of ECM protease inhibitors. The fibrinolysis system is essential in ECM accumulation and fibrosis. Inhibition of fibrinolysis results in the accumulation of fibrin and ECM. Plasminogen activator inhibitor-1 (PAI-1) is the key inhibitor of fibrinolysis. The PAI-promoter contains several transcription factor binding sites including an AP-1 and Smad binding elements that promote PAI-1 induction by TGF-β. PAI-1 is the primary inhibitor of both tissue-type (TPA) and urokinase-type plasminogen (uPA) activator. Thus, TGF-β and PAI-1 work in tandem to produce the characteristic tissue of fibrosis.

In the bleomycin-induced model of pulmonary fibrosis (PF), mice in which the PAI-1 gene is deleted are protected from developing PF. Additionally, adenovirus-mediated transfer of the uPA gene to the lung significantly reduces the production of lung hydroxyproline and attenuated the bleomycin-induced increase in lung collagen, both hallmarks of fibrosis. The TGF-β signaling pathway is complex. TGF-β family members bind to specific pairs of receptor serine/threonine kinases. Upon binding, the ligand acts to assemble two type I and two type II receptors into a complex. The type II receptor phosphorylates the type I receptor that subsequently phosphorylates the intracellular substrates Smad 2 and Smad 3. This complex then binds Smad 4 and translocates to the nucleus for signal propagation. TGF-β can also activate AP-1 transcription via the MAPK pathway. TGF-β may originally act as a "healing molecule" in the lung or liver after initial inflammation and injury to the tissue. However, with continued inflammation/injury the balance may be shifted to excessive fibroproliferation and ECM deposition, leading to an "endless healing" process and development of fibrosis. Thus, complete inhibition of TGF-β could initially undermine the healing process.

TGF-β is highly expressed in airway epithelium and macrophages of small airways in patients with COPD. Using anti-inflammatory therapies, such as corticosteroids and interferon-γ, to treat PF has been disappointing due to variable efficacy and significant adverse effects. Therefore, an important goal is to identify small molecules that interact with previously identified molecular pathways (i.e. TGF-β signaling) involved in the development of fibrosis to prevent the progression or reverse the fibrosis seen in patients.

Wnt Signaling and Human Disease

Vertebrate Wnt proteins are homologues of the Drosophila wingless gene and have been shown to play important roles in regulating cell differentiation, proliferation, and polarity. Cadigan, K.M. et al., Genes Dev. 11:3286-3305 (1997); Parr, B.A. et al., Curr. Opin. Genet. Dev. 4:523-528 (1994); Smalley, M. J. et al., Cancer Met. Rev. 18:215-230 (1999); and Willert, K. et al., Curr. Opin. Genet. Dev. 8:95-102 (1998). Wnt proteins are cysteine-rich secreted glycoproteins that signal through at least three known pathways. The best understood of these, commonly called the canonical pathway, involves binding of Wnt proteins to frizzled cell surface receptors and low-density lipoprotein cell surface co-receptors, thereby inhibiting glycogensynthase kinase 313 (GSK-313) phosphorylation of the cytoskeletal protein β-catenin. This hypophosphorylated β-catenin is then translocated to the nucleus, where it binds to members of the LEFITCF family of transcription factors. Binding of β-catenin converts LEF/TCF factors from repressors to activators, thereby switching on cell-specific gene transcription. The other two pathways that Wnt proteins can signal through either activate calmodulin kinase 11 and protein kinase C (known as the Wnt/Ca++pathway) or jun N-terminal kinase (also known as the planar cell polarity pathway).

Several components of the Wnt pathway have been implicated in tumorigenesis in humans and mice, and studies of those have in turn identified a role for β-catenin. Wnt1 was first identified from a retroviral integration in mice that caused mammary tumors. Tsukamoto, A.S. et al., Cell 55:619-625 (1988); and Jue, S.F. et al., Mol. Cell. Biol. 12:321-328 (1992). Overexpression of protein kinase CK2 in the mammary gland, which potentiates β-catenin-dependent Wnt signaling, also increases the incidence of mammary tumors in transgenic mice. Landesman-Bollag, E. et al., Oncogene 20:3247-3257 (2001); and Song, D. H. et al., J. Biol. Chem. 275:23790-23797 (2000). Gut epithelia has revealed the most extensive correlation between Wnt signaling and tumorigenesis. Several reports have described mutations in β-catenin itself in some colon tumors and these mutations occur in or near the GSK-313 phosphorylation sites. Polakis, P. et al., Adv. Exp. Med. Biol. 470:23-32 (1999); and Morin, P.J. et al., Science 275:1787-1790 (1997). Chilosi and colleagues (Chilosi, M. et al., Am. J. Pathol. 162:1495-1502, 2003) investigated β-catenin mutations in IPF patients but did not identify any. This is consistent with a mechanism in which the aberrant activation of the Wnt pathway is a response and not a cause of IPF.

Lung Development and Wnt Signaling

In the mouse, the lung arises from the primitive foregut endoderm starting at approximately E9.5 during mouse development. (Warburton, D. et al., Mech. Dev. 92:55-81, 2000.) This primitive epithelium is surrounded by mesodermally derived multipotent mesenchymal cells, which in time will differentiate into several cell lineages including bronchial and vascular smooth muscle, pulmonary fibroblasts, and endothelial cells of the vasculature. During gestation, the airway epithelium evolves and grows through a process termed branching morphogenesis. This process results in the three-dimensional arborized network of airways required to generate to sufficient surface area for postnatal respiration. Mouse embryonic lung development can be divided into at least four stages: embryonic (E9.5 to E12.5), pseudoglandular (EI2.5 to E16.0), canalicular (EI6.0 to EI7.5), and saccular/alveolar (EI7.5 to postnatal).

During development, epithelial-mesenchymal signaling plays an important role in the regulation of both epithelial and mesenchymal cell differentiation and development. Several important signaling molecules are expressed in the airway epithelium and signal to the adjacent mesenchyme including members of the bone morphogenetic family (BMP-4), transforming growth factor family (TGF-β1, -2), and sonic hedgehog (SHH). In turn, the mesenchyme expresses several signaling molecules such as FGF-7, -9, and -10, important for lung epithelial development and proliferation. Gain of function and loss of function experiments in mice have demonstrated an important role for each of these factors in regulating lung epithelial and mesenchymal proliferation and differentiation. Bellusci, S., et al., Development 1997, 124:4867-

4878; Simonet, W.S., et al., Proc. Nat. Acad. Sci. USA 1995, 92:12461-12465; Clark, JC., et al., Am. J. Physiol. 2001, 280:L705-L715; Min, H., et al., Genes Dev. 1998, 12:3156-3161; Motoyama, 1., et al., Nat. Genet. 1998,20:54-57; Litingtung, Y, et al., Nat. Genet. 1998,20:58-61; Pepicelli, C.V., et al., Curr. Biol. 1998, 8:1083-1086; Weaver, M., et al., Development 1999, 126:4005-4015.

Wnt signaling also plays a role during lung development. Several Wnt genes are expressed in the developing and adult lung including Wnt2, Wnt2b/13, Wnt7b, Wnt5a, and Wntll. Kispert, A., et al., Development 1996, 122:3627-3637; Lin, Y., et al., Dev. Dyn. 2001, 222:26-39; Monkley, S. J, et al., Development 1996, 122:3343-3353; Yamaguchi, T.P., et al., Development 1999, 126:1211-1223; Weidenfeld, J., et al., J. Biol. Chem. 2002, 277:21061-21070. Of these, Wnt5a and Wnt7b are expressed at high levels exclusively in the developing airway epithelium during lung development. Wnt2, Wnt5a, and Wnt7b have been inactivated through homologous recombination in mice. Wnt2-null mice do not display an overt lung phenotype and Wnt5a null mice have late-stage lung maturation defects, corresponding to expression of Wnt5a later in lung development. (Monkley, (1996); Li, C. et al., Dev. Biol. 248:68-81 (2002). Inactivation of Wnt7b results in either early embryo demise because of defects in extra-embryonic tissues or perinatal demise because of defects in lung development. Parr, B.A., et al., Dev. Biol. 237:324-332 (2001); Shu, W. et al., Development 129:4831-4842 (2002)). These lung defects include decreased mesenchymal proliferation, lung hypoplasia caused by reduced branching, and pulmonary vascular smooth muscle defects leading to blood vessel hemorrhage in the lung (Shu, W. (2002)). Thus, Wnt signaling regulates important aspects of both epithelial and mesenchymal development during gestation, likely through both autocrine and paracrine signaling mechanisms.

Accumulation of nuclear β-catenin has been observed in both epithelial and mesenchymal (myofibroblasts) cell lineages in adult human lung. Other reports support these observations during mouse lung development. (Tebar, M., el al., Mech. Dev. 109:437-440 (2001)). Type 2 pneumocytes appear to express high levels of β-catenin both in the embryo and in the adult. (Tebar, 2001). Type 2 cells are precursors of type 1 cells, which form the thin diffusible stratum important for gas exchange in the lung. Type 2 cells have been shown to re-enter the cell cycle, grow, and differentiate into type 1 cells in some models of lung re-epithelialization. (Borok, Z. et al., Am. J. Respir. Cell Mol. Biol. 12:50-55 (1995); Danto, S.I. et al., Am. J. Respir. Cell Mol. Biol. 12:497-502 (1995)).

Importantly, type 2 cells proliferate excessively during-idiopathic fibrosis (IPF) and other proliferative lung diseases, and increased nuclear β-catenin in these cells suggests that Wnt signaling regulates this proliferation. (Kawanami, O., et al., Lab. Invest. 46:39-53 (1982); Kasper, M. et al., Histol. Histopathol. 11:463-483 (1996)). Increased proliferation of type 2 cells in IPF may also inhibit their differentiation into type 1 cells because excessive proliferation is often antagonistic to cellular differentiation. In this context, it is important to note that expression of certain important transcriptional and signaling regulators in the lung decreases with gestational age. Forced overexpression of some of these such as BMP-4, GATA6, and Foxa2 results in aberrant lung development that exhibits many aspects of arrested lung epithelial maturity. (Weaver, 1999; Koutsourakis, M. et al., Mech. Dev. 105: 105-114,2001; Zhou, L. et al., Dev. Dyn. 210:305-314, 1997). Thus, a careful balance of the correct spatial and temporal expression of certain regulatory genes is required for normal lung development, and improper activation of these pathways can result in severe defects in epithelial differentiation.

Nuclear β-catenin is found in the mesenchyme adjacent to the airway epithelium (Chilosi, 2003), and this is significant especially because these cells appear to be myofibroblastic in nature and may contribute to bronchial and vascular smooth muscle in the lung. Although Wnt signals in these mesenchymal cells could be autocrine in nature, it is just as likely that the mesenchymal cells are responding to a paracrine signal from the airway epithelium where Wnts such as Wnt5a and Wnt7b are expressed. In this way, the epithelium may be responsible for causing the aberrant activation of Wnt signaling in adjacent mesenchyme, leading to increased fibrosis and damage to the lung. This is particularly relevant because of the increase in the number of type 2 cells in the airways of IPF patients. This may also be reflective of a switch to an embryonic phenotype in the alveolus, where type 1 cells are rare. In turn, this would result in an increase in expression of several genes', including Wnts such as Wnt7b, whose expression is dramatically down-regulated in postntal development. (Weidenfeld, 2002; Shu, 2002.) The increased level of Wnts may inhibit the proper differentiation of more mature alveolar cells such as type 1 cells, impairing the repair process.

Because nuclear translocation of β-catenin is a result of Wnt signaling activity, its presence in cells such as distal airway epithelium and in mesenchyme adjacent to airway. Epithelium suggests that epithelial-mesenchymal Wnt signaling is active and likely plays an important role during both lung development and disease states such as IPF.

Regulation of Cell-Matrix Interactions by Wnt Signaling

A link has been shown between Wnt signaling and regulation of cell-matrix interactions including cell adhesion and migration. In particular, Wnt signaling has been shown to affect cell motility and invasiveness of melanoma cells. (Weeraratna, A.T. et al., Cancer Cell 1:279-288 (2002)). In this system, melanoma cells overexpressing Wnt5a displayed increased adhesiveness, which correlated to a reorganized actin cytoskeleton (Weer, 2002). These data suggest that Wnt5a expression correlates directly with the metastatic ability of melanoma tumors. In IPF lung tissue (Chilosi, 2003), the important extracellular matrix metalloproteinase matrilysin was overexpressed in some of the cells containing high levels of nuclear β-catenin. This is supported by previous studies showing that matrilysin is a molecular target of Wnt signaling. (Crawford, H.C., Oncogene 18:2883-2891, 1999.) Matrilysin has been linked to a role in carcinogenesis both in intestinal and endometrial tumors. Increased matrilysin expression strongly correlates with increased nuclear β-catenin expression and inhibition of this nuclear translocation results in decreased matrilysin expression. (Crawford, 1999.) Without being bound by a specific hypothesis, the mechanism may involve increased degradation of the extracellular matrix from increased matrilysin expression, leading to decreased cell adhesion and increased cell motility. In IPF, this might reduce the ability of both epithelial and mesenchymal cells to properly restructure the alveolar architecture after injury. In addition, extracellular matrix integrity may be required for type 1 cell differentiation, because of their flattened morphology and the very large surface area that they cover in the alveolus. This process may contribute to an increase in type 2 cell proliferation, which in turn could decrease type 1 cell differentiation.

Wnt Signaling and IPF

Without being bound by a specific hypothesis, several models could explain the finding that Wnt signaling is aberrantly activated in IPF. First, unregulated activation of the Wnt signaling pathway could be a physiological response to either lung injury or the repair process, possibly because of the requirement of the Wnt pathway for proliferation in cells such as type 2 alveolar epithelium and adjoining myofibroblasts. In this model, Wnt signaling should deactivate once the repair process is complete, leading to a return to normal proliferation. In the second model, aberrant Wnt signaling is the initiating event leading to increased cell proliferation in type 2 cells, which may inhibit their ability to differentiate into type 1 cells and restructure the alveolar architecture properly. Either injury-induced or spontaneous mutations in certain components of the canonical Wnt pathway or in regulatory molecules that regulate this pathway may result in this dysregulation of cell proliferation. The fact that nuclear β-catenin is up-regulated in other lung proliferative diseases suggests that the previous data (Chilosi, 2003) may be a response and not a primary causative event in IPF. Moreover, the unregulated proliferation in type 2 cells and mesenchymal fibroblasts along with the increased presence of nuclear β-catenin suggests that the Wnt pathway is continuously stimulated in lung diseases such as IPF and that inhibitors of Wnt signaling may provide a means to control this proliferation. Increased nuclear β-catenin was detected in the mesenchyme adjacent to the airway epithelium, described as myofibroblasts. (Chilosi, 2003.) These myofibroblastscan induce apoptosis in neighboring epithelial cells in vitro and in vivo, probably through degradation of the extracellular matrix. (Uhal, B.D. et al., Am. J. Physiol. 275:L1192-L1199, 1998; Uhal, B.D.et al., Am. J. Physiol. 269:L819-L828, 1995; Selman,. M. et al., Am. J. Physiol. 279:L562-L574, 2000.) In addition, in IPF there appears to be either a lack of re-epithelialization or an increase in type 2 cells with little if any maturation of type 1 cells, leading to injured areas with exposed mesodermal components or re-epithelialized with immature type 2 cells. Since it has been demonstrated that type 2 cells express high levels of TGF-β1, which is a profibrotic cytokine, in IPF either scenario would inhibit the proper re-epithelialization of these injured areas, causing more fibrosis. (Kapanci, Y., et al., Am. J. Respir. Crit. Care Med. 152:2163-2169, 1995; Khalil, N., et al., Am. J. Respir. Cell Mol. Biol. 5: 155-162, 1991.) This process could go unchecked and eventually lead to massive changes in tissue architecture, eventual tissue destruction, and loss of lung function.

Connective tissue growth factor (CTGF) is a 36 to 38 kD cysteine-rich peptide containing 349 amino acids. It belongs to the CCN (CTGF, cyr 61/cef 10, nov) family of growth factors. The gene for CTGF was originally cloned from a human umbilical endothelial cell cDNA library. CTGF has been detected in endothelial cells, fibroblasts, cartilaginous cells, smooth muscle cells, and some cancer cell lines. Earlier studies revealed that TGF-β1 increases CTGF mRNA markedly in human foreskin fibroblasts. PDGF, EGF, and FGF were also shown to induce CTGF expression, but their effects were only transient and weak.

Connective tissue growth factor has diverse bioactivities. Depending on cell types, CTGF was shown to trigger mitogenesis, chemotaxis, ECM production, apoptosis, and angiogenesis. In earlier studies, CTGF was noted to have mitogenic and chemotactic effects on fibroblasts. CTGF was also reported to enhance the mRNA expression of α1(I) collagen, fibronectin, and αs integrin in fibroblasts. The finding that TGF-β increases CTGF synthesis and that TGF-β and CTGF share many functions is consistent with the hypothesis that CTGF is a downstream mediator of TGF-β.

The mechanism by which CTGF exerts its effects on cells, especially its signal transduction, is still unclear. CTGF was reported to bind to the surface of fibroblasts with high affinity, and this binding was competed with recombinant PDGF BB. This suggests that CTGF binds to a certain class of PDGF receptors, or that there is some cross reactivity of PDGF BB with CTGF receptors.

Connective tissue growth factor mRNA has been detected in fibroblasts of sclerotic lesions of patients with systemic sclerosis. In patients with localized scleroderma, CTGF mRNA was detected in fibroblasts in tissues from sclerotic stage more than the inflammatory stage, which suggests a close correlation between CTGF and fibrosis. Similar results were also obtained in keloid and other fibrotic diseases. Subsequently, expression of CTGF has been reported in a variety of fibrosis, such as liver fibrosis, pulmonary fibrosis, and heart fibrosis.

CTGF is also implicated in dermal fibrosis of scleroderma. However, the detailed role of CTGF in fibrosis is still unclear. Further studies are needed to clarify this point.

The CCN family comprises cysteine-rich 61 (CYR61/CCN1), connective tissue growth factor (CTGF/CCN2), nephroblastoma overexpressed (NOV/CCN3), and Wnt-induced secreted proteins-1 (WISP-1/CCN4), -2 (WISP-2/CCN5) and -3 (WISP-3/CCN6). These proteins stimulate mitosis, adhesion, apoptosis, extracellular matrix production, growth arrest and migration of multiple cell types. Many of these activities probably occur through the ability of CCN proteins to bind and activate cell surface integrins.

Connective tissue growth factor (CTGF) has been identified as a potential target of Wnt and BMP signaling. It has been confirmed by microarray results, and demonstrated that CTGF was up-regulated at the early stage of B:MP~9 and Wnt3A stimulations and that Wnt3A-regulated CTGF expression was β-catenin-dependent.

Each of the above conditions can benefit from treatment with one or more compounds of the present invention. Each of the types of fibrosis described above can be treated with one or more compounds of the present invention.

The following non-limiting examples illustrate the compounds, compositions, and methods of use of this invention.

EXAMPLES

The present invention will be further specifically explained with reference to Examples. However, the scope of the present invention is not limited to the following Examples. In the Examples, for thin layer chromatography (TLC), Pre-coated Silica Gel 60 F254 (produced by Merck, product number: 5715-1M)) was used. After development with chloroform:methanol (1:0 to 1:1) or ethyl acetate:hexane (1:0 to 0:1), spots were observed by UV irradiation (254 nm) or color development with ninhydrine or phosphomoribdic acid solution in ethanol. For drying organic solvent, anhydrous magnesium sulfate or anhydrous sodium sulfate was used. As for column chromatography, the indication of "Büch" means use of Büch sepacore preparative chromatography system (produced by Büch), and one or several columns selected from cartridge columns Si6M-12×75 mm, 12×150 mm, 40×75 mm and 40×150 mm produced by the same manufacturer were used depending on the amount of sample. As for column chromatography, the indication of "Purif" means use of Moritex Purif preparative chromatography system (produced by Moritex), and one or several columns selected from cartridge columns 20, 35, 60, 200 and 400 produced by the same manufacturer were used depending on the amount of sample. For flash column chromatography, Silica gel 60N (spherical shape, neutral, 40 to 100 μm, produced by Kanto Chemicals) was used. Preparative thin layer chromatography (hereinafter abbreviated as "PTLC") was performed by using one or several plates of PLC Plate Silica Gel 60 F254 (20×20 cm, thickness: 2 mm, concentration zone: 4 cm, produced by Merck, product number: 13793-1M) depending on the amount of sample.

The indication of "LCMS" means that mass spectrum was measured by liquid chromatography-mass spectrometry (LC/MS). Platform-LC type mass spectrometry apparatus ZQ2000 (produced by Micromass) was used as the mass spectrometer, and the measurement was performed by the electrospray ionization (ESI) method. As a liquid chromatography apparatus, an apparatus produced by Waters was used. As a separation column, Develosil C30-UG-5 (50×4.6 mm, Nomura Kagaku Co., Ltd.) for method "A" or Agilent ZOBAX SB-C (2.1×50 mm, Agilent) for methods "B", "C", "D", "E", "F", "G" and "H" in the tables mentioned below was used. Elution was performed at a flow rate of 1 ml/minute, and Solution A=water [containing 0.1% (v/v) formic acid] and Solution B=acetonitrile [containing 0.1% (v/v) formic acid] for method "A" were used as solvents. Another method elution was perfomed as shown below.

For method "B"
Column: Agilent ZOBAX SB-C18 3.5 μm, 2.1×50 mm
Temperature: 40° C.
Mobile Phase: A=water containing 0.1% TFA, solution B=acetonitrile containing 0.05% TFA
Flow Rate: 0.6 mL/min
Gradient: 0-3.4 min linear 0~100% of B;
3.4 min-3.9 min, isocratic 100% of B;
3.91 min-4.5 min, isocratic 0% of B For method "C"
Column: Agilent ZOBAX SB-C18 3.5 μm, 2.1×50 mm
Temperature: 50° C.
Mobile Phase: A=water containing 0.1% TFA, solution B=acetonitrile containing 0.05% TFA
Flow Rate: 0.8 mL/min
Gradient: 0-3.4 min linear 1~100% of B;
3.4 min-3.9 min, isocratic 100% of B;
3.91 min-4.5 min, isocratic 1% of B For method "D"
Column: Agilent ZOBAX SB-C18 3.5 μm, 2.1×50 mm
Temperature: 50° C.
Mobile Phase: A=water containing 0.1% TFA, solution B=acetonitrile containing 0.05% TFA
Flow Rate: 0.8 mL/min
Gradient: 0-3.4 min linear 10~100% of B;
3.4 min-3.9 min, isocratic 100% of B;
3.91 min-4.5 min, isocratic 10% of B For method "E"
Column: Agilent ZOBAX SB-C18 3.5 μm, 2.1×50 mm
Temperature: 50° C.
Mobile Phase: A=water containing 0.1% TFA, solution B=acetonitrile containing 0.05% TFA
Flow Rate: 0.8 mL/min
Gradient: 0-3.4 min linear 25~100% of B;
3.4 min-3.9 min, isocratic 100% of B;
3.91 min-4.5 min, isocratic 25% of B For method "F"
Column: Agilent ZOBAX SB-C18 3.5 μm, 2.1×50 mm
Temperature: 50° C.
Mobile Phase: A=water containing 0.1% TFA, solution B=acetonitrile containing 0.05% TFA
Flow Rate: 0.8 mL/min
Gradient: 0-3.4 min linear 40~100% of B;
3.4 min-3.9 min, isocratic 100% of B;
3.91 min-4.5 min, isocratic 40% of B For method "G"
Column: Waters X Bridge Shield PR18 5 μm, 2.1×50 mm
Temperature: 40° C.
Mobile Phase: C=water containing 0.05% $NH_3H_2O$, solution D=acetonitrile
Flow Rate: 0.8 mL/min
Gradient: 0-3.4 min linear 5~100% of D;
3.4 min-3.9 min, isocratic 100% of D;
3.91 min-4.5 min, isocratic 5% of D For method "H"
Column: Waters X Bridge Shield PR18 5 μm, 2.1×50 mm
Temperature: 40° C.
Mobile Phase: C=water containing 0.05% $NH_3H_2O$, solution D=acetonitrile
Flow Rate: 0.8 mL/min
Gradient: 0-3.4 min linear 15~100% of D;
3.4 min-3.9 min, isocratic 100% of D;
3.91 min-4.5 min, isocratic 15% of D Example XXIII-1

Synthesis of tert-butyl 2-(1,3-dioxoisoindolin-2-yloxy)acetate (Compound XXIII-1)

To a solution of N-hydroxyphthalimide (16.31 g, 100 mmol) in dichloromethane (300 ml) was added triethylamine (20.91 ml, 150 mmol) and the mixture was stirred at 0° C. tert-Butyl bromoacetate (14.77 ml, 100 mmol) was added and the mixture was stirred at room temperature for 1 hr. The reaction mixture was diluted with chloroform (100 ml) and washed with water (300 ml). The organic layer was washed with brine (300 ml) and dried over magnesium sulfate and filtered. The filtrate was concentrated in vacuo. n-Hexane: ethyl acetate (80:20, 100 ml) was added to the residue and the obtained precipitate was collected by filtration to obtain the title compound (26.72 g, 96%).

Example XIV-1

Synthesis of ethyl 2-(1-allylhydrazinyl)-2-methylpropanoate (Compound XIV-1)

To a solution of 70%-allylhydrazine (7.73 ml, 75 mmol) and triethylamine (1048 ml, 75 mmol) in chloroform (25 ml) was added ethyl 2-bromo-2-methylpropanoate (9.75 g, 50 mmol) and the mixture was sittred for 1 hr and then refluxed overnight. The reaction mixture was diluted with ethylacetate (150 ml) and washed with water (100 ml) and brine (100 ml). Then the organic layer was dried over magnesium sulfate and filtered. The filtrate was concentrated in vacuo. The crude residue was subjected to silica gel column chromatography (eluent: chloroform:methanol=95:5) to obtain the title compound (5.0 g, 54%).

Example XIV-2

Synthesis of ethyl 2-methyl-2-(1-methylhydrazinyl)propanoate (Compound XIV-2)

According to the procedure described in the synthesis method of Compound XIV-1, methylhydrazine (7.12 g, 150 mmol) was reacted with ethyl 2-bromo-2-methylpropanoate (19.51 g, 100 mmol) to obtain the title compound (15.54 g, 96%).

Example XIV-3

Synthesis of ethyl 1-(aminomethyl)cyclopropanecarboxylate (Compound XIV-3)

To a solution of ethyl 1-cyanocyclopropanecarboxylate (1 g, 7.18 mmol) in ethanol-water-conc. ammonia solution (7 ml-350 µl-1 ml) was added raney nickel (ca. 350 µl) and the mixture was sittred for 24 hr at 50° C. The reaction mixture was filtered through Celite and the filtrate was concentrated in vacuo to obtain the title compound (690 mg, 67%).

Example XIV-4

Synthesis of ethyl 3-amino-2,2-dimethylpropanoate (Compound XIV-4)

According to the procedure described in the synthesis method of Compound XIV-3 with the modification that the reaction was carried out for 3 days, ethyl 2-cyano-2-methylpropanoate (2.91 ml, 20 mmol) was hydrogenated with raney nickel (600 mg) to obtain the title compound (2.90 g, 100%).

Example XIV-5

Synthesis of tert-butyl 2-(aminooxy)acetate (Compound XIV-5)

To a solution of tert-butyl 2-(1,3-dioxoisoindolin-2-yloxy)acetate (Compound XXIII-1) (13.86 g, 50 mmol) in methanol:tetrahydrofuran (2:3, 150 ml) was added hydrazine monohydrate (7.28 ml, 150 mmol) and the mixture was stirred at room temperature for 1 hr. The reaction mixture was concentrated in vacuo and the residue was diluted with ethyl acetate (300 ml) and the mixture was washed with sat. NaHCO$_3$ aq. (300 ml). The organic layer was washed with brine (300 ml), dried over magnesium sulfate and filtered. The filtrate was concentrated in vacuo to obtain the title compound (6.40 g, 87%).

Example V-1

Synthesis of ethyl 2-(1-allyl-2-(benzylcarbamoyl)hydrazinyl)-2-methylpropanoate (Compound V-1)

To a solution of ethyl 2-(1-allylhydrazinyl)-2-methylpropanoate (Compound XIV-1) (4.33 g, 23.25 mmol) in THF was added benzyl isocyanate (2.87 ml, 23.25 mmol) and the mixture was stirred at room temperature overnight. The reaction mixture was diluted with ethyl acetate (100 ml) and the mixture was washed with water (100 ml) and brine (100 ml). Then the organic layer was dried over magnesium sulfate and filtered. The filtrate was concentrated in vacuo. The crude residue was subjected to silica gel column chromatography (eluent: n-hexane:ethylacetate=1:1 to 1:2) to obtain the title compound (2.55 g, 35%).

Example V-2

Synthesis of ethyl 2-(2-(benzylcarbamoyl)-1-methylhydrazinyl)-2-methylpropanoate (Compound V-2)

According to the procedure described in the synthesis method of Compound V-1, ethyl 2-methyl-2-(1-methylhydrazinyl)propanoate (10.27 g, 77.8 mmol) was reacted with benzyl isocyanate (15.53 g, 116.7 mmol) to obtain the title compound (12.97 g, 57%).

Example V-3

Synthesis of ethyl 1-((3-benzylureido)methyl)cyclopropanecarboxylate (Compound V-3)

According to the procedure described in the synthesis method of Compound V-1 with the modification that the reaction solvent was changed to CH$_2$Cl$_2$ and DIPEA (1.6 ml, 9.3 mmol) was added, ethyl 1-(aminomethyl)cyclopropanecarboxylate (880 mg, 6.2 mmol) was reacted with benzyl isocyanate (1.15 ml, 8.0 mmol) to obtain the title compound (1.64 g, 106%).

Example V-4

Synthesis of ethyl 3-(3-benzylureido)-2,2-dimethylpropanoate (Compound V-4)

According to the procedure described in the synthesis method of Compound V-3, ethyl 3-amino-2,2-dimethylpropanoate (2.90 mg, 20 mmol) was reacted with benzyl isocyanate (1.24 ml, 10 mmol) to obtain the title compound (1.68 g, 30%).

Example V-5

Synthesis of tert-butyl 2-(3-(pyridin-4-ylmethyl)ureidooxy)acetate (Compound V-5)

A solution of 4-nitrophenyl chloroformate (12.09 g, 60 mmol) in dichloromethane (200 ml) was stirred at 0° C. for 10 min. A solution of tert-butyl 2-(aminooxy)acetate (Compound XIV-5) (7.36 g, 50 mmol) in dichloromethane (100 ml) and triethylamine (9.06 ml, 65 mmol) were added to the reaction mixture and the mixture was stirred at room temperature for 0.5 hr. The reaction mixture was washed with water (300 ml) and brine (300 ml). The organic layer was dried over magnesium sulfate and filtered. The filtrate was concentrated in vacuo to give the desired product (15.14 g, 97%).

A solution of the above product (4.68 g, 15 mmol) in dichloromethane (75 ml) was stirred at 0° C. for 10 min. 4-Picolylamine (2.73 ml, 27 mmol) was added to the reaction mixture and the mixture was stirred at room temperature for 2 hr. The reaction mixture was washed with sat. NaHCO$_3$ aq. (75 ml), water (75 ml) and brine (75 ml), dried over magnesium sulfate and filtered. The filtrate was concentrated in vacuo. The residue was purified by Büch silica gel column chromatography (eluent: ethyl acetate only) to obtain the title compound (0.94 g, 22%).

Example V-6

Synthesis of tert-butyl 2-(3-(4-chlorobenzyl)ureidooxy)acetate (Compound V-6)

A solution of 4-nitrophenyl chloroformate (12.09 g, 60 mmol) in dichloromethane (200 ml) was stirred at 0° C. for 10 min. A solution of tert-butyl 2-(aminooxy)acetate (Compound XIV-5) (7.36 g, 50 mmol) in dichloromethane (100 ml) and triethylamine (9.06 ml, 65 mmol) were added to the reaction mixture and the mixture was stirred at room temperature for 0.5 hr. The reaction mixture was washed with water (300 ml) and brine (300 ml). The organic layer was dried with magnesium sulfate and filtered. The filtrate was concentrated in vacuo to give the desired product (15.14 g, 97%).

A solution of the above product (4.68 g, 15 mmol) in dichloromethane (75 ml) was stirred at 0° C. for 10 min. 4-Chlorobenzylamine (3.28 ml, 27 mmol) was added to the solution and the mixture was stirred at room temperature for 1.5 hr. The reaction mixture was washed with sat. NaHCO$_3$ aq. (75 ml), water (75 ml), 10% citric acid aq. (75 ml) and brine (75 ml), dried over magnesium sulfate and filtered. The filtrate was concentrated in vacuo. The residue was purified by Büch silica gel column chromatography (eluent: n-hexane:ethyl acetate=100:0 to 60:40) to obtain the title compound (1.66 g, 35%).

Example V-7

Synthesis of tert-butyl 2-(3-(naphthalen-1-ylmethyl)ureidooxy)acetate (Compound V-7)

A solution of 4-nitrophenyl chloroformate (12.09 g, 60 mmol) in dichloromethane (200 ml) was stirred at 0° C. for 10 min. A solution of tert-butyl 2-(aminooxy)acetate (Compound XIV-5) (7.36 g, 50 mmol) in dichloromethane (100 ml) and triethylamine (9.06 ml, 65 mmol) were added and the mixture was stirred at room temperature for 0.5 hr. The reaction mixture was washed with water (300 ml) and brine (300 ml). The organic layer was dried over magnesium sulfate and filtered. The layer was concentrated in vacuo to give the desired product (15.14 g, 97%).

A solution of the above product (4.68 g, 15 mmol) in dichloromethane (75 ml) was stirred at 0° C. for 10 min. 1-Naphthylmethylamine (3.89 ml, 27 mmol) was added to the reaction mixture and the mixture was stirred at room temperature for 1 hr. The reaction mixture was washed with sat. NaHCO$_3$ aq. (75 ml), water (75 ml), 10% citric acid aq. (75 ml) and brine (75 ml), dried over magnesium sulfate and filtered. The filtrate was concentrated in vacuo. The residue was purified by Büch silica gel column chromatography (eluent: n-hexane:ethyl acetate=100:0 to 60:40) to obtain the title compound (1.10 g, 22%).

Example V-8

Synthesis of tert-butyl 2-(3-ethylureidooxy)acetate (Compound V-8)

A solution of 4-nitrophenyl chloroformate (12.09 g, 60 mmol) in dichloromethane (200 ml) was stirred at 0° C. for 10 min. A solution of tert-butyl 2-(aminooxy)acetate (Compound XIV-5) (7.36 g, 50 mmol) in dichloromethane (100 ml) and triethylamine (9.06 ml, 65 mmol) were added and the mixture was stirred at room temperature for 0.5 hr. The reaction mixture was washed with water (300 ml) and brine (300 ml). The organic layer was dried over magnesium sulfate and filtered and the filtrate was concentrated in vacuo to give the desired product (15.14 g, 97%).

The solution of the above product (4.68 g, 15 mmol) in dichloromethane (75 ml) was stirred at 0° C. for 10 min. Ethylamine (70% aq. solution) (2.17 ml, 27 mmol) was added to the reaction mixture and the mixture was stirred at room temperature for 1 hr. The reaction mixture was washed with sat. NaHCO$_3$ aq. (75 ml), water (75 ml), 10% citric acid aq. (75 ml) and brine (75 ml), dried over magnesium sulfate and filtered. The filtrate was concentrated in vacuo. The residue was purified by Büch silica gel column chromatography (eluent: n-hexane:ethyl acetate=100:0 to 60:40) to obtain the title compound (0.74 g, 23%).

Example VI-1

Synthesis of 1-((3-benzylureido)methyl)cyclopropanecarboxylic acid (Compound VI-1)

To the solution of ethyl 1-((3-benzylureido)methyl)cyclopropanecarboxylate (Compound V-3) (1.6 g, 5.8 mmol) in tetrahydrofuran/methanol/water (2:3:1, 20 ml), lithium hydroxide monohydrate (487 mg, 11.6 mmol) was added and the mixture was stirred at room temperature for 3 hr. The reaction mixture was diluted with water (25 ml) and washed with ether (25 ml). The aqueous layer was acidified with 10%-citric acid (15 ml) and extracted with chloroform (30 ml). The organic layer was washed with brine (25 ml) and dried over magnesium sulfate and then filtered. The filtrate was concentrated in vacuo to obtain the title compound (1.08 g, 77%).

Example VI-2

Synthesis of 3-(3-benzylureido)-3-methylbutanoic acid (Compound VI-2)

To a solution of 3-amino-3-methylbutanoic acid (5.86 g, 34.2 mmol) in THF was added benzyl isocyanate (5.87 ml, 47.5 mmol) and the mixture was stirred at room temperature overnight. The reaction mixture was diluted with ethyl acetate (100 ml) and washed with water (100 ml) and brine (100 ml). Then the organic layer was dried over magnesium sulfate and filtered. The filtrate was concentrated in vacuo. The crude residue was subjected to silica gel column chromatography (eluent: chloroform:methanol=95:5) to obtain the title compound (5.73 g, 67%).

Example VI-3

Synthesis of 3-(3-benzylureido)-2,2-dimethylpropanoic acid (Compound VI-3)

According to the procedure described in the synthesis method of Compound VI-1, ethyl 3-(3-benzylureido)-2,2-dimethylpropanoate (Compound V-4) (840 mg, 3.0 mmol) was reacted with lithium hydroxide monohydrate (151 mg, 3.6 mmol) to obtain the title compound (381 mg, 50.7%).

Example VI-4

Synthesis of 2-(1-allyl-2-(benzylcarbamoyl)hydrazinyl)-2-methylpropanoic acid (Compound VI-4)

To a solution of ethyl 2-(1-allyl-2-(benzylcarbamoyl)hydrazinyl)-2-methylpropanoate (Compound V-1) (958.2 mg, 3.0 mmol) in tetrahydrofuran/methanol/water (2:3:1, 15 ml), lithium hydroxide monohydrate (251.8 mg, 6.0 mmol) was added and the mixture was stirred at room temperature for 3 hr. The reaction mixture was diluted with water (25 ml) and washed with ether (25 ml). The aqueous layer was acidified with 10%-citric acid (15 ml) and extracted with chloroform (30 ml). The organic layer was washed with brine (25 ml) and dried over magnesium sulfate and then filtered. The filtrate was concentrated in vacuo to obtain the title compound (724 mg, 83%).

Example VI-5

Synthesis of 2-(2-(benzylcarbamoyl)-1-methylhydrazinyl)-2-methylpropanoic acid (Compound VI-5)

According to the procedure described in the synthesis method of Compound VI-4, ethyl 2-(2-(benzylcarbamoyl)-1-methylhydrazinyl)-2-methylpropanoate (Compound V-2) (2.932 g, 10 mmol) was reacted with lithium hydroxide monohydrate (839.2 mg, 20 mmol) to obtain the title compound (975.1 mg, 37%).

Example VI-6

Synthesis of 2-(3-benzylureidooxy)acetic acid (Compound VI-6)

To a solution of 2-(aminooxy)acetic acid (5 g, 46 mmol) and triethylamine (3.17 ml, 23 mmol) in dichloromethane (60 ml) and tetrahydrofuran (60 ml) was added benzyl isocyanate (5.43 ml, 44 mmol) and the mixture was stirred at room temperature overnight. The reaction mixture was diluted with ethyl acetate (400 ml) and washed with water (300 ml) and brine (200 ml). The organic layer was washed with 1N-sodium hydroxide aq. (60 ml). The aqueous layer was acidified with 1N-HCl aq. (70 ml) and extracted with ethyl acetate (300 ml). The organic layer was washed with brine (200 ml), dried over magnesium sulfate and filtered. The filtrate was concentrated in vacuo and ether (50 ml) and n-hexane (150 ml) were added for precipitation to obtain the title compound (3.2 g, 33%).

Example VI-7

Synthesis of 2-(benzyloxycarbonylaminooxy)acetic acid (Compound VI-7)

A solution of carboxymethoxyl amine hemihydrochloride (5.47 g, 50 mmol) in water (100 ml) was stirred at room temperature for 0.5 hr. Sodium bicarbonate (12.6 g, 150 mmol) and a solution of benzyl chloroformate (8.57 ml, 60 mmol) in tetrahydrofuran (25 ml) were added and the mixture was stirred at room temperature for 21 hr. The reaction mixture was diluted with diethyl ether (250 ml) and washed with 1N-NaOH aq. (50 ml). The aqueous layer was acidified with 5N-HCl aq. (25 ml) and extracted with ethyl acetate (250 ml). The organic layer was washed with water (250 ml) and brine (250 ml), dried over magnesium sulfate and filtered. The filtrate was concentrated in vacuo to obtain the title compound (8.35 g, 74%).

Example VI-8

Synthesis of 2-(phenylmethylsulfonamidooxy)acetic acid (Compound VI-8)

A solution of carboxymethoxyl amine hemihydrochloride (4.37 g, 40 mmol) in water (100 ml) was stirred at room temperature for 0.5 hr. Sodium bicarbonate (16.8 g, 200 mmol) and a solution of benzylsulfonyl chloride (8.01 g, 42 mmol) in tetrahydrofuran (50 ml) were added and the mixture was stirred at room temperature for 23 hr. The reaction mixture was diluted with diethyl ether (100 ml) and washed with 2N-NaOH aq. (25 ml). The aqueous layer was acidified with 5N-HCl aq. (12 ml) and extracted with ethyl acetate (100 ml). The organic layer was washed with water (100 ml) and brine (100 ml), dried over magnesium sulfate and filtered. The filtrate was concentrated in vacuo to obtain the title compound (4.01 g, 41%).

Example VI-9

Synthesis of 2-(3-(pyridin-4-ylmethyl)ureidooxy) acetic acid (Compound VI-9)

To a solution of tert-butyl 2-(3-(pyridin-4-ylmethyl)ureidooxy)acetate (Compound V-5) (42.2 mg, 0.15 mmol) in tetrahydrofuran (1 ml) was added 4N HCl/dioxane (2 ml) and the mixture was stirred at room temperature for 3 days. The reaction mixture was concentrated in vacuo to obtain the title compound (34 mg, 100%).

Example VI-10

Synthesis of 2-(3-(4-chlorobenzyl)ureidooxy)acetic acid (Compound VI-10)

According to the procedure described in the synthesis method of Compound VI-9, tert-butyl 2-(3-(4-chlorobenzyl) ureidooxy)acetate (Compound V-6) (47.2 mg, 0.15 mmol) was reacted with 4N HCl/dioxane (2 ml) to obtain the title compound (39 mg, 100%).

Example VI-11

Synthesis of 2-(3-(naphthalen-1-ylmethyl)ureidooxy) acetic acid (Compound VI-11)

According to the procedure described in the synthesis method of Compound VI-9, tert-butyl 2-(3-(naphthalen-1-ylmethyl)ureidooxy)acetate (Compound V-7) (50 mg, 0.15 mmol) was reacted with 4N HCl/dioxane (2 ml) to obtain the title compound (41 mg, 100%).

Example VI-12

Synthesis of 2-(3-ethylureidooxy)acetic acid (Compound VI-12)

According to the procedure described in the synthesis method of Compound VI-9, tert-butyl 2-(3-ethylureidooxy) acetate (Compound V-8) (33 mg, 0.15 mmol) was reacted with 4N HCl/dioxane (2 ml) to obtain the title compound (24 mg, 100%).

Example XVIII-1

Synthesis of (S)-1,1-diethoxypropan-2-amine (Compound XVIII-1)

To a solution of N-methoxy-N-methylamine hydrochloride (21.95 g, 225 mmol) in 1N sodium hydroxide (225 ml) were added (S)-2-(benzyloxycarbonylamino)propanoic acid (33.48 g, 150 mmol) and a solution of 4-(4,6-dimethoxy-1,3,5-triazin-2-yl)-4-methylmorpholinium chloride (62.26 g, 225 mmol) in acetonitrile (225 ml) and the mixture was stirred at room temperature for 2 hr. The reaction mixture was concentrated in vacuo and the residue was diluted with ethyl acetate (600 ml) and the mixture was washed with water (300 ml) and brine (300 ml). The organic layer was dried over magnesium sulfate and filtered and the filtrate was concentrated in vacuo to obtain (S)-benzyl 1-(methoxy(methyl)amino)-1-oxopropan-2-ylcarbamate (42.33 g, 93%).

To a solution of (S)-benzyl 1-(methoxy(methyl)amino)-1-oxopropan-2-ylcarbamate (5.33 g, 20.0 mmol) in tetrahydrofuran (40 ml) was added a 2M solution of lithium alminium hydride in tetrahydrofuran (10 ml) at 0° C. for 0.5 hr. The resulting solution was stirred at room temperature for 2 hr. The reaction mixture was cooled to 0° C. and saturated ammonium chloride aq. (10 ml) was added dropwise. The precipitate was filtered on Celite and washed with methanol (50 ml). The filtrate was concentrated in vacuo and the residue was diluted with ethyl acetate (200 ml) and the mixture was washed with water (100 ml) and brine (100 ml). The organic layer was dried over magnesium sulfate and filtered and the filtrate was concentrated in vacuo. The residue was diluted with ethanol (50 ml) and 4N hydrochloric acid in dioxane (0.25 ml) was added. The reaction mixture was refluxed for 18 hr and concentrated in vacuo. The residue was diluted with ethyl acetate (200 ml) and the mixture was washed with saturated sodium bicarbonate (200 ml) and brine (200 ml). The organic layer was dried with magnesium sulfate and filtered and the filtrate was concentrated in vacuo. The residue was purified by silica gel column chromatography (eluent: n-hexane:ethyl acetate=100:0 to 80:20) to obtain (S)-benzyl 1,1-diethoxypropan-2-ylcarbamate (3.55 g, 63%, 2 steps).

To a solution of (S)-benzyl 1,1-diethoxypropan-2-ylcarbamate (844 mg, 3.00 mmol) in methanol (50 ml) was added 5% palladium on carbon (30 mg) and the mixture was stirred at room temperature for 2 hr under hydrogen atmosphere. The reaction mixture was filtered on Celite and washed with methanol (200 ml) and the filtrate was concentrated in vacuo to obtain the title compound (442 mg, 100%).

Example XIX-1

Synthesis of 5-chlorothieno[3,2-b]pyridine-3-carbaldehyde (Compound XIX-1)

To a solution of phosphoryl chrolide (14.9 ml, 160 mmol) in dimethylformamide (45 ml) was added portionwise N-(2-oxotetrahydrothiophen-3-yl)acetamide (12.74 g, 80 mmol) and the mixture was stirred at 90° C. for 2 hr. The reaction mixture was poured into ice water (400 ml) and followed by, addition of saturated sodium acetate (500 ml). The solution was extracted by ethyl acetate (1000 ml). The organic layer was washed with water (300 ml), water (400 ml) and brine (200 ml). Then the organic layer was dried over magnesium sulfate, filtered and the filtrate was concentrated in vacuo. The residue was crystallized by addition of ethyl acetate/ether (1:1, 200 ml) and the crystals were collected by filtration to obtain the title compound (3.55 g, 18%).

Example XX-1

Synthesis of 4-Bromomethyl-2-bis(tert-butoxycarbonyl)aminobenzothiazole (Compound XX-1)

To a solution of 2-amino-4-methylbenzothiazole (5.01 g, 30.5 mmol) in tetrahydrofuran (100 ml) were added triethylamine (8.50 ml, 61 mmol), di-tert-butyl dicarbonate (9.11 ml, 39.7 mmol) and 4-dimethylaminopyridine (745 mg, 6.1 mmol) and the mixture was stirred at room temperature overnight. The reaction mixture was concentrated in vacuo and the residue was diluted with ethyl acetate (300 ml). The organic layer was washed with 10% citric acid (300 ml), water (300 ml), saturated aqueous sodium bicarbonate (300 ml) and brine (100 ml). Then the organic layer was dried over magnesium sulfate, filtered and the filtrate was concentrated in vacuo. The crude residue was subjected to silica gel column chromatography (eluent: n-hexane:ethyl acetate=95:5 to 90:10 each) to obtain 2-(bis(tert-butoxycarbonyl)amino)-4-methylbenzothiazole (3.74 g, 34%).

To a solution of 2-(bis(tert-butoxycarbonyl)amino)-4-methylbenzothiazole (1.09 g, 3.00 mmol) in carbon tetrachloride (15 ml) were added N-bromosuccinimide (694 mg, 3.90 mmol) and 2,2'-azobis(isobutyronitrile) (99 mg, 0.20 mmol) and the mixture was stirred under nitrogen atomsphere at 80° C. for 2 hr. The reaction mixture was allowed to cool to room temperature and concentrated in vacuo. The crude residue was subjected to column chromatography (eluent: n-hexane:chloroform=60:40 to 50:50) to obtain the title compound (1.26 g, 95%).

Example IX-1

Synthesis of tert-butyl 4-((2,2-diethoxyethylamino)methyl)benzo[d]thiazol-2-ylcarbamate (Compound IX-1)

To a solution of 2,2-diethoxyethanamine (8.72 ml, 60.0 mmol) in acetonitrile (300 ml) were added 4-bromomethyl-2-bis(tert-butoxycarbonyl)aminobenzothiazole (Compound XIX-1) (1.33 g, 3.00 mmol) and potassium carbonate (3.14 g, 18.0 mmol) and the mixture was stirred at room temperature overnight. The reaction mixture was concentrated in vacuo and the residue was diluted with ethyl acetate (300 ml) and the mixture was washed with water (300 ml) and brine (200 ml). The organic layer was dried over magnesium sulfate (5 g) and filtered. The filtrate was concentrated in vacuo and the residue was purified by silica gel column chromatography (eluent: chloroform:methanol=100:0 to 80:20) to obtain the title compound (1.01 g, yield: 85%).

Example IX-2

Synthesis of 2,2-diethoxy-N-(naphthalen-1-ylmethyl)ethanamine (Compound IX-2)

To a solution of 1-naphthaldehyde (2.2 ml, 16.0 mmol) in tetrahydrofuran (6 ml) was added 2,2-diethoxyethanamine (2.9 ml, 20.0 mmol) and the mixture was stirred at room temperature 0.5 hr. And then sodium triacetoxyborohydride (10.6 g, 50 mmol) was added and the mixture was stirred for additional 4 hr. The reaction mixture was diluted with ethyl acetate (200 ml) and washed with saturated aqueous sodium bicarbonate (200 ml), water (200 ml) and brine (200 ml). The organic layer was dried over magnesium sulfate (5 g) and filtered. The filtrate was concentrated in vacuo and the residue was purified by silica gel column chromatography (eluent: n-hexane:ethyl acetate=100:0 to 70:30) to obtain the title compound (3.0 g, 46%).

Example IX-3

Synthesis of 2,2-diethoxy-N-(quinolin-8-ylmethyl)ethanamine (Compound IX-3)

According to the procedure described in the synthesis method of Compound IX-2 with the modification that the reaction was carried out overnight, 2,2-diethoxyethanamine (2.18 ml, 15 mmol) was reacted with 8-quinolinecarboxaldehyde (1.89 g, 12 mmol) to obtain the title compound (3.0 g, 73%).

Example IX-4

Synthesis of 2,2-diethoxy-N-(quinolin-4-ylmethyl)ethanamine (Compound IX-4)

According to the procedure described in the synthesis method of Compound IX-2 with the modification that the reaction was carried out overnight, 2,2-diethoxyethanamine (3.64 ml, 25 mmol) was reacted with 4-quinolinecarboxaldehyde (3.14 g, 20 mmol) to obtain the title compound (6.0 g, 88%).

Example IX-5

Synthesis of (S)-tert-butyl 4-((1,1-diethoxypropan-2-ylamino)methyl)benzo[d]thiazol-2-ylcarbamate (Compound IX-5)

To a solution of (S)-1,1-diethoxypropan-2-amine (Compound XVIII-1) (442 mg, 3.00 mmol) in acetonitrile (5 ml) were added 4-bromomethyl-2-bis(tert-butoxycarbonyl)aminobenzothiazole (Compound XX-1) (133 mg, 0.30 mmol) and potassium carbonate (62 mg, 0.45 mmol) and the mixture was stirred at 65° C. for 2 hr. The reaction mixture was concentrated in vacuo and the residue was diluted with ethyl acetate (100 ml) and the mixture was washed with water (100 ml) and brine (100 ml). The organic layer was dried over magnesium sulfate and filtered. The filtrate was concentrated in vacuo and the residue was purified by silica gel column chromatography (eluent: chloroform:methanol=100:0 to 95:5) to obtain the title compound (173 mg, yield: 71%).

Example IX-6

Synthesis of (S)-1,1-diethoxy-N-(naphthalen-1-ylmethyl)propan-2-amine (Compound IX-6)

To a solution of (S)-1,1-diethoxypropan-2-amine (Compound XVIII-1) (682 mg, 3.55 mmol) in tetrahydrofuran (2 ml) was added 1-naphthaldehyde (554 mg, 3.55 mmol) and the mixture was stirred at room temperature for 0.5 hr. The reaction mixture was diluted with tetrahydrofuran (3 ml) and sodium triacetoxyborohydride (829 mg, 3.91 mmol) was added and the mixture was stirred at room temperature for 18 hr. The reaction mixture was diluted with ethyl acetate (50 ml) and washed with saturated aqueous sodium bicarbonate (50 ml) twice, water (50 ml) twice and brine (50 ml) twice. The organic layer was dried over magnesium sulfate and filtered and the filtrate was concentrated in vacuo to obtain the title compound (685 mg, 67.1%).

Example IX-7

Synthesis of (S)-1,1-diethoxy-N-(quinolin-8-ylmethyl)propan-2-amine (Compound IX-7)

According to the procedure described in the synthesis is method of Compound IX-6, (S)-1,1-diethoxypropan-2-amine (Compound XVIII-1) (442 mg, 3.00 mmol) was reacted with 8-quinolinecarboaldehyde (393 mg, 2.50 mmol) to obtain the title compound (649 mg, 90.7%).

Example IX-8

Synthesis of (S)—N-(benzo[c][1,2,5]thiadiazol-4-ylmethyl)-1,1-diethoxypropan-2-amine (Compound IX-8)

According to the procedure described in the synthesis method of Compound IX-5, (S)-1,1-diethoxypropan-2-amine (Compound XVIII-1) (883 mg, 6.0 mmol) was reacted with benzo[c][1,2,5]thiadiazole-4-carbaldehyde (837 mg, 5.1 mmol) to obtain the title compound (1.41 g, 95%).

Example IX-9

Synthesis of (S)-1,1-diethoxy-N-(isoquinolin-5-ylmethyl)propan-2-amine (Compound IX-9)

According to the procedure described in the synthesis method of Compound IX-6, (S)-1,1-diethoxypropan-2-amine (Compound XVIII-1) (883 mg, 6.0 mmol) was reacted with isoquinoline-5-carbaldehyde (802 mg, 5.1 mmol) to obtain the title compound (1.37 g, 95%).

Example IX-10

Synthesis of (S)—N-(benzo[b]thiophen-3-ylmethyl)-1,1-diethoxypropan-2-amine (Compound IX-10)

According to the procedure described in the synthesis method of Compound IX-6, (S)-1,1-diethoxypropan-2-amine (Compound XVIII-1) (883 mg, 6.0 mmol) was reacted with benzo[b]thiophene-3-carbaldehyde (827 mg, 5.1 mmol) to obtain the title compound (1.45 g, 97%).

Example IX-11

Synthesis of (S)—N-((5-chlorothieno[3,2-b]pyridin-3-yl)methyl)-1,1-diethoxypropan-2-amine (Compound IX-11)

According to the procedure described in the synthesis method of Compound IX-6, (S)-1,1-diethoxypropan-2-amine (Compound XVIII-1) (1.98 g, 13.4 mmol) was reacted with 5-chlorothieno[3,2-b]pyridine-3-carbaldehyde (Compound XIX-1) (1.98 g, 10 mmol) and the obtained residue was purified by Büch silica gel column chromatography (eluent: chloroform:methanol=98:2 to 95:5) to obtain the title compound (996 mg, 30%).

Example IX-12

Synthesis of (S)-1,1-diethoxy-N-(quinoxalin-5-ylmethyl)propan-2-amine (Compound IX-12)

According to the procedure described in the synthesis method of Compound IX-6, (S)-1,1-diethoxypropan-2-amine (Compound XVIII-1) (1.57 g, 10.0 mmol) was reacted with quinoxaline-5-carbaldehyde (1.34 g, 8.5 mmol) to obtain the title compound (1.93 g, 78%).

Example IX-13

Synthesis of N-benzyl-2,2-diethoxyethanamine (Compound IX-13)

According to the procedure described in the synthesis method of Compound IX-2, 2,2-diethoxyethanamine (72.7 ml, 500 mmol) was reacted with benzaldehyde (50.7 ml, 500 mmol) and the obtained residue was purified by silica gel column chromatography (eluent: n-hexane:ethyl acetate=50:50 and 0:100) to obtain the title compound (47.5 g, 42%).

Example IX-14

Synthesis of (R)-2,2-diethoxy-N-(1-phenylethyl)ethanamine (Compound IX-14)

According to the procedure described in the synthesis method of Compound IX-1, 2-bromo-1,1-diethoxyethane (41.3 ml, 270 mmol) was reacted with (R)-(+)-1-phenylethylamine (66.6 g, 550 mmol) and the obtained residue was purified by silica gel column chromatography (eluent: n-hexane:ethyl acetate=5:1 and 1:1) to obtain the title compound (46.0 g, 70%).

Example IX-15

Synthesis of 2,2-diethoxy-N-(pyridin-4-ylmethyl)ethanamine (Compound IX-15)

According to the procedure described in the synthesis method of Compound IX-2, 2,2-diethoxyethanamine (162.8 ml, 1120 mmol) was reacted with 4-pyridinecarboxaldehyde (120 g, 1120 mmol) and the obtained residue was purified by silica gel column chromatography (eluent: ethyl acetate and ethyl acetate:ethanol=15:1) to obtain the title compound (110 g, 44%).

Example IX-16

Synthesis of 2,2-diethoxy-N-(pyridin-2-ylmethyl)ethanamine (Compound IX-16)

According to the procedure described in the synthesis method of Compound IX-1, 2-bromo-1,1-diethoxyethane (34.6 ml, 230 mmol) was reacted with 2-picolylamine (50 g, 460 mmol) and the obtained residue was purified by silica gel column chromatography (eluent: ethyl acetate:ethanol=10:1) to obtain the title compound (34.0 g, 65%)

Example IX-17

Synthesis of N-(2,4-difluorobenzyl)-2,2-diethoxyethanamine (Compound IX-17)

According to the procedure described in the synthesis method of Compound IX-2, 2,2-diethoxyethanamine (75.6 ml, 520 mmol) was reacted with 2,4-difluorobenzaldehyde (75 g, 520 mmol) and the obtained residue was purified by silica gel column chromatography (eluent: n-hexane:ethyl acetate=5:1 and 3:1) to obtain the title compound (50.0 g, 36%).

Example IX-18

Synthesis of N-(benzo[b]thiophen-3-ylmethyl)-2,2-diethoxyethanamine (Compound IX-18)

According to the procedure described in the synthesis method of Compound IX-2 with the modification that the reaction was carried out overnight, 2,2-diethoxyethanamine (8.72 ml, 60 mmol) was reacted with benzothiophene-3-carboxyaldehyde (8.11 g, 50 mmol) and the obtained residue was purified by silica gel column chromatography (eluent: n-hexane:ethyl acetate=90:10 to 80:20) to obtain the title compound (21.6 g, 86%).

Example IX-19

Synthesis of N-(2,2-diethoxyethyl)-3-methylbutan-1-amine (Compound IX-19)

According to the procedure described in the synthesis method of Compound IX-5 with the modification that the reaction was carried out overnight, 2,2-diethoxyethanamine (2.91 ml, 20 mmol) was reacted with isoamylbromide (1.26 ml, 10 mmol) and the obtained residue was purified by Büch silica gel column chromatography (eluent: n-hexane:ethyl acetate=90:10 to 80:20) to obtain the title compound (1.57 g, 77%).

Example IX-20

Synthesis of 2,2-diethoxy-N-phenethylethanamine (Compound IX-20)

According to the procedure described in the synthesis method of Compound IX-1, 2,2-diethoxyethanamine (5.82 ml, 40 mmol) was reacted with (2-bromoethyl)benzene (2.70 ml, 20 mmol) and the obtained residue was purified by Büch silica gel column chromatography (chloroform only) to obtain the title compound (4.45 g, 94%).

Example IX-21

Synthesis of N-(2,2-diethoxyethyl)-3-phenylpropan-1-amine (Compound IX-21)

According to the procedure described in the synthesis method of Compound IX-1, 2,2-diethoxyethanamine (5.82 ml, 40 mmol) was reacted with 3-phenylpropyl bromide (3.02 ml, 20 mmol) and the obtained residue was purified by Büch silica gel column chromatography (eluent: chloroform only) to obtain the title compound (1.37 g, 27%).

Example IX-22

Synthesis of N-(2,2-diethoxyethyl)-3,3-diphenylpropan-1-amine (Compound IX-22)

According to the procedure described in the synthesis method of Compound IX-1, 2,2-diethoxyethanamine (5.82 ml, 40 mmol) was reacted with 3,3-diphenylpropyl bromide (5.50 g, 20 mmol) and the obtained residue was purified by Büch silica gel column chromatography (eluent: n-hexane:ethyl acetate=90:10 to 80:20) to obtain the title compound (3.98 g, 61%).

Example IX-23

Synthesis of 2,2-diethoxy-N-(naphthalen-2-ylmethyl)ethanamine (Compound IX-23)

According to the procedure described in the synthesis method of Compound IX-1, 2,2-diethoxyethanamine (5.82 ml, 40 mmol) was reacted with 2-(bromomethyl)naphthalene (4.42 g, 20 mmol) and the obtained residue was purified by Büch silica gel column chromatography (eluent: n-hexane: ethyl acetate=90:10 to 80:20) to obtain the title compound (4.24 g, 78%).

Example IX-24

Synthesis of N-(cyclohexylmethyl)-2,2-diethoxyethanamine (Compound IX-24)

According to the procedure described in the synthesis method of Compound IX-5 with the modification that the reaction was carried out overnight, 2,2-diethoxyethanamine (5.82 ml, 40 mmol) was reacted with bromomethylcyclohexane (2.77 ml, 20 mmol) and the obtained residue was purified by Büch silica gel column chromatography (eluent: chloroform:methanol=100:0 to 98:2) to obtain the title compound (1.36 g, 30%).

Example IX-25

Synthesis of 2,2-diethoxy-N-(2-(tetrahydro-2H-pyran-2-yloxy)ethyl)ethanamine (Compound IX-25)

According to the procedure described in the synthesis method of Compound IX-5 with the modification that the reaction was carried out overnight, 2,2-diethoxyethanamine (5.82 ml, 40 mmol) was reacted with 2-(2-bromoethoxy) tetrahydro-2H-pyran (3.03 ml, 20 mmol) and the obtained residue was purified by Bach silica gel column chromatography (eluent: chloroform:methanol=100:0 to 98:2) to obtain the title compound (1.59 g, 30%).

Example IX-26

Synthesis of tert-butyl 3-(2,2-diethoxyethylamino)propanoate (Compound IX-26)

According to the procedure described in the synthesis method of Compound IX-1, 2,2-diethoxyethanamine (5.82 ml, (40 mmol) was reacted with tert-butyl 3-bromopropionate (3.34 ml, 20 mmol) and the obtained residue was purified by Büch silica gel column chromatography (eluent: chloroform only) to obtain the title compound (1.33 g, 25%).

Example IX-27

Synthesis of methyl 3-(2,2-diethoxyethylamino)propanoate (Compound IX-27)

According to the procedure described in the synthesis method of Compound IX-5 with the modification that the reaction was carried out overnight, 2,2-diethoxyethanamine (8.72 ml, 60 mmol) was reacted with methyl 3-bromopropionate (3.27 ml, 30 mmol) and the obtained residue was purified by Büch silica gel column chromatography (eluent: chloroform:methanol=100:0 to 98:2) to obtain the title compound (1.75 g, 27%).

Example III-1

Synthesis of (S)-(9H-fluoren-9-yl)methyl 3-(4-tert-butoxyphenyl)-1-((2,2-diethoxyethyl)(2-tert-butoxycarbonylaminobenzothiazole-4-ylmethyl)amino)-1-oxopropan-2-ylcarbamate (Compound III-1)

To a solution of (S)-2-(((9H-fluoren-9-yl)methoxy)carbonylamino)-3-(4-tert-butoxyphenyl)propanoic acid (919 mg, 2.0 mmol), hydroxybenzotriazol (203 mg, 1.5 mmol) and 1-ethyl-3-(3-dimethylaminopropyl)carbodiimide (383 mg, 2.0 mmol) in dichloromethane (7 ml) tert-butyl 4-((2,2-diethoxyethylamino)methyl)benzo[d]thiazol-2-ylcarbamate (Compound IX-1) (273 mg, 1.0 mmol) and 4-dimethylaminopyridine (61 mg, 0.5 mmol) in dichloromethane (2 ml) was added and the mixture was stirred at room temperature for 4 hr. The reaction mixture was diluted with ethyl acetate (50 ml) and washed with saturated aqueous sodium bicarbonate (50 ml), water (50 ml) and brine (50 ml). The organic layer was dried over magnesium sulfate and filtered. The filtrate was concentrated in vacuo and the residue was purified by silica gel column chromatography (eluent: n-hexane:ethyl acetate=5:1 to 2:1) to obtain the title compound (1.0 g, yield: 100%).

Example III-2

Synthesis of (S)-(9H-fluoren-9-yl)methyl 3-(4-tert-butoxyphenyl)-1-((2,2-diethoxyethyl)(naphthalen-1-ylmethyl)amino)-1-oxopropan-2-ylcarbamate (Compound III-2)

According to the procedure described in the synthesis method of Compound III-1, 2,2-diethoxy-N-(naphthalen-1-ylmethyl)ethanamine (Compound IX-2) (2.73 g, 10 mmol) was coupled with (S)-2-(((9H-fluoren-9-yl)methoxy)carbonylamino)-3-(4-tert-butoxyphenyl)propanoic acid (6.89 g, 15 mmol) and the obtained residue was purified by silica gel column chromatography (eluent: n-hexane:ethyl acetate=8:2 to 6:4) to obtain the title compound (6.46 g, 90%).

Example III-3

Synthesis of (S)-(9H-fluoren-9-yl)methyl 3-(4-tert-butoxyphenyl)-1-((2,2-diethoxyethyl)(quinolin-8-ylmethyl)amino)-1-oxopropan-2-ylcarbamate (Compound III-3)

According to the procedure described in the synthesis method of Compound III-1, 2,2-diethoxy-N-(quinolin-8-ylmethyl)ethanamine (Compound IX-3) (1.37 g, 5 mmol) was coupled with (S)-2-(((9H-fluoren-9-yl)methoxy)carbonylamino)-3-(4-tert-butoxyphenyl)propanoic acid (2.76 g, 6 mmol) and the obtained residue was purified by silica gel column chromatography (eluent: n-hexane:ethyl acetate=7:3 to 5:5) to obtain the title compound (0.62 g, 17%).

Example III-4

Synthesis of (S)-(9H-fluoren-9-yl)methyl 3-(4-tert-butoxyphenyl)-1-((2,2-diethoxyethyl)(quinolin-4-ylmethyl)amino)-1-oxopropan-2-ylcarbamate (Compound III-4)

According to the procedure described in the synthesis method of Compound III-1, 2,2-diethoxy-N-(quinolin-4-ylmethyl)ethanamine (Compound IX-4) (274 mg, 1.0 mmol) was coupled with (S)-2-(((9H-fluoren-9-yl)methoxy)carbonylamino)-3-(4-tert-butoxyphenyl)propanoic acid (689 g, 1.5 mmol) and the obtained residue was purified by silica gel column chromatography (eluent: n-hexane:ethyl acetate=5:1 to 2:1) to obtain the title compound (546 mg, 76%).

Example III-5

Synthesis of (9H-fluoren-9-yl)methyl(S)-3-(4-tert-butoxyphenyl)-1-(((S)-1,1-diethoxypropan-2-yl)(2-tert-butoxycarbonyl)aminobenzothiazol-4-ylmethyl)amino)-1-oxopropan-2-ylcarbamate (Compound III-5)

To a solution of (S)-2-(((9H-fluoren-9-yl)methoxy)carbonylamino)-3-(4-tert-butoxyphenyl) propanoic acid (101 mg, 0.22 mmol) and O-(7-azabenzotriazol-1-yl)-1,1,3,3-tetramethyluronium hexafluorphosphate (84 mg, 0.22 mmol) in dichloromethane (1 ml) was added a solution of (S)-tert-butyl 4-(1,1-diethoxypropan-2-ylamino)methyl)benzo[d]thiazol-2-ylcarbamate (Compound IX-5)(82 mg, 0.2 mmol) and N,N-diisopropylethylamine (38 μl, 0.22 mmol) in dichloromethane (1 ml) and the mixture was stirred at room temperature overnight. The reaction mixture was diluted with ethyl acetate (50 ml) and washed with saturated sodium bicarbonate (50 ml), water (50 ml) and brine (50 ml). The organic layer was dried over magnesium sulfate and filtered. The filtrate was concentrated in vacuo and the residue was purified by silica gel column chromatography (eluent: n-hexane:ethyl acetate=9:1 to 7:3) to obtain the title compound (85.8 mg, 50%).

Example III-6

Synthesis of (9H-fluoren-9-yl)methyl(S)-3-(4-tert-butoxyphenyl)-1-(((S)-1,1-diethoxypropan-2-yl)(naphthalen-1-ylmethyl)amino)-1-oxopropan-2-ylcarbamate (Compound III-6)

According to the procedure described in the synthesis method of Compound III-5, (S)-1,1-diethoxy-N-(naphthalen-1-ylmethyl)propan-2-amine (Compound IX-6) (686 mg, 2.4 mmol) was coupled with (S)-2-(((9H-fluoren-9-yl)methoxy)carbonylamino)-3-(4-tert-butoxyphenyl)propanoic acid (1.15 g, 2.51 mmol) and the obtained residue was purified by Büch silica gel column chromatography (eluent: n-hexane:ethyl acetate=7:3) to obtain the title compound (1.384 g, 79%).

Example III-7

Synthesis of (9H-fluoren-9-yl)methyl(S)-3-(4-tert-butoxyphenyl)-1-(((S)-1,1-diethoxypropan-2-yl)(quinolin-8-ylmethyl)amino)-1-oxopropan-2-ylcarbamate (Compound III-7)

According to the procedure described in the synthesis method of Compound III-5, (S)-1,1-diethoxy-N-(quinolin-8-ylmethyl)propan-2-amine (Compound IX-7) (1.33 g, 4.6 mmol) was coupled with (S)-2-(((9H-fluoren-9-yl)methoxy)carbonylamino)-3-(4-tert-butoxyphenyl)propanoic acid (2.22 g, 4.84 mmol) and the obtained residue was purified by Büch silica gel column chromatography (eluent: n-hexane:ethyl acetate=4:6) to obtain the title compound (2.41 g, 68%).

Example III-8

Synthesis of (9H-fluoren-9-yl)methyl(S)-1-((benzo[c][1,2,5]thiadiazol-4-ylmethyl)((S)-1,1-diethoxypropan-2-yl)amino)-3-(4-tert-butoxyphenyl)-1-oxopropan-2-ylcarbamate (Compound III-8)

According to the procedure described in the synthesis method of Compound III-5, (S)—N-(benzo[c][1,2,5]thiadiazol-4-ylmethyl)-1,1-diethoxypropan-2-amine (Compound IX-8) (1.41 g, 4.78 mmol) was coupled with (S)-2-(((9H-fluoren-9-yl)methoxy)carbonylamino)-3-(4-tert-butoxyphenyl)propanoic acid (2.4 g, 5.23 mmol) and the obtained residue was purified by Büch silica gel column chromatography (eluent: n-hexane:ethyl acetate=7:3) to obtain the title compound (2.38% g, 68%).

Example III-9

Synthesis of (9H-fluoren-9-yl)methyl(S)-3-(4-tert-butoxyphenyl)-1-(((S)-1,1-diethoxypropan-2-yl)(isoquinolin-5-ylmethyl)amino)-1-oxopropan-2-ylcarbamate (Compound III-9)

According to the procedure described in the synthesis method of Compound III-5, (S)-1,1-diethoxy-N-(isoquinolin-5-ylmethyl)propan-2-amine (Compound IX-9) (1.98 g, 5.21 mmol) was coupled with (S)-2-(((9H-fluoren-9-yl)methoxy)carbonylamino)-3-(4-tert-butoxyphenyl)propanoic acid (2.4 g, 5.21 mmol) and the obtained residue was purified by Büch silica gel column chromatography (eluent: n-hexane:ethyl acetate=7:3) to obtain the title compound (2.92 g, 76%).

Example III-10

Synthesis of (9H-fluoren-9-yl)methyl(S)-1-((benzo[b]thiophen-3-ylmethyl)((S)-1,1-diethoxypropan-2-yl)amino)-3-(4-tert-butoxyphenyl)-1-oxopropan-2-ylcarbamate (Compound III-10)

According to the procedure described in the synthesis method of Compound III-5, (S)—N-(benzo[b]thiophen-3-ylmethyl)-1,1-diethoxypropan-2-amine (Compound IX-10) (1.45 g, 4.941 mmol) was coupled with (S)-2-(((9H-fluoren-9-yl)methoxy)carbonylamino)-3-(4-tert-butoxyphenyl)propanoic acid (2.50 g, 5.44 mmol) and the obtained residue was purified by Büch silica gel column chromatography (eluent: n-hexane:ethyl acetate=7:3) to obtain the title compound (2.36 g, 59%).

Example III-11

Synthesis of (9H-fluoren-9-yl)methyl(S)-3-(4-tert-butoxyphenyl)-1-(((5-chlorothieno[3,2-b]pyridin-3-yl)methyl)((S)-1,1-diethoxypropan-2-yl)amino)-1-oxopropan-2-ylcarbamate (Compound III-11)

According to the procedure described in the synthesis method of Compound III-5, (S)—N-((5-chlorothieno[3,2-b]pyridin-3-yl)methyl)-1,1-diethoxypropan-2-amine (Compound IX-11) (996 mg, 3.03 mmol) was coupled with (S)-2-(((9H-fluoren-9-yl)methoxy)carbonylamino)-3-(4-tert-butoxyphenyl)propanoic acid (1.53 g, 3.33 mmol) and the obtained residue was purified by Büch silica gel column chromatography (eluent: chloroform:methanol=98:2) to obtain the title compound (1.29% g, 55%).

Example III-12

Synthesis of (9H-fluoren-9-yl)methyl(S)-3-(4-tert-butoxyphenyl)-1-(((S)-1,1-diethoxypropan-2-yl)(quinoxalin-5-ylmethyl)amino)-1-oxopropan-2-ylcarbamate (Compound III-12)

According to the procedure described in the synthesis method of Compound III-5, (S)-1,1-diethoxy-N-(quinoxalin- 5-ylmethyl)propan-2-amine (Compound IX-12) (1.93 g, 6.65 mmol) was coupled with (S)-2-(((9H-fluoren-9-yl)methoxy)carbonylamino)-3-(4-tert-butoxyphenyl)propanoic acid (3.36 g, 7.31 mmol) and the obtained residue was purified by Büch silica gel column chromatography (eluent: chloroform:methanol=100:0 to 98:2) to obtain the title compound (2.35 g, 48%).

Example III-13

Synthesis of (S)-(9H-fluoren-9-yl)methyl 1-(benzyl (2,2-diethoxyethyl)amino)-3-(4-tert-butoxyphenyl)-1-oxopropan-2-ylcarbamate (Compound III-13)

According to the procedure described in the synthesis method of Compound III-1, N-benzyl-2,2-diethoxyethanamine (Compound IX-13) (43.3 g, 190 mmol) was coupled with (S)-2-(((9H-fluoren-9-yl)methoxy)carbonylamino)-3-(4-tert-butoxyphenyl)propanoic acid (128.6 g, 280 mmol) and the obtained residue was purified by silica gel column chromatography (eluent: n-hexane:ethyl acetate=4:1) to obtain the title compound (55.0 g, 43%).

Example III-14

Synthesis of (9H-fluoren-9-yl)methyl(S)-3-(4-tert-butoxyphenyl)-1-((2,2-diethoxyethyl)((R)-1-phenylethyl)amino)-1-oxopropan-2-ylcarbamate (Compound III-14)

According to the procedure described in the synthesis method of Compound III-5, (R)-2,2-diethoxy-N-(1-phenylethyl)ethanamine (Compound IX-14) (50.0 g, 210 mmol) was coupled with (S)-2-(((9H-fluoren-9-yl)methoxy)carbonylamino)-3-(4-tert-butoxyphenyl)propanoic acid (101.1 g, 220 mmol) and the obtained residue was purified by silica gel column chromatography (eluent: n-hexane:ethyl acetate=4:1) to obtain the title compound (125.0 g, 87%).

Example III-15

Synthesis of (S)-(9H-fluoren-9-yl)methyl 3-(4-tert-butoxyphenyl)-1-((2,2-diethoxyethyl)(pyridin-4-ylmethyl)amino)-1-oxopropan-2-ylcarbamate (Compound III-15)

According to the procedure described in the synthesis method of Compound III-5, 2,2-diethoxy-N-(pyridin-4-ylmethyl)ethanamine (Compound IX-15) (70.8 g, 315 mmol) was coupled with (S)-2-(((9H-fluoren-9-yl)methoxy)carbonylamino)-3-(4-tert-butoxyphenyl)propanoic acid (128.6 g, 280 mmol) and the obtained residue was purified by silica gel column chromatography (eluent: n-hexane:ethyl acetate=1:1 to 0:100) to obtain the title compound (160.0 g, 76%).

Example III-16

Synthesis of (S)-(9H-fluoren-9-yl)methyl 3-(4-tert-butoxyphenyl)-1-((2,2-diethoxyethyl)(pyridin-2-ylmethyl)amino)-1-oxopropan-2-ylcarbamate (Compound III-16)

According to the procedure described in the synthesis method of Compound III-5, 2,2-diethoxy-N-(pyridin-2-ylmethyl)ethanamine (Compound IX-16) (34.0 g, 150 mmol) was coupled with (S)-2-(((9H-fluoren-9-yl)methoxy)carbonylamino)-3-(4-tert-butoxyphenyl)propanoic acid (72.3 g, 150 mmol) and the obtained residue was purified by silica gel column chromatography (eluent: n-hexane:ethyl acetate=3:1) to obtain the title compound (90.0 g, 90%).

Example III-17

Synthesis of (S)-(9H-fluoren-9-yl)methyl 3-(4-tert-butoxyphenyl)-1-((2,2-diethoxyethyl)(2,4-difluorobenzyl)amino)-1-oxopropan-2-ylcarbamate (Compound III-17)

According to the procedure described in the synthesis method of Compound III-1 with the modification that the reaction was carried out overnight, N-(2,4-difluorobenzyl)-2,2-diethoxyethanamine (Compound IX-17) (49.3 g, 190 mmol) was coupled with (S)-2-(((9H-fluoren-9-yl)methoxy)carbonylamino)-3-(4-tert-butoxyphenyl)propanoic acid (128.6 g, 280 mmol) and the obtained residue was purified by silica gel column chromatography (eluent: n-hexane:ethyl acetate=4:1) to obtain the title compound (49.0 g, 36%).

Example III-18

Synthesis of (9H-fluoren-9-yl)methyl(S)-1-(((S)-1,1-diethoxypropan-2-yl)(quinolin-8-ylmethyl)amino)-3-(4-hydroxy-2,6dimethylphenyl)-1-oxopropan-2-ylcarbamate (Compound III-18)

To a solution of (S)-2-(((9H-fluoren-9-yl)methoxy)carbonylamino)-3-(4-hydroxy-2,6-dimethylphenyl)propanoic acid (907 mg, 2.1 mmol) and (S)-1,1-diethoxy-N-(quinolin-8-ylmethyl)propan-2-amine (Compound IX-7) (577 mg, 2.0 mmol) in dichloromethane (10 ml) was added 4-(4,6-dimethoxy-1,3,5-triazin-2-yl)-4-methylmorpholinium chloride (660 mg, 2.1 mmol) and the mixture was stirred at room temperature for 5 hr. The reaction mixture was diluted with ethyl acetate (50 ml) and washed with saturated sodium bicarbonate (50 ml), water (50 ml) and brine (50 ml). The organic layer was dried over magnesium sulfate and filtered. The filtrate was concentrated in vacuo and the residue was purified by silica gel column chromatography (eluent: n-hexane:ethyl acetate=1:1) to obtain the title compound (775 mg, 55%).

Typical examples of the compound III of the present invention that can be given by reacting and treating corresponding starting compounds using any of the methods described in the present specification are shown in Table C3. The compounds were prepared according to the preparation methods of the compound numbers (e.g., "III-1") shown in the columns of "Syn" in the table. In the columns of purification, "Büch" indicates use of Büch sepacore preparative chromatography system and "w/o" indicates without column chromatography. In the columns of yield, "-" indicates yield was not determined. "Int_IX" means an intermediate compound numbers and "Int_X" is corresponding carboxylic acid.

TABLE C3

| Ex. No. | chemical name | purification | syn. | yield (%) | Int_IX | Int_X |
|---|---|---|---|---|---|---|
| III-19 | (S)-(9H-fluoren-9-yl)methyl 1-(benzyl(2,2-diethoxyethyl)amino)-1-oxopropan-2-ylcarbamate | Buch | III-1 | 43 | 13 | Fmoc-Ala-OH |
| III-20 | N-Benzyl-N-(2,2-dimethoxyethyl)-6-(tert-butoxycarbonylamino)-2-(S)-(9H-fluoren-9-yl)methoxycarbonylaminohexamide | Buch | III-1 | 84 | 13 | Fmoc-Lys(Boc)-OH |

TABLE C3-continued

| Ex. No. | chemical name | purification | syn. | yield (%) | Int_IX | Int_X |
|---|---|---|---|---|---|---|
| III-21 | (S)-tert-butyl 3-(((9H-fluoren-9-yl)methoxy)carbonylamino)-4-(benzyl(2,2-diethoxyethyl)amino-4-oxobutanoate | Buch | III-1 | 63 | 13 | Fmoc-Asp(OtBu)-OH |
| III-22 | (S)-(9H-fluoren-9-yl)methyl 1-(benzyl(2,2-diethoxyethyl)amino)-1,4-dioxo-4-(tritylamino)butan-2-ylcarbamate | Buch | III-1 | 76 | 13 | Fmoc-Asn(Trt)-OH |
| III-23 | (S)-(9H-fluoren-9-yl)methyl 1-((2,2-diethoxyethyl)(naphthalen-1-ylmethyl)amino)-1-oxopropan-2-ylcarbamate | Buch | III-1 | 49 | 2 | Fmoc-Ala-OH |
| III-24 | N-(naphthalen-1-ylmethyl)-N-(2,2-dimethoxyethyl)-6-(tert-butoxycarbonylamino)-2-(S)-(9H-fluoren-9-yl)methoxycarbonylaminohexamide | Buch | III-1 | 59 | 2 | Fmoc-Lys(Boc)-OH |
| III-25 | (S)-tert-butyl 3-(((9H-fluoren-9-yl)methoxy)carbonylamino)-4-((2,2-diethoxyethyl)(naphthalen-1-ylmethyl)amino)-4-oxobutanoate | Buch | III-1 | 44 | 2 | Fmoc-Asp(OtBu)-OH |
| III-26 | (S)-(9H-fluoren-9-yl)methyl 1-((2,2-diethoxyethyl)(naphthalen-1-ylmethyl)amino)-1,4-dioxo-4-(tritylamino)butan-2-ylcarbamate | Buch | III-1 | 25 | 2 | Fmoc-Asn(Trt)-OH |
| III-27 | (S)-(9H-fluoren-9-yl)methyl 1-((2,2-diethoxyethyl)(quinolin-8-ylmethyl)amino)-1-oxopropan-2-ylcarbamate | Buch | III-1 | 64 | 3 | Fmoc-Ala-OH |
| III-28 | N-(quinolin-8-ylmethyl)-N-(2,2-dimethoxyethyl)-6-(tert-butoxycarbonylamino)-2-(S)-(9H-fluoren-9-yl)methoxycarbonylaminohexamide | Buch | III-1 | 80 | 3 | Fmoc-Lys(Boc)-OH |
| III-29 | (S)-tert-butyl 3-(((9H-fluoren-9-yl)methoxy)carbonylamino)-4-((2,2-diethoxyethyl)(quinolin-8-ylmethyl)amino)-4-oxobutanoate | Buch | III-1 | 79 | 3 | Fmoc-Asp(OtBu)-OH |
| III-30 | (S)-(9H-fluoren-9-yl)methyl 1-((2,2-diethoxyethyl)(quinolin-8-ylmethyl)amino)-1,4-dioxo-4-(tritylamino)butan-2-ylcarbamate | Buch | III-1 | 31 | 3 | Fmoc Asn(Trt)-OH |
| III-31 | (S)-(9H-fluoren-9-yl)methyl 1-((benzo[b]thiophen-3-ylmethyl)(2,2-diethoxyethyl)amino)-1-oxopropan-2-ylcarbamate | Buch | III-1 | 66 | 18 | Fmoc-Ala-OH |
| III-32 | (S)-(9H-fluoren-9-yl)methyl 1-((benzo[b]thiophen-3-ylmethyl)(2,2-diethoxyethyl)amino)-3-(4-tert-butoxyphenyl)-1-oxopropan-2-ylcarbamate | Buch | III-1 | 71 | 18 | Fmoc-Tyr(tBu)-OH |
| III-33 | N-(benzo[b]thiophen-3-ylmethyl)-N-(2,2-dimethoxyethyl)-6-(tert-butoxycarbonylamino)-2-(S)-(9H-fluoren-9-yl)methoxycarbonylaminohexamide | Buch | III-1 | 53 | 18 | Fmoc-Lys(Boc)-OH |
| III-34 | (S)-tert-butyl 3-(((9H-fluoren-9-yl)methoxy)carbonylamino)-4-(benzo[b]thiophen-3-ylmethyl)(2,2-diethoxyethyl)amino)-4-oxobutanoate | Buch | III-1 | 60 | 18 | Fmoc-Asp(OtBu)-OH |
| III-35 | (S)-(9H-fluoren-9-yl)methyl 1-((benzo[b]thiophen-3-ylmethyl)(2,2-diethoxyethyl)amino)-1,4-dioxo-4-(tritylamino)butan-2-ylcarbamate | Buch | III-1 | 53 | 18 | Fmoc-Asn(Trt)-OH |
| III-36 | (S)-(9H-fluoren-9-yl)methyl 1-((2,2-diethoxyethyl)(isopentyl)amino)-1-oxopropan-2-ylcarbamate | w/o | III-1 | — | 19 | Fmoc-Ala-OH |
| III-37 | (S)-(9H-fluoren-9-yl)methyl 3-(4-tert-butoxyphenyl)-1-((2,2-diethoxyethyl)(isopentyl)amino)-1-oxopropan-2-ylcarbamate | w/o | III-1 | — | 19 | Fmoc-Tyr(tBu)-OH |
| III-38 | N-isopentyl-N-(2,2-dimethoxyethyl)-6-(tert-butoxycarbonylamino)-2-(S)-(9H-fluoren-9-yl)methoxycarbonylaminohexamide | w/o | III-1 | — | 19 | Fmoc-Lys(Boc)-OH |
| III-39 | (S)-tert-butyl 3-(((9H-fluoren-9-yl)methoxy)carbonylamino)-4-((2,2-diethoxyethyl)(isopentyl)amino)-4-oxobutanoate | w/o | III-1 | — | 19 | Fmoc-Asp(OtBu)-OH |
| III-40 | (S)-(9H-fluoren-9-yl)methyl 1-((2,2-diethoxyethyl)(isopentyl)amino)-1,4-dioxo-4-(tritylamino)butan-2-ylcarbamate | w/o | III-1 | — | 19 | Fmoc-Asn(Trt)-OH |
| III-41 | (S)-(9H-fluoren-9-yl)methyl 3-tert-butoxy-1-((2,2-diethoxyethyl)(isopentyl)amino)-1-oxopropan-2-ylcarbamate | w/o | III-1 | — | 19 | Fmoc-Ser(tBu)-OH |
| III-42 | (S)-(9H-fluoren-9-yl)methyl 1-((2,2-diethoxyethyl)(isopentyl)amino)-4-methyl-1-oxopentan-2-ylcarbamate | w/o | III-1 | — | 19 | Fmoc-L-Leu-OH |
| III-43 | (S)-(9H-fluoren-9-yl)methyl 2-((2,2-diethoxyethyl)(isopentyl)amino)-2-oxo-1-phenylethylcarbamate | w/o | III-1 | — | 19 | Fmoc-Phg-OH |
| III-44 | (S)-(9H-fluoren-9-yl)methyl 1-((2,2-diethoxyethyl)(isopentyl)amino)-1-oxo-3-phenylpropan-2-ylcarbamate | w/o | III-1 | — | 19 | Fmoc-Phe-OH |
| III-45 | (S)-(9H-fluoren-9-yl)methyl 1-((2,2-diethoxyethyl)(isopentyl)amino)-1-oxo-4-phenylbutan-2-ylcarbamate | w/o | III-1 | — | 19 | Fmoc-Hph-OH |
| III-46 | (S)-(9H-fluoren-9-yl)methyl 3-(benzyloxy)-1-((2,2-diethoxyethyl)(isopentyl)amino)-1-oxopropan-2-ylcarbamate | w/o | III-1 | — | 19 | Fmoc-Ser(Bzl)-OH |

TABLE C3-continued

| Ex. No. | chemical name | purification | syn. | yield (%) | Int_IX | Int_X |
|---|---|---|---|---|---|---|
| III-47 | (S)-(9H-fluoren-9-yl)methyl 1-((2,2-diethoxyethyl)(isopentyl)amino)-3-(naphthalen-1-yl)-1-oxopropan-2-ylcarbamate | w/o | III-1 | — | 19 | Fmoc-Ala(1-Naph)-OH |
| III-48 | (S)-(9H-fluoren-9-yl)methyl 1-((2,2-diethoxyethyl)(isopentyl)amino)-3-(naphthalen-2-yl)-1-oxopropan-2-ylcarbamate | w/o | III-1 | — | 19 | Fmoc-Ala(2-Naph)-OH |
| III-49 | (S)-(9H-fluoren-9-yl)methyl 1-((2,2-diethoxyethyl)(phenethyl)amino)-1-oxopropan-2-ylcarbamate | w/o | III-1 | — | 20 | Fmoc-Ala-OH |
| III-50 | (S)-(9H-fluoren-9-yl)methyl 3-(4-tert-butoxyphenyl)-1-((2,2-diethoxyethyl)(phenethyl)amino)-1-oxopropan-2-ylcarbamate | w/o | III-1 | — | 20 | Fmoc-Tyr(tBu)-OH |
| III-51 | N-phenethyl-N-(2,2-dimethoxyethyl)-6-(tert-butoxycarbonylamino)-2-(S)-(9H-fluoren-9-yl)methoxycarbonylaminohexamide | w/o | III-1 | — | 20 | Fmoc-Lys(Boc)-OH |
| III-52 | (S)-tert-butyl 3-(((9H-fluoren-9-yl)methoxy)carbonylamino)-4-((2,2-diethoxyethyl)(phenethyl)amino)-4-oxobutanoate | w/o | III-1 | — | 20 | Fmoc-Asp(OtBu)-OH |
| III-53 | (S)-(9H-fluoren-9-yl)methyl 1-((2,2-diethoxyethyl)(phenethyl)amino)-1,4-dioxo-4-(tritylamino)butan-2-ylcarbamate | w/o | III-1 | — | 20 | Fmoc-Asn(Trt)-OH |
| III-54 | (S)-(9H-fluoren-9-yl)methyl 3-tert-butoxy-1-((2,2-diethoxyethyl)(phenethyl)amino)-1-oxopropan-2-ylcarbamate | w/o | III-1 | — | 20 | Fmoc-Ser(tBu)-OH |
| III-55 | (S)-(9H-fluoren-9-yl)methyl 1-((2,2-diethoxyethyl)(phenethyl)amino)-4-methyl-1-oxopentan-2-ylcarbamate | w/o | III-1 | — | 20 | Fmoc-L-Leu-OH |
| III-56 | (S)-(9H-fluoren-9-yl)methyl 2-((2,2-diethoxyethyl)(phenethyl)amino)-2-oxo-1-phenylethylcarbamate | w/o | III-1 | — | 20 | Fmoc-Phg-OH |
| III-57 | (S)-(9H-fluoren-9-yl)methyl 1-((2,2-diethoxyethyl)(phenethyl)amino)-1-oxo-3-phenylpropan-2-ylcarbamate | w/o | III-1 | — | 20 | Fmoc-Phe-OH |
| III-58 | (S)-(9H-fluoren-9-yl)methyl 1-((2,2-diethoxyethyl)(phenethyl)amino)-1-oxo-4-phenylbutan-2-ylcarbamate | w/o | III-1 | — | 20 | Fmoc-Hph-OH |
| III-59 | (S)-(9H-fluoren-9-yl)methyl 3-(benzyloxy)-1-((2,2-diethoxyethyl)(phenethyl)amino)-1-oxopropan-2-ylcarbamate | w/o | III-1 | — | 20 | Fmoc-Ser(Bzl)-OH |
| III-60 | (S)-(9H-fluoren-9-yl)methyl 1-((2,2-diethoxyethyl)(phenethyl)amino)-3-(naphthalen-1-yl)-1-oxopropan-2-ylcarbamate | w/o | III-1 | — | 20 | Fmoc-Ala(1-Naph)-OH |
| III-61 | (S)-(9H-fluoren-9-yl)methyl 1-((2,2-diethoxyethyl)(phenethyl)amino)-3-(naphthalen-2-yl)-1-oxopropan-2-ylcarbamate | w/o | III-1 | — | 20 | Fmoc-Ala(2-Naph)-OH |
| III-62 | (S)-(9H-fluoren-9-yl)methyl 1-((2,2-diethoxyethyl)(3-phenylpropyl)amino)-1-oxopropan-2-ylcarbamate | w/o | III-1 | — | 21 | Fmoc-Ala-OH |
| III-63 | (S)-(9H-fluoren-9-yl)methyl 3-(4-tert-butoxyphenyl)-1-((2,2-diethoxyethyl)(3-phenylpropyl)amino)-1-oxopropan-2-ylcarbamate | w/o | III-1 | — | 21 | Fmoc-Tyr(tBu)-OH |
| III-64 | N-phenylpropyl-N-(2,2-dimethoxyethyl)-6-(tert-butoxycarbonylamino)-2-(S)-(9H-fluoren-9-yl)methoxycarbonylaminohexamide | w/o | III-1 | — | 21 | Fmoc-Lys(Boc)-OH |
| III-65 | (S)-tert-butyl 3-(((9H-fluoren-9-yl)methoxy)carbonylamino)-4-((2,2-diethoxyethyl)(3-phenylpropyl)amino)-4-oxobutanoate | w/o | III-1 | — | 21 | Fmoc-Asp(OtBu)-OH |
| III-66 | (S)-(9H-fluoren-9-yl)methyl 1-((2,2-diethoxyethyl)(3-phenylpropyl)amino)-1,4-dioxo-4-(tritylamino)butan-2-ylcarbamate | w/o | III-1 | — | 21 | Fmoc-Asn(Trt)-OH |
| III-67 | (S)-(9H-fluoren-9-yl)methyl 3-tert-butoxy-1-((2,2-diethoxyethyl)(3-phenylpropyl)amino)-1-oxopropan-2-ylcarbamate | w/o | III-1 | — | 21 | Fmoc-Ser(tBu)-OH |
| III-68 | (S)-(9H-fluoren-9-yl)methyl 1-((2,2-diethoxyethyl)(3-phenylpropyl)amino)-4-methyl-1-oxopentan-2-ylcarbamate | w/o | III-1 | — | 21 | Fmoc-L-Leu-OH |
| III-69 | (S)-(9H-fluoren-9-yl)methyl 2-((2,2-diethoxyethyl)(3-phenylpropyl)amino)-2-oxo-1-phenylethylcarbamate | w/o | III-1 | — | 21 | Fmoc-Phg-OH |
| III-70 | (S)-(9H-fluoren-9-yl)methyl 1-((2,2-diethoxyethyl)(3-phenylpropyl)amino)-1-oxo-3-phenylpropan-2-ylcarbamate | w/o | III-1 | — | 21 | Fmoc-Phe-OH |
| III-71 | (S)-(9H-fluoren-9-yl)methyl 1-((2,2-diethoxyethyl)(3-phenylpropyl)amino)-1-oxo-4-phenylbutan-2-ylcarbamate | w/o | III-1 | — | 21 | Fmoc-Hph-OH |
| III-72 | (S)-(9H-fluoren-9-yl)methyl 3-(benzyloxy)-1-((2,2-diethoxyethyl)(3-phenylpropyl)amino)-1-oxopropan-2-ylcarbamate | w/o | III-1 | — | 21 | Fmoc-Ser(Bzl)-OH |
| III-73 | (S)-(9H-fluoren-9-yl)methyl 1-((2,2-diethoxyethyl)(3-phenylpropyl)amino)-3-(naphthalen-1-yl)-1-oxopropan-2-ylcarbamate | w/o | III-1 | — | 21 | Fmoc-Ala(1-Naph)-OH |

TABLE C3-continued

| Ex. No. | chemical name | purification | syn. | yield (%) | Int_IX | Int_X |
|---|---|---|---|---|---|---|
| III-74 | (S)-(9H-fluoren-9-yl)methyl 1-((2,2-diethoxyethyl)(3-phenylpropyl)amino)-3-(naphthalen-2-yl)-1-oxopropan-2-ylcarbamate | w/o | III-1 | — | 21 | Fmoc-Ala(2-Naph)-OH |
| III-75 | (S)-(9H-fluoren-9-yl)methyl 1-((2,2-diethoxyethyl)(3,3-diphenylpropyl)amino)-1-oxopropan-2-ylcarbamate | w/o | III-1 | — | 22 | Fmoc-Ala-OH |
| III-76 | (S)-(9H-fluoren-9-yl)methyl 3-(4-tert-butoxyphenyl)-1-((2,2-diethoxyethyl)(3,3-diphenylpropyl)amino)-1-oxopropan-2-ylcarbamate | w/o | III-1 | — | 22 | Fmoc-Tyr(tBu)-OH |
| III-77 | N-(3,3-diphenylpropyl)-N-(2,2-dimethoxyethyl)-6-(tert-butoxycarbonylamino)-2-(S)-(9H-fluoren-9-yl)methoxycarbonylaminohexamide | w/o | III-1 | — | 22 | Fmoc-Lys(Boc)-OH |
| III-78 | (S)-tert-butyl 3-(((9H-fluoren-9-yl)methoxy)carbonylamino)-4-((2,2-diethoxyethyl)(3,3-diphenylpropyl)amino)-4-oxobutanoate | w/o | III-1 | — | 22 | Fmoc-Asp(OtBu)-OH |
| III-79 | (S)-(9H-fluoren-9-yl)methyl 1-((2,2-diethoxyethyl)(3,3-diphenylpropyl)amino)-1,4-dioxo-4-(tritylamino)butan-2-ylcarbamate | w/o | III-1 | — | 22 | Fmoc-Asn(Trt)-OH |
| III-80 | (S)-(9H-fluoren-9-yl)methyl 3-tert-butoxy-1-((2,2-diethoxyethyl)(3,3-diphenylpropyl)amino)-1-oxopropan-2-ylcarbamate | w/o | III-1 | — | 22 | Fmoc-Ser(tBu)-OH |
| III-81 | (S)-(9H-fluoren-9-yl)methyl 1-((2,2-diethoxyethyl)(3,3-diphenylpropyl)amino)-4-methyl-1-oxopentan-2-ylcarbamate | w/o | III-1 | — | 22 | Fmoc-L-Leu-OH |
| III-82 | (S)-(9H-fluoren-9-yl)methyl 2-((2,2-diethoxyethyl)(3,3-diphenylpropyl)amino)-2-oxo-1-phenylethylcarbamate | w/o | III-1 | — | 22 | Fmoc-Phg-OH |
| III-83 | (S)-(9H-fluoren-9-yl)methyl 1-((2,2-diethoxyethyl)(3,3-diphenylpropyl)amino)-1-oxo-3-phenylpropan-2-ylcarbamate | w/o | III-1 | — | 22 | Fmoc-Phe-OH |
| III-84 | (S)-(9H-fluoren-9-yl)methyl 1-((2,2-diethoxyethyl)(3,3-diphenylpropyl)amino)-1-oxo-4-phenylbutan-2-ylcarbamate | w/o | III-1 | — | 22 | Fmoc-Hph-OH |
| III-85 | (S)-(9H-fluoren-9-yl)methyl 3-(benzyloxy)-1-((2,2-diethoxyethyl)(3,3-diphenylpropyl)amino)-1-oxopropan-2-ylcarbamate | w/o | III-1 | — | 22 | Fmoc-Ser(Bzl)-OH |
| III-86 | (S)-(9H-fluoren-9-yl)methyl 1-((2,2-diethoxyethyl)(3,3-diphenylpropyl)amino)-3-(naphthalen-1-yl)-1-oxopropan-2-ylcarbamate | w/o | III-1 | — | 22 | Fmoc-Ala(1-Naph)-OH |
| III-87 | (S)-(9H-fluoren-9-yl)methyl 1-((2,2-diethoxyethyl)(3,3-diphenylpropyl)amino)-3-(naphthalen-2-yl)-1-oxopropan-2-ylcarbamate | w/o | III-1 | — | 22 | Fmoc-Ala(2-Naph)-OH |
| III-88 | (S)-(9H-fluoren-9-yl)methyl 1-((2,2-diethoxyethyl)(naphthalen-2-ylmethyl)amino)-1-oxopropan-2-ylcarbamate | w/o | III-1 | — | 23 | Fmoc-Ala-OH |
| III-89 | (S)-(9H-fluoren-9-yl)methyl 3-(4-tert-butoxyphenyl)-1-((2,2-diethoxyethyl)(naphthalen-2-ylmethyl)amino)-1-oxopropan-2-ylcarbamate | w/o | III-1 | — | 23 | Fmoc-Tyr(tBu)-OH |
| III-90 | N-(naphthalen-2-ylmethyl)-N-(2,2-dimethoxyethyl)-6-(tert-butoxycarbonylamino)-2-(S)-(9H-fluoren-9-yl)methoxycarbonylaminohexamide | w/o | III-1 | — | 23 | Fmoc-Lys(Boc)-OH |
| III-91 | (S)-tert-butyl 3-(((9H-fluoren-9-yl)methoxy)carbonylamino)-4-((2,2-diethoxyethyl)(naphthalen-2-ylmethyl)amino)-4-oxobutanoate | w/o | III-1 | — | 23 | Fmoc-Asp(OtBu)-OH |
| III-92 | (S)-(9H-fluoren-9-yl)methyl 1-((2,2-diethoxyethyl)(naphthalen-2-ylmethyl)amino)-1,4-dioxo-4-(tritylamino)butan-2-ylcarbamate | w/o | III-1 | — | 23 | Fmoc-Asn(Trt)-OH |
| III-93 | (S)-(9H-fluoren-9-yl)methyl 3-tert-butoxy-1-((2,2-diethoxyethyl)(naphthalen-2-ylmethyl)amino)-1-oxopropan-2-ylcarbamate | w/o | III-1 | — | 23 | Fmoc-Ser(tBu)-OH |
| III-94 | (S)-(9H-fluoren-9-yl)methyl 1-((2,2-diethoxyethyl)(naphthalen-2-ylmethyl)amino)-4-methyl-1-oxopentan-2-ylcarbamate | w/o | III-1 | — | 23 | Fmoc-L-Leu-OH |
| III-95 | (S)-(9H-fluoren-9-yl)methyl 2-((2,2-diethoxyethyl)(naphthalen-2-ylmethyl)amino)-2-oxo-1-phenylethylcarbamate | w/o | III-1 | — | 23 | Fmoc-Phg-OH |
| III-96 | (S)-(9H-fluoren-9-yl)methyl 1-((2,2-diethoxyethyl)(naphthalen-2-ylmethyl)amino)-1-oxo-3-phenylpropan-2-ylcarbamate | w/o | III-1 | — | 23 | Fmoc-Phe-OH |
| III-97 | (S)-(9H-fluoren-9-yl)methyl 1-((2,2-diethoxyethyl)(naphthalen-2-ylmethyl)amino)-1-oxo-4-phenylbutan-2-ylcarbamate | w/o | III-1 | — | 23 | Fmoc-Hph-OH |
| III-98 | (S)-(9H-fluoren-9-yl)methyl 3-(benzyloxy)-1-((2,2-diethoxyethyl)(naphthalen-2-ylmethyl)amino)-1-oxopropan-2-ylcarbamate | w/o | III-1 | — | 23 | Fmoc-Ser(Bzl)-OH |
| III-99 | (S)-(9H-fluoren-9-yl)methyl 1-((2,2-diethoxyethyl)(naphthalen-2-ylmethyl)amino)-3-(naphthalen-1-yl)-1-oxopropan-2-ylcarbamate | w/o | III-1 | — | 23 | Fmoc-Ala(1-Naph)-OH |

TABLE C3-continued

| Ex. No. | chemical name | purification | syn. | yield (%) | Int_IX | Int_X |
|---|---|---|---|---|---|---|
| III-100 | (S)-(9H-fluoren-9-yl)methyl 1-((2,2-diethoxyethyl)(naphthalen-2-ylmethyl)amino)-3-(naphthalen-2-yl)-1-oxopropan-2-ylcarbamate | w/o | III-1 | — | 23 | Fmoc-Ala(2-Naph)-OH |
| III-101 | (S)-(9H-fluoren-9-yl)methyl 1-((2,2-diethoxyethyl)(pyridin-4-ylmethyl)amino)-1-oxopropan-2-ylcarbamate | w/o | III-1 | — | 15 | Fmoc-Ala-OH |
| III-102 | N-(pyridin-4-ylmethyl)-N-(2,2-dimethoxyethyl)-6-(tert-butoxycarbonylamino)-2-(S)-(9H-fluoren-9-yl)methoxycarbonylaminohexamide | w/o | III-1 | — | 15 | Fmoc-Lys(Boc)-OH |
| III-103 | (S)-tert-butyl 3-(((9H-fluoren-9-yl)methoxy)carbonylamino)-4-((2,2-diethoxyethyl)(pyridin-4-ylmethyl)amino)-4-oxobutanoate | w/o | III-1 | — | 15 | Fmoc-Asp(OtBu)-OH |
| III-104 | (S)-(9H-fluoren-9-yl)methyl 1-((2,2-diethoxyethyl)(pyridin-4-ylmethyl)amino)-1,4-dioxo-4-(tritylamino)butan-2-ylcarbamate | w/o | III-1 | — | 15 | Fmoc-Asn(Trt)-OH |
| III-105 | (S)-(9H-fluoren-9-yl)methyl 3-tert-butoxy-1-((2,2-diethoxyethyl)(pyridin-4-ylmethyl)amino)-1-oxopropan-2-ylcarbamate | w/o | III-1 | — | 15 | Fmoc-Ser(tBu)-OH |
| III-106 | (S)-(9H-fluoren-9-yl)methyl 1-((2,2-diethoxyethyl)(pyridin-4-ylmethyl)amino)-4-methyl-1-oxopentan-2-ylcarbamate | w/o | III-1 | — | 15 | Fmoc-L-Leu-OH |
| III-107 | (S)-(9H-fluoren-9-yl)methyl 2-((2,2-diethoxyethyl)(pyridin-4-ylmethyl)amino)-2-oxo-1-phenylethylcarbamate | w/o | III-1 | — | 15 | Fmoc-Phg-OH |
| III-108 | (S)-(9H-fluoren-9-yl)methyl 1-((2,2-diethoxyethyl)(pyridin-4-ylmethyl)amino)-1-oxo-3-phenylpropan-2-ylcarbamate | w/o | III-1 | — | 15 | Fmoc-Phe-OH |
| III-109 | (S)-(9H-fluoren-9-yl)methyl 1-((2,2-diethoxyethyl)(pyridin-4-ylmethyl)amino)-1-oxo-4-phenylbutan-2-ylcarbamate | w/o | III-1 | — | 15 | Fmoc-Hph-OH |
| III-110 | (S)-(9H-fluoren-9-yl)methyl 3-(benzyloxy)-1-((2,2-diethoxyethyl)(pyridin-4-ylmethyl)amino)-1-oxopropan-2-ylcarbamate | w/o | III-1 | — | 15 | Fmoc-Ser(Bzl)-OH |
| III-111 | (S)-(9H-fluoren-9-yl)methyl 1-((2,2-diethoxyethyl)(pyridin-4-ylmethyl)amino)-3-(naphthalen-1-yl)-1-oxopropan-2-ylcarbamate | w/o | III-1 | — | 15 | Fmoc-Ala(1-Naph)-OH |
| III-112 | (S)-(9H-fluoren-9-yl)methyl 1-((2,2-diethoxyethyl)(pyridin-4-ylmethyl)amino)-3-(naphthalen-2-yl)-1-oxopropan-2-ylcarbamate | w/o | III-1 | — | 15 | Fmoc-Ala(2-Naph)-OH |
| III-113 | (S)-(9H-fluoren-9-yl)methyl 1-((cyclohexylmethyl)(2,2-diethoxyethyl)amino)-1-oxopropan-2-ylcarbamate | w/o | III-1 | — | 24 | Fmoc-Ala-OH |
| III-114 | (S)-(9H-fluoren-9-yl)methyl 3-(4-tert-butoxyphenyl)-1-((cyclohexylmethyl)(2,2-diethoxyethyl)amino)-1-oxopropan-2-ylcarbamate | w/o | III-1 | — | 24 | Fmoc-Tyr(tBu)-OH |
| III-115 | N-cyclohexylmethyl-N-(2,2-dimethoxyethyl)-6-(tert-butoxycarbonylamino)-2-(S)-(9H-fluoren-9-yl)methoxycarbonylaminohexamide | w/o | III-1 | — | 24 | Fmoc-Lys(Boc)-OH |
| III-116 | (S)-tert-butyl 3-(((9H-fluoren-9-yl)methoxy)carbonylamino)-4-((cyclohexylmethyl)(2,2-diethoxyethyl)amino)-4-oxobutanoate | w/o | III-1 | — | 24 | Fmoc-Asp(OtBu)-OH |
| III-117 | (S)-(9H-fluoren-9-yl)methyl 1-((cyclohexylmethyl)(2,2-diethoxyethyl)amino)-1,4-dioxo-4-(tritylamino)butan-2-ylcarbamate | w/o | III-1 | — | 24 | Fmoc-Asn(Trt)-OH |
| III-118 | (S)-(9H-fluoren-9-yl)methyl 3-tert-butoxy-1-((cyclohexylmethyl)(2,2-diethoxyethyl)amino)-1-oxopropan-2-ylcarbamate | w/o | III-1 | — | 24 | Fmoc-Ser(tBu)-OH |
| III-119 | (S)-(9H-fluoren-9-yl)methyl 1-((cyclohexylmethyl)(2,2-diethoxyethyl)amino)-4-methyl-1-oxopentan-2-ylcarbamate | w/o | III-1 | — | 24 | Fmoc-L-Leu-OH |
| III-120 | (S)-(9H-fluoren-9-yl)methyl 2-((cyclohexylmethyl)(2,2-diethoxyethyl)amino)-2-oxo-1-phenylethylcarbamate | w/o | III-1 | — | 24 | Fmoc-Phg-OH |
| III-121 | (S)-(9H-fluoren-9-yl)methyl 1-((cyclohexylmethyl)(2,2-diethoxyethyl)amino)-1-oxo-3-phenylpropan-2-ylcarbamate | w/o | III-1 | — | 24 | Fmoc-Phe-OH |
| III-122 | (S)-(9H-fluoren-9-yl)methyl 1-((cyclohexylmethyl)(2,2-diethoxyethyl)amino)-1-oxo-4-phenylbutan-2-ylcarbamate | w/o | III-1 | — | 24 | Fmoc-Hph-OH |
| III-123 | (S)-(9H-fluoren-9-yl)methyl 3-(benzyloxy)-1-((cyclohexylmethyl)(2,2-diethoxyethyl)amino)-1-oxopropan-2-ylcarbamate | w/o | III-1 | — | 24 | Fmoc-Ser(Bzl)-OH |
| III-124 | (S)-(9H-fluoren-9-yl)methyl 1-((cyclohexylmethyl)(2,2-diethoxyethyl)amino)-3-(naphthalen-1-yl)-1-oxopropan-2-ylcarbamate | w/o | III-1 | — | 24 | Fmoc-Ala(1-Naph)-OH |
| III-125 | (S)-(9H-fluoren-9-yl)methyl 1-((cyclohexylmethyl)(2,2-diethoxyethyl)amino)-3-(naphthalen-2-yl)-1-oxopropan-2-ylcarbamate | w/o | III-1 | — | 24 | Fmoc-Ala(2-Naph)-OH |
| III-126 | (9H-fluoren-9-yl)methyl (2S)-1-((2,2-diethoxyethyl)(2-(tetrahydro-2H-pyran-2-yloxy)ethyl)amino)-1-oxopropan-2-ylcarbamate | w/o | III-1 | — | 25 | Fmoc-Ala-OH |
| III-127 | (9H-fluoren-9-yl)methyl (2S)-3-(4-tert-butoxyphenyl)-1-((2,2-diethoxyethyl)(2-(tetrahydro-2H-pyran-2-yloxy)ethyl)amino)-1-oxopropan-2-ylcarbamate | w/o | III-1 | — | 25 | Fmoc Tyr(tBu)-OH |
| III-128 | N-(2-(tetrahydro-2H-pyran-2-yloxy)ethyl)-N-(2,2-dimethoxyethyl)-6-(tert-butoxycarbonylamino)-2-(S)-(9H-fluoren-9-yl)methoxycarbonylaminohexamide | w/o | III-1 | — | 25 | Fmoc-Lys(Boc)-OH |

TABLE C3-continued

| Ex. No. | chemical name | purification | syn. | yield (%) | Int_IX | Int_X |
|---|---|---|---|---|---|---|
| III-129 | (3S)-tert-butyl 3-(((9H-fluoren-9-yl)methoxy)carbonylamino)-4-((2,2-diethoxyethyl)(2-(tetrahydro-2H-pyran-2-yloxy)ethyl)amino)-4-oxobutanoate | w/o | III-1 | — | 25 | Fmoc-Asp(OtBu)-OH |
| III-130 | (9H-fluoren-9-yl)methyl (2S)-1-((2,2-diethoxyethyl)(2-(tetrahydro-2H-pyran-2-yloxy)ethyl)amino)-1,4-dioxo-4-(tritylamino)butan-2-ylcarbamate | w/o | III-1 | — | 25 | Fmoc-Asn(Trt)-OH |
| III-131 | (9H-fluoren-9-yl)methyl (2S)-3-tert-butoxy-1-((2,2-diethoxyethyl)(2-(tetrahydro-2H-pyran-2-yloxy)ethyl)amino)-1-oxopropan-2-ylcarbamate | w/o | III-1 | — | 25 | Fmoc-Ser(tBu)-OH |
| III-132 | (9H-fluoren-9-yl)methyl (2S)-1-((2,2-diethoxyethyl)(2-(tetrahydro-2H-pyran-2-yloxy)ethyl)amino)-4-methyl-1-oxopentan-2-ylcarbamate | w/o | III-1 | — | 25 | Fmoc-L-Leu-OH |
| III-133 | (9H-fluoren-9-yl)methyl (1S)-2-((2,2-diethoxyethyl)(2-(tetrahydro-2H-pyran-2-yloxy)ethyl)amino)-2-oxo-1-phenylethylcarbamate | w/o | III-1 | — | 25 | Fmoc-Phg-OH |
| III-134 | (9H-fluoren-9-yl)methyl (2S)-1-((2,2-diethoxyethyl)(2-(tetrahydro-2H-pyran-2-yloxy)ethyl)amino)-1-oxo-3-phenylpropan-2-ylcarbamate | w/o | III-1 | — | 25 | Fmoc-Phe-OH |
| III-135 | (9H-fluoren-9-yl)methyl (2S)-1-((2,2-diethoxyethyl)(2-(tetrahydro-2H-pyran-2-yloxy)ethyl)amino)-1-oxo-4-phenylbutan-2-ylcarbamate | w/o | III-1 | — | 25 | Fmoc-Hph-OH |
| III-136 | (9H-fluoren-9-yl)methyl (2S)-3-(benzyloxy)-1-((2,2-diethoxyethyl)(2-(tetrahydro-2H-pyran-2-yloxy)ethyl)amino)-1-oxopropan-2-ylcarbamate | w/o | III-1 | — | 25 | Fmoc-Ser(Bzl)-OH |
| III-137 | (9H-fluoren-9-yl)methyl (2S)-1-((2,2-diethoxyethyl)(2-(tetrahydro-2H-pyran-2-yloxy)ethyl)amino)-3-(naphthalen-1-yl)-1-oxopropan-2-ylcarbamate | w/o | III-1 | — | 25 | Fmoc-Ala(1-Naph)-OH |
| III-138 | (9H-fluoren-9-yl)methyl (2S)-1-((2,2-diethoxyethyl)(2-(tetrahydro-2H-pyran-2-yloxy)ethyl)amino)-3-(naphthalen-2-yl)-1-oxopropan-2-ylcarbamate | w/o | III-1 | — | 25 | Fmoc-Ala(2-Naph)-OH |
| III-139 | (S)-tert-butyl 3-(2-(((9H-fluoren-9-yl)methoxy)carbonylamino)-N-(2,2-diethoxyethyl)propanamido)propanoate | w/o | III-1 | — | 26 | Fmoc-Ala-OH |
| III-140 | (S)-tert-butyl 3-(2-(((9H-fluoren-9-yl)methoxy)carbonylamino)-3-(4-tert-butoxyphenyl)-N-(2,2-diethoxyethyl)propanamido)propanoate | w/o | III-1 | — | 26 | Fmoc-Tyr(tBu)-OH |
| III-141 | (S)-tert-butyl 3-(2-(((9H-fluoren-9-yl)methoxy)carbonylamino)-6-(tert-butoxycarbonylamino)-N-(2,2-diethoxyethyl)hexanamido)propanoate | w/o | III-1 | — | 26 | Fmoc-Lys(Boc)-OH |
| III-142 | (S)-tert-butyl 3-(((9H-fluoren-9-yl)methoxy)carbonylamino)-4-((3-tert-butoxy-3-oxopropyl)(2,2-diethoxyethyl)amino)-4-oxobutanoate | w/o | III-1 | — | 26 | Fmoc-Asp(OtBu)-OH |
| III-143 | (S)-tert-butyl 3-(2-(((9H-fluoren-9-yl)methoxy)carbonylamino)-N-(2,2-diethoxyethyl)-4-oxo-4-(tritylamino)butanamido)propanoate | w/o | III-1 | — | 26 | Fmoc-Asn(Trt)-OH |
| III-144 | (S)-tert-butyl 3-(2-(((9H-fluoren-9-yl)methoxy)carbonylamino)-3-tert-butoxy-N-(2,2-diethoxyethyl)propanamido)propanoate | w/o | III-1 | — | 26 | Fmoc-Ser(tBu)-OH |
| III-145 | (S)-tert-butyl 3-(2-(((9H-fluoren-9-yl)methoxy)carbonylamino)-N-(2,2-diethoxyethyl)-4-methylpentanamido)propanoate | w/o | III-1 | — | 26 | Fmoc-L-Leu-OH |
| III-146 | (S)-tert-butyl 3-(2-(((9H-fluoren-9-yl)methoxy)carbonylamino)-N-(2,2-diethoxyethyl)-2-phenylacetamido)propanoate | w/o | III-1 | — | 26 | Fmoc-Phg-OH |
| III-147 | (S)-tert-butyl 3-(2-(((9H-fluoren-9-yl)methoxy)carbonylamino)-N-(2,2-diethoxyethyl)-3-phenylpropanamido)propanoate | w/o | III-1 | — | 26 | Fmoc-Phe-OH |
| III-148 | (S)-tert-butyl 3-(2-(((9H-fluoren-9-yl)methoxy)carbonylamino)-N-(2,2-diethoxyethyl)-4-phenylbutanamido)propanoate | w/o | III-1 | — | 26 | Fmoc-Hph-OH |
| III-149 | (S)-tert-butyl 3-(2-(((9H-fluoren-9-yl)methoxy)carbonylamino)-3-(benzyloxy)-N-(2,2-diethoxyethyl)propanamido)propanoate | w/o | III-1 | — | 26 | Fmoc-Ser(Bzl)-OH |
| III-150 | (S)-tert-butyl 3-(2-(((9H-fluoren-9-yl)methoxy)carbonylamino)-N-(2,2-diethoxyethyl)-3-(naphthalen-1-yl)propanamido)propanoate | w/o | III-1 | — | 26 | Fmoc-Ala(1-Naph)-OH |
| III-151 | (S)-tert-butyl 3-(2-(((9H-fluoren-9-yl)methoxy)carbonylamino)-N-(2,2-diethoxyethyl)-3-(naphthalen-2-yl)propanamido)propanoate | w/o | III-1 | — | 26 | Fmoc-Ala(2-Naph)-OH |
| III-152 | (S)-methyl 3-(2-(((9H-fluoren-9-yl)methoxy)carbonylamino)-N-(2,2-diethoxyethyl)propanamido)propanoate | w/o | III-1 | — | 27 | Fmoc-Ala-OH |
| III-153 | (S)-methyl 3-(2-(((9H-fluoren-9-yl)methoxy)carbonylamino)-3-(4-tert-butoxyphenyl)-N-(2,2-diethoxyethyl)propanamido)propanoate | w/o | III-1 | — | 27 | Fmoc-Tyr(tBu)-OH |
| III-154 | (S)-methyl 3-(2-(((9H-fluoren-9-yl)methoxy)carbonylamino)-6-(tert-butoxycarbonylamino)-N-(2,2-diethoxyethyl)hexanamido)propanoate | w/o | III-1 | — | 27 | Fmoc-Lys(Boc)-OH |

TABLE C3-continued

| Ex. No. | chemical name | purification | syn. | yield (%) | Int_IX | Int_X |
|---|---|---|---|---|---|---|
| III-155 | (S)-tert-butyl 3-(((9H-fluoren-9-yl)methoxy)carbonylamino)-4-((2,2-diethoxyethyl)(3-methoxy-3-oxopropyl)amino)-4-oxobutanoate | w/o | III-1 | — | 27 | Fmoc-Asp(OtBu)-OH |
| III-156 | (S)-methyl 3-(2-(((9H-fluoren-9-yl)methoxy)carbonylamino)-N-(2,2-diethoxyethyl)-4-oxo-4-(tritylamino)butanamido)propanoate | w/o | III-1 | — | 27 | Fmoc-Asn(Trt)-OH |
| III-157 | (S)-methyl 3-(2-(((9H-fluoren-9-yl)methoxy)carbonylamino)-3-tert-butoxy-N-(2,2-diethoxyethyl)propanamido)propanoate | w/o | III-1 | — | 27 | Fmoc-Ser(tBu)-OH |
| III-158 | (S)-methyl 3-(2-(((9H-fluoren-9-yl)methoxy)carbonylamino)-N-(2,2-diethoxyethyl)-4-methylpentanamido)propanoate | w/o | III-1 | — | 27 | Fmoc-L-Leu-OH |
| III-159 | (S)-methyl 3-(2-(((9H-fluoren-9-yl)methoxy)carbonylamino)-N-(2,2-diethoxyethyl)-2-phenylacetamido)propanoate | w/o | III-1 | — | 27 | Fmoc-Phg-OH |
| III-160 | (S)-methyl 3-(2-(((9H-fluoren-9-yl)methoxy)carbonylamino)-N-(2,2-diethoxyethyl)-3-phenylpropanamido)propanoate | w/o | III-1 | — | 27 | Fmoc-Phe-OH |
| III-161 | (S)-methyl 3-(2-(((9H-fluoren-9-yl)methoxy)carbonylamino)-N-(2,2-diethoxyethyl)-4-phenylbutanamido)propanoate | w/o | III-1 | — | 27 | Fmoc-Hph-OH |
| III-162 | (S)-methyl 3-(2-(((9H-fluoren-9-yl)methoxy)carbonylamino)-3-(benzyloxy)-N-(2,2-diethoxyethyl)propanamido)propanoate | w/o | III-1 | — | 27 | Fmoc-Ser(Bzl)-OH |
| III-163 | (S)-methyl 3-(2-(((9H-fluoren-9-yl)methoxy)carbonylamino)-N-(2,2-diethoxyethyl)-3-(naphthalen-1-yl)propanamido)propanoate | w/o | III-1 | — | 27 | Fmoc-Ala(1-Naph)-OH |
| III-164 | (S)-methyl 3-(2-(((9H-fluoren-9-yl)methoxy)carbonylamino)-N-(2,2-diethoxyethyl)-3-(naphthalen-2-yl)propanamido)propanoate | w/o | III-1 | — | 27 | Fmoc-Ala(2-Naph)-OH |

Example IV-1

Synthesis of (S)-2-amino-3-(4-tert-butoxyphenyl)-N-(2,2-diethoxyethyl)-N-(2-tert-butoxycarbonylaminobenzothiazole-4-ylmethyl)propanamide (Compound IV-1)

To a solution of (S)-(9H-fluoren-9-yl)methyl 3-(4-tert-butoxyphenyl)-1-((2,2-diethoxyethyl)(2-tert-butoxycarbonylaminobenzothiazole-4-ylmethyl)amino)-1-oxopropan-2-ylcarbamate (Compound III-1) (482 mg, 0.58 mmol) was added 25%-piperidine/dichloromethane (4 ml) and the mixture was stirred at room temperature for 1 hr. The reaction mixture was concentrated in vacuo and the residue was purified by silica gel column chromatography (eluent: n-hexane:ethyl acetate=9:1, chloroform:methanol=100:0 and 8:2) to obtain the title compound (353.2 mg, 99%).

Example IV-2

Synthesis of (S)-2-amino-3-(4-tert-butoxyphenyl)-N-(2,2-diethoxyethyl)-N-(naphthalen-1-ylmethyl)propanamide (Compound IV-2)

According to the procedure described in the synthesis method of Compound IV-1, (S)-(9H-fluoren-9-yl)methyl 3-(4-tert-butoxyphenyl)-1-((2,2-diethoxyethyl)(naphthalen-1-ylmethyl)amino)-1-oxopropan-2-ylcarbamate (Compound III-2) (740 mg, 1.0 mmol) was treated with piperidine and the obtained residue was purified by silica gel column chromatography (eluent: n-hexane:ethyl acetate=9:1, chloroform:methanol=100:0 and 8:2) to obtain the title compound (556.1 mg, 112%).

Example IV-3

Synthesis of (S)-2-amino-3-(4-tert-butoxyphenyl)-N-(2,2-diethoxyethyl)-N-(quinolin-8-ylmethyl)propanamide (Compound IV-3)

According to the procedure described in the synthesis method of Compound IV-1, (S)-(9H-fluoren-9-yl)methyl 3-(4-tert-butoxyphenyl)-1-((2,2-diethoxyethyl)(quinolin-8-ylmethyl)amino)-1-oxopropan-2-ylcarbamate (Compound III-3) (740 mg, 1.0 mmol) was treated with piperidine and the obtained residue was purified by silica gel column chromatography (eluent: n-hexane:ethyl acetate=9:1, chloroform:methanol=100:0 and 8:2) to obtain the title compound (596.1 mg, 100%).

Example IV-4

Synthesis of (S)-2-amino-3-(4-tert-butoxyphenyl)-N-(2,2-diethoxyethyl)-N-(quinolin-4-ylmethyl)propanamide (Compound IV-4)

According to the procedure described in the synthesis method of Compound IV-1, (S)-(9H-fluoren-9-yl)methyl 3-(4-tert-butoxyphenyl)-1-((2,2-diethoxyethyl)(quinolin-4-ylmethyl)amino)-1-oxopropan-2-ylcarbamate (Compound III-4) (358 mg, 0.5 mmol) was treated with piperidine and the obtained residue was purified on silica gel column chromatography (eluent: n-hexane:ethyl acetate=9:1, chloroform:methanol=100:0 and 8:2) to obtain the title compound (241 mg, 95%).

Example IV-5

Synthesis of (S)-2-amino-3-(4-tert-butoxyphenyl)-N-((S)-1,1-diethoxypropan-2-yl)-N-(2-tert-butoxycarbonyl)aminobenzothiazol-4-ylmethyl)propanamide (Compound IV-5)

According to the procedure described in the synthesis method of Compound IV-1, (9H-fluoren-9-yl)methyl(S)-3-(4-tert-butoxyphenyl)-1-(((S)-1,1-diethoxypropan-2-yl)(2-tert-butoxycarbonyl)aminobenzothiazol-4-ylmethyl)amino)-1-oxopropan-2-ylcarbamate (Compound III-5) (85 mg, 0.1 mmol) was treated with piperidine and the obtained residue was purified by silica gel column chromatography

Example IV-6

Synthesis of (S)-2-amino-3-(4-tert-butoxyphenyl)-N-((S)-1,1-diethoxypropan-2-yl)-N-(naphthalen-1-ylmethyl)propanamide (Compound IV-6)

According to the procedure described in the synthesis method of Compound IV-1, (9H-fluoren-9-yl)methyl(S)-3-(4-tert-butoxyphenyl)-1-MS)-1,1-diethoxypropan-2-yl)(naphthalen-1-ylmethyl)amino)-1-oxopropan-2-ylcarbamate (Compound III-6) (1.34 g, 1.84 mmol) was treated with piperidine and the obtained residue was purified by silica gel column chromatography (eluent: n-hexane:ethyl acetate=9:1, chloroform:methanol=100:0 and 8:2) to obtain the title compound (928 mg, 99%).

Example IV-7

Synthesis of (S)-2-amino-3-(4-tert-butoxyphenyl)-N—((S)-1,1-diethoxypropan-2-yl)-N-(quinolin-8-ylmethyl)propanamide (Compound IV-7)

According to the procedure described in the synthesis method of Compound IV-1, (9H-fluoren-9-yl)methyl(S)-3-(4-tert-butoxyphenyl)-1-(((S)-1,1-diethoxypropan-2-yl)(quinolin-8-ylmethyl)amino)-1-oxopropan-2-ylcarbamate (Compound III-7) (2.41 g, 3.31 mmol) was treated with piperidine and the obtained residue was purified by silica gel column chromatography (eluent: n-hexane:ethyl acetate=chloroform:methanol=100:0 and 8:2) to obtain the title compound (1.29 g, 77%).

Example IV-8

Synthesis of (S)-2-amino-N-(benzo[c][1,2,5]thiadiazol-4-ylmethyl)-3-(4-tert-butoxyphenyl)-N-((S)-1,1-diethoxypropan-2-yl)propanamide (Compound IV-8)

According to the procedure described in the synthesis method of Compound IV-1, (9H-fluoren-9-yl)methyl(S)-1-((benzo[c][1,2,5]thiadiazol-4-ylmethyl)((S)-1,1-diethoxypropan-2-yl)amino)-3-(4-tert-butoxyphenyl)-1-oxopropan-2-ylcarbamate (Compound III-8) (509 mg, 0.69 mmol) was treated with piperidine and the obtained residue was purified by silica gel column chromatography (eluent: n-hexane:ethyl acetate=9:1, chloroform:methanol=100:0 and 8:2) to obtain the title compound (496 mg, 139%).

Example IV-9

Synthesis of (S)-2-amino-3-(4-tert-butoxyphenyl)-N-((S)-1,1-diethoxypropan-2-yl)-N-(isoquinolin-5-ylmethyl)propanamide (Compound IV-9)

According to the procedure described in the synthesis method of Compound IV-1, (9H-fluoren-9-yl)methyl(S)-3-(4-tert-butoxyphenyl)-1-MS)-1,1-diethoxypropan-2-yl)(isoquinolin-5-ylmethyl)amino)-1-oxopropan-2-ylcarbamate (Compound III-9) (508 mg, 0.70 mmol) was treated with piperidine and the obtained residue was purified by silica gel column chromatography (eluent: n-hexane:ethyl acetate=9:1, chloroform:methanol=100:0 and 8:2) to obtain the title compound (406 mg, 114%).

Example IV-10

Synthesis of (S)-2-amino-N-(benzo[b]thiophen-3-ylmethyl)-3-(4-tert-butoxyphenyl)-N-((S)-1,1-diethoxypropan-2-yl)propanamide (Compound IV-10)

According to the procedure described in the synthesis method of Compound IV-1, (9H-fluoren-9-yl)methyl(S)-1-((benzo[b]thiophen-3-ylmethyl)((S)-1,1-diethoxypropan-2-yl)amino)-3-(4-tert-butoxyphenyl)-1-oxopropan-2-ylcarbamate (Compound III-10) (500 mg, 0.68 mmol) was treated with piperidine and the obtained residue was purified by silica gel column chromatography (eluent: n-hexane:ethyl acetate=9:1, chloroform:methanol=100:0 and 8:2) to obtain the title compound (339 mg, 98%).

Example IV-11

Synthesis of (S)-2-amino-3-(4-tert-butoxyphenyl)-N-((5-chlorothieno[3,2-b]pyridin-3-yl)methyl)-N-((S)-1,1-diethoxypropan-2-yl)propanamide (Compound IV-11)

According to the procedure described in the synthesis method of Compound IV-1, (9H-fluoren-9-yl)methyl(S)-3-(4-tert-butoxyphenyl)-1-(((5-chlorothieno[3,2-b]pyridin-3-yl)methyl)((S)-1,1-diethoxypropan-2-yl)amino)-1-oxopropan-2-ylcarbamate (Compound III-11) (512 mg, 0.66 mmol) was treated with piperidine and the obtained residue was purified by silica gel column chromatography (eluent: n-hexane:ethyl acetate=9:1, chloroform:methanol=100:0 and 8:2) to obtain the title compound (429 mg, 119%).

Example IV-12

Synthesis of (S)-2-amino-3-(4-tert-butoxyphenyl)-N-((S)-1,1-diethoxypropan-2-yl)-N-(quinoxalin-5-ylmethyl)propanamide (Compound IV-12)

According to the procedure described in the synthesis method of Compound IV-1, (9H-fluoren-9-yl)methyl(S)-3-(4-tert-butoxyphenyl)-1-(((S)-1,1-diethoxypropan-2-yl)(quinoxalin-5-ylmethyl)amino)-1-oxopropan-2-ylcarbamate (Compound III-12) (586 mg, 0.80 mmol) was treated with piperidine and the obtained residue was purified by silica gel column chromatography (eluent: n-hexane:ethyl acetate=9:1, chloroform:methanol=100:0 and 8:2) to obtain the title compound (288 mg, 71%).

Example IV-13

Synthesis of (S)-2-amino-N-benzyl-3-(4-tert-butoxyphenyl)-N-(2,2-diethoxyethyl)propanamide (Compound IV-13)

According to the procedure described in the synthesis method of Compound IV-1, (S)-(9H-fluoren-9-yl)methyl 1-(benzyl(2,2-diethoxyethyl)amino)-3-(4-tert-butoxyphenyl)-1-oxopropan-2-ylcarbamate (Compound III-13) (3.22 g, 4.8 mmol) was treated with piperidine and the obtained residue was purified by silica gel column chromatography (eluent: n-hexane:ethyl acetate=9:1, chloroform:methanol=100:0 and 8:2) to obtain the title compound (2.26 g, 106%).

(eluent: n-hexane:ethyl acetate=9:1, chloroformmethanol=100:0 and 8:2) to obtain the title compound (51.1 mg, 81%).

Example IV-14

Synthesis of (S)-2-amino-3-(4-tert-butoxyphenyl)-N-(2,2-diethoxyethyl)-N-((R)-1-phenylethyl)propanamide (Compound IV-14)

According to the procedure described in the synthesis method of Compound IV-1, (9H-fluoren-9-yl)methyl(S)-3-(4-tert-butoxyphenyl)-1-((2,2-diethoxyethyl)((R)-1-phenylethyl)amino)-1-oxopropan-2-ylcarbamate (Compound III-14) (3.08 g, 4.5 mmol) was treated with piperidine and the obtained residue was purified by silica gel column chromatography (eluent: n-hexane:ethyl acetate=9:1, chloroform:methanol=100:0 and 8:2) to obtain the title compound (1.99 g, 97%).

Example IV-15

Synthesis of (S)-2-amino-3-(4-tert-butoxyphenyl)-N-(2,2-diethoxyethyl)-N-(pyridin-4-ylmethyl)propanamide (Compound IV-15)

According to the procedure described in the synthesis method of Compound IV-1, (S)-(9H-fluoren-9-yl)methyl 3-(4-tert-butoxyphenyl)-1-((2,2-diethoxyethyl)(pyridin-4-ylmethyl)amino)-1-oxopropan-2-ylcarbamate (Compound III-15) (3.1 g, 4.6 mmol) was treated with piperidine and the obtained residue was purified by silica gel column chromatography (eluent: n-hexane:ethyl acetate=9:1, chloroform:methanol=100:0 and 8:2) to obtain the title compound (1.98 g, 97%).

Example IV-16

Synthesis of (S)-2-amino-3-(4-tert-butoxyphenyl)-N-(2,2-diethoxyethyl)-N-(pyridin-2-ylmethyl)propanamide (Compound IV-16)

According to the procedure described in the synthesis method of Compound IV-1, (S)-(9H-fluoren-9-yl)methyl 3-(4-tert-butoxyphenyl)-1-((2,2-diethoxyethyl)(pyridin-2-ylmethyl)amino)-1-oxopropan-2-ylcarbamate (Compound III-16) (3.12 g, 4.6 mmol) was treated with piperidine and the obtained residue was purified by silica gel column chromatography (eluent: n-hexane:ethyl acetate=9:1, chloroform:methanol=100:0 and 8:2) to obtain the title compound (1.97 g, 97%).

Example IV-17

Synthesis of (S)-2-amino-3-(4-tert-butoxyphenyl)-N-(2,2-diethoxyethyl)-N-(2,4-difluorobenzyl)propanamide (Compound IV-17)

According to the procedure described in the synthesis method of Compound IV-1, (S)-(9H-fluoren-9-yl)methyl 3-(4-tert-butoxyphenyl)-1-((2,2-diethoxyethyl)(2,4-difluorobenzyl)amino)-1-oxopropan-2-ylcarbamate (Compound III-17) (3.08 g, 4.4 mmol) was treated with piperidine and the obtained residue was purified by silica gel column chromatography (eluent: n-hexane:ethyl acetate=9:1, chloroform:methanol=100:0 and 8:2) to obtain the title compound (2.33 g, 158%).

Example IV-18

Synthesis of (S)-2-amino-N—((S)-1,1-diethoxypropan-2-yl)-3-(4-hydroxy-2,6-dimethylphenyl)-N-(quinolin-8-ylmethyl)propanamide (Compound IV-18)

According to the procedure described in the synthesis method of Compound IV-1, (9H-fluoren-9-yl)methyl(S)-1-(((S)-1,1-diethoxypropan-2-yl)(quinolin-8-ylmethyl)amino)-3-(4-hydroxy-2,6-dimethylphenyl)-1-oxopropan-2-ylcarbamate (Compound III-18) (512 mg, 0.73 mmol) was treated with piperidine and the obtained residue was purified by silica gel column chromatography (eluent: n-hexane:ethyl acetate=9:1, chloroform:methanol=100:0 and 8:2) to obtain the title compound (404 mg, 115%).

Typical examples of the compound IV of the present invention that can be given by reacting and treating corresponding starting compounds using any of the methods described in the present specification are shown in Table C4. The compounds were prepared according to the preparation methods of the compound numbers (e.g., "IV-1") shown in the columns of "Syn" in the table. In the columns of weight, number indicates weight (mg) of the obtained desired product. In the columns of yield, number indicates yield (%) of the desired product. "Int" means an intermediate compound number.

TABLE C4

| Ex. No. | chemical name | syn. | weight (mg) | yield (%) | Int |
|---|---|---|---|---|---|
| IV-19 | (S)-2-amino-N-benzyl-N-(2,2-diethoxyethyl)propanamide | IV-1 | 640 | 100 | III-19 |
| IV-20 | (S)-tert-butyl 5-amino-6-(benzyl(2,2-diethoxyethyl)amino)-6-oxohexylcarbamate | IV-1 | 1980 | 104 | III-20 |
| IV-21 | (S)-tert-butyl 3-amino-4-(benzyl(2,2-diethoxyethyl)amino)-4-oxobutanoate | IV-1 | 1250 | 101 | III-21 |
| IV-22 | (S)-2-amino-N1-benzyl-N1-(2,2-diethoxyethyl)-N4-tritylsuccinamide | IV-1 | 2110 | 96 | III-22 |
| IV-23 | (S)-2-amino-N-(2,2-diethoxyethyl)-N-(naphthalen-1-ylmethyl)propanamide | IV-1 | 670 | 97 | III-23 |
| IV-24 | (S)-tert-butyl 5-amino-6-((2,2-diethoxyethyl)(naphthalen-1-ylmethyl)amino)-6-oxohexylcarbamate | IV-1 | 1160 | 116 | III-24 |
| IV-25 | (S)-tert-butyl 3-amino-4-((2,2-diethoxyethyl)(naphthalen-1-ylmethyl)amino)-4-oxobutanoate | IV-1 | 770 | 87 | III-25 |
| IV-26 | (S)-2-amino-N1-(2,2-diethoxyethyl)-N1-(naphthalen-1-ylmethyl)-N4-tritylsuccinamide | IV-1 | 810 | 129 | III-26 |
| IV-27 | (S)-2-amino-N-(2,2-diethoxyethyl)-N-(quinolin-8-ylmethyl)propanamide | IV-1 | 1020 | 46 | III-27 |

TABLE C4-continued

| Ex. No. | chemical name | syn. | weight (mg) | yield (%) | Int |
|---|---|---|---|---|---|
| IV-28 | (S)-tert-butyl 5-amino-6-((2,2-diethoxyethyl)(quinolin-8-ylmethyl)amino)-6-oxohexylcarbamate | IV-1 | 1750 | 44 | III-28 |
| IV-29 | (S)-tert-butyl 3-amino-4-((2,2-diethoxyethyl)(quinolin-8-ylmethyl)amino)-4-oxobutanoate | IV-1 | 930 | 26 | III-29 |
| IV-30 | (S)-2-amino-N1-(2,2-diethoxyethyl)-N1-(quinolin-8-ylmethyl)-N4-tritylsuccinamide | IV-1 | 1520 | 77 | III-30 |
| IV-31 | (S)-2-amino-N-(benzo[b]thiophen-3-ylmethyl)-N-(2,2-diethoxyethyl)propanamide | IV-1 | 1890 | 81 | III-31 |
| IV-32 | (S)-2-amino-N-(benzo[b]thiophen-3-ylmethyl)-3-(4-tert-butoxyphenyl)-N-(2,2-diethoxyethyl)propanamide | IV-1 | 2140 | 60 | III-32 |
| IV-33 | (S)-tert-butyl 5-amino-6-((benzo[b]thiophen-3-ylmethyl)(2,2-diethoxyethyl)amino)-6-oxohexylcarbamate | IV-1 | 2560 | 95 | III-33 |
| IV-34 | (S)-tert-butyl 3-amino-4-((benzo[b]thiophen-3-ylmethyl)(2,2-diethoxyethyl)amino)-4-oxobutanoate | IV-1 | 2510 | 93 | III-34 |
| IV-35 | (S)-2-amino-N1-(benzo[b]thiophen-3-ylmethyl)-N1-(2,2-diethoxyethyl)-N4-tritylsuccinamide | IV-1 | 2680 | 80 | III-35 |
| IV-36 | (S)-2-amino-N-(2,2-diethoxyethyl)-N-isopentylpropanamide | IV-1 | 89.2 | 54 | III-36 |
| IV-37 | (S)-2-amino-3-(4-tert-butoxyphenyl)-N-(2,2-diethoxyethyl)-N-isopentylpropanamide | IV-1 | 201.3 | 79 | III-37 |
| IV-38 | (S)-tert-butyl 5-amino-6-((2,2-diethoxyethyl)(isopentyl)amino)-6-oxohexylcarbamate | IV-1 | 179.2 | 69 | III-38 |
| IV-39 | (S)-tert-butyl 3-amino-4-((2,2-diethoxyethyl)(isopentyl)amino)-4-oxobutanoate | IV-1 | 120.1 | 53 | III-39 |
| IV-40 | (S)-2-amino-N1-(2,2-diethoxyethyl)-N1-isopentyl-N4-tritylsuccinamide | IV-1 | 248.2 | 74 | III-40 |
| IV-41 | (S)-2-amino-3-tert-butoxy-N-(2,2-diethoxyethyl)-N-isopentylpropanamide | IV-1 | 111.6 | 54 | III-41 |
| IV-42 | (S)-2-amino-N-(2,2-diethoxyethyl)-N-isopentyl-4-methylpentanamide | IV-1 | 93.7 | 49 | III-42 |
| IV-43 | (S)-2-amino-N-(2,2-diethoxyethyl)-N-isopentyl-2-phenylacetamide | IV-1 | 146.8 | 73 | III-43 |
| IV-44 | (S)-2-amino-N-(2,2-diethoxyethyl)-N-isopentyl-3-phenylpropanamide | IV-1 | 116.9 | 56 | III-44 |
| IV-45 | (S)-2-amino-N-(2,2-diethoxyethyl)-N-isopentyl-4-phenylbutanamide | IV-1 | 106.9 | 49 | III-45 |
| IV-46 | (S)-2-amino-3-(benzyloxy)-N-(2,2-diethoxyethyl)-N-isopentylpropanamide | IV-1 | 122.5 | 54 | III-46 |
| IV-47 | (S)-2-amino-N-(2,2-diethoxyethyl)-N-isopentyl-3-(naphthalen-1-yl)propanamide | IV-1 | 131.9 | 55 | III-47 |
| IV-48 | (S)-2-amino-N-(2,2-diethoxyethyl)-N-isopentyl-3-(naphthalen-2-yl)propanamide | IV-1 | 97.9 | 41 | III-48 |
| IV-49 | (S)-2-amino-N-(2,2-diethoxyethyl)-N-phenethylpropanamide | IV-1 | 134.3 | 73 | III-49 |
| IV-50 | (S)-2-amino-3-(4-tert-butoxyphenyl)-N-(2,2-diethoxyethyl)-N-phenethylpropanamide | IV-1 | 209.5 | 76 | III-50 |
| IV-51 | (S)-tert-butyl 5-amino-6-((2,2-diethoxyethyl)(phenethyl)amino)-6-oxohexylcarbamate | IV-1 | 99.1 | 36 | III-51 |
| IV-52 | (S)-tert-butyl 3-amino-4-((2,2-diethoxyethyl)(phenethyl)amino)-4-oxobutanoate | IV-1 | 131.4 | 54 | III-52 |
| IV-53 | (S)-2-amino-N1-(2,2-diethoxyethyl)-N1-phenethyl-N4-tritylsuccinamide | IV-1 | 319.1 | 90 | III-53 |
| IV-54 | (S)-2-amino-3-tert-butoxy-N-(2,2-diethoxyethyl)-N-phenethylpropanamide | IV-1 | 106.7 | 47 | III-54 |
| IV-55 | (S)-2-amino-N-(2,2-diethoxyethyl)-4-methyl-N-phenethylpentanamide | IV-1 | 89.0 | 42 | III-55 |
| IV-56 | (S)-2-amino-N-(2,2-diethoxyethyl)-N-phenethyl-2-phenylacetamide | IV-1 | 64.4 | 29 | III-56 |
| IV-57 | (S)-2-amino-N-(2,2-diethoxyethyl)-N-phenethyl-3-phenylpropanamide | IV-1 | 109.2 | 47 | III-57 |
| IV-58 | (S)-2-amino-N-(2,2-diethoxyethyl)-N-phenethyl-4-phenylbutanamide | IV-1 | 99.5 | 42 | III-58 |
| IV-59 | (S)-2-amino-3-(benzyloxy)-N-(2,2-diethoxyethyl)-N-phenethylpropanamide | IV-1 | 110.7 | 45 | III-59 |
| IV-60 | (S)-2-amino-N-(2,2-diethoxyethyl)-3-(naphthalen-1-yl)-N-phenethylpropanamide | IV-1 | 145.3 | 56 | III-60 |
| IV-61 | (S)-2-amino-N-(2,2-diethoxyethyl)-3-(naphthalen-2-yl)-N-phenethylpropanamide | IV-1 | 121.5 | 47 | III-61 |
| IV-62 | (S)-2-amino-N-(2,2-diethoxyethyl)-N-(3-phenylpropyl)propanamide | IV-1 | 140.8 | 73 | III-62 |

TABLE C4-continued

| Ex. No. | chemical name | syn. | weight (mg) | yield (%) | Int |
|---|---|---|---|---|---|
| IV-63 | (S)-2-amino-3-(4-tert-butoxyphenyl)-N-(2,2-diethoxyethyl)-N-(3-phenylpropyl)propanamide | IV-1 | 130.4 | 46 | III-63 |
| IV-64 | (S)-tert-butyl 5-amino-6-((2,2-diethoxyethyl)(3-phenylpropyl)amino)-6-oxohexylcarbamate | IV-1 | 189.0 | 66 | III-64 |
| IV-65 | (S)-tert-butyl 3-amino-4-((2,2-diethoxyethyl)(3-phenylpropyl)amino)-4-oxobutanoate | IV-1 | 40.2 | 16 | III-65 |
| IV-66 | (S)-2-amino-N1-(2,2-diethoxyethyl)-N1-(3-phenylpropyl)-N4-tritylsuccinamide | IV-1 | 131.7 | 36 | III-66 |
| IV-67 | (S)-2-amino-3-tert-butoxy-N-(2,2-diethoxyethyl)-N-(3-phenylpropyl)propanamide | IV-1 | 99.3 | 42 | III-67 |
| IV-68 | (S)-2-amino-N-(2,2-diethoxyethyl)-4-methyl-N-(3-phenylpropyl)pentanamide | IV-1 | 142.7 | 65 | III-68 |
| IV-69 | (S)-2-amino-N-(2,2-diethoxyethyl)-2-phenyl-N-(3-phenylpropyl)acetamide | IV-1 | 86.5 | 37 | III-69 |
| IV-70 | (S)-2-amino-N-(2,2-diethoxyethyl)-3-phenyl-N-(3-phenylpropyl)propanamide | IV-1 | 153.9 | 64 | III-70 |
| IV-71 | (S)-2-amino-N-(2,2-diethoxyethyl)-4-phenyl-N-(3-phenylpropyl)butanamide | IV-1 | 129.7 | 52 | III-71 |
| IV-72 | (S)-2-amino-3-(benzyloxy)-N-(2,2-diethoxyethyl)-N-(3-phenylpropyl)propanamide | IV-1 | 157.4 | 61 | III-72 |
| IV-73 | (S)-2-amino-N-(2,2-diethoxyethyl)-3-(naphthalen-1-yl)-N-(3-phenylpropyl)propanamide | IV-1 | 88.1 | 33 | III-73 |
| IV-74 | (S)-2-amino-N-(2,2-diethoxyethyl)-3-(naphthalen-2-yl)-N-(3-phenylpropyl)propanamide | IV-1 | 78.2 | 29 | III-74 |
| IV-75 | (S)-2-amino-N-(2,2-diethoxyethyl)-N-(3,3-diphenylpropyl)propanamide | IV-1 | 184.4 | 77 | III-75 |
| IV-76 | (S)-2-amino-3-(4-tert-butoxyphenyl)-N-(2,2-diethoxyethyl)-N-(3,3-diphenylpropyl)propanamide | IV-1 | 201.6 | 61 | III-76 |
| IV-77 | (S)-tert-butyl 5-amino-6-((2,2-diethoxyethyl)(3,3-diphenylpropyl)amino)-6-oxohexylcarbamate | IV-1 | 144.8 | 43 | III-77 |
| IV-78 | (S)-tert-butyl 3-amino-4-((2,2-diethoxyethyl)(3,3-diphenylpropyl)amino)-4-oxobutanoate | IV-1 | 221.8 | 74 | III-78 |
| IV-79 | (S)-2-amino-N1-(2,2-diethoxyethyl)-N1-(3,3-diphenylpropyl)-N4-tritylsuccinamide | IV-1 | 355.6 | 87 | III-79 |
| IV-80 | (S)-2-amino-3-tert-butoxy-N-(2,2-diethoxyethyl)-N-(3,3-diphenylpropyl)propanamide | IV-1 | 112.5 | 40 | III-80 |
| IV-81 | (S)-2-amino-N-(2,2-diethoxyethyl)-N-(3,3-diphenylpropyl)-4-methylpentanamide | IV-1 | 125.3 | 47 | III-81 |
| IV-82 | (S)-2-amino-N-(2,2-diethoxyethyl)-N-(3,3-diphenylpropyl)-2-phenylacetamide | IV-1 | 91.0 | 33 | III-82 |
| IV-83 | (S)-2-amino-N-(2,2-diethoxyethyl)-N-(3,3-diphenylpropyl)-3-phenylpropanamide | IV-1 | 106.3 | 37 | III-83 |
| IV-84 | (S)-2-amino-N-(2,2-diethoxyethyl)-N-(3,3-diphenylpropyl)-4-phenylbutanamide | IV-1 | 154.7 | 53 | III-84 |
| IV-85 | (S)-2-amino-3-(benzyloxy)-N-(2,2-diethoxyethyl)-N-(3,3-diphenylpropyl)propanamide | IV-1 | 187.1 | 62 | III-85 |
| IV-86 | (S)-2-amino-N-(2,2-diethoxyethyl)-N-(3,3-diphenylpropyl)-3-(naphthalen-1-yl)propanamide | IV-1 | 186.4 | 59 | III-86 |
| IV-87 | (S)-2-amino-N-(2,2-diethoxyethyl)-N-(3,3-diphenylpropyl)-3-(naphthalen-2-yl)propanamide | IV-1 | 185.8 | 59 | III-87 |
| IV-88 | (S)-2-amino-N-(2,2-diethoxyethyl)-N-(naphthalen-2-ylmethyl)propanamide | IV-1 | 125.1 | 61 | III-88 |
| IV-89 | (S)-2-amino-3-(4-tert-butoxyphenyl)-N-(2,2-diethoxyethyl)-N-(naphthalen-2-ylmethyl)propanamide | IV-1 | 215.2 | 73 | III-89 |
| IV-90 | (S)-tert-butyl 5-amino-6-((2,2-diethoxyethyl)(naphthalen-2-ylmethyl)amino)-6-oxohexylcarbamate | IV-1 | 193.4 | 64 | III-90 |
| IV-91 | (S)-tert-butyl 3-amino-4-((2,2-diethoxyethyl)(naphthalen-2-ylmethyl)amino)-4-oxobutanoate | IV-1 | 154.8 | 58 | III-91 |
| IV-92 | (S)-2-amino-N1-(2,2-diethoxyethyl)-N1-(naphthalen-2-ylmethyl)-N4-tritylsuccinamide | IV-1 | 191.9 | 51 | III-92 |
| IV-93 | (S)-2-amino-3-tert-butoxy-N-(2,2-diethoxyethyl)-N-(naphthalen-2-ylmethyl)propanamide | IV-1 | 160.7 | 64 | III-93 |
| IV-94 | (S)-2-amino-N-(2,2-diethoxyethyl)-4-methyl-N-(naphthalen-2-ylmethyl)pentanamide | IV-1 | 154.2 | 67 | III-94 |
| IV-95 | (S)-2-amino-N-(2,2-diethoxyethyl)-N-(naphthalen-2-ylmethyl)-2-phenylacetamide | IV-1 | 167.2 | 69 | III-95 |
| IV-96 | (S)-2-amino-N-(2,2-diethoxyethyl)-N-(naphthalen-2-ylmethyl)-3-phenylpropanamide | IV-1 | 165.5 | 66 | III-96 |
| IV-97 | (S)-2-amino-N-(2,2-diethoxyethyl)-N-(naphthalen-2-ylmethyl)-4-phenylbutanamide | IV-1 | 163.8 | 63 | III-97 |
| IV-98 | (S)-2-amino-3-(benzyloxy)-N-(2,2-diethoxyethyl)-N-(naphthalen-2-ylmethyl)propanamide | IV-1 | 194.2 | 72 | III-98 |

TABLE C4-continued

| Ex. No. | chemical name | syn. | weight (mg) | yield (%) | Int |
|---|---|---|---|---|---|
| IV-99 | (S)-2-amino-N-(2,2-diethoxyethyl)-3-(naphthalen-1-yl)-N-(naphthalen-2-ylmethyl)propanamide | IV-1 | 155.3 | 55 | III-99 |
| IV-100 | (S)-2-amino-N-(2,2-diethoxyethyl)-3-(naphthalen-2-yl)-N-(naphthalen-2-ylmethyl)propanamide | IV-1 | 197.8 | 70 | III-100 |
| IV-101 | (S)-2-amino-N-(2,2-diethoxyethyl)-N-(pyridin-4-ylmethyl)propanamide | IV-1 | 135.3 | 76 | III-101 |
| IV-102 | (S)-tert-butyl 5-amino-6-((2,2-diethoxyethyl)(pyridin-4-ylmethyl)amino)-6-oxohexylcarbamate | IV-1 | 95.8 | 35 | III-102 |
| IV-103 | (S)-tert-butyl 3-amino-4-((2,2-diethoxyethyl)(pyridin-4-ylmethyl)amino)-4-oxobutanoate | IV-1 | 75.5 | 32 | III-103 |
| IV-104 | (S)-2-amino-N1-(2,2-diethoxyethyl)-N1-(pyridin-4-ylmethyl)-N4-tritylsuccinamide | IV-1 | 153.9 | 44 | III-104 |
| IV-105 | (S)-2-amino-3-tert-butoxy-N-(2,2-diethoxyethyl)-N-(pyridin-4-ylmethyl)propanamide | IV-1 | 155.4 | 71 | III-105 |
| IV-106 | (S)-2-amino-N-(2,2-diethoxyethyl)-4-methyl-N-(pyridin-4-ylmethyl)pentanamide | IV-1 | 216.7 | 107 | III-106 |
| IV-107 | (S)-2-amino-N-(2,2-diethoxyethyl)-2-phenyl-N-(pyridin-4-ylmethyl)acetamide | IV-1 | 173.7 | 81 | III-107 |
| IV-108 | (S)-2-amino-N-(2,2-diethoxyethyl)-3-phenyl-N-(pyridin-4-ylmethyl)propanamide | IV-1 | 86.9 | 39 | III-108 |
| IV-109 | (S)-2-amino-N-(2,2-diethoxyethyl)-4-phenyl-N-(pyridin-4-ylmethyl)butanamide | IV-1 | 121.4 | 52 | III-109 |
| IV-110 | (S)-2-amino-3-(benzyloxy)-N-(2,2-diethoxyethyl)-N-(pyridin-4-ylmethyl)propanamide | IV-1 | 190.6 | 79 | III-110 |
| IV-111 | (S)-2-amino-N-(2,2-diethoxyethyl)-3-(naphthalen-1-yl)-N-(pyridin-4-ylmethyl)propanamide | IV-1 | 168.2 | 67 | III-111 |
| IV-112 | (S)-2-amino-N-(2,2-diethoxyethyl)-3-(naphthalen-2-yl)-N-(pyridin-4-ylmethyl)propanamide | IV-1 | 138.4 | 55 | III-112 |
| IV-113 | (S)-2-amino-N-(cyclohexylmethyl)-N-(2,2-diethoxyethyl)propanamide | IV-1 | 180.3 | 100 | III-113 |
| IV-114 | (S)-2-amino-3-(4-tert-butoxyphenyl)-N-(cyclohexylmethyl)-N-(2,2-diethoxyethyl)propanamide | IV-1 | 92.2 | 34 | III-114 |
| IV-115 | (S)-tert-butyl 5-amino-6-((cyclohexylmethyl)(2,2-diethoxyethyl)amino)-6-oxohexylcarbamate | IV-1 | 94.3 | 34 | III-115 |
| IV-116 | (S)-tert-butyl 3-amino-4-((cyclohexylmethyl)(2,2-diethoxyethyl)amino)-4-oxobutanoate | IV-1 | 227.5 | 95 | III-116 |
| IV-117 | (S)-2-amino-N1-(cyclohexylmethyl)-N1-(2,2-diethoxyethyl)-N4-tritylsuccinamide | IV-1 | 106.4 | 30 | III-117 |
| IV-118 | (S)-2-amino-3-tert-butoxy-N-(cyclohexylmethyl)-N-(2,2-diethoxyethyl)propanamide | IV-1 | 92.7 | 42 | III-118 |
| IV-119 | (S)-2-amino-N-(cyclohexylmethyl)-N-(2,2-diethoxyethyl)-4-methylpentanamide | IV-1 | 217.8 | 106 | III-119 |
| IV-120 | (S)-2-amino-N-(cyclohexylmethyl)-N-(2,2-diethoxyethyl)-2-phenylacetamide | IV-1 | 172.9 | 80 | III-120 |
| IV-121 | (S)-2-amino-N-(cyclohexylmethyl)-N-(2,2-diethoxyethyl)-3-phenylpropanamide | IV-1 | 88.6 | 39 | III-121 |
| IV-122 | (S)-2-amino-N-(cyclohexylmethyl)-N-(2,2-diethoxyethyl)-4-phenylbutanamide | IV-1 | 75.2 | 32 | III-122 |
| IV-123 | (S)-2-amino-3-(benzyloxy)-N-(cyclohexylmethyl)-N-(2,2-diethoxyethyl)propanamide | IV-1 | 225.8 | 93 | III-123 |
| IV-124 | (S)-2-amino-N-(cyclohexylmethyl)-N-(2,2-diethoxyethyl)-3-(naphthalen-1-yl)propanamide | IV-1 | 92.5 | 36 | III-124 |
| IV-125 | (S)-2-amino-N-(cyclohexylmethyl)-N-(2,2-diethoxyethyl)-3-(naphthalen-2-yl)propanamide | IV-1 | 72.7 | 28 | III-125 |
| IV-126 | (2S)-2-amino-N-(2,2-diethoxyethyl)-N-(2-(tetrahydro-2H-pyran-2-yloxy)ethyl)propanamide | IV-1 | 108.6 | 54 | III-126 |
| IV-127 | (2S)-2-amino-3-(4-tert-butoxphenyl)-N-(2,2-diethoxyethyl)-N-(2-(tetrahydro-2H-pyran-2-yloxy)ethyl)propanamide | IV-1 | 148.6 | 52 | III-127 |
| IV-128 | tert-butyl (5S)-5-amino-6-((2,2-diethoxyethyl)(2-(tetrahydro-2H-pyran-2-yloxy)ethyl)amino)-6-oxohexylcarbamate | IV-1 | 104.7 | 36 | III-128 |
| IV-129 | (3S)-tert-butyl 3-amino-4-((2,2-diethoxyethyl)(2-(tetrahydro-2H-pyran-2-yloxy)ethyl)amino)-4-oxobutanoate | IV-1 | 119.1 | 46 | III-129 |
| IV-130 | (2S)-2-amino-N1-(2,2-diethoxyethyl)-N1-(2-(tetrahydro-2H-pyran-2-yloxy)ethyl)-N4-tritylsuccinamide | IV-1 | 145.2 | 39 | III-130 |
| IV-131 | (2S)-2-amino-3-tert-butoxy-N-(2,2-diethoxyethyl)-N-(2-(tetrahydro-2H-pyran-2-yloxy)ethyl)propanamide | IV-1 | 132.6 | 55 | III-131 |
| IV-132 | (2S)-2-amino-N-(2,2-diethoxyethyl)-4-methyl-N-(2-(tetrahydro-2H-pyran-2-yloxy)ethyl)pentanamide | IV-1 | 85.4 | 38 | III-132 |

TABLE C4-continued

| Ex. No. | chemical name | syn. | weight (mg) | yield (%) | Int |
|---|---|---|---|---|---|
| IV-133 | (2S)-2-amino-N-(2,2-diethoxyethyl)-2-phenyl-N-(2-(tetrahydro-2H-pyran-2-yloxy)ethyl)acetamide | IV-1 | 131.2 | 55 | III-133 |
| IV-134 | (2S)-2-amino-N-(2,2-diethoxyethyl)-3-phenyl-N-(2-(tetrahydro-2H-pyran-2-yloxy)ethyl)propanamide | IV-1 | 95.2 | 39 | III-134 |
| IV-135 | (2S)-2-amino-N-(2,2-diethoxyethyl)-4-phenyl-N-(2-(tetrahydro-2H-pyran-2-yloxy)ethyl)butanamide | IV-1 | 76.8 | 30 | III-135 |
| IV-136 | (2S)-2-amino-3-(benzyloxy)-N-(2,2-diethoxyethyl)-N-(2-(tetrahydro-2H-pyran-2-yloxy)ethyl)propanamide | IV-1 | 85.1 | 32 | III-136 |
| IV-137 | (2S)-2-amino-N-(2,2-diethoxyethyl)-3-(naphthalen-1-yl)-N-(2-(tetrahydro-2H-pyran-2-yloxy)ethyl)propanamide | IV-1 | 76.1 | 28 | III-137 |
| IV-138 | (2S)-2-amino-N-(2,2-diethoxyethyl)-3-(naphthalen-2-yl)-N-(2-(tetrahydro-2H-pyran-2-yloxy)ethyl)propanamide | IV-1 | 132.9 | 48 | III-138 |
| IV-139 | (S)-tert-butyl 3-(2-amino-N-(2,2-diethoxyethyl)propanamido)propanoate | IV-1 | 152 | 76 | III-139 |
| IV-140 | (S)-tert-butyl 3-(2-amino-3-(4-tert-butoxyphenyl)-N-(2,2-diethoxyethyl)propanamido)propanoate | IV-1 | 225.1 | 78 | III-140 |
| IV-141 | (S)-tert-butyl 3-(2-amino-6-(tert-butoxycarbonylamino)-N-(2,2-diethoxyethyl)hexanamido)propanoate | IV-1 | 89.1 | 30 | III-141 |
| IV-142 | (S)-tert-butyl 3-amino-4-((3-tert-butoxy-3-oxopropyl)(2,2-diethoxyethyl)amino)-4-oxobutanoate | IV-1 | 111.6 | 43 | III-142 |
| IV-143 | (S)-tert-butyl 3-(2-amino-N-(2,2-diethoxyethyl)-4-oxo-4-(tritylamino)butanamido)propanoate | IV-1 | 53.2 | 14 | III-143 |
| IV-144 | (S)-tert-butyl 3-(2-amino-3-tert-butoxy-N-(2,2-diethoxyethyl)propanamido)propanoate | IV-1 | 95.6 | 39 | III-144 |
| IV-145 | (S)-tert-butyl 3-(2-amino-N-(2,2-diethoxyethyl)-4-methylpentanamido)propanoate | IV-1 | 140.8 | 63 | III-145 |
| IV-146 | (S)-tert-butyl 3-(2-amino-N-(2,2-diethoxyethyl)-2-phenylacetamido)propanoate | IV-1 | 108.4 | 46 | III-146 |
| IV-147 | (S)-tert-butyl 3-(2-amino-N-(2,2-diethoxyethyl)-3-phenylpropanamido)propanoate | IV-1 | 160.4 | 65 | III-147 |
| IV-148 | (S)-tert-butyl 3-(2-amino-N-(2,2-diethoxyethyl)-4-phenylbutanamido)propanoate | IV-1 | 135.8 | 54 | III-148 |
| IV-149 | (S)-tert-butyl 3-(2-amino-3-(benzyloxy)-N-(2,2-diethoxyethyl)propanamido)propanoate | IV-1 | 156.6 | 60 | III-149 |
| IV-150 | (S)-tert-butyl 3-(2-amino-N-(2,2-diethoxyethyl)-3-(naphthalen-1-yl)propanamido)propanoate | IV-1 | 56.6 | 21 | III-150 |
| IV-151 | (S)-tert-butyl 3-(2-amino-N-(2,2-diethoxyethyl)-3-(naphthalen-2-yl)propanamido)propanoate | IV-1 | 59.7 | 22 | III-151 |
| IV-152 | (S)-methyl 3-(2-amino-N-(2,2-diethoxyethyl)propanamido)propanoate | IV-1 | 147.9 | 85 | III-152 |
| IV-153 | (S)-methyl 3-(2-amino-3-(4-tert-butoxyphenyl)-N-(2,2-diethoxyethyl)propanamido)propanoate | IV-1 | 76.3 | 29 | III-153 |
| IV-154 | (S)-methyl 3-(2-amino-6-(tert-butoxycarbonylamino)-N-(2,2-diethoxyethyl)hexanamido)propanoate | IV-1 | 94.4 | 35 | III-154 |
| IV-155 | (S)-tert-butyl 3-amino-4-((2,2-diethoxyethyl)(3-methoxy-3-oxopropyl)amino)-4-oxobutanoate | IV-1 | 72.2 | 31 | III-155 |
| IV-156 | (S)-methyl 3-(2-amino-N-(2,2-diethoxyethyl)-4-oxo-4-(tritylamino)butanamido)propanoate | IV-1 | 76.9 | 22 | III-156 |
| IV-157 | (S)-methyl 3-(2-amino-3-tert-butoxy-N-(2,2-diethoxyethyl)propanamido)propanoate | IV-1 | 124.6 | 57 | III-157 |
| IV-158 | (S)-methyl 3-(2-amino-N-(2,2-diethoxyethyl)-4-methytpentanamido)propanoate | IV-1 | 97.3 | 49 | III-158 |
| IV-159 | (S)-methyl 3-(2-amino-N-(2,2-diethoxyethyl)-2-phenylacetamido)propanoate | IV-1 | 69.6 | 33 | III-159 |
| IV-160 | (S)-methyl 3-(2-amino-N-(2,2-diethoxyethyl)-3-phenylpropanamido)propanoate | IV-1 | 143.0 | 65 | III-160 |
| IV-161 | (S)-methyl 3-(2-amino-N-(2,2-diethoxyethyl)-4-phenylbutanamido)propanoate | IV-1 | 101.3 | 44 | III-161 |
| IV-162 | (S)-methyl 3-(2-amino-3-(benzyloxy)-N-(2,2-diethoxyethyl)propanamido)propanoate | IV-1 | 178.4 | 75 | III-162 |
| IV-163 | (S)-methyl 3-(2-amino-N-(2,2-diethoxyethyl)-3-(naphthalen-1-yl)propanamido)propanoate | IV-1 | 70.7 | 28 | III-163 |
| IV-164 | (S)-methyl 3-(2-amino-N-(2,2-diethoxyethyl)-3-(naphthalen-2-yl)propanamido)propanoate | IV-1 | 61.0 | 24 | III-164 |

Example II-1

Synthesis of (S)-1-((3-benzylureido)methyl)-N-(3-(4-tert-butoxyphenyl)-1-((2,2-diethoxyethyl)(naphthalen-1-ylmethyl)amino)-1-oxopropan-2-yl)cyclopropanecarboxamide (Compound II-1)

To a solution of 1-((3-benzylureido)methyl)cyclopropanecarboxylic acid (Compound VI-1) (182 mg, 0.77 mmol), hydroxybenzotriazol (126 mg, 0.51 mmol) and 1-ethyl-3-(3-dimethylaminopropyl)carbodiimide (98 mg, 0.51% mmol) in dichloromethane (1.5 ml) was added a solution of (S)-2-amino-3-(4-tert-butoxyphenyl)-N-(2,2-diethoxyethyl)-N-(naphthalen-1-ylmethyl)propanamide (Compound IV-2) (125 mg, 0.25 mmol) and 4-dimethylaminopyridine (16 mg, 0.13 mmol) in dichloromethane (1.5 ml) and the mixture was stirred at room temperature overnight. The reaction mixture was diluted with ethyl acetated (150 ml) and washed with saturated sodium bicarbonate (50 ml), water (10 ml) and brine (15 ml). The organic layer was dried over magnesium sulfate and filtered. The filtrate was concentrated in vacuo and the residue was purified by Purif silica gel column chromatography (eluent: n-hexanae:ethylacetate=50:50 to 0:100) to obtain the title compound (175 mg, 97%).

Example II-2

Synthesis of (S)-tert-butyl 4-((2-(1-((3-benzylureido)methyl)cyclopropanecarboxamido)-3-(4-tert-butoxyphenyl)-N-(2,2-diethoxyethyl)propanamido)methyl)benzo[d]thiazol-2-ylcarbamate (Compound II-2)

According to the procedure described in the synthesis method of Compound II-1, 1-((3-benzylureido)methyl)cyclopropanecarboxylic acid (Compound VI-1) (74 mg, 0.3 mmol) was coupled with (S)-2-amino-3-(4-tert-butoxyphenyl)-N-(2,2-diethoxyethyl)-N-(2-tert-butoxycarbonyl)aminobenzothiazol-4-ylmethyl)propanamide (Compound IV-1) (92 mg, 0.15 mmol) and the obtained residue was purified by Purif silica gel column chromatography (eluent: n-hexane:ethylacetate=50:50 to 0:100) to obtain the title compound (135 mg, 107%).

Example II-3

Synthesis of (S)-1-((3-benzylureido)methyl)-N-(3-(4-tert-butoxyphenyl)-1-((2,2-diethoxyethyl)(quinolin-8-ylmethyl)amino)-1-oxopropan-2-yl)cyclopropanecarboxamide (Compound II-3)

According to the procedure described in the synthesis method of Compound II-1, 1-((3-benzylureido)methyl)cyclopropanecarboxylic acid (Compound VI-1) (154 mg, 0.62 mmol) was coupled with (S)-2-amino-3-(4-tert-butoxyphenyl)-N-(2,2-diethoxyethyl)-N-(quinolin-8-ylmethyl)propanamide (Compound IV-3) (153 mg, 0.31 mmol) and the obtained residue was purified by Purif silica gel column chromatography (eluent: n-hexane:ethylacetate=50:50 to 0:100) to obtain the title compound (181 mg, 81%).

Example II-4

Synthesis of (S)-1-((3-benzylureido)methyl)-N-(3-(4-tert-butoxyphenyl)-1-((2,2-diethoxyethyl)(quinolin-4-ylmethyl)amino)-1-oxopropan-2-yl)cyclopropanecarboxamide (Compound II-4)

According to the procedure described in the synthesis method of Compound II-1, 1-((3-benzylureido)methyl)cyclopropanecarboxylic acid (Compound VI-1) (174 mg, 0.35 mmol) was coupled with (S)-2-amino-3-(4-tert-butoxyphenyl)-N-(2,2-diethoxyethyl)-N-(quinolin-4-ylmethyl)propanamide (Compound IV-4) (173 mg, 0.7 mmol) and the obtained residue was purified by Purif silica gel column chromatography (eluent: n-hexane:ethylacetate=50:50 to 0:100) to obtain the title compound (182 mg, 72%).

Example II-5

Synthesis of (S)-3-(3-benzylureido)-N-(3-(4-tert-butoxyphenyl)-1-((2,2-diethoxyethyl)(naphthalen-1-ylmethyl)amino)-1-oxopropan-2-yl)-3-methylbutanamide (Compound II-5)

According to the procedure described in the synthesis method of Compound II-1, 3-(3-benzylureido)-3-methylbutanoic acid (Compound VI-2) (170 mg, 0.68 mmol) was coupled with (S)-2-amino-3-(4-tert-butoxyphenyl)-N-(2,2-diethoxyethyl)-N-(naphthalen-1-ylmethyl)propanamide (Compound IV-2) (223 mg, 0.45 mmol) and the obtained residue was purified by silica gel column chromatography (eluent: n-hexane:ethylacetate=50:50 to 0:100) to obtain the title compound (289 mg, 89%).

Example II-6

Synthesis of (S)-tert-butyl 4-(9-(4-tert-butoxybenzyl)-11-(2,2-diethoxyethyl)-5,5-dimethyl-3,7,10-trioxo-1-phenyl-2,4,8,11-tetraazadodecan-12-yl)benzo[d]thiazol-2-ylcarbamate (Compound II-6)

According to the procedure described in the synthesis method of Compound II-1, 3-(3-benzylureido)-3-methylbutanoic acid (Compound VI-2) (30 mg, 0.12 mmol) was coupled with (S)-2-amino-3-(4-tert-butoxyphenyl)-N-(2,2-diethoxyethyl)-N-(2-tert-butoxycarbonyl)aminobenzothiazol-4-ylmethyl)propanamide (Compound IV-1) (61 mg, 0.1 mmol) and the obtained residue was purified by silica gel column chromatography (eluent: chloroform:methanol=100:0 to 95:5) to obtain the title compound (35.7 mg, 42%).

Example II-7

Synthesis of (S)-3-(3-benzylureido)-N-(3-(4-tert-butoxyphenyl)-1-((2,2-diethoxyethyl)(quinolin-8-ylmethyl)amino)-1-oxopropan-2-yl)-2,2-dimethylpropanamide (Compound II-7)

According to the procedure described in the synthesis method of Compound II-1, 3-(3-benzylureido)-2,2-dimethylpropanoic acid (Compound VI-3) (152 mg, 0.61 mmol) was coupled with (S)-2-amino-3-(4-tert-butoxyphenyl)-N-(2,2-diethoxyethyl)-N-(quinolin-8-ylmethyl)propanamide (Compound IV-3) (200 mg, 0.41 mmol) and the obtained residue was purified by silica gel column chromatography (eluent: chloroform:methanol=90:10) to obtain the title compound (258.1 mg, 88%).

Example II-8

Synthesis of (S)-3-(3-benzylureido)-N-(3-(4-tert-butoxyphenyl)-1-((2,2-diethoxyethyl)(naphthalen-1-ylmethyl)amino)-1-oxopropan-2-yl)-2,2-dimethylpropanamide (Compound II-8)

According to the procedure described in the synthesis method of Compound II-1, 3-(3-benzylureido)-2,2-dimethylpropanoic acid (Compound VI-3) (150 mg, 0.60 mmol) was coupled with(S)-2-amino-3-(4-tert-butoxyphenyl)-N-(2,2- diethoxyethyl)-N-(naphthalen-1-ylmethyl)propanamide (Compound IV-2) (246 mg, 0.50 mmol) and the obtained residue was purified by silica gel column chromatography (n-hexane:ethylacetate=70:30 to 50:50) to obtain the title compound (360 mg, 99%).

Example II-9

Synthesis of (S)-tert-butyl 4-(9-(4-tert-butoxybenzyl)-11-(2,2-diethoxyethyl)-6,6-dimethyl-3,7,10-trioxo-1-phenyl-2,4,8,11-tetraazadodecan-12-yl)benzo[d]thiazol-2-ylcarbamate (Compound II-9)

According to the procedure described in the synthesis method of Compound II-1, 3-(3-benzylureido)-2,2-dimethylpropanoic acid (Compound VI-3) (150 mg, 0.60 mmol) was coupled with (S)-2-amino-3-(4-tert-butoxyphenyl)-N-(2,2-diethoxyethyl)-N-(2-tert-butoxycarbonyl)aminobenzothiazol-4-ylmethyl)propanamide (Compound IV-1) (307 mg, 0.50 mmol) and the obtained residue was purified by silica gel column chromatography (eluent: n-hexane:ethylacetate=70:30 to 50:50) to obtain the title compound (339 mg, 80%).

Example II-10

Synthesis of (S)-2-allyl-N-benzyl-2-(1-(3-(4-tert-butoxyphenyl)-1-((2,2-diethoxyethyl)(naphthalen-1-ylmethyl)amino)-1-oxopropan-2-ylamino)-2-methyl-1-oxopropan-2-yl)hydrazinecarboxamide (Compound II-10)

According to the procedure described in the synthesis method of Compound II-1, 2-(1-allyl-2-(benzylcarbamoyl)hydrazinyl)-2-methylpropanoic acid (Compound VI-4) (317 mg, 1.1 mmol) was coupled with (S)-2-amino-3-(4-tert-butoxyphenyl)-N-(2,2-diethoxyethyl)-N-(naphthalen-1-ylmethyl)propanamide (Compound IV-2) (502 mg, 0.73 mmol) and the obtained residue was purified by silica gel column chromatography (eluent: chloroform:methanol=97:3) to obtain the title compound (716 mg, 128%).

Example II-11

Synthesis of (S)-2-(2-(3-benzylureidooxy)acetamido)-3-(4-tert-butoxyphenyl)-N-(2,2-diethoxyethyl)-N-(naphthalen-1-ylmethyl)propanamide (Compound II-11)

According to the procedure described in the synthesis method of Compound II-1, 2-(3-benzylureidooxy)acetic acid (Compound VI-6) (247 mg, 1.0 mmol) was coupled with (S)-2-amino-3-(4-tert-butoxyphenyl)-N-(2,2-diethoxyethyl)-N-(naphthalen-1-ylmethyl)propanamide (Compound IV-2) (502 mg, 1.0 mmol) and the obtained residue was purified by silica gel column chromatography (eluent: chloroform:methanol=98:2 to 97:3) to obtain the title compound (381 mg, 52%).

Example II-12

Synthesis of (S)-tert-butyl 4-(9-(4-tert-butoxybenzyl)-11-(2,2-diethoxyethyl)-3,7,10-trioxo-1-phenyl-5-oxa-2,4,8,11-tetraazadodecan-12-yl)benzo[d]thiazol-2-ylcarbamate (Compound II-12)

According to the procedure described in the synthesis method of Compound II-1, 2-(3-benzylureidooxy)acetic acid (Compound VI-6) (350 mg, 1.4 mmol) was coupled with (S)-2-amino-3-(4-tert-butoxyphenyl)-N-(2,2-diethoxyethyl)-N-(2-tert-butoxycarbonyl)aminobenzothiazol-4-ylmethyl)propanamide (Compound IV-1) (887 mg, 1.4 mmol) and the obtained residue was purified by silica gel column chromatography (eluent: chloroform:methanol=97:3) to obtain the title compound (656 mg, 54%).

Example II-13

Synthesis of (S)—N-benzyl-2-(1-(3-(4-tert-butoxyphenyl)-1-((2,2-diethoxyethyl)(naphthalen-1-ylmethyl)amino)-1-oxopropan-2-ylamino)-2-methyl-1-oxopropan-2-yl)-2-methylhydrazinecarboxamide (Compound II-13)

According to the procedure described in the synthesis method of Compound II-1, 2-(2-(benzylcarbamoyl)-1-methylhydrazinyl)-2-methylpropanoic acid (Compound VI-5) (441 mg, 1.67 mmol) was coupled with (S)-2-amino-3-(4-tert-butoxyphenyl)-N-(2,2-diethoxyethyl)-N-(naphthalen-1-ylmethyl)propanamide (Compound IV-2) (544.6 mg, 1.11 mmol) and the obtained residue was purified by silica gel column chromatography (eluent: chloroform:methanol=98:2) to obtain the title compound (476 mg, 58%).

Example II-14

Synthesis of (S)—N-benzyl-2-(2-(3-benzylureidooxy)acetamido)-N-(2,2-diethoxyethyl)propanamide (Compound II-14)

To a solution of 2-(3-benzylureidooxy)acetic acid (Compound VI-6) (53.8 mg, 0.24 mmol) and hydroxybenzotriazol (40.5 mg, 0.3 mmol) in dichloromethane (1 ml) were added 1-ethyl-3-(3-dimethylaminopropyl)carbodiimide (57.5 mg, 0.3 mmol) and 4-dimethylaminopyridine (2.4 mg, 0.02 mmol) and the mixture was stirred at room temperature for 0.5 hr. A solution of (S)-2-amino-N-benzyl-N-(2,2-diethoxyethyl)propanamide (Compound IV-19) (58.9 mg, 0.2 mmol) in dichloromethane (1 ml) was added to the reaction mixture and the mixture was stirred at room temperature for 18 hr. The reaction mixture was washed with sat. NaHCO$_3$ aq. (1 ml), water (1 ml) and brine (1 ml). The organic layer was filtered on Celite (1 g) and magnesium sulfate (150 mg). The filtrate was concentrated in vacuo and the residue was purified with PTLC (development solvent: chloroform:methanol=98:2) to obtain the titled compound (60 mg, 80%).

Typical examples of the compound having general formula II of the present invention that can be obtained by reacting and treating corresponding intermediates using any of the methods described in the present specification including the examples described above are shown in Table C2. In the following general formula II, $R^{91}$ and $R^{92}$ are ethyl, $R^3$, B and E are hydrogen, A is —(CHR$^7$)—, and G is oxygen. The compounds were prepared according to the preparation methods of the compound numbers (e.g., "II-14") shown in the columns of "Syn" in the tables, and "Int_1" and "Int_2" indicates intermediate compound numbers. In the column of "$R^1$", "$R^7$" and "$R^2$" indicate chemical groups in the general formula II. In the columns of yield, number indicates yield (%) of the desired product.

Genaral fomula (II)

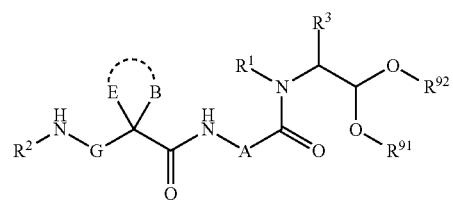

TABLE C2

| Ex. No. | R¹ | R⁷ | R² | Int_1 | Int_2 | syn. | yield (%) |
|---|---|---|---|---|---|---|---|
| II-14 | Benzyl | Methyl | Benzylaminocarbonyl | IV-19 | VI-6 | II-14 | 80 |
| II-15 | Benzyl | 4-tert-butoxybenzyl | Benzylaminocarbonyl | IV-13 | VI-6 | II-14 | 88 |
| II-16 | Benzyl | tert-butoxycarbonylaminobutyl | Benzylaminocarbonyl | IV-20 | VI-6 | II-14 | 85 |
| II-17 | Benzyl | 2-tert-butoxy-2-oxoethyl | Benzylaminocarbonyl | IV-21 | VI-6 | II-14 | 67 |
| II-18 | Benzyl | 2-oxo-2-(tritylamino)ethyl | Benzylaminocarbonyl | IV-22 | VI-6 | II-14 | 56 |
| II-19 | naphthalen-1-ylmethyl | Methyl | Benzylaminocarbonyl | IV-23 | VI-6 | II-14 | 58 |
| II-20 | naphthalen-1-ylmethyl | tert-butoxycarbonylaminobutyl | Benzylaminocarbonyl | IV-24 | VI-6 | II-14 | 59 |
| II-21 | naphthalen-1-ylmethyl | 2-tert-butoxy-2-oxoethyl | Benzylaminocarbonyl | IV-25 | VI-6 | II-14 | 98 |
| II-22 | naphthalen-1-ylmethyl | 2-oxo-2-(tritylamino)ethyl | Benzylaminocarbonyl | IV-26 | VI-6 | II-14 | 48 |
| II-23 | quinolin-8-ylmethyl | Methyl | Benzylaminocarbonyl | IV-27 | VI-6 | II-14 | 39 |
| II-24 | quinolin-8-ylmethyl | tert-butoxycarbonylaminobutyl | Benzylaminocarbonyl | IV-28 | VI-6 | II-14 | 35 |
| II-25 | quinolin-8-ylmethyl | 2-tert-butoxy-2-oxoethyl | Benzylaminocarbonyl | IV-29 | VI-6 | II-14 | 45 |
| II-26 | quinolin-8-ylmethyl | 2-oxo-2-(tritylamino)ethyl | Benzylaminocarbonyl | IV-30 | VI-6 | II-14 | 20 |
| II-27 | benzo[b]thiophen-3-ylmethyl | Methyl | Benzylaminocarbonyl | IV-31 | VI-6 | II-14 | 34 |
| II-28 | benzo[b]thiophen-3-ylmethyl | 4-tert-butoxybenzyl | Benzylaminocarbonyl | IV-32 | VI-6 | II-14 | 60 |
| II-29 | benzo[b]thiophen-3-ylmethyl | tert-butoxycarbonylaminobutyl | Benzylaminocarbonyl | IV-33 | VI-6 | II-14 | 62 |
| II-30 | benzo[b]thiophen-3-ylmethyl | 2-tert-butoxy-2-oxoethyl | Benzylaminocarbonyl | IV-34 | VI-6 | II-14 | 42 |
| II-31 | benzo[b]thiophen-3-ylmethyl | 2-oxo-2-(tritylamino)ethyl | Benzylaminocarbonyl | IV-35 | VI-6 | II-14 | 56 |
| II-32 | Benzyl | Methyl | N-(pyridin-4-ylmethyl)aminocarbonyl | IV-19 | VI-9 | II-14 | 55 |
| II-33 | Benzyl | Methyl | N-(4-chlorobenzyl)aminocarbonyl | IV-19 | VI-10 | II-14 | 52 |
| II-34 | Benzyl | Methyl | N-(naphthalen-1-ylmethyl)aminocarbonyl | IV-19 | VI-11 | II-14 | 55 |
| II-35 | Benzyl | Methyl | N-ethylaminocarbonyl | IV-19 | VI-12 | II-14 | 56 |
| II-36 | Benzyl | 4-tert-butoxybenzyl | N-(pyridin-4-ylmethyl)aminocarbonyl | IV-13 | VI-9 | II-14 | 37 |
| II-37 | Benzyl | 4-tert-butoxybenzyl | N-(4-chlorobenzyl)aminocarbonyl | IV-13 | VI-10 | II-14 | 37 |
| II-38 | Benzyl | 4-tert-butoxybenzyl | N-(naphthalen-1-ylmethyl)aminocarbonyl | IV-13 | VI-11 | II-14 | 32 |
| II-39 | Benzyl | 4-tert-butoxybenzyl | N-ethylaminocarbonyl | IV-13 | VI-12 | II-14 | 41 |
| II-40 | Benzyl | tert-butoxycarbonylaminobutyl | N-(pyridin-4-ylmethyl)aminocarbonyl | IV-20 | VI-9 | II-14 | 26 |
| II-41 | Benzyl | tert-butoxycarbonylaminobutyl | N-(4-chlorobenzyl)aminocarbonyl | IV-20 | VI-10 | II-14 | 26 |
| II-42 | Benzyl | tert-butoxycarbonylaminobutyl | N-(naphthalen-1-ylmethyl)aminocarbonyl | IV-20 | VI-11 | II-14 | 38 |
| II-43 | Benzyl | tert-butoxycarbonylaminobutyl | N-ethylaminocarbonyl | IV-20 | VI-12 | II-14 | 43 |
| II-44 | Benzyl | 2-tert-butoxy-2-oxoethyl | N-(pyridin-4-ylmethyl)aminocarbonyl | IV-21 | VI-9 | II-14 | 18 |
| II-45 | Benzyl | 2-tert-butoxy-2-oxoethyl | N-(4-chlorobenzyl)aminocarbonyl | IV-21 | VI-10 | II-14 | 28 |
| II-46 | Benzyl | 2-tert-butoxy-2-oxoethyl | N-(naphthalen-1-ylmethyl)aminocarbonyl | IV-21 | VI-11 | II-14 | 33 |
| II-47 | Benzyl | 2-tert-butoxy-2-oxoethyl | N-ethylaminocarbonyl | IV-21 | VI-12 | II-14 | 42 |
| II-48 | Benzyl | 2-oxo-2-(tritylamino)ethyl | N-(pyridin-4-ylmethyl)aminocarbonyl | IV-22 | VI-9 | II-14 | 10 |
| II-49 | Benzyl | 2-oxo-2-(tritylamino)ethyl | N-(4-chlorobenzyl)aminocarbonyl | IV-22 | VI-10 | II-14 | 17 |
| II-50 | Benzyl | 2-oxo-2-(tritylamino)ethyl | N-(naphthalen-1-ylmethyl)aminocarbonyl | IV-22 | VI-11 | II-14 | 16 |
| II-51 | Benzyl | 2-oxo-2-(tritylamino)ethyl | N-ethylaminocarbonyl | IV-22 | VI-12 | II-14 | 27 |
| II-52 | naphthalen-1-ylmethyl | Methyl | N-(pyridin-4-ylmethyl)aminocarbonyl | IV-23 | VI-9 | II-14 | 26 |
| II-53 | naphthalen-1-ylmethyl | Methyl | N-(4-chlorobenzyl)aminocarbonyl | IV-23 | VI-10 | II-14 | 36 |
| II-54 | naphthalen-1-ylmethyl | Methyl | N-(naphthalen-1-ylmethyl)aminocarbonyl | IV-23 | VI-11 | II-14 | 46 |
| II-55 | naphthalen-1-ylmethyl | Methyl | N-ethylaminocarbonyl | IV-23 | VI-12 | II-14 | 54 |
| II-56 | naphthalen-1-ylmethyl | 4-tert-butoxybenzyl | N-(pyridin-4-ylmethyl)aminocarbonyl | IV-2 | VI-9 | II-14 | 35 |
| II-57 | naphthalen-1-ylmethyl | 4-tert-butoxybenzyl | N-(4-chlorobenzyl)aminocarbonyl | IV-2 | VI-10 | II-14 | 17 |
| II-58 | naphthalen-1-ylmethyl | 4-tert-butoxybenzyl | N-(naphthalen-1-ylmethyl)aminocarbonyl | IV-2 | VI-11 | II-14 | 39 |

TABLE C2-continued

| Ex. No. | R¹ | R⁷ | R² | Int_1 | Int_2 | syn. | yield (%) |
|---|---|---|---|---|---|---|---|
| II-59 | naphthalen-1-ylmethyl | 4-tert-butoxybenzyl | N-ethylaminocarbonyl | IV-2 | VI-12 | II-14 | 70 |
| II-60 | naphthalen-1-ylmethyl | tert-butoxycarbonylamino butyl | N-(pyridin-4-ylmethyl)aminocarbonyl | IV-24 | VI-9 | II-14 | 37 |
| II-61 | naphthalen-1-ylmethyl | tert-butoxycarbonylamino butyl | N-(4-chlorobenzyl)aminocarbonyl | IV-24 | VI-10 | II-14 | 42 |
| II-62 | naphthalen-1-ylmethyl | tert-butoxycarbonylamino butyl | N-(naphthalen-1-ylmethyl)aminocarbonyl | IV-24 | VI-11 | II-14 | 48 |
| II-63 | naphthalen-1-ylmethyl | tert-butoxycarbonylamino butyl | N-ethylaminocarbonyl | IV-24 | VI-12 | II-14 | 56 |
| II-64 | naphthalen-1-ylmethyl | 2-tert-butoxy-2-oxoethyl | N-(pyridin-4-ylmethyl)aminocarbonyl | IV-25 | VI-9 | II-14 | 28 |
| II-65 | naphthalen-1-ylmethyl | 2-tert-butoxy-2-oxoethyl | N-(4-chlorobenzyl)aminocarbonyl | IV-25 | VI-10 | II-14 | 51 |
| II-66 | naphthalen-1-ylmethyl | 2-tert-butoxy-2-oxoethyl | N-(naphthalen-1-ylmethyl)aminocarbonyl | IV-25 | VI-11 | II-14 | 60 |
| II-67 | naphthalen-1-ylmethyl | 2-tert-butoxy-2-oxoethyl | N-ethylaminocarbonyl | IV-25 | VI-12 | II-14 | 50 |
| II-68 | naphthalen-1-ylmethyl | 2-oxo-2-(tritylamino)ethyl | N-(pyridin-4-ylmethyl)aminocarbonyl | IV-26 | VI-9 | II-14 | 28 |
| II-69 | naphthalen-1-ylmethyl | 2-oxo-2-(tritylamino)ethyl | N-(4-chlorobenzyl)aminocarbonyl | IV-26 | VI-10 | II-14 | 31 |
| II-70 | naphthalen-1-ylmethyl | 2-oxo-2-(tritylamino)ethyl | N-(naphthalen-1-ylmethyl)aminocarbonyl | IV-26 | VI-11 | II-14 | 30 |
| II-71 | naphthalen-1-ylmethyl | 2-oxo-2-(tritylamino)ethyl | N-ethylaminocarbonyl | IV-26 | VI-12 | II-14 | 19 |
| II-72 | quinolin-8-ylmethyl | Methyl | N-(pyridin-4-ylmethyl)aminocarbonyl | IV-27 | VI-9 | II-14 | 31 |
| II-73 | quinolin-8-ylmethyl | Methyl | N-(4-chlorobenzyl)aminocarbonyl | IV-27 | VI-10 | II-14 | 100 |
| II-74 | quinolin-8-ylmethyl | Methyl | N-(naphthalen-1-ylmethyl)aminocarbonyl | IV-27 | VI-11 | II-14 | 26 |
| II-75 | quinolin-8-ylmethyl | Methyl | N-ethylaminocarbonyl | IV-27 | VI-12 | II-14 | 26 |
| II-76 | quinolin-8-ylmethyl | 4-tert-butoxybenzyl | N-(pyridin-4-ylmethyl)aminocarbonyl | IV-3 | VI-9 | II-14 | 13 |
| II-77 | quinolin-8-ylmethyl | 4-tert-butoxybenzyl | N-(4-chlorobenzyl)aminocarbonyl | IV-3 | VI-10 | II-14 | 100 |
| II-78 | quinolin-8-ylmethyl | 4-tert-butoxybenzyl | N-(naphthalen-1-ylmethyl)aminocarbonyl | IV-3 | VI-11 | II-14 | 21 |
| II-79 | quinolin-8-ylmethyl | 4-tert-butoxybenzyl | N-ethylaminocarbonyl | IV-3 | VI-12 | II-14 | 16 |
| II-80 | quinolin-8-ylmethyl | tert-butoxycarbonylamino butyl | N-(pyridin-4-ylmethyl)aminocarbonyl | IV-28 | VI-9 | II-14 | 26 |
| II-81 | quinolin-8-ylmethyl | tert-butoxycarbonylamino butyl | N-(4-chlorobenzyl)aminocarbonyl | IV-28 | VI-10 | II-14 | 32 |
| II-82 | quinolin-8-ylmethyl | tert-butoxycarbonylamino butyl | N-(naphthalen-1-ylmethyl)aminocarbonyl | IV-28 | VI-11 | II-14 | 36 |
| II-83 | quinolin-8-ylmethyl | tert-butoxycarbonylamino butyl | N-ethylaminocarbonyl | IV-28 | VI-12 | II-14 | 33 |
| II-84 | quinolin-8-ylmethyl | 2-tert-butoxy-2-oxoethyl | N-(pyridin-4-ylmethyl)aminocarbonyl | IV-29 | VI-9 | II-14 | 24 |
| II-85 | quinolin-8-ylmethyl | 2-tert-butoxy-2-oxoethyl | N-(4-chlorobenzyl)aminocarbonyl | IV-29 | VI-10 | II-14 | 36 |
| II-86 | quinolin-8-ylmethyl | 2-tert-butoxy-2-oxoethyl | N-(naphthalen-1-ylmethyl)aminocarbonyl | IV-29 | VI-11 | II-14 | 34 |
| II-87 | quinolin-8-ylmethyl | 2-tert-butoxy-2-oxoethyl | N-ethylaminocarbonyl | IV-29 | VI-12 | II-14 | 37 |
| II-88 | quinolin-8-ylmethyl | 2-oxo-2-(tritylamino)ethyl | N-(pyridin-4-ylmethyl)aminocarbonyl | IV-30 | VI-9 | II-14 | 8 |
| II-89 | quinolin-8-ylmethyl | 2-oxo-2-(tritylamino)ethyl | N-(4-chlorobenzyl)aminocarbonyl | IV-30 | VI-10 | II-14 | 21 |
| II-90 | quinolin-8-ylmethyl | 2-oxo-2-(tritylamino)ethyl | N-(naphthalen-1-ylmethyl)aminocarbonyl | IV-30 | VI-11 | II-14 | 22 |
| II-91 | quinolin-8-ylmethyl | 2-oxo-2-(tritylamino)ethyl | N-ethylaminocarbonyl | IV-30 | VI-12 | II-14 | 24 |
| II-92 | benzo[b]thiophen-3-ylmethyl | Methyl | N-(pyridin-4-ylmethyl)aminocarbonyl | IV-31 | VI-9 | II-14 | 44 |
| II-93 | benzo[b]thiophen-3-ylmethyl | Methyl | N-(4-chlorobenzyl)aminocarbonyl | IV-31 | VI-10 | II-14 | 43 |
| II-94 | benzo[b]thiophen-3-ylmethyl | Methyl | N-(naphthalen-1-ylmethyl)aminocarbonyl | IV-31 | VI-11 | II-14 | 48 |
| II-95 | benzo[b]thiophen-3-ylmethyl | Methyl | N-ethylaminocarbonyl | IV-31 | VI-12 | II-14 | 61 |
| II-96 | benzo[b]thiophen-3-ylmethyl | 4-tert-butoxybenzyl | N-(pyridin-4-ylmethyl)aminocarbonyl | IV-32 | VI-9 | II-14 | 44 |
| II-97 | benzo[b]thiophen-3-ylmethyl | 4-tert-butoxybenzyl | N-(4-chlorobenzyl)aminocarbonyl | IV-32 | VI-10 | II-14 | 43 |
| II-98 | benzo[b]thiophen-3-ylmethyl | 4-tert-butoxybenzyl | N-(naphthalen-1-ylmethyl)aminocarbonyl | IV-32 | VI-11 | II-14 | 42 |
| II-99 | benzo[b]thiophen-3-ylmethyl | 4-tert-butoxybenzyl | N-ethylaminocarbonyl | IV-32 | VI-12 | II-14 | 59 |

TABLE C2-continued

| Ex. No. | R¹ | R⁷ | R² | Int_1 | Int_2 | syn. | yield (%) |
|---|---|---|---|---|---|---|---|
| II-100 | benzo[b]thiophen-3-ylmethyl | tert-butoxycarbonylaminobutyl | N-(pyridin-4-ylmethyl)aminocarbonyl | IV-33 | VI-9 | II-14 | 54 |
| II-101 | benzo[b]thiophen-3-ylmethyl | tert-butoxycarbonylaminobutyl | N-(4-chlorobenzyl)aminocarbonyl | IV-33 | VI-10 | II-14 | 63 |
| II-102 | benzo[b]thiophen-3-ylmethyl | tert-butoxycarbonylaminobutyl | N-(naphthalen-1-ylmethyl)aminocarbonyl | IV-33 | VI-11 | II-14 | 51 |
| II-103 | benzo[b]thiophen-3-ylmethyl | tert-butoxycarbonylaminobutyl | N-ethylaminocarbonyl | IV-33 | VI-12 | II-14 | 56 |
| II-104 | benzo[b]thiophen-3-ylmethyl | 2-tert-butoxy-2-oxoethyl | N-(pyridin-4-ylmethyl)aminocarbonyl | IV-34 | VI-9 | II-14 | 43 |
| II-105 | benzo[b]thiophen-3-ylmethyl | 2-tert-butoxy-2-oxoethyl | N-(4-chlorobenzyl)aminocarbonyl | IV-34 | VI-10 | II-14 | 44 |
| II-106 | benzo[b]thiophen-3-ylmethyl | 2-tert-butoxy-2-oxoethyl | N-(naphthalen-1-ylmethyl)aminocarbonyl | IV-34 | VI-11 | II-14 | 50 |
| II-107 | benzo[b]thiophen-3-ylmethyl | 2-tert-butoxy-2-oxoethyl | N-ethylaminocarbonyl | IV-34 | VI-12 | II-14 | 62 |
| II-108 | benzo[b]thiophen-3-ylmethyl | 2-oxo-2-(tritylamino)ethyl | N-(pyridin-4-ylmethyl)aminocarbonyl | IV-35 | VI-9 | II-14 | 38 |
| II-109 | benzo[b]thiophen-3-ylmethyl | 2-oxo-2-(tritylamino)ethyl | N-(4-chlorobenzyl)aminocarbonyl | IV-35 | VI-10 | II-14 | 51 |
| II-110 | benzo[b]thiophen-3-ylmethyl | 2-oxo-2-(tritylamino)ethyl | N-(naphthalen-1-ylmethyl)aminocarbonyl | IV-35 | VI-11 | II-14 | 54 |
| II-111 | benzo[b]thiophen-3-ylmethyl | 2-oxo-2-(tritylamino)ethyl | N-ethylaminocarbonyl | IV-35 | VI-12 | II-14 | 52 |
| II-112 | isopentyl | Methyl | benzyloxycarbonyl | IV-36 | VI-7 | II-14 | 41 |
| II-113 | isopentyl | 4-tert-butoxybenzyl | benzyloxycarbonyl | IV-37 | VI-7 | II-14 | 30 |
| II-114 | isopentyl | tert-butoxycarbonylaminobutyl | benzyloxycarbonyl | IV-38 | VI-7 | II-14 | 34 |
| II-115 | isopentyl | 2-tert-butoxy-2-oxoethyl | benzyloxycarbonyl | IV-39 | VI-7 | II-14 | 33 |
| II-116 | isopentyl | 2-oxo-2-(tritylamino)ethyl | benzyloxycarbonyl | IV-40 | VI-7 | II-14 | 16 |
| II-117 | isopentyl | 2-tert-butoxyethyl | benzyloxycarbonyl | IV-41 | VI-7 | II-14 | 47 |
| II-118 | isopentyl | 2-methylpropyl | benzyloxycarbonyl | IV-42 | VI-7 | II-14 | 50 |
| II-119 | isopentyl | Phenyl | benzyloxycarbonyl | IV-43 | VI-7 | II-14 | 44 |
| II-120 | isopentyl | Benzyl | benzyloxycarbonyl | IV-44 | VI-7 | II-14 | 53 |
| II-121 | isopentyl | phenethyl | benzyloxycarbonyl | IV-45 | VI-7 | II-14 | 51 |
| II-122 | isopentyl | benzyloxymethyl | benzyloxycarbonyl | IV-46 | VI-7 | II-14 | 50 |
| II-123 | isopentyl | naphthalen-1-ylmethyl | benzyloxycarbonyl | IV-47 | VI-7 | II-14 | 43 |
| II-124 | isopentyl | naphthalen-2-ylmethyl | benzyloxycarbonyl | IV-48 | VI-7 | II-14 | 46 |
| II-125 | phenethyl | Methyl | benzyloxycarbonyl | IV-49 | VI-7 | II-14 | 41 |
| II-126 | phenethyl | 4-tert-butoxybenzyl | benzyloxycarbonyl | IV-50 | VI-7 | II-14 | 37 |
| II-127 | phenethyl | tert-butoxycarbonylaminobutyl | benzyloxycarbonyl | IV-51 | VI-7 | II-14 | 30 |
| II-128 | phenethyl | 2-tert-butoxy-2-oxoethyl | benzyloxycarbonyl | IV-52 | VI-7 | II-14 | 38 |
| II-129 | phenethyl | 2-oxo-2-(tritylamino)ethyl | benzyloxycarbonyl | IV-53 | VI-7 | II-14 | 12 |
| II-130 | phenethyl | 2-tert-butoxyethyl | benzyloxycarbonyl | IV-54 | VI-7 | II-14 | 46 |
| II-131 | phenethyl | 2-methylpropyl | benzyloxycarbonyl | IV-55 | VI-7 | II-14 | 49 |
| II-132 | phenethyl | Phenyl | benzyloxycarbonyl | IV-56 | VI-7 | II-14 | 40 |
| II-133 | phenethyl | Benzyl | benzyloxycarbonyl | IV-57 | VI-7 | II-14 | 42 |
| II-134 | phenethyl | phenethyl | benzyloxycarbonyl | IV-58 | VI-7 | II-14 | 40 |
| II-135 | phenethyl | benzyloxymethyl | benzyloxycarbonyl | IV-59 | VI-7 | II-14 | 50 |
| II-136 | phenethyl | naphthalen-1-ylmethyl | benzyloxycarbonyl | IV-60 | VI-7 | II-14 | 47 |
| II-137 | phenethyl | naphthalen-2-ylmethyl | benzyloxycarbonyl | IV-61 | VI-7 | II-14 | 45 |
| II-138 | phenylpropyl | Methyl | benzyloxycarbonyl | IV-62 | VI-7 | II-14 | 49 |
| II-139 | phenylpropyl | 4-tert-butoxybenzyl | benzyloxycarbonyl | IV-63 | VI-7 | II-14 | 35 |
| II-140 | phenylpropyl | tert-butoxycarbonylaminobutyl | benzyloxycarbonyl | IV-64 | VI-7 | II-14 | 40 |
| II-141 | phenylpropyl | 2-tert-butoxy-2-oxoethyl | benzyloxycarbonyl | IV-65 | VI-7 | II-14 | 32 |
| II-142 | phenylpropyl | 2-oxo-2-(tritylamino)ethyl | benzyloxycarbonyl | IV-66 | VI-7 | II-14 | 13 |
| II-143 | phenylpropyl | 2-tert-butoxyethyl | benzyloxycarbonyl | IV-67 | VI-7 | II-14 | 24 |
| II-144 | phenylpropyl | 2-methylpropyl | benzyloxycarbonyl | IV-68 | VI-7 | II-14 | 45 |
| II-145 | phenylpropyl | Phenyl | benzyloxycarbonyl | IV-69 | VI-7 | II-14 | 31 |
| II-146 | phenylpropyl | Benzyl | benzyloxycarbonyl | IV-70 | VI-7 | II-14 | 46 |
| II-147 | phenylpropyl | phenethyl | benzyloxycarbonyl | IV-71 | VI-7 | II-14 | 44 |
| II-148 | phenylpropyl | benzyloxymethyl | benzyloxycarbonyl | IV-72 | VI-7 | II-14 | 43 |
| II-149 | phenylpropyl | naphthalen-1-ylmethyl | benzyloxycarbonyl | IV-73 | VI-7 | II-14 | 23 |
| II-150 | phenylpropyl | naphthalen-2-ylmethyl | benzyloxycarbonyl | IV-74 | VI-7 | II-14 | 49 |
| II-151 | 3,3-diphenylpropyl | Methyl | benzyloxycarbonyl | IV-75 | VI-7 | II-14 | 44 |

TABLE C2-continued

| Ex. No. | R¹ | R⁷ | R² | Int_1 | Int_2 | syn. | yield (%) |
|---|---|---|---|---|---|---|---|
| II-152 | 3,3-diphenylpropyl | 4-tert-butoxybenzyl | benzyloxycarbonyl | IV-76 | VI-7 | II-14 | 41 |
| II-153 | 3,3-diphenylpropyl | tert-butoxycarbonylamino butyl | benzyloxycarbonyl | IV-77 | VI-7 | II-14 | 40 |
| II-154 | 3,3-diphenylpropyl | 2-tert-butoxy-2-oxoethyl | benzyloxycarbonyl | IV-78 | VI-7 | II-14 | 42 |
| II-155 | 3,3-diphenylpropyl | 2-oxo-2-(tritylamino)ethyl | benzyloxycarbonyl | IV-79 | VI-7 | II-14 | 15 |
| II-156 | 3,3-diphenylpropyl | 2-tert-butoxyethyl | benzyloxycarbonyl | IV-80 | VI-7 | II-14 | 51 |
| II-157 | 3,3-diphenylpropyl | 2-methylpropyl | benzyloxycarbonyl | IV-81 | VI-7 | II-14 | 62 |
| II-158 | 3,3-diphenylpropyl | Phenyl | benzyloxycarbonyl | IV-82 | VI-7 | II-14 | 30 |
| II-159 | 3,3-diphenylpropyl | Benzyl | benzyloxycarbonyl | IV-83 | VI-7 | II-14 | 45 |
| II-160 | 3,3-diphenylpropyl | phenethyl | benzyloxycarbonyl | IV-84 | VI-7 | II-14 | 49 |
| II-161 | 3,3-diphenylpropyl | benzyloxymethyl | benzyloxycarbonyl | IV-85 | VI-7 | II-14 | 52 |
| II-162 | 3,3-diphenylpropyl | naphthalen-1-ylmethyl | benzyloxycarbonyl | IV-86 | VI-7 | II-14 | 46 |
| II-163 | 3,3-diphenylpropyl | naphthalen-2-ylmethyl | benzyloxycarbonyl | IV-87 | VI-7 | II-14 | 51 |
| II-164 | naphthalen-2-ylmethyl | Methyl | benzyloxycarbonyl | IV-88 | VI-7 | II-14 | 47 |
| II-165 | naphthalen-2-ylmethyl | 4-tert-butoxybenzyl | benzyloxycarbonyl | IV-89 | VI-7 | II-14 | 37 |
| II-166 | naphthalen-2-ylmethyl | tert-butoxycarbonylamino butyl | benzyloxycarbonyl | IV-90 | VI-7 | II-14 | 52 |
| II-167 | naphthalen-2-ylmethyl | 2-tert-butoxy-2-oxoethyl | benzyloxycarbonyl | IV-91 | VI-7 | II-14 | 32 |
| II-168 | naphthalen-2-ylmethyl | 2-oxo-2-(tritylamino)ethyl | benzyloxycarbonyl | IV-92 | VI-7 | II-14 | 33 |
| II-169 | naphthalen-2-ylmethyl | 2-tert-butoxyethyl | benzyloxycarbonyl | IV-93 | VI-7 | II-14 | 48 |
| II-170 | naphthalen-2-ylmethyl | 2-methylpropyl | benzyloxycarbonyl | IV-94 | VI-7 | II-14 | 45 |
| II-171 | naphthalen-2-ylmethyl | Phenyl | benzyloxycarbonyl | IV-95 | VI-7 | II-14 | 34 |
| II-172 | naphthalen-2-ylmethyl | Benzyl | benzyloxycarbonyl | IV-96 | VI-7 | II-14 | 35 |
| II-173 | naphthalen-2-ylmethyl | phenethyl | benzyloxycarbonyl | IV-97 | VI-7 | II-14 | 43 |
| II-174 | naphthalen-2-ylmethyl | benzyloxymethyl | benzyloxycarbonyl | IV-98 | VI-7 | II-14 | 39 |
| II-175 | naphthalen-2-ylmethyl | naphthalen-1-ylmethyl | benzyloxycarbonyl | IV-99 | VI-7 | II-14 | 27 |
| II-176 | naphthalen-2-ylmethyl | naphthalen-2-ylmethyl | benzyloxycarbonyl | IV-100 | VI-7 | II-14 | 20 |
| II-177 | pyridin-4-ylmethyl | Methyl | benzyloxycarbonyl | IV-101 | VI-7 | II-14 | 47 |
| II-178 | pyridin-4-ylmethyl | 4-tert-butoxybenzyl | benzyloxycarbonyl | IV-15 | VI-7 | II-14 | 12 |
| II-179 | pyridin-4-ylmethyl | tert-butoxycarbonylamino butyl | benzyloxycarbonyl | IV-102 | VI-7 | II-14 | 20 |
| II-180 | pyridin-4-ylmethyl | 2-tert-butoxy-2-oxoethyl | benzyloxycarbonyl | IV-103 | VI-7 | II-14 | 31 |
| II-181 | pyridin-4-ylmethyl | 2-oxo-2-(tritylamino)ethyl | benzyloxycarbonyl | IV-104 | VI-7 | II-14 | 20 |
| II-182 | pyridin-4-ylmethyl | 2-tert-butoxyethyl | benzyloxycarbonyl | IV-105 | VI-7 | II-14 | 31 |
| II-183 | pyridin-4-ylmethyl | 2-methylpropyl | benzyloxycarbonyl | IV-106 | VI-7 | II-14 | 29 |
| II-184 | pyridin-4-ylmethyl | Phenyl | benzyloxycarbonyl | IV-107 | VI-7 | II-14 | 22 |
| II-185 | pyridin-4-ylmethyl | Benzyl | benzyloxycarbonyl | IV-108 | VI-7 | II-14 | 25 |
| II-186 | pyridin-4-ylmethyl | phenethyl | benzyloxycarbonyl | IV-109 | VI-7 | II-14 | 28 |
| II-187 | pyridin-4-ylmethyl | benzyloxymethyl | benzyloxycarbonyl | IV-110 | VI-7 | II-14 | 20 |
| II-188 | pyridin-4-ylmethyl | naphthalen-1-ylmethyl | benzyloxycarbonyl | IV-111 | VI-7 | II-14 | 20 |
| II-189 | pyridin-4-ylmethyl | naphthalen-2-ylmethyl | benzyloxycarbonyl | IV-112 | VI-7 | II-14 | 35 |
| II-190 | cyclohexylmethyl | Methyl | benzyloxycarbonyl | IV-113 | VI-7 | II-14 | 50 |
| II-191 | cyclohexylmethyl | 4-tert-butoxybenzyl | benzyloxycarbonyl | IV-114 | VI-7 | II-14 | 30 |
| II-192 | cyclohexylmethyl | tert-butoxycarbonylamino butyl | benzyloxycarbonyl | IV-115 | VI-7 | II-14 | 37 |
| II-193 | cyclohexylmethyl | 2-tert-butoxy-2-oxoethyl | benzyloxycarbonyl | IV-116 | VI-7 | II-14 | 42 |
| II-194 | cyclohexylmethyl | 2-oxo-2-(tritylamino)ethyl | benzyloxycarbonyl | IV-117 | VI-7 | II-14 | 40 |
| II-195 | cyclohexylmethyl | 2-tert-butoxyethyl | benzyloxycarbonyl | IV-118 | VI-7 | II-14 | 39 |
| II-196 | cyclohexylmethyl | 2-methylpropyl | benzyloxycarbonyl | IV-119 | VI-7 | II-14 | 31 |
| II-197 | cyclohexylmethyl | Phenyl | benzyloxycarbonyl | IV-120 | VI-7 | II-14 | 34 |
| II-198 | cyclohexylmethyl | Benzyl | benzyloxycarbonyl | IV-121 | VI-7 | II-14 | 40 |
| II-199 | cyclohexylmethyl | phenethyl | benzyloxycarbonyl | IV-122 | VI-7 | II-14 | 21 |
| II-200 | cyclohexylmethyl | benzyloxymethyl | benzyloxycarbonyl | IV-123 | VI-7 | II-14 | 37 |
| II-201 | cyclohexylmethyl | naphthalen-1-ylmethyl | benzyloxycarbonyl | IV-124 | VI-7 | II-14 | 26 |
| II-202 | cyclohexylmethyl | naphthalen-2-ylmethyl | benzyloxycarbonyl | IV-125 | VI-7 | II-14 | 35 |
| II-203 | 2-(tetrahydro-2H-pyran-2-yloxy)ethyl | Methyl | benzyloxycarbonyl | IV-126 | VI-7 | II-14 | 42 |
| II-204 | 2-(tetrahydro-2H-pyran-2-yloxy)ethyl | 4-tert-butoxybenzyl | benzyloxycarbonyl | IV-127 | VI-7 | II-14 | 30 |
| II-205 | 2-(tetrahydro-2H-pyran-2-yloxy)ethyl | tert-butoxycarbonylamino butyl | benzyloxycarbonyl | IV-128 | VI-7 | II-14 | 26 |
| II-206 | 2-(tetrahydro-2H-pyran-2-yloxy)ethyl | 2-tert-butoxy-2-oxoethyl | benzyloxycarbonyl | IV-129 | VI-7 | II-14 | 18 |
| II-207 | 2-(tetrahydro-2H-pyran-2-yloxy)ethyl | 2-oxo-2-(tritylamino)ethyl | benzyloxycarbonyl | IV-130 | VI-7 | II-14 | 11 |
| II-208 | 2-(tetrahydro-2H-pyran-2-yloxy)ethyl | 2-tert-butoxyethyl | benzyloxycarbonyl | IV-131 | VI-7 | II-14 | 29 |

TABLE C2-continued

| Ex. No. | R¹ | R⁷ | R² | Int_1 | Int_2 | syn. | yield (%) |
|---|---|---|---|---|---|---|---|
| II-209 | 2-(tetrahydro-2H-pyran-2-yloxy)ethyl | 2-methylpropyl | benzyloxycarbonyl | IV-132 | VI-7 | II-14 | 28 |
| II-210 | 2-(tetrahydro-2H-pyran-2-yloxy)ethyl | Phenyl | benzyloxycarbonyl | IV-133 | VI-7 | II-14 | 15 |
| II-211 | 2-(tetrahydro-2H-pyran-2-yloxy)ethyl | Benzyl | benzyloxycarbonyl | IV-134 | VI-7 | II-14 | 34 |
| II-212 | 2-(tetrahydro-2H-pyran-2-yloxy)ethyl | phenethyl | benzyloxycarbonyl | IV-135 | VI-7 | II-14 | 31 |
| II-213 | 2-(tetrahydro-2H-pyran-2-yloxy)ethyl | benzyloxymethyl | benzyloxycarbonyl | IV-136 | VI-7 | II-14 | 34 |
| II-214 | 2-(tetrahydro-2H-pyran-2-yloxy)ethyl | naphthalen-1-ylmethyl | benzyloxycarbonyl | IV-137 | VI-7 | II-14 | 21 |
| II-215 | 2-(tetrahydro-2H-pyran-2-yloxy)ethyl | naphthalen-2-ylmethyl | benzyloxycarbonyl | IV-138 | VI-7 | II-14 | 25 |
| II-216 | 3-tert-butoxy-3-oxopropyl | Methyl | benzyloxycarbonyl | IV-139 | VI-7 | II-14 | 50 |
| II-217 | 3-tert-butoxy-3-oxopropyl | 4-tert-butoxybenzyl | benzyloxycarbonyl | IV-140 | VI-7 | II-14 | 25 |
| II-218 | 3-tert-butoxy-3-oxopropyl | tert-butoxycarbonylamino butyl | benzyloxycarbonyl | IV-141 | VI-7 | II-14 | 46 |
| II-219 | 3-tert-butoxy-3-oxopropyl | 2-tert-butoxy-2-oxoethyl | benzyloxycarbonyl | IV-142 | VI-7 | II-14 | 32 |
| II-220 | 3-tert-butoxy-3-oxopropyl | 2-oxo-2-(tritylamino)ethyl | benzyloxycarbonyl | IV-143 | VI-7 | II-14 | 18 |
| II-221 | 3-tert-butoxy-3-oxopropyl | 2-tert-butoxyethyl | benzyloxycarbonyl | IV-144 | VI-7 | II-14 | 33 |
| II-222 | 3-tert-butoxy-3-oxopropyl | 2-methylpropyl | benzyloxycarbonyl | IV-145 | VI-7 | II-14 | 39 |
| II-223 | 3-tert-butoxy-3-oxopropyl | Phenyl | benzyloxycarbonyl | IV-146 | VI-7 | II-14 | 25 |
| II-224 | 3-tert-butoxy-3-oxopropyl | Benzyl | benzyloxycarbonyl | IV-147 | VI-7 | II-14 | 40 |
| II-225 | 3-tert-butoxy-3-oxopropyl | phenethyl | benzyloxycarbonyl | IV-148 | VI-7 | II-14 | 30 |
| II-226 | 3-tert-butoxy-3-oxopropyl | benzyloxymethyl | benzyloxycarbonyl | IV-149 | VI-7 | II-14 | 39 |
| II-227 | 3-tert-butoxy-3-oxopropyl | naphthalen-1-ylmethyl | benzyloxycarbonyl | IV-150 | VI-7 | II-14 | 25 |
| II-228 | 3-tert-butoxy-3-oxopropyl | naphthalen-2-ylmethyl | benzyloxycarbonyl | IV-151 | VI-7 | II-14 | 39 |
| II-229 | 3-methoxy-3-oxopropyl | Methyl | benzyloxycarbonyl | IV-152 | VI-7 | II-14 | 50 |
| II-230 | 3-methoxy-3-oxopropyl | 4-tert-butoxybenzyl | benzyloxycarbonyl | IV-153 | VI-7 | II-14 | 37 |
| II-231 | 3-methoxy-3-oxopropyl | tert-butoxycarbonylamino butyl | benzyloxycarbonyl | IV-154 | VI-7 | II-14 | 13 |
| II-232 | 3-methoxy-3-oxopropyl | 2-tert-butoxy-2-oxoethyl | benzyloxycarbonyl | IV-155 | VI-7 | II-14 | 16 |
| II-233 | 3-methoxy-3-oxopropyl | 2-oxo-2-(tritylamino)ethyl | benzyloxycarbonyl | IV-156 | VI-7 | II-14 | 21 |
| II-234 | 3-methoxy-3-oxopropyl | 2-tert-butoxyethyl | benzyloxycarbonyl | IV-157 | VI-7 | II-14 | 10 |
| II-235 | 3-methoxy-3-oxopropyl | 2-methylpropyl | benzyloxycarbonyl | IV-158 | VI-7 | II-14 | 32 |
| II-236 | 3-methoxy-3-oxopropyl | Phenyl | benzyloxycarbonyl | IV-159 | VI-7 | II-14 | 13 |
| II-237 | 3-methoxy-3-oxopropyl | Benzyl | benzyloxycarbonyl | IV-160 | VI-7 | II-14 | 34 |
| II-238 | 3-methoxy-3-oxopropyl | phenethyl | benzyloxycarbonyl | IV-161 | VI-7 | II-14 | 26 |
| II-239 | 3-methoxy-3-oxopropyl | benzyloxymethyl | benzyloxycarbonyl | IV-162 | VI-7 | II-14 | 30 |
| II-240 | 3-methoxy-3-oxopropyl | naphthalen-1-ylmethyl | benzyloxycarbonyl | IV-163 | VI-7 | II-14 | 20 |
| II-241 | 3-methoxy-3-oxopropyl | naphthalen-2-ylmethyl | benzyloxycarbonyl | IV-164 | VI-7 | II-14 | 34 |
| II-242 | isopentyl | Methyl | Benzylsulfonyl | IV-36 | VI-8 | II-14 | 51 |
| II-243 | isopentyl | 4-tert-butoxybenzyl | Benzylsulfonyl | IV-37 | VI-8 | II-14 | 27 |
| II-244 | isopentyl | tert-butoxycarbonylamino butyl | Benzylsulfonyl | IV-38 | VI-8 | II-14 | 38 |
| II-245 | isopentyl | 2-tert-butoxy-2-oxoethyl | Benzylsulfonyl | IV-39 | VI-8 | II-14 | 32 |
| II-246 | isopentyl | 2-oxo-2-(tritylamino)ethyl | Benzylsulfonyl | IV-40 | VI-8 | II-14 | 9 |
| II-247 | isopentyl | 2-tert-butoxyethyl | Benzylsulfonyl | IV-41 | VI-8 | II-14 | 49 |

TABLE C2-continued

| Ex. No. | R¹ | R⁷ | R² | Int_1 | Int_2 | syn. | yield (%) |
|---|---|---|---|---|---|---|---|
| II-248 | isopentyl | 2-methylpropyl | Benzylsulfonyl | IV-42 | VI-8 | II-14 | 47 |
| II-249 | isopentyl | Phenyl | Benzylsulfonyl | IV-43 | VI-8 | II-14 | 35 |
| II-250 | isopentyl | Benzyl | Benzylsulfonyl | IV-44 | VI-8 | II-14 | 53 |
| II-251 | isopentyl | phenethyl | Benzylsulfonyl | IV-45 | VI-8 | II-14 | 44 |
| II-252 | isopentyl | benzyloxymethyl | Benzylsulfonyl | IV-46 | VI-8 | II-14 | 46 |
| II-253 | isopentyl | naphthalen-1-ylmethyl | Benzylsulfonyl | IV-47 | VI-8 | II-14 | 33 |
| II-254 | isopentyl | naphthalen-2-ylmethyl | Benzylsulfonyl | IV-48 | VI-8 | II-14 | 43 |
| II-255 | phenethyl | Methyl | Benzylsulfonyl | IV-49 | VI-8 | II-14 | 55 |
| II-256 | phenethyl | 4-tert-butoxybenzyl | Benzylsulfonyl | IV-50 | VI-8 | II-14 | 28 |
| II-257 | phenethyl | tert-butoxycarbonylaminobutyl | Benzylsulfonyl | IV-51 | VI-8 | II-14 | 29 |
| II-258 | phenethyl | 2-tert-butoxy-2-oxoethyl | Benzylsulfonyl | IV-52 | VI-8 | II-14 | 22 |
| II-259 | phenethyl | 2-oxo-2-(tritylamino)ethyl | Benzylsulfonyl | IV-53 | VI-8 | II-14 | 8 |
| II-260 | phenethyl | 2-tert-butoxyethyl | Benzylsulfonyl | IV-54 | VI-8 | II-14 | 34 |
| II-261 | phenethyl | 2-methylpropyl | Benzylsulfonyl | IV-55 | VI-8 | II-14 | 46 |
| II-262 | phenethyl | Phenyl | Benzylsulfonyl | IV-56 | VI-8 | II-14 | 26 |
| II-263 | phenethyl | Benzyl | Benzylsulfonyl | IV-57 | VI-8 | II-14 | 39 |
| II-264 | phenethyl | phenethyl | Benzylsulfonyl | IV-58 | VI-8 | II-14 | 33 |
| II-265 | phenethyl | benzyloxymethyl | Benzylsulfonyl | IV-59 | VI-8 | II-14 | 40 |
| II-266 | phenethyl | naphthalen-1-ylmethyl | Benzylsulfonyl | IV-60 | VI-8 | II-14 | 31 |
| II-267 | phenethyl | naphthalen-2-ylmethyl | Benzylsulfonyl | IV-61 | VI-8 | II-14 | 28 |
| II-268 | phenylpropyl | Methyl | Benzylsulfonyl | IV-62 | VI-8 | II-14 | 50 |
| II-269 | phenylpropyl | 4-tert-butoxybenzyl | Benzylsulfonyl | IV-63 | VI-8 | II-14 | 25 |
| II-270 | phenylpropyl | tert-butoxycarbonylaminobutyl | Benzylsulfonyl | IV-64 | VI-8 | II-14 | 34 |
| II-271 | phenylpropyl | 2-tert-butoxy-2-oxoethyl | Benzylsulfonyl | IV-65 | VI-8 | II-14 | 55 |
| II-272 | phenylpropyl | 2-oxo-2-(tritylamino)ethyl | Benzylsulfonyl | IV-66 | VI-8 | II-14 | 14 |
| II-273 | phenylpropyl | 2-tert-butoxyethyl | Benzylsulfonyl | IV-67 | VI-8 | II-14 | 19 |
| II-274 | phenylpropyl | 2-methylpropyl | Benzylsulfonyl | IV-68 | VI-8 | II-14 | 38 |
| II-275 | phenylpropyl | Phenyl | Benzylsulfonyl | IV-69 | VI-8 | II-14 | 19 |
| II-276 | phenylpropyl | Benzyl | Benzylsulfonyl | IV-70 | VI-8 | II-14 | 33 |
| II-277 | phenylpropyl | phenethyl | Benzylsulfonyl | IV-71 | VI-8 | II-14 | 26 |
| II-278 | phenylpropyl | benzyloxymethyl | Benzylsulfonyl | IV-72 | VI-8 | II-14 | 33 |
| II-279 | phenylpropyl | naphthalen-1-ylmethyl | Benzylsulfonyl | IV-73 | VI-8 | II-14 | 16 |
| II-280 | phenylpropyl | naphthalen-2-ylmethyl | Benzylsulfonyl | IV-74 | VI-8 | II-14 | 48 |
| II-281 | 3,3-diphenylpropyl | Methyl | Benzylsulfonyl | IV-75 | VI-8 | II-14 | 43 |
| II-282 | 3,3-diphenylpropyl | 4-tert-butoxybenzyl | Benzylsulfonyl | IV-76 | VI-8 | II-14 | 24 |
| II-283 | 3,3-diphenylpropyl | tert-butoxycarbonylaminobutyl | Benzylsulfonyl | IV-77 | VI-8 | II-14 | 28 |
| II-284 | 3,3-diphenylpropyl | 2-tert-butoxy-2-oxoethyl | Benzylsulfonyl | IV-78 | VI-8 | II-14 | 20 |
| II-285 | 3,3-diphenylpropyl | 2-oxo-2-(tritylamino)ethyl | Benzylsulfonyl | IV-79 | VI-8 | II-14 | 8 |
| II-286 | 3,3-diphenylpropyl | 2-tert-butoxyethyl | Benzylsulfonyl | IV-80 | VI-8 | II-14 | 36 |
| II-287 | 3,3-diphenylpropyl | 2-methylpropyl | Benzylsulfonyl | IV-81 | VI-8 | II-14 | 52 |
| II-288 | 3,3-diphenylpropyl | Phenyl | Benzylsulfonyl | IV-82 | VI-8 | II-14 | 17 |
| II-289 | 3,3-diphenylpropyl | Benzyl | Benzylsulfonyl | IV-83 | VI-8 | II-14 | 26 |
| II-290 | 3,3-diphenylpropyl | phenethyl | Benzylsulfonyl | IV-84 | VI-8 | II-14 | 28 |
| II-291 | 3,3-diphenylpropyl | benzyloxymethyl | Benzylsulfonyl | IV-85 | VI-8 | II-14 | 33 |
| II-292 | 3,3-diphenylpropyl | naphthalen-1-ylmethyl | Benzylsulfonyl | IV-86 | VI-8 | II-14 | 27 |
| II-293 | 3,3-diphenylpropyl | naphthalen-2-ylmethyl | Benzylsulfonyl | IV-87 | VI-8 | II-14 | 35 |
| II-294 | naphthalen-2-ylmethyl | Methyl | Benzylsulfonyl | IV-88 | VI-8 | II-14 | 48 |
| II-295 | naphthalen-2-ylmethyl | 4-tert-butoxybenzyl | Benzylsulfonyl | IV-89 | VI-8 | II-14 | 61 |
| II-296 | naphthalen-2-ylmethyl | tert-butoxycarbonylaminobutyl | Benzylsulfonyl | IV-90 | VI-8 | II-14 | 65 |
| II-297 | naphthalen-2-ylmethyl | 2-tert-butoxy-2-oxoethyl | Benzylsulfonyl | IV-91 | VI-8 | II-14 | 64 |
| II-298 | naphthalen-2-ylmethyl | 2-oxo-2-(tritylamino)ethyl | Benzylsulfonyl | IV-92 | VI-8 | II-14 | 54 |
| II-299 | naphthalen-2-ylmethyl | 2-tert-butoxyethyl | Benzylsulfonyl | IV-93 | VI-8 | II-14 | 58 |
| II-300 | naphthalen-2-ylmethyl | 2-methylpropyl | Benzylsulfonyl | IV-94 | VI-8 | II-14 | 56 |
| II-301 | naphthalen-2-ylmethyl | Phenyl | Benzylsulfonyl | IV-95 | VI-8 | II-14 | 65 |
| II-302 | naphthalen-2-ylmethyl | Benzyl | Benzylsulfonyl | IV-96 | VI-8 | II-14 | 62 |
| II-303 | naphthalen-2-ylmethyl | phenethyl | Benzylsulfonyl | IV-97 | VI-8 | II-14 | 54 |
| II-304 | naphthalen-2-ylmethyl | benzyloxymethyl | Benzylsulfonyl | IV-98 | VI-8 | II-14 | 58 |
| II-305 | naphthalen-2-ylmethyl | naphthalen-1-ylmethyl | Benzylsulfonyl | IV-99 | VI-8 | II-14 | 51 |
| II-306 | naphthalen-2-ylmethyl | naphthalen-2-ylmethyl | Benzylsulfonyl | IV-100 | VI-8 | II-14 | 59 |
| II-307 | pyridin-4-ylmethyl | Methyl | Benzylsulfonyl | IV-101 | VI-8 | II-14 | 51 |
| II-308 | pyridin-4-ylmethyl | 4-tert-butoxybenzyl | Benzylsulfonyl | IV-15 | VI-8 | II-14 | 8 |
| II-309 | pyridin-4-ylmethyl | tert-butoxycarbonylaminobutyl | Benzylsulfonyl | IV-102 | VI-8 | II-14 | 17 |
| II-310 | pyridin-4-ylmethyl | 2-tert-butoxy-2-oxoethyl | Benzylsulfonyl | IV-103 | VI-8 | II-14 | 48 |

TABLE C2-continued

| Ex. No. | R¹ | R⁷ | R² | Int_1 | Int_2 | syn. | yield (%) |
|---|---|---|---|---|---|---|---|
| II-311 | pyridin-4-ylmethyl | 2-oxo-2-(tritylamino)ethyl | Benzylsulfonyl | IV-104 | VI-8 | II-14 | 13 |
| II-312 | pyridin-4-ylmethyl | 2-tert-butoxyethyl | Benzylsulfonyl | IV-105 | VI-8 | II-14 | 17 |
| II-313 | pyridin-4-ylmethyl | 2-methylpropyl | Benzylsulfonyl | IV-106 | VI-8 | II-14 | 27 |
| II-314 | pyridin-4-ylmethyl | Phenyl | Benzylsulfonyl | IV-107 | VI-8 | II-14 | 22 |
| II-315 | pyridin-4-ylmethyl | Benzyl | Benzylsulfonyl | IV-108 | VI-8 | II-14 | 24 |
| II-316 | pyridin-4-ylmethyl | phenethyl | Benzylsulfonyl | IV-109 | VI-8 | II-14 | 27 |
| II-317 | pyridin-4-ylmethyl | benzyloxymethyl | Benzylsulfonyl | IV-110 | VI-8 | II-14 | 15 |
| II-318 | pyridin-4-ylmethyl | naphthalen-1-ylmethyl | Benzylsulfonyl | IV-111 | VI-8 | II-14 | 15 |
| II-319 | pyridin-4-ylmethyl | naphthalen-2-ylmethyl | Benzylsulfonyl | IV-112 | VI-8 | II-14 | 22 |
| II-320 | cyclohexylmethyl | Methyl | Benzylsulfonyl | IV-113 | VI-8 | II-14 | 50 |
| II-321 | cyclohexylmethyl | 4-tert-butoxybenzyl | Benzylsulfonyl | IV-114 | VI-8 | II-14 | 18 |
| II-322 | cyclohexylmethyl | tert-butoxycarbonylamino butyl | Benzylsulfonyl | IV-115 | VI-8 | II-14 | 33 |
| II-323 | cyclohexylmethyl | 2-tert-butoxy-2-oxoethyl | Benzylsulfonyl | IV-116 | VI-8 | II-14 | 22 |
| II-324 | cyclohexylmethyl | 2-oxo-2-(tritylamino)ethyl | Benzylsulfonyl | IV-117 | VI-8 | II-14 | 47 |
| II-325 | cyclohexylmethyl | 2-tert-butoxyethyl | Benzylsulfonyl | IV-118 | VI-8 | II-14 | 35 |
| II-326 | cyclohexylmethyl | 2-methylpropyl | Benzylsulfonyl | IV-119 | VI-8 | II-14 | 29 |
| II-327 | cyclohexylmethyl | Phenyl | Benzylsulfonyl | IV-120 | VI-8 | II-14 | 23 |
| II-328 | cyclohexylmethyl | Benzyl | Benzylsulfonyl | IV-121 | VI-8 | II-14 | 26 |
| II-329 | cyclohexylmethyl | phenethyl | Benzylsulfonyl | IV-122 | VI-8 | II-14 | 9 |
| II-330 | cyclohexylmethyl | benzyloxymethyl | Benzylsulfonyl | IV-123 | VI-8 | II-14 | 32 |
| II-331 | cyclohexylmethyl | naphthalen-1-ylmethyl | Benzylsulfonyl | IV-124 | VI-8 | II-14 | 15 |
| II-332 | cyclohexylmethyl | naphthalen-2-ylmethyl | Benzylsulfonyl | IV-125 | VI-8 | II-14 | 46 |
| II-333 | 2-(tetrahydro-2H-pyran-2-yloxy)ethyl | Methyl | Benzylsulfonyl | IV-126 | VI-8 | II-14 | 52 |
| II-334 | 2-(tetrahydro-2H-pyran-2-yloxy)ethyl | 4-tert-butoxybenzyl | Benzylsulfonyl | IV-127 | VI-8 | II-14 | 26 |
| II-335 | 2-(tetrahydro-2H-pyran-2-yloxy)ethyl | tert-butoxycarbonylamino butyl | Benzylsulfonyl | IV-128 | VI-8 | II-14 | 25 |
| II-336 | 2-(tetrahydro-2H-pyran-2-yloxy)ethyl | 2-tert-butoxy-2-oxoethyl | Benzylsulfonyl | IV-129 | VI-8 | II-14 | 17 |
| II-337 | 2-(tetrahydro-2H-pyran-2-yloxy)ethyl | 2-oxo-2-(tritylamino)ethyl | Benzylsulfonyl | IV-130 | VI-8 | II-14 | 12 |
| II-338 | 2-(tetrahydro-2H-pyran-2-yloxy)ethyl | 2-tert-butoxyethyl | Benzylsulfonyl | IV-131 | VI-8 | II-14 | 24 |
| II-339 | 2-(tetrahydro-2H-pyran-2-yloxy)ethyl | 2-methylpropyl | Benzylsulfonyl | IV-132 | VI-8 | II-14 | 24 |
| II-340 | 2-(tetrahydro-2H-pyran-2-yloxy)ethyl | Phenyl | Benzylsulfonyl | IV-133 | VI-8 | II-14 | 13 |
| II-341 | 2-(tetrahydro-2H-pyran-2-yloxy)ethyl | Benzyl | Benzylsulfonyl | IV-134 | VI-8 | II-14 | 23 |
| II-342 | 2-(tetrahydro-2H-pyran-2-yloxy)ethyl | phenethyl | Benzylsulfonyl | IV-135 | VI-8 | II-14 | 48 |
| II-343 | 2-(tetrahydro-2H-pyran-2-yloxy)ethyl | benzyloxymethyl | Benzylsulfonyl | IV-136 | VI-8 | II-14 | 19 |
| II-344 | 2-(tetrahydro-2H-pyran-2-yloxy)ethyl | naphthalen-1-ylmethyl | Benzylsulfonyl | IV-137 | VI-8 | II-14 | 100 |
| II-345 | 2-(tetrahydro-2H-pyran-2-yloxy)ethyl | naphthalen-2-ylmethyl | Benzylsulfonyl | IV-138 | VI-8 | II-14 | 100 |
| II-346 | 3-tert-butoxy-3-oxopropyl | Methyl | Benzylsulfonyl | IV-139 | VI-8 | II-14 | 54 |
| II-347 | 3-tert-butoxy-3-oxopropyl | 4-tert-butoxybenzyl | Benzylsulfonyl | IV-140 | VI-8 | II-14 | 100 |
| II-348 | 3-tert-butoxy-3-oxopropyl | tert-butoxycarbonylamino butyl | Benzylsulfonyl | IV-141 | VI-8 | II-14 | 100 |
| II-349 | 3-tert-butoxy-3-oxopropyl | 2-tert-butoxy-2-oxoethyl | Benzylsulfonyl | IV-142 | VI-8 | II-14 | 100 |
| II-350 | 3-tert-butoxy-3-oxopropyl | 2-oxo-2-(tritylamino)ethyl | Benzylsulfonyl | IV-143 | VI-8 | II-14 | 100 |
| II-351 | 3-tert-butoxy-3-oxopropyl | 2-tert-butoxyethyl | Benzylsulfonyl | IV-144 | VI-8 | II-14 | 100 |
| II-352 | 3-tert-butoxy-3-oxopropyl | 2-methylpropyl | Benzylsulfonyl | IV-145 | VI-8 | II-14 | 100 |
| II-353 | 3-tert-butoxy-3-oxopropyl | Phenyl | Benzylsulfonyl | IV-146 | VI-8 | II-14 | 100 |
| II-354 | 3-tert-butoxy-3-oxopropyl | Benzyl | Benzylsulfonyl | IV-147 | VI-8 | II-14 | 100 |
| II-355 | 3-tert-butoxy-3-oxopropyl | phenethyl | Benzylsulfonyl | IV-148 | VI-8 | II-14 | 20 |
| II-356 | 3-tert-butoxy-3-oxopropyl | benzyloxymethyl | Benzylsulfonyl | IV-149 | VI-8 | II-14 | 36 |

TABLE C2-continued

| Ex. No. | R¹ | R⁷ | R² | Int_1 | Int_2 | syn. | yield (%) |
|---|---|---|---|---|---|---|---|
| II-357 | 3-tert-butoxy-3-oxopropyl | naphthalen-1-ylmethyl | Benzylsulfonyl | IV-150 | VI-8 | II-14 | 43 |
| II-358 | 3-tert-butoxy-3-oxopropyl | naphthalen-2-ylmethyl | Benzylsulfonyl | IV-151 | VI-8 | II-14 | 51 |
| II-359 | 3-methoxy-3-oxopropyl | Methyl | Benzylsulfonyl | IV-152 | VI-8 | II-14 | 50 |
| II-360 | 3-methoxy-3-oxopropyl | 4-tert-butoxybenzyl | Benzylsulfonyl | IV-153 | VI-8 | II-14 | 44 |
| II-361 | 3-methoxy-3-oxopropyl | 2-tert-butoxy-2-oxoethyl | Benzylsulfonyl | IV-155 | VI-8 | II-14 | 11 |
| II-362 | 3-methoxy-3-oxopropyl | 2-oxo-2-(tritylamino)ethyl | Benzylsulfonyl | IV-156 | VI-8 | II-14 | 40 |
| II-363 | 3-methoxy-3-oxopropyl | 2-methylpropyl | Benzylsulfonyl | IV-158 | VI-8 | II-14 | 17 |
| II-364 | 3-methoxy-3-oxopropyl | Phenyl | Benzylsulfonyl | IV-159 | VI-8 | II-14 | 14 |
| II-365 | 3-methoxy-3-oxopropyl | Benzyl | Benzylsulfonyl | IV-160 | VI-8 | II-14 | 32 |
| II-366 | 3-methoxy-3-oxopropyl | phenethyl | Benzylsulfonyl | IV-161 | VI-8 | II-14 | 22 |
| II-367 | 3-methoxy-3-oxopropyl | benzyloxymethyl | Benzylsulfonyl | IV-162 | VI-8 | II-14 | 25 |
| II-368 | 3-methoxy-3-oxopropyl | naphthalen-1-ylmethyl | Benzylsulfonyl | IV-163 | VI-8 | II-14 | 53 |
| II-369 | 3-methoxy-3-oxopropyl | naphthalen-2-ylmethyl | Benzylsulfonyl | IV-164 | VI-8 | II-14 | 57 |

Example I-1

Synthesis of N-benzyl-6'-(4-hydroxybenzyl)-8'-(naphthalen-1-ylmethyl)-4',7'-dioxohexahydrospiro[cyclopropane-1,3'-pyrazino[1,2-a]pyrimidine]-1'(2'H)-carboxamide (Compound I-1)

To (S)-1-((3-benzylureido)methyl)-N-(3-(4-tert-butoxyphenyl)-1-2,2-diethoxyethyl)(naphthalen-1-ylmethyl)amino)-1-oxopropan-2-Yl)cyclopropanecarboxamide (Compound II-1)(188 mg, 0.26 mmol) was added 10%-HCOOH/water (2.0 ml) and the mixture was stirred at room temperature overnight. The reaction mixture was concentrated in vacuo and the residue was purified by silica gel column chromatography (eluent:chloroform:methanol=100:0 to 90:10) to obtain the title compound (47 mg, 29%).

Typical examples of the compound I of the present invention that can be given by reacting and treating corresponding starting compounds using any of the methods described in the present specification are shown in Table C1. The compounds were prepared according to the preparation methods of the compound numbers (e.g., "I-1") shown in the columns of "Syn" in the tables. "Int" means an intermediate compound number. In the tables mentioned below, data indicated by "RT" mean data of liquid chromatography retention time. In the columns of "Mass", data of mass spectrometry are shown (the indication "N.D" means that no molecular ion peak was detected). In the columns of "method", elution conditions of the liquid chromatography are described. For the indication of retention time in the liquid chromatography, the indication "A" for elution condition means that measurement was performed by elution with a linear gradient of 5 to 100% (v/v) Solution B from 0 minute to 5 minutes and then with 100% Solution B until 6 minutes. Another indications "B", "C", "D", "E", "F", "G" and "H" for elution condition in the tables are mentioned above.

TABLE C1

| Ex. No. | chemical name | Syn. | Int | method | RT | Mass |
|---|---|---|---|---|---|---|
| I-1 | N-benzyl-6'-(4-hydroxybenzyl)-8'-(naphthalen-1-ylmethyl)-4',7'-dioxohexahydrospiro[cyclopropane-1,3'-pyrazino[1,2-a]pyrimidine]-1'(2'H)-carboxamide | I-1 | II-1 | A | 4.51 | 575.1 |
| I-2 | 8'-((2-aminobenzo[d]thiazol-4-yl)methyl)-N-benzyl-6'-(4-hydroxybenzyl)-4',7'-dioxohexahydrospiro[cyclopropane-1,3'-pyrazino[1,2-a]pyrimidine]-1'(2'H)-carboxamide | I-1 | II-2 | A | 3.78 | 597.1 |
| I-3 | N-benzyl-6'-(4-hydroxybenzyl)-4',7'-dioxo-8'-(quinolin-8-ylmethyl)hexahydrospiro[cyclopropane-1,3'-pyrazino[1,2-a]pyrimidine]-1'(2'H)-carboxamide | I-1 | II-3 | A | 4.47 | 576.1 |
| I-4 | N-benzyl-6'-(4-hydroxybenzyl)-4',7'-dioxo-8'-(quinolin-4-ylmethyl)hexahydrospiro[cyclopropane-1,3'-pyrazino[1,2-a]pyrimidine]-1'(2'H)-carboxamide | I-1 | II-4 | A | 4.46 | 576.1 |
| I-5 | N-benzyl-6-(4-hydroxybenzyl)-2,2-dimethyl-8-(naphthalen-1-ylmethyl)-4,7-dioxooctahydro-1H-pyrimido[1,2-a]pyrazine-1-carboxamide | I-1 | II-5 | A | 4.49 | 577.1 |
| I-6 | 8-((2-aminobenzo[d]thiazol-4-yl)methyl)-N-benzyl-6-(4-hydroxybenzyl)-2,2-dimethyl-4,7-dioxooctahydro-1H-pyrimido[1,2-a]pyrazine-1-carboxamide | I-1 | II-6 | A | 3.89 | 599.1 |

TABLE C1-continued

| Ex. No. | chemical name | Syn. | Int | method | RT | Mass |
|---|---|---|---|---|---|---|
| I-7 | N-benzyl-6-(4-hydroxybenzyl)-2,2-dimethyl-4,7-dioxo-8-(quinolin-8-ylmethyl)octahydro-1H-pyrimido[1,2-a]pyrazine-1-carboxamide | I-1 | II-7 | A | 4.45 | 578.1 |
| I-8 | N-benzyl-6-(4-hydroxybenzyl)-3,3-dimethyl-8-(naphthalen-1-ylmethyl)-4,7-dioxooctahydro-1H-pyrimido[1,2-a]pyrazine-1-carboxamide | I-1 | II-8 | A | 4.77 | 577.3 |
| I-9 | 8-((2-aminobenzo[d]thiazol-4-yl)methyl)-N-benzyl-6-(4-hydroxybenzyl)-3,3-dimethyl-4,7-dioxooctahydro-1H-pyrimido[1,2-a]pyrazine-1-carboxamide | I-1 | II-9 | A | 3.60 | 599.1 |
| I-10 | 2-allyl-N-benzyl-6-(4-hydroxybenzyl)-3,3-dimethyl-8-(naphthalen-1-ylmethyl)-4,7-dioxooctahydro-1H-pyrazino[2,1-c][1,2,4]triazine-1-carboxamide | I-1 | II-10 | A | 5.13 | 618.2 |
| I-11 | N-benzyl-6-(4-hydroxybenzyl)-8-(naphthalen-1-ylmethyl)-4,7-dioxohexahydropyrazino[2,1-c][1,2,4]oxadiazine-1(6H)-carboxamide | I-1 | II-11 | A | 4.77 | 551.2 |
| I-12 | 8-((2-aminobenzo[d]thiazol-4-yl)methyl)-N-benzyl-6-(4-hydroxybenzyl)-4,7-dioxohexahydropyrazino[2,1-c][1,2,4]oxadiazine-1(6H)-carboxamide | I-1 | II-12 | A | 3.72 | 573.1 |
| I-13 | N-benzyl-6-(4-hydroxybenzyl)-2,3,3-trimethyl-8-(naphthalen-1-ylmethyl)-4,7-dioxooctahydro-1H-pyrazino[2,1-c][1,2,4]triazine-1-carboxamide | I-1 | II-13 | A | 4.93 | 592.2 |
| I-14 | N,8-dibenzyl-6-methyl-4,7-dioxohexahydropyrazino[2,1-c][1,2,4]oxadiazine-1(6H)-carboxamide | I-1 | II-14 | A | 4.17 | 409.5 |
| I-15 | N,8-dibenzyl-6-(4-hydroxybenzyl)-4,7-dioxohexahydropyrazino[2,1-c][1,2,4]oxadiazine-1(6H)-carboxamide | I-1 | II-15 | A | 4.29 | 501.5 |
| I-16 | 6-(4-aminobutyl)-N,8-dibenzyl-4,7-dioxohexahydropyrazino[2,1-c][1,2,4]oxadiazine-1(6H)-carboxamide | I-1 | II-16 | A | 3.06 | 466.5 |
| I-17 | 2-(8-benzyl-1-(benzylcarbamoyl)-4,7-dioxooctahydropyrazino[2,1-c][1,2,4]oxadiazin-6-yl)acetic acid | I-1 | II-17 | A | 3.93 | 453.5 |
| I-18 | 6-(2-amino-2-oxoethyl)-N,8-dibenzyl-4,7-dioxohexahydropyrazino[2,1-c][1,2,4]oxadiazine-1(6H)-carboxamide | I-1 | II-18 | A | 3.72 | 452.5 |
| I-19 | N-benzyl-6-methyl-8-(naphthalen-1-ylmethyl)-4,7-dioxohexahydropyrazino[2,1-c][1,2,4]oxadiazine-1(6H)-carboxamide | I-1 | II-19 | A | 4.65 | 459.5 |
| I-20 | 6-(4-aminobutyl)-N-benzyl-8-(naphthalen-1-ylmethyl)-4,7-dioxohexahydropyrazino[2,1-c][1,2,4]oxadiazine-1(6H)-carboxamide | I-1 | II-20 | A | 3.30 | 516.6 |
| I-21 | 2-(1-(benzylcarbamoyl)-8-(naphthalen-1-ylmethyl)-4,7-dioxooctahydropyrazino[2,1-c][1,2,4]oxadiazin-6-yl)acetic acid | I-1 | II-21 | A | 4.37 | 503.5 |
| I-22 | 6-(2-amino-2-oxoethyl)-N-benzyl-8-(naphthalen-1-ylmethyl)-4,7-dioxohexahydropyrazino[2,1-c][1,2,4]oxadiazine-1(6H)-carboxamide | I-1 | II-22 | A | 4.15 | 502.5 |
| I-23 | N-benzyl-6-methyl-4,7-dioxo-8-(quinolin-8-ylmethyl)hexahydropyrazino[2,1-c][1,2,4]oxadiazine-1(6H)-carboxamide | I-1 | II-23 | A | 3.74 | 460.5 |
| I-24 | 6-(4-aminobutyl)-N-benzyl-4,7-dioxo-8-(quinolin-8-ylmethyl)hexahydropyrazino[2,1-c][1,2,4]oxadiazine-1(6H)-carboxamide | I-1 | II-24 | A | 2.92 | 517.6 |
| I-25 | 2-(1-(benzylcarbamoyl)-4,7-dioxo-8-(quinolin-8-ylmethyl)octahydropyrazino[2,1-c][1,2,4]oxadiazin-6-yl)acetic acid | I-1 | II-25 | A | 3.44 | 504.5 |
| I-26 | 6-(2-amino-2-oxoethyl)-N-benzyl-4,7-dioxo-8-(quinolin-8-ylmethyl)hexahydropyrazino[2,1-c][1,2,4]oxadiazine-1(6H)-carboxamide | I-1 | II-26 | A | 3.24 | 503.5 |
| I-27 | 8-(benzo[b]thiophen-3-ylmethyl)-N-benzyl-6-methyl-4,7-dioxohexahydropyrazino[2,1-c][1,2,4]oxadiazine-1(6H)-carboxamide | I-1 | II-27 | A | 4.61 | 465.5 |
| I-28 | 8-(benzo[b]thiophen-3-ylmethyl)-N-benzyl-6-(4-hydroxybenzyl)-4,7-dioxohexahydropyrazino[2,1-c][1,2,4]oxadiazine-1(6H)-carboxamide | I-1 | II-28 | A | 4.71 | 557.6 |
| I-29 | 6-(4-aminobutyl)-8-(benzo[b]thiophen-3-ylmethyl)-N-benzyl-4,7-dioxohexahydropyrazino[2,1-c][1,2,4]oxadiazine-1(6H)-carboxamide | I-1 | II-29 | A | 3.32 | 522.6 |
| I-30 | 2-(8-(benzo[b]thiophen-3-ylmethyl)-1-(benzylcarbamoyl)-4,7-dioxooctahydropyrazino[2,1-c][1,2,4]oxadiazin-6-yl)acetic acid | I-1 | II-30 | A | 4.33 | 509.5 |
| I-31 | 6-(2-amino-2-oxoethyl)-8-(benzo[b]thiophen-3-ylmethyl)-N-benzyl-4,7-dioxohexahydropyrazino[2,1-c][1,2,4]oxadiazine-1(6H)-carboxamide | I-1 | II-31 | A | 4.13 | 508.6 |
| I-32 | 8-benzyl-6-methyl-4,7-dioxo-N-(pyridin-4-ylmethyl)hexahydropyrazino[2,1-c][1,2,4]oxadiazine-1(6H)-carboxamide | I-1 | II-32 | A | 2.50 | 410.4 |
| I-33 | 8-benzyl-N-(4-chlorobenzyl)-6-methyl-4,7-dioxohexahydropyrazino[2,1-c][1,2,4]oxadiazine-1(6H)-carboxamide | I-1 | II-33 | A | 4.50 | 443.9 |

TABLE C1-continued

| Ex. No. | chemical name | Syn. | Int | method | RT | Mass |
|---|---|---|---|---|---|---|
| I-34 | 8-benzyl-6-methyl-N-(naphthalen-1-ylmethyl)-4,7-dioxohexahydropyrazino[2,1-c][1,2,4]oxadiazine-1(6H)-carboxamide | I-1 | II-34 | A | 4.70 | 459.5 |
| I-35 | 8-benzyl-N-ethyl-6-methyl-4,7-dioxohexahydropyrazino[2,1-c][1,2,4]oxadiazine-1(6H)-carboxamide | I-1 | II-35 | A | 3.48 | 347.4 |
| I-36 | 8-benzyl-6-(4-hydroxybenzyl)-4,7-dioxo-N-(pyridin-4-ylmethyl)hexahydropyrazino[2,1-c][1,2,4]oxadiazine-1(6H)-carboxamide | I-1 | II-36 | A | 2.71 | 502.5 |
| I-37 | 8-benzyl-N-(4-chlorobenzyl)-6-(4-hydroxybenzyl)-4,7-dioxohexahydropyrazino[2,1-c][1,2,4]oxadiazine-1(6H)-carboxamide | I-1 | II-37 | A | 4.56 | 536.0 |
| I-38 | 8-benzyl-6-(4-hydroxybenzyl)-N-(naphthalen-1-ylmethyl)-4,7-dioxohexahydropyrazino[2,1-c][1,2,4]oxadiazine-1(6H)-carboxamide | I-1 | II-38 | A | 4.71 | 551.6 |
| I-39 | 8-benzyl-N-ethyl-6-(4-hydroxybenzyl)-4,7-dioxohexahydropyrazino[2,1-c][1,2,4]oxadiazine-1(6H)-carboxamide | I-1 | II-39 | A | 3.72 | 439.5 |
| I-40 | 6-(4-aminobutyl)-8-benzyl-4,7-dioxo-N-(pyridin-4-ylmethyl)hexahydropyrazino[2,1-c][1,2,4]oxadiazine-1(6H)-carboxamide | I-1 | II-40 | A | 2.07 | 467.5 |
| I-41 | 6-(4-aminobutyl)-8-benzyl-N-(4-chlorobenzyl)-4,7-dioxohexahydropyrazino[2,1-c][1,2,4]oxadiazine-1(6H)-carboxamide | I-1 | II-41 | A | 3.26 | 501.0 |
| I-42 | 6-(4-aminobutyl)-8-benzyl-N-(naphthalen-1-ylmethyl)-4,7-dioxohexahydropyrazino[2,1-c][1,2,4]oxadiazine-1(6H)-carboxamide | I-1 | II-42 | A | 3.34 | 516.6 |
| I-43 | 6-(4-aminobutyl)-8-benzyl-N-ethyl-4,7-dioxohexahydropyrazino[2,1-c][1,2,4]oxadiazine-1(6H)-carboxamide | I-1 | II-43 | A | 2.67 | 404.5 |
| I-44 | 2-(8-benzyl-4,7-dioxo-1-(pyridin-4-ylmethylcarbamoyl)octahydropyrazino[2,1-c][1,2,4]oxadiazin-6-yl)acetic acid | I-1 | II-44 | A | 2.40 | 454.4 |
| I-45 | 2-(8-benzyl-1-(4-chlorobenzylcarbamoyl)-4,7-dioxooctahydropyrazino[2,1-c][1,2,4]oxadiazin-6-yl)acetic acid | I-1 | II-45 | A | 4.21 | 487.9 |
| I-46 | 2-(8-benzyl-1-(naphthalen-1-ylmethylcarbamoyl)-4,7-dioxooctahydropyrazino[2,1-c][1,2,4]oxadiazin-6-yl)acetic acid | I-1 | II-46 | A | 4.37 | 503.5 |
| I-47 | 2-(8-benzyl-1-(ethylcarbamoyl)-4,7-dioxooctahydropyrazino[2,1-c][1,2,4]oxadiazin-6-yl)acetic acid | I-1 | II-47 | A | 3.30 | 391.4 |
| I-48 | 6-(2-amino-2-oxoethyl)-8-benzyl-4,7-dioxo-N-(pyridin-4-ylmethyl)hexahydropyrazino[2,1-c][1,2,4]oxadiazine-1(6H)-carboxamide | I-1 | II-48 | A | 3.74 | 453.5 |
| I-49 | 6-(2-amino-2-oxoethyl)-8-benzyl-N-(4-chlorobenzyl)-4,7-dioxohexahydropyrazino[2,1-c][1,2,4]oxadiazine-1(6H)-carboxamide | I-1 | II-49 | A | 4.01 | 486.9 |
| I-50 | 6-(2-amino-2-oxoethyl)-8-benzyl-N-(naphthalen-1-ylmethyl)-4,7-dioxohexahydropyrazino[2,1-c][1,2,4]oxadiazine-1(6H)-carboxamide | I-1 | II-50 | A | 4.19 | 502.5 |
| I-51 | 6-(2-amino-2-oxoethyl)-8-benzyl-N-ethyl-4,7-dioxohexahydropyrazino[2,1-c][1,2,4]oxadiazine-1(6H)-carboxamide | I-1 | II-51 | A | 3.12 | 390.4 |
| I-52 | 6-methyl-8-(naphthalen-1-ylmethyl)-4,7-dioxo-N-(pyridin-4-ylmethyl)hexahydropyrazino[2,1-c][1,2,4]oxadiazine-1(6H)-carboxamide | I-1 | II-52 | A | 2.90 | 460.5 |
| I-53 | N-(4-chlorobenzyl)-6-methyl-8-(naphthalen-1-ylmethyl)-4,7-dioxohexahydropyrazino[2,1-c][1,2,4]oxadiazine-1(6H)-carboxamide | I-1 | II-53 | A | 4.93 | 494.0 |
| I-54 | 6-methyl-N,8-bis(naphthalen-1-ylmethyl)-4,7-dioxohexahydropyrazino[2,1-c][1,2,4]oxadiazine-1(6H)-carboxamide | I-1 | II-54 | A | 5.12 | 509.6 |
| I-55 | N-ethyl-6-methyl-8-(naphthalen-1-ylmethyl)-4,7-dioxohexahydropyrazino[2,1-c][1,2,4]oxadiazine-1(6H)-carboxamide | I-1 | II-55 | A | 4.05 | 397.4 |
| I-56 | 6-(4-hydroxybenzyl)-8-(naphthalen-1-ylmethyl)-4,7-dioxo-N-(pyridin-4-ylmethyl)hexahydropyrazino[2,1-c][1,2,4]oxadiazine-1(6H)-carboxamide | I-1 | II-56 | A | 3.14 | 552.6 |
| I-57 | N-(4-chlorobenzyl)-6-(4-hydroxybenzyl)-8-(naphthalen-1-ylmethyl)-4,7-dioxohexahydropyrazino[2,1-c][1,2,4]oxadiazine-1(6H)-carboxamide | I-1 | II-57 | A | 5.00 | 586.0 |
| I-58 | 6-(4-hydroxybenzyl)-N,8-bis(naphthalen-1-ylmethyl)-4,7-dioxohexahydropyrazino[2,1-c][1,2,4]oxadiazine-1(6H)-carboxamide | I-1 | II-58 | A | 5.17 | 601.7 |
| I-59 | N-ethyl-6-(4-hydroxybenzyl)-8-(naphthalen-1-ylmethyl)-4,7-dioxohexahydropyrazino[2,1-c][1,2,4]oxadiazine-1(6H)-carboxamide | I-1 | II-59 | A | 4.25 | 489.5 |
| I-60 | 6-(4-aminobutyl)-8-(naphthalen-1-ylmethyl)-4,7-dioxo-N-(pyridin-4-ylmethyl)hexahydropyrazino[2,1-c][1,2,4]oxadiazine-1(6H)-carboxamide | I-1 | II-60 | A | 2.47 | 517.6 |

TABLE C1-continued

| Ex. No. | chemical name | Syn. | Int | method | RT | Mass |
|---|---|---|---|---|---|---|
| I-61 | 6-(4-aminobutyl)-N-(4-chlorobenzyl)-8-(naphthalen-1-ylmethyl)-4,7-dioxohexahydropyrazino[2,1-c][1,2,4]oxadiazine-1(6H)-carboxamide | I-1 | II-61 | A | 3.50 | 551.0 |
| I-62 | 6-(4-aminobutyl)-N,8-bis(naphthalen-1-ylmethyl)-4,7-dioxohexahydropyrazino[2,1-c][1,2,4]oxadiazine-1(6H)-carboxamide | I-1 | II-62 | A | 3.58 | 566.7 |
| I-63 | 6-(4-aminobutyl)-N-ethyl-8-(naphthalen-1-ylmethyl)-4,7-dioxohexahydropyrazino[2,1-c][1,2,4]oxadiazine-1(6H)-carboxamide | I-1 | II-63 | A | 3.02 | 454.5 |
| I-64 | 2-(8-(naphthalen-1-ylmethyl)-4,7-dioxo-1-(pyridin-4-ylmethylcarbamoyl)octahydropyrazino[2,1-c][1,2,4]oxadiazin-6-yl)acetic acid | I-1 | II-64 | A | 2.86 | 504.5 |
| I-65 | 2-(1-(4-chlorobenzylcarbamoyl)-8-(naphthalen-1-ylmethyl)-4,7-dioxooctahydropyrazino[2,1-c][1,2,4]oxadiazin-6-yl)acetic acid | I-1 | II-65 | A | 4.63 | 538.0 |
| I-66 | 2-(8-(naphthalen-1-ylmethyl)-1-(naphthalen-1-ylmethylcarbamoyl)-4,7-dioxooctahydropyrazino[2,1-c][1,2,4]oxadiazin-6-yl)acetic acid | I-1 | II-66 | A | 4.79 | 553.6 |
| I-67 | 2-(1-(ethylcarbamoyl)-8-(naphthalen-1-ylmethyl)-4,7-dioxooctahydropyrazino[2,1-c][1,2,4]oxadiazin-6-yl)acetic acid | I-1 | II-67 | A | 3.82 | 441.4 |
| I-68 | 6-(2-amino-2-oxoethyl)-8-(naphthalen-1-ylmethyl)-4,7-dioxo-N-(pyridin-4-ylmethyl)hexahydropyrazino[2,1-c][1,2,4]oxadiazine-1(6H)-carboxamide | I-1 | II-68 | A | 2.73 | 503.5 |
| I-69 | 6-(2-amino-2-oxoethyl)-N-(4-chlorobenzyl)-8-(naphthalen-1-ylmethyl)-4,7-dioxohexahydropyrazino[2,1-c][1,2,4]oxadiazine-1(6H)-carboxamide | I-1 | II-69 | A | 4.43 | 537.0 |
| I-70 | 6-(2-amino-2-oxoethyl)-N,8-bis(naphthalen-1-ylmethyl)-4,7-dioxohexahydropyrazino[2,1-c][1,2,4]oxadiazine-1(6H)-carboxamide | I-1 | II-70 | A | 4.61 | 552.6 |
| I-71 | 6-(2-amino-2-oxoethyl)-N-ethyl-8-(naphthalen-1-ylmethyl)-4,7-dioxohexahydropyrazino[2,1-c][1,2,4]oxadiazine-1(6H)-carboxamide | I-1 | II-71 | A | 3.62 | 440.5 |
| I-72 | 6-methyl-4,7-dioxo-N-(pyridin-4-ylmethyl)-8-(quinolin-8-ylmethyl)hexahydropyrazino[2,1-c][1,2,4]oxadiazine-1(6H)-carboxamide | I-1 | II-72 | A | 2.09 | 461.5 |
| I-73 | N-(4-chlorobenzyl)-6-methyl-4,7-dioxo-8-(quinolin-8-ylmethyl)hexahydropyrazino[2,1-c][1,2,4]oxadiazine-1(6H)-carboxamide | I-1 | II-73 | A | 4.07 | 494.9 |
| I-74 | 6-methyl-N-(naphthalen-1-ylmethyl)-4,7-dioxo-8-(quinolin-8-ylmethyl)hexahydropyrazino[2,1-c][1,2,4]oxadiazine-1(6H)-carboxamide | I-1 | II-74 | A | 4.31 | 510.6 |
| I-75 | N-ethyl-6-methyl-4,7-dioxo-8-(quinolin-8-ylmethyl)hexahydropyrazino[2,1-c][1,2,4]oxadiazine-1(6H)-carboxamide | I-1 | II-75 | A | 2.94 | 398.4 |
| I-76 | 6-(4-hydroxybenzyl)-4,7-dioxo-N-(pyridin-4-ylmethyl)-8-(quinolin-8-ylmethyl)hexahydropyrazino[2,1-c][1,2,4]oxadiazine-1(6H)-carboxamide | I-1 | II-76 | A | 2.55 | 553.6 |
| I-77 | N-(4-chlorobenzyl)-6-(4-hydroxybenzyl)-4,7-dioxo-8-(quinolin-8-ylmethyl)hexahydropyrazino[2,1-c][1,2,4]oxadiazine-1(6H)-carboxamide | I-1 | II-77 | A | 4.25 | 587.0 |
| I-78 | 6-(4-hydroxybenzyl)-N-(naphthalen-1-ylmethyl)-4,7-dioxo-8-(quinolin-8-ylmethyl)hexahydropyrazino[2,1-c][1,2,4]oxadiazine-1(6H)-carboxamide | I-1 | II-78 | A | 4.47 | 602.7 |
| I-79 | N-ethyl-6-(4-hydroxybenzyl)-4,7-dioxo-8-(quinolin-8-ylmethyl)hexahydropyrazino[2,1-c][1,2,4]oxadiazine-1(6H)-carboxamide | I-1 | II-79 | A | 3.30 | 490.5 |
| I-80 | 6-(4-aminobutyl)-4,7-dioxo-N-(pyridin-4-ylmethyl)-8-(quinolin-8-ylmethyl)hexahydropyrazino[2,1-c][1,2,4]oxadiazine-1(6H)-carboxamide | I-1 | II-80 | A | 2.03 | 518.6 |
| I-81 | 6-(4-aminobutyl)-N-(4-chlorobenzyl)-4,7-dioxo-8-(quinolin-8-ylmethyl)hexahydropyrazino[2,1-c][1,2,4]oxadiazine-1(6H)-carboxamide | I-1 | II-81 | A | 3.14 | 552.0 |
| I-82 | 6-(4-aminobutyl)-N-(naphthalen-1-ylmethyl)-4,7-dioxo-8-(quinolin-8-ylmethyl)hexahydropyrazino[2,1-c][1,2,4]oxadiazine-1(6H)-carboxamide | I-1 | II-82 | A | 3.26 | 567.7 |
| I-83 | 6-(4-aminobutyl)-N-ethyl-4,7-dioxo-8-(quinolin-8-ylmethyl)hexahydropyrazino[2,1-c][1,2,4]oxadiazine-1(6H)-carboxamide | I-1 | II-83 | A | 2.49 | 455.5 |
| I-84 | 2-(4,7-dioxo-1-(pyridin-4-ylmethylcarbamoyl)-8-(quinolin-8-ylmethyl)octahydropyrazino[2,1-c][1,2,4]oxadiazin-6-yl)acetic acid | I-1 | II-84 | A | 2.13 | 505.5 |
| I-85 | 2-(1-(4-chlorobenzylcarbamoyl)-4,7-dioxo-8-(quinolin-8-ylmethyl)octahydropyrazino[2,1-c][1,2,4]oxadiazin-6-yl)acetic acid | I-1 | II-85 | A | 3.78 | 539.0 |
| I-86 | 2-(1-(naphthalen-1-ylmethylcarbamoyl)-4,7-dioxo-8-(quinolin-8-ylmethyl)octahydropyrazino[2,1-c][1,2,4]oxadiazin-6-yl)acetic acid | I-1 | II-86 | A | 3.97 | 554.6 |

TABLE C1-continued

| Ex. No. | chemical name | Syn. | Int | method | RT | Mass |
|---|---|---|---|---|---|---|
| I-87 | 2-(1-(ethylcarbamoyl)-4,7-dioxo-8-(quinolin-8-ylmethyl)octahydropyrazino[2,1-c][1,2,4]oxadiazin-6-yl)acetic acid | I-1 | II-87 | A | 2.75 | 442.4 |
| I-88 | 6-(2-amino-2-oxoethyl)-4,7-dioxo-N-(pyridin-4-ylmethyl)-8-(quinolin-8-ylmethyl)hexahydropyrazino[2,1-c][1,2,4]oxadiazine-1(6H)-carboxamide | I-1 | II-88 | A | 3.54 | 504.5 |
| I-89 | 6-(2-amino-2-oxoethyl)-N-(4-chlorobenzyl)-4,7-dioxo-8-(quinolin-8-ylmethyl)hexahydropyrazino[2,1-c][1,2,4]oxadiazine-1(6H)-carboxamide | I-1 | II-89 | A | 3.56 | 538.0 |
| I-90 | 6-(2-amino-2-oxoethyl)-N-(naphthalen-1-ylmethyl)-4,7-dioxo-8-(quinolin-8-ylmethyl)hexahydropyrazino[2,1-c][1,2,4]oxadiazine-1(6H)-carboxamide | I-1 | II-90 | A | 3.72 | 553.6 |
| I-91 | 6-(2-amino-2-oxoethyl)-N-ethyl-4,7-dioxo-8-(quinolin-8-ylmethyl)hexahydropyrazino[2,1-c][1,2,4]oxadiazine-1(6H)-carboxamide | I-1 | II-91 | A | 2.59 | 441.5 |
| I-92 | 8-(benzo[b]thiophen-3-ylmethyl)-6-methyl-4,7-dioxo-N-(pyridin-4-ylmethyl)hexahydropyrazino[2,1-c][1,2,4]oxadiazine-1(6H)-carboxamide | I-1 | II-92 | A | 2.88 | 466.5 |
| I-93 | 8-(benzo[b]thiophen-3-ylmethyl)-N-(4-chlorobenzyl)-6-methyl-4,7-dioxohexahydropyrazino[2,1-c][1,2,4]oxadiazine-1(6H)-carboxamide | I-1 | II-93 | A | 4.91 | 500.0 |
| I-94 | 8-(benzo[b]thiophen-3-ylmethyl)-6-methyl-N-(naphthalen-1-ylmethyl)-4,7-dioxohexahydropyrazino[2,1-c][1,2,4]oxadiazine-1(6H)-carboxamide | I-1 | II-94 | A | 5.12 | 515.6 |
| I-95 | 8-(benzo[b]thiophen-3-ylmethyl)-N-ethyl-6-methyl-4,7-dioxohexahydropyrazino[2,1-c][1,2,4]oxadiazine-1(6H)-carboxamide | I-1 | II-95 | A | 4.01 | 403.5 |
| I-96 | 8-(benzo[b]thiophen-3-ylmethyl)-6-(4-hydroxybenzyl)-4,7-dioxo-N-(pyridin-4-ylmethyl)hexahydropyrazino[2,1-c][1,2,4]oxadiazine-1(6H)-carboxamide | I-1 | II-96 | A | 3.12 | 558.6 |
| I-97 | 8-(benzo[b]thiophen-3-ylmethyl)-N-(4-chlorobenzyl)-6-(4-hydroxybenzyl)-4,7-dioxohexahydropyrazino[2,1-c][1,2,4]oxadiazine-1(6H)-carboxamide | I-1 | II-97 | A | 4.95 | 592.1 |
| I-98 | 8-(benzo[b]thiophen-3-ylmethyl)-6-(4-hydroxybenzyl)-N-(naphthalen-1-ylmethyl)-4,7-dioxohexahydropyrazino[2,1-c][1,2,4]oxadiazine-1(6H)-carboxamide | I-1 | II-98 | A | 5.12 | 607.7 |
| I-99 | 8-(benzo[b]thiophen-3-ylmethyl)-N-ethyl-6-(4-hydroxybenzyl)-4,7-dioxohexahydropyrazino[2,1-c][1,2,4]oxadiazine-1(6H)-carboxamide | I-1 | II-99 | A | 4.21 | 495.6 |
| I-100 | 6-(4-aminobutyl)-8-(benzo[b]thiophen-3-ylmethyl)-4,7-dioxo-N-(pyridin-4-ylmethyl)hexahydropyrazino[2,1-c][1,2,4]oxadiazine-1(6H)-carboxamide | I-1 | II-100 | A | 2.43 | 523.6 |
| I-101 | 6-(4-aminobutyl)-8-(benzo[b]thiophen-3-ylmethyl)-N-(4-chlorobenzyl)-4,7-dioxohexahydropyrazino[2,1-c][1,2,4]oxadiazine-1(6H)-carboxamide | I-1 | II-101 | A | 3.48 | 557.1 |
| I-102 | 6-(4-aminobutyl)-8-(benzo[b]thiophen-3-ylmethyl)-N-(naphthalen-1-ylmethyl)-4,7-dioxohexahydropyrazino[2,1-c][1,2,4]oxadiazine-1(6H)-carboxamide | I-1 | II-102 | A | 3.54 | 572.7 |
| I-103 | 6-(4-aminobutyl)-8-(benzo[b]thiophen-3-ylmethyl)-N-ethyl-4,7-dioxohexahydropyrazino[2,1-c][1,2,4]oxadiazine-1(6H)-carboxamide | I-1 | II-103 | A | 2.98 | 460.6 |
| I-104 | 2-(8-(benzo[b]thiophen-3-ylmethyl)-4,7-dioxo-1-(pyridin-4-ylmethylcarbamoyl)octahydropyrazino[2,1-c][1,2,4]oxadiazin-6-yl)acetic acid | I-1 | II-104 | A | 2.82 | 510.5 |
| I-105 | 2-(8-(benzo[b]thiophen-3-ylmethyl)-1-(4-chlorobenzylcarbamoyl)-4,7-dioxooctahydropyrazino[2,1-c][1,2,4]oxadiazin-6-yl)acetic acid | I-1 | II-105 | A | 4.58 | 544.0 |
| I-106 | 2-(8-(benzo[b]thiophen-3-ylmethyl)-1-(naphthalen-1-ylmethylcarbamoyl)-4,7-dioxooctahydropyrazino[2,1-c][1,2,4]oxadiazin-6-yl)acetic acid | I-1 | II-106 | A | 4.77 | 559.6 |
| I-107 | 2-(8-(benzo[b]thiophen-3-ylmethyl)-1-(ethylcarbamoyl)-4,7-dioxooctahydropyrazino[2,1-c][1,2,4]oxadiazin-6-yl)acetic acid | I-1 | II-107 | A | 3.78 | 447.5 |
| I-108 | 6-(2-amino-2-oxoethyl)-8-(benzo[b]thiophen-3-ylmethyl)-4,7-dioxo-N-(pyridin-4-ylmethyl)hexahydropyrazino[2,1-c][1,2,4]oxadiazine-1(6H)-carboxamide | I-1 | II-108 | A | 2.71 | 509.6 |
| I-109 | 6-(2-amino-2-oxoethyl)-8-(benzo[b]thiophen-3-ylmethyl)-N-(4-chlorobenzyl)-4,7-dioxohexahydropyrazino[2,1-c][1,2,4]oxadiazine-1(6H)-carboxamide | I-1 | II-109 | A | 4.41 | 543.0 |
| I-110 | 6-(2-amino-2-oxoethyl)-8-(benzo[b]thiophen-3-ylmethyl)-N-(naphthalen-1-ylmethyl)-4,7-dioxohexahydropyrazino[2,1-c][1,2,4]oxadiazine-1(6H)-carboxamide | I-1 | II-110 | A | 4.55 | 558.6 |
| I-111 | 6-(2-amino-2-oxoethyl)-8-(benzo[b]thiophen-3-ylmethyl)-N-ethyl-4,7-dioxohexahydropyrazino[2,1-c][1,2,4]oxadiazine-1(6H)-carboxamide | I-1 | II-111 | A | 3.58 | 446.5 |
| I-112 | benzyl 8-isopentyl-6-methyl-4,7-dioxohexahydropyrazino[2,1-c][1,2,4]oxadiazine-1(6H)-carboxylate | I-1 | II-112 | A | 4.65 | 390.4 |

TABLE C1-continued

| Ex. No. | chemical name | Syn. | Int | method | RT | Mass |
|---|---|---|---|---|---|---|
| I-113 | benzyl 6-(4-hydroxybenzyl)-8-isopentyl-4,7-dioxohexahydropyrazino[2,1-c][1,2,4]oxadiazine-1(6H)-carboxylate | I-1 | II-113 | A | 4.73 | 482.5 |
| I-114 | benzyl 6-(4-aminobutyl)-8-isopentyl-4,7-dioxohexahydropyrazino[2,1-c][1,2,4]oxadiazine-1(6H)-carboxylate | I-1 | II-114 | A | 3.30 | 447.5 |
| I-115 | 2-(1-(benzyloxycarbonyl)-8-isopentyl-4,7-dioxooctahydropyrazino[2,1-c][1,2,4]oxadiazin-6-yl)acetic acid | I-1 | II-115 | A | 4.35 | 434.5 |
| I-116 | benzyl 6-(2-amino-2-oxoethyl)-8-isopentyl-4,7-dioxohexahydropyrazino[2,1-c][1,2,4]oxadiazine-1(6H)-carboxylate | I-1 | II-116 | A | 4.13 | 433.5 |
| I-117 | benzyl 6-(hydroxymethyl)-8-isopentyl-4,7-dioxohexahydropyrazino[2,1-c][1,2,4]oxadiazine-1(6H)-carboxylate | I-1 | II-117 | A | 4.33 | 406.4 |
| I-118 | benzyl 6-isobutyl-8-isopentyl-4,7-dioxohexahydropyrazino[2,1-c][1,2,4]oxadiazine-1(6H)-carboxylate | I-1 | II-118 | A | 5.32 | 432.5 |
| I-119 | benzyl 8-isopentyl-4,7-dioxo-6-phenylhexahydropyrazino[2,1-c][1,2,4]oxadiazine-1(6H)-carboxylate | I-1 | II-119 | A | 5.16 | 452.5 |
| I-120 | benzyl 6-benzyl-8-isopentyl-4,7-dioxohexahydropyrazino[2,1-c][1,2,4]oxadiazine-1(6H)-carboxylate | I-1 | II-120 | A | 5.26 | 466.5 |
| I-121 | benzyl 8-isopentyl-4,7-dioxo-6-phenethylhexahydropyrazino[2,1-c][1,2,4]oxadiazine-1(6H)-carboxylate | I-1 | II-121 | A | 5.40 | 480.6 |
| I-122 | benzyl 6-(benzyloxymethyl)-8-isopentyl-4,7-dioxohexahydropyrazino[2,1-c][1,2,4]oxadiazine-1(6H)-carboxylate | I-1 | II-122 | A | 5.40 | 496.6 |
| I-123 | benzyl 8-isopentyl-6-(naphthalen-1-ylmethyl)-4,7-dioxohexahydropyrazino[2,1-c][1,2,4]oxadiazine-1(6H)-carboxylate | I-1 | II-123 | A | 5.18 | 516.6 |
| I-124 | benzyl 8-isopentyl-6-(naphthalen-2-ylmethyl)-4,7-dioxohexahydropyrazino[2,1-c][1,2,4]oxadiazine-1(6H)-carboxylate | I-1 | II-124 | A | 5.24 | 516.6 |
| I-125 | benzyl 6-methyl-4,7-dioxo-8-phenethylhexahydropyrazino[2,1-c][1,2,4]oxadiazine-1(6H)-carboxylate | I-1 | II-125 | A | 4.59 | 424.5 |
| I-126 | benzyl 6-(4-hydroxybenzyl)-4,7-dioxo-8-phenethylhexahydropyrazino[2,1-c][1,2,4]oxadiazine-1(6H)-carboxylate | I-1 | II-126 | A | 4.63 | 516.6 |
| I-127 | benzyl 6-(4-aminobutyl)-4,7-dioxo-8-phenethylhexahydropyrazino[2,1-c][1,2,4]oxadiazine-1(6H)-carboxylate | I-1 | II-127 | A | 3.28 | 481.6 |
| I-128 | 2-(1-(benzyloxycarbonyl)-4,7-dioxo-8-phenethyloctahydropyrazino[2,1-c][1,2,4]oxadiazin-6-yl)acetic acid | I-1 | II-128 | A | 4.33 | 468.5 |
| I-129 | benzyl 6-(2-amino-2-oxoethyl)-4,7-dioxo-8-phenethylhexahydropyrazino[2,1-c][1,2,4]oxadiazine-1(6H)-carboxylate | I-1 | II-129 | A | 4.11 | 467.5 |
| I-130 | benzyl 6-(hydroxymethyl)-4,7-dioxo-8-phenethylhexahydropyrazino[2,1-c][1,2,4]oxadiazine-1(6H)-carboxylate | I-1 | II-130 | A | 4.29 | 440.5 |
| I-131 | benzyl 6-isobutyl-4,7-dioxo-8-phenethylhexahydropyrazino[2,1-c][1,2,4]oxadiazine-1(6H)-carboxylate | I-1 | II-131 | A | 5.18 | 466.5 |
| I-132 | benzyl 4,7-dioxo-8-phenethyl-6-phenylhexahydropyrazino[2,1-c][1,2,4]oxadiazine-1(6H)-carboxylate | I-1 | II-132 | A | 5.10 | 486.5 |
| I-133 | benzyl 6-benzyl-4,7-dioxo-8-phenethylhexahydropyrazino[2,1-c][1,2,4]oxadiazine-1(6H)-carboxylate | I-1 | II-133 | A | 5.22 | 500.6 |
| I-134 | benzyl 4,7-dioxo-6,8-diphenethylhexahydropyrazino[2,1-c][1,2,4]oxadiazine-1(6H)-carboxylate | I-1 | II-134 | A | 5.36 | 514.6 |
| I-135 | benzyl 6-(benzyloxymethyl)-4,7-dioxo-8-phenethylhexahydropyrazino[2,1-c][1,2,4]oxadiazine-1(6H)-carboxylate | I-1 | II-135 | A | 5.32 | 530.6 |
| I-136 | benzyl 6-(naphthalen-1-ylmethyl)-4,7-dioxo-8-phenethylhexahydropyrazino[2,1-c][1,2,4]oxadiazine-1(6H)-carboxylate | I-1 | II-136 | A | 5.14 | 550.6 |
| I-137 | benzyl 6-(naphthalen-2-ylmethyl)-4,7-dioxo-8-phenethylhexahydropyrazino[2,1-c][1,2,4]oxadiazine-1(6H)-carboxylate | I-1 | II-137 | A | 5.20 | 550.6 |
| I-138 | benzyl 6-methyl-4,7-dioxo-8-(3-phenylpropyl)hexahydropyrazino[2,1-c][1,2,4]oxadiazine-1(6H)-carboxylate | I-1 | II-138 | A | 4.38 | 438.5 |
| I-139 | benzyl 6-(4-hydroxybenzyl)-4,7-dioxo-8-(3-phenylpropyl)hexahydropyrazino[2,1-c][1,2,4]oxadiazine-1(6H)-carboxylate | I-1 | II-139 | A | 4.83 | 530.6 |
| I-140 | benzyl 6-(4-aminobutyl)-4,7-dioxo-8-(3-phenylpropyl)hexahydropyrazino[2,1-c][1,2,4]oxadiazine-1(6H)-carboxylate | I-1 | II-140 | A | 3.42 | 495.6 |
| I-141 | 2-(1-(benzyloxycarbonyl)-4,7-dioxo-8-(3-phenylpropyl)octahydropyrazino[2,1-c][1,2,4]oxadiazin-6-yl)acetic acid | I-1 | II-141 | A | 4.51 | 482.5 |

TABLE C1-continued

| Ex. No. | chemical name | Syn. | Int | method | RT | Mass |
|---|---|---|---|---|---|---|
| I-142 | benzyl 6-(2-amino-2-oxoethyl)-4,7-dioxo-8-(3-phenylpropyl)hexahydropyrazino[2,1-c][1,2,4]oxadiazine-1(6H)-carboxylate | I-1 | II-142 | A | 4.33 | 481.5 |
| I-143 | benzyl 6-(hydroxymethyl)-4,7-dioxo-8-(3-phenylpropyl)hexahydropyrazino[2,1-c][1,2,4]oxadiazine-1(6H)-carboxylate | I-1 | II-143 | A | 4.51 | 454.5 |
| I-144 | benzyl 6-isobutyl-4,7-dioxo-8-(3-phenylpropyl)hexahydropyrazino[2,1-c][1,2,4]oxadiazine-1(6H)-carboxylate | I-1 | II-144 | A | 5.38 | 480.6 |
| I-145 | benzyl 4,7-dioxo-6-phenyl-8-(3-phenylpropyl)hexahydropyrazino[2,1-c][1,2,4]oxadiazine-1(6H)-carboxylate | I-1 | II-145 | A | 5.28 | 500.6 |
| I-146 | benzyl 6-benzyl-4,7-dioxo-8-(3-phenylpropyl)hexahydropyrazino[2,1-c][1,2,4]oxadiazine-1(6H)-carboxylate | I-1 | II-146 | A | 5.38 | 514.6 |
| I-147 | benzyl 4,7-dioxo-6-phenethyl-8-(3-phenylpropyl)hexahydropyrazino[2,1-c][1,2,4]oxadiazine-1(6H)-carboxylate | I-1 | II-147 | A | 5.52 | 528.6 |
| I-148 | benzyl 6-(benzyloxymethyl)-4,7-dioxo-8-(3-phenylpropyl)hexahydropyrazino[2,1-c][1,2,4]oxadiazine-1(6H)-carboxylate | I-1 | II-148 | A | 5.48 | 544.6 |
| I-149 | benzyl 6-(naphthalen-1-ylmethyl)-4,7-dioxo-8-(3-phenylpropyl)hexahydropyrazino[2,1-c][1,2,4]oxadiazine-1(6H)-carboxylate | I-1 | II-149 | A | 5.24 | 564.6 |
| I-150 | benzyl 6-(naphthalen-2-ylmethyl)-4,7-dioxo-8-(3-phenylpropyl)hexahydropyrazino[2,1-c][1,2,4]oxadiazine-1(6H)-carboxylate | I-1 | II-150 | A | 5.30 | 564.6 |
| I-151 | benzyl 8-(3,3-diphenylpropyl)-6-methyl-4,7-dioxohexahydropyrazino[2,1-c][1,2,4]oxadiazine-1(6H)-carboxylate | I-1 | II-151 | A | 5.20 | 514.6 |
| I-152 | benzyl 8-(3,3-diphenylpropyl)-6-(4-hydroxybenzyl)-4,7-dioxohexahydropyrazino[2,1-c][1,2,4]oxadiazine-1(6H)-carboxylate | I-1 | II-152 | A | 5.20 | 606.7 |
| I-153 | benzyl 6-(4-aminobutyl)-8-(3,3-diphenylpropyl)-4,7-dioxohexahydropyrazino[2,1-c][1,2,4]oxadiazine-1(6H)-carboxylate | I-1 | II-153 | A | 3.68 | 571.7 |
| I-154 | 2-(1-(benzyloxycarbonyl)-8-(3,3-diphenylpropyl)-4,7-dioxooctahydropyrazino[2,1-c][1,2,4]oxadiazin-6-yl)acetic acid | I-1 | II-154 | A | 4.93 | 558.6 |
| I-155 | benzyl 6-(2-amino-2-oxoethyl)-8-(3,3-diphenylpropyl)-4,7-dioxohexahydropyrazino[2,1-c][1,2,4]oxadiazine-1(6H)-carboxylate | I-1 | II-155 | A | 4.75 | 557.6 |
| I-156 | benzyl 8-(3,3-diphenylpropyl)-6-(hydroxymethyl)-4,7-dioxohexahydropyrazino[2,1-c][1,2,4]oxadiazine-1(6H)-carboxylate | I-1 | II-156 | A | 4.93 | 530.6 |
| I-157 | benzyl 8-(3,3-diphenylpropyl)-6-isobutyl-4,7-dioxohexahydropyrazino[2,1-c][1,2,4]oxadiazine-1(6H)-carboxylate | I-1 | II-157 | A | 5.68 | 556.7 |
| I-158 | benzyl 8-(3,3-diphenylpropyl)-4,7-dioxo-6-phenylhexahydropyrazino[2,1-c][1,2,4]oxadiazine-1(6H)-carboxylate | I-1 | II-158 | A | 5.60 | 576.7 |
| I-159 | benzyl 6-benzyl-8-(3,3-diphenylpropyl)-4,7-dioxohexahydropyrazino[2,1-c][1,2,4]oxadiazine-1(6H)-carboxylate | I-1 | II-159 | A | 5.70 | 590.7 |
| I-160 | benzyl 8-(3,3-diphenylpropyl)-4,7-dioxo-6-phenethylhexahydropyrazino[2,1-c][1,2,4]oxadiazine-1(6H)-carboxylate | I-1 | II-160 | A | 5.78 | 604.7 |
| I-161 | benzyl 6-(benzyloxymethyl)-8-(3,3-diphenylpropyl)-4,7-dioxohexahydropyrazino[2,1-c][1,2,4]oxadiazine-1(6H)-carboxylate | I-1 | II-161 | A | 5.78 | 620.7 |
| I-162 | benzyl 8-(3,3-diphenylpropyl)-6-(naphthalen-1-ylmethyl)-4,7-dioxohexahydropyrazino[2,1-c][1,2,4]oxadiazine-1(6H)-carboxylate | I-1 | II-162 | A | 5.60 | 640.7 |
| I-163 | benzyl 8-(3,3-diphenylpropyl)-6-(naphthalen-2-ylmethyl)-4,7-dioxohexahydropyrazino[2,1-c][1,2,4]oxadiazine-1(6H)-carboxylate | I-1 | II-163 | A | 5.64 | 640.7 |
| I-164 | benzyl 6-methyl-8-(naphthalen-2-ylmethyl)-4,7-dioxohexahydropyrazino[2,1-c][1,2,4]oxadiazine-1(6H)-carboxylate | I-1 | II-164 | A | 4.95 | 460.5 |
| I-165 | benzyl 6-(4-hydroxybenzyl)-8-(naphthalen-2-ylmethyl)-4,7-dioxohexahydropyrazino[2,1-c][1,2,4]oxadiazine-1(6H)-carboxylate | I-1 | II-165 | A | 4.91 | 552.6 |
| I-166 | benzyl 6-(4-aminobutyl)-8-(naphthalen-2-ylmethyl)-4,7-dioxohexahydropyrazino[2,1-c][1,2,4]oxadiazine-1(6H)-carboxylate | I-1 | II-166 | A | 3.48 | 517.6 |
| I-167 | 2-(1-(benzyloxycarbonyl)-8-(naphthalen-2-ylmethyl)-4,7-dioxooctahydropyrazino[2,1-c][1,2,4]oxadiazin-6-yl)acetic acid | I-1 | II-167 | A | 4.65 | 504.5 |

TABLE C1-continued

| Ex. No. | chemical name | Syn. | Int | method | RT | Mass |
|---|---|---|---|---|---|---|
| I-168 | benzyl 6-(2-amino-2-oxoethyl)-8-(naphthalen-2-ylmethyl)-4,7-dioxohexahydropyrazino[2,1-c][1,2,4]oxadiazine-1(6H)-carboxylate | I-1 | II-168 | A | 4.41 | 503.5 |
| I-169 | benzyl 6-(hydroxymethyl)-8-(naphthalen-2-ylmethyl)-4,7-dioxohexahydropyrazino[2,1-c][1,2,4]oxadiazine-1(6H)-carboxylate | I-1 | II-169 | A | 4.61 | 476.5 |
| I-170 | benzyl 6-isobutyl-8-(naphthalen-2-ylmethyl)-4,7-dioxohexahydropyrazino[2,1-c][1,2,4]oxadiazine-1(6H)-carboxylate | I-1 | II-170 | A | 5.52 | 502.6 |
| I-171 | benzyl 8-(naphthalen-2-ylmethyl)-4,7-dioxo-6-phenylhexahydropyrazino[2,1-c][1,2,4]oxadiazine-1(6H)-carboxylate | I-1 | II-171 | A | 5.46 | 522.6 |
| I-172 | benzyl 6-benzyl-8-(naphthalen-2-ylmethyl)-4,7-dioxohexahydropyrazino[2,1-c][1,2,4]oxadiazine-1(6H)-carboxylate | I-1 | II-172 | A | 5.54 | 536.6 |
| I-173 | benzyl 8-(naphthalen-2-ylmethyl)-4,7-dioxo-6-phenethylhexahydropyrazino[2,1-c][1,2,4]oxadiazine-1(6H)-carboxylate | I-1 | II-173 | A | 5.06 | 550.6 |
| I-174 | benzyl 6-(benzyloxymethyl)-8-(naphthalen-2-ylmethyl)-4,7-dioxohexahydropyrazino[2,1-c][1,2,4]oxadiazine-1(6H)-carboxylate | I-1 | II-174 | A | 5.58 | 566.6 |
| I-175 | benzyl 6-(naphthalen-1-ylmethyl)-8-(naphthalen-2-ylmethyl)-4,7-dioxohexahydropyrazino[2,1-c][1,2,4]oxadiazine-1(6H)-carboxylate | I-1 | II-175 | A | 5.38 | 586.6 |
| I-176 | benzyl 6,8-bis(naphthalen-2-ylmethyl)-4,7-dioxohexahydropyrazino[2,1-c][1,2,4]oxadiazine-1(6H)-carboxylate | I-1 | II-176 | A | 5.38 | 586.6 |
| I-177 | benzyl 6-methyl-4,7-dioxo-8-(pyridin-4-ylmethyl)hexahydropyrazino[2,1-c][1,2,4]oxadiazine-1(6H)-carboxylate | I-1 | II-177 | A | 2.77 | 411.4 |
| I-178 | benzyl 6-(4-hydroxybenzyl)-4,7-dioxo-8-(pyridin-4-ylmethyl)hexahydropyrazino[2,1-c][1,2,4]oxadiazine-1(6H)-carboxylate | I-1 | II-178 | A | 2.96 | 503.5 |
| I-179 | benzyl 6-(4-aminobutyl)-4,7-dioxo-8-(pyridin-4-ylmethyl)hexahydropyrazino[2,1-c][1,2,4]oxadiazine-1(6H)-carboxylate | I-1 | II-179 | A | 2.23 | 468.5 |
| I-180 | 2-(1-(benzyloxycarbonyl)-4,7-dioxo-8-(pyridin-4-ylmethyl)octahydropyrazino[2,1-c][1,2,4]oxadiazin-6-yl)acetic acid | I-1 | II-180 | A | 2.65 | 455.4 |
| I-181 | benzyl 6-(2-amino-2-oxoethyl)-4,7-dioxo-8-(pyridin-4-ylmethyl)hexahydropyrazino[2,1-c][1,2,4]oxadiazine-1(6H)-carboxylate | I-1 | II-181 | A | 2.53 | 454.4 |
| I-182 | benzyl 6-(hydroxymethyl)-4,7-dioxo-8-(pyridin-4-ylmethyl)hexahydropyrazino[2,1-c][1,2,4]oxadiazine-1(6H)-carboxylate | I-1 | II-182 | A | 2.61 | 427.4 |
| I-183 | benzyl 6-isobutyl-4,7-dioxo-8-(pyridin-4-ylmethyl)hexahydropyrazino[2,1-c][1,2,4]oxadiazine-1(6H)-carboxylate | I-1 | II-183 | A | 3.32 | 453.5 |
| I-184 | benzyl 4,7-dioxo-6-phenyl-8-(pyridin-4-ylmethyl)hexahydropyrazino[2,1-c][1,2,4]oxadiazine-1(6H)-carboxylate | I-1 | II-184 | A | 3.26 | 473.5 |
| I-185 | benzyl 6-benzyl-4,7-dioxo-8-(pyridin-4-ylmethyl)hexahydropyrazino[2,1-c][1,2,4]oxadiazine-1(6H)-carboxylate | I-1 | II-185 | A | 3.34 | 487.5 |
| I-186 | benzyl 4,7-dioxo-6-phenethyl-8-(pyridin-4-ylmethyl)hexahydropyrazino[2,1-c][1,2,4]oxadiazine-1(6H)-carboxylate | I-1 | II-186 | A | 3.55 | 501.5 |
| I-187 | benzyl 6-(benzyloxymethyl)-4,7-dioxo-8-(pyridin-4-ylmethyl)hexahydropyrazino[2,1-c][1,2,4]oxadiazine-1(6H)-carboxylate | I-1 | II-187 | A | 3.43 | 517.5 |
| I-188 | benzyl 6-(naphthalen-1-ylmethyl)-4,7-dioxo-8-(pyridin-4-ylmethyl)hexahydropyrazino[2,1-c][1,2,4]oxadiazine-1(6H)-carboxylate | I-1 | II-188 | A | 3.38 | 537.6 |
| I-189 | benzyl 6-(naphthalen-2-ylmethyl)-4,7-dioxo-8-(pyridin-4-ylmethyl)hexahydropyrazino[2,1-c][1,2,4]oxadiazine-1(6H)-carboxylate | I-1 | II-189 | A | 3.34 | 537.6 |
| I-190 | benzyl 8-(cyclohexylmethyl)-6-methyl-4,7-dioxohexahydropyrazino[2,1-c][1,2,4]oxadiazine-1(6H)-carboxylate | I-1 | II-190 | A | 5.02 | 416.5 |
| I-191 | benzyl 8-(cyclohexylmethyl)-6-(4-hydroxybenzyl)-4,7-dioxohexahydropyrazino[2,1-c][1,2,4]oxadiazine-1(6H)-carboxylate | I-1 | II-191 | A | 4.98 | 508.6 |
| I-192 | benzyl 6-(4-aminobutyl)-8-(cyclohexylmethyl)-4,7-dioxohexahydropyrazino[2,1-c][1,2,4]oxadiazine-1(6H)-carboxylate | I-1 | II-192 | A | 3.43 | 473.6 |
| I-193 | 2-(1-(benzyloxycarbonyl)-8-(cyclohexylmethyl)-4,7-dioxooctahydropyrazino[2,1-c][1,2,4]oxadiazin-6-yl)acetic acid | I-1 | II-193 | A | 4.63 | 460.5 |

TABLE C1-continued

| Ex. No. | chemical name | Syn. | Int | method | RT | Mass |
|---|---|---|---|---|---|---|
| I-194 | benzyl 6-(2-amino-2-oxoethyl)-8-(cyclohexylmethyl)-4,7-dioxohexahydropyrazino[2,1-c][1,2,4]oxadiazine-1(6H)-carboxylate | I-1 | II-194 | A | 4.35 | 459.5 |
| I-195 | benzyl 8-(cyclohexylmethyl)-6-(hydroxymethyl)-4,7-dioxohexahydropyrazino[2,1-c][1,2,4]oxadiazine-1(6H)-carboxylate | I-1 | II-195 | A | 4.63 | 432.5 |
| I-196 | benzyl 8-(cyclohexylmethyl)-6-isobutyl-4,7-dioxohexahydropyrazino[2,1-c][1,2,4]oxadiazine-1(6H)-carboxylate | I-1 | II-196 | A | 5.54 | 458.6 |
| I-197 | benzyl 8-(cyclohexylmethyl)-4,7-dioxo-6-phenylhexahydropyrazino[2,1-c][1,2,4]oxadiazine-1(6H)-carboxylate | I-1 | II-197 | A | 5.46 | 478.6 |
| I-198 | benzyl 6-benzyl-8-(cyclohexylmethyl)-4,7-dioxohexahydropyrazino[2,1-c][1,2,4]oxadiazine-1(6H)-carboxylate | I-1 | II-198 | A | 5.54 | 492.6 |
| I-199 | benzyl 8-(cyclohexylmethyl)-4,7-dioxo-6-phenethylhexahydropyrazino[2,1-c][1,2,4]oxadiazine-1(6H)-carboxylate | I-1 | II-199 | A | 5.68 | 506.6 |
| I-200 | benzyl 6-(benzyloxymethyl)-8-(cyclohexylmethyl)-4,7-dioxohexahydropyrazino[2,1-c][1,2,4]oxadiazine-1(6H)-carboxylate | I-1 | II-200 | A | 5.66 | 522.6 |
| I-201 | benzyl 8-(cyclohexylmethyl)-6-(naphthalen-1-ylmethyl)-4,7-dioxohexahydropyrazino[2,1-c][1,2,4]oxadiazine-1(6H)-carboxylate | I-1 | II-201 | A | 5.44 | 542.6 |
| I-202 | benzyl 8-(cyclohexylmethyl)-6-(naphthalen-2-ylmethyl)-4,7-dioxohexahydropyrazino[2,1-c][1,2,4]oxadiazine-1(6H)-carboxylate | I-1 | II-202 | A | 5.52 | 542.6 |
| I-203 | benzyl 8-(2-hydroxyethyl)-6-methyl-4,7-dioxohexahydropyrazino[2,1-c][1,2,4]oxadiazine-1(6H)-carboxylate | I-1 | II-203 | A | 2.53 | 364.4 |
| I-204 | benzyl 6-(4-hydroxybenzyl)-8-(2-hydroxyethyl)-4,7-dioxohexahydropyrazino[2,1-c][1,2,4]oxadiazine-1(6H)-carboxylate | I-1 | II-204 | A | 3.89 | 456.5 |
| I-205 | benzyl 6-(4-aminobutyl)-8-(2-hydroxyethyl)-4,7-dioxohexahydropyrazino[2,1-c][1,2,4]oxadiazine-1(6H)-carboxylate | I-1 | II-205 | A | 2.69 | 421.5 |
| I-206 | 2-(1-(benzyloxycarbonyl)-8-(2-hydroxyethyl)-4,7-dioxooctahydropyrazino[2,1-c][1,2,4]oxadiazin-6-yl)acetic acid | I-1 | II-206 | A | 3.18 | 408.4 |
| I-207 | benzyl 6-(2-amino-2-oxoethyl)-8-(2-hydroxyethyl)-4,7-dioxohexahydropyrazino[2,1-c][1,2,4]oxadiazine-1(6H)-carboxylate | I-1 | II-207 | A | 3.02 | 407.4 |
| I-208 | benzyl 8-(2-hydroxyethyl)-6-(hydroxymethyl)-4,7-dioxohexahydropyrazino[2,1-c][1,2,4]oxadiazine-1(6H)-carboxylate | I-1 | II-208 | A | 3.36 | 380.4 |
| I-209 | benzyl 8-(2-hydroxyethyl)-6-isobutyl-4,7-dioxohexahydropyrazino[2,1-c][1,2,4]oxadiazine-1(6H)-carboxylate | I-1 | II-209 | A | 4.47 | 406.4 |
| I-210 | benzyl 8-(2-hydroxyethyl)-4,7-dioxo-6-phenylhexahydropyrazino[2,1-c][1,2,4]oxadiazine-1(6H)-carboxylate | I-1 | II-210 | A | 4.35 | 426.4 |
| I-211 | benzyl 6-benzyl-8-(2-hydroxyethyl)-4,7-dioxohexahydropyrazino[2,1-c][1,2,4]oxadiazine-1(6H)-carboxylate | I-1 | II-211 | A | 4.49 | 440.5 |
| I-212 | benzyl 8-(2-hydroxyethyl)-4,7-dioxo-6-phenethylhexahydropyrazino[2,1-c][1,2,4]oxadiazine-1(6H)-carboxylate | I-1 | II-212 | A | 4.67 | 454.5 |
| I-213 | benzyl 6-(benzyloxymethyl)-8-(2-hydroxyethyl)-4,7-dioxohexahydropyrazino[2,1-c][1,2,4]oxadiazine-1(6H)-carboxylate | I-1 | II-213 | A | 4.17 | 470.5 |
| I-214 | benzyl 8-(2-hydroxyethyl)-6-(naphthalen-1-ylmethyl)-4,7-dioxohexahydropyrazino[2,1-c][1,2,4]oxadiazine-1(6H)-carboxylate | I-1 | II-214 | A | 4.93 | 490.5 |
| I-215 | benzyl 8-(2-hydroxyethyl)-6-(naphthalen-2-ylmethyl)-4,7-dioxohexahydropyrazino[2,1-c][1,2,4]oxadiazine-1(6H)-carboxylate | I-1 | II-215 | A | 4.93 | 490.5 |
| I-216 | 3-(1-(benzyloxycarbonyl)-6-methyl-4,7-dioxohexahydropyrazino[2,1-c][1,2,4]oxadiazin-8(1H)-yl)propanoic acid | I-1 | II-216 | A | 3.46 | 392.4 |
| I-217 | 3-(1-(benzyloxycarbonyl)-6-(4-hydroxybenzyl)-4,7-dioxohexahydropyrazino[2,1-c][1,2,4]oxadiazin-8(1H)-yl)propanoic acid | I-1 | II-217 | A | 3.58 | 484.5 |
| I-218 | 3-(6-(4-aminobutyl)-1-(benzyloxycarbonyl)-4,7-dioxohexahydropyrazino[2,1-c][1,2,4]oxadiazin-8(1H)-yl)propanoic acid | I-1 | II-218 | A | 2.61 | 449.5 |
| I-219 | 3-(1-(benzyloxycarbonyl)-6-(carboxymethyl)-4,7-dioxohexahydropyrazino[2,1-c][1,2,4]oxadiazin-8(1H)-yl)propanoic acid | I-1 | II-219 | A | 3.30 | 436.4 |

TABLE C1-continued

| Ex. No. | chemical name | Syn. | Int | method | RT | Mass |
|---|---|---|---|---|---|---|
| I-220 | 3-(6-(2-amino-2-oxoethyl)-1-(benzyloxycarbonyl)-4,7-dioxohexahydropyrazino[2,1-c][1,2,4]oxadiazin-8(1H)-yl)propanoic acid | I-1 | II-220 | A | 3.14 | 435.4 |
| I-221 | 3-(1-(benzyloxycarbonyl)-6-(hydroxymethyl)-4,7-dioxohexahydropyrazino[2,1-c][1,2,4]oxadiazin-8(1H)-yl)propanoic acid | I-1 | II-221 | A | 3.24 | 408.4 |
| I-222 | 3-(1-(benzyloxycarbonyl)-6-isobutyl-4,7-dioxohexahydropyrazino[2,1-c][1,2,4]oxadiazin-8(1H)-yl)propanoic acid | I-1 | II-222 | A | 4.10 | 434.5 |
| I-223 | 3-(1-(benzyloxycarbonyl)-4,7-dioxo-6-phenylhexahydropyrazino[2,1-c][1,2,4]oxadiazin-8(1H)-yl)propanoic acid | I-1 | II-223 | A | 4.00 | 454.4 |
| I-224 | 3-(6-benzyl-1-(benzyloxycarbonyl)-4,7-dioxohexahydropyrazino[2,1-c][1,2,4]oxadiazin-8(1H)-yl)propanoic acid | I-1 | II-224 | A | 4.13 | 468.5 |
| I-225 | 3-(1-(benzyloxycarbonyl)-4,7-dioxo-6-phenethylhexahydropyrazino[2,1-c][1,2,4]oxadiazin-8(1H)-yl)propanoic acid | I-1 | II-225 | A | 4.32 | 482.5 |
| I-226 | 3-(1-(benzyloxycarbonyl)-6-(benzyloxymethyl)-4,7-dioxohexahydropyrazino[2,1-c][1,2,4]oxadiazin-8(1H)-yl)propanoic acid | I-1 | II-226 | A | 4.25 | 498.5 |
| I-227 | 3-(1-(benzyloxycarbonyl)-6-(naphthalen-1-ylmethyl)-4,7-dioxohexahydropyrazino[2,1-c][1,2,4]oxadiazin-8(1H)-yl)propanoic acid | I-1 | II-227 | A | 4.13 | 518.5 |
| I-228 | 3-(1-(benzyloxycarbonyl)-6-(naphthalen-2-ylmethyl)-4,7-dioxohexahydropyrazino[2,1-c][1,2,4]oxadiazin-8(1H)-yl)propanoic acid | I-1 | II-228 | A | 4.15 | 518.5 |
| I-229 | benzyl 8-(3-methoxy-3-oxopropyl)-6-methyl-4,7-dioxohexahydropyrazino[2,1-c][1,2,4]oxadiazine-1(6H)-carboxylate | I-1 | II-229 | A | 3.89 | 406.4 |
| I-230 | benzyl 6-(4-hydroxybenzyl)-8-(3-methoxy-3-oxopropyl)-4,7-dioxohexahydropyrazino[2,1-c][1,2,4]oxadiazine-1(6H)-carboxylate | I-1 | II-230 | A | 3.98 | 498.5 |
| I-231 | benzyl 6-(4-aminobutyl)-8-(3-methoxy-3-oxopropyl)-4,7-dioxohexahydropyrazino[2,1-c][1,2,4]oxadiazine-1(6H)-carboxylate | I-1 | II-231 | A | 2.88 | 463.5 |
| I-232 | 2-(1-(benzyloxycarbonyl)-8-(3-methoxy-3-oxopropyl)-4,7-dioxooctahydropyrazino[2,1-c][1,2,4]oxadiazin-6-yl)acetic acid | I-1 | II-232 | A | 3.14 | 450.4 |
| I-233 | benzyl 6-(2-amino-2-oxoethyl)-8-(3-methoxy-3-oxopropyl)-4,7-dioxohexahydropyrazino[2,1-c][1,2,4]oxadiazine-1(6H)-carboxylate | I-1 | II-233 | A | 3.44 | 449.4 |
| I-234 | benzyl 6-(hydroxymethyl)-8-(3-methoxy-3-oxopropyl)-4,7-dioxohexahydropyrazino[2,1-c][1,2,4]oxadiazine-1(6H)-carboxylate | I-1 | II-234 | A | 3.58 | 422.4 |
| I-235 | benzyl 6-isobutyl-8-(3-methoxy-3-oxopropyl)-4,7-dioxohexahydropyrazino[2,1-c][1,2,4]oxadiazine-1(6H)-carboxylate | I-1 | II-235 | A | 4.51 | 448.5 |
| I-236 | benzyl 8-(3-methoxy-3-oxopropyl)-4,7-dioxo-6-phenylhexahydropyrazino[2,1-c][1,2,4]oxadiazine-1(6H)-carboxylate | I-1 | II-236 | A | 4.45 | 468.5 |
| I-237 | benzyl 6-benzyl-8-(3-methoxy-3-oxopropyl)-4,7-dioxohexahydropyrazino[2,1-c][1,2,4]oxadiazine-1(6H)-carboxylate | I-1 | II-237 | A | 4.53 | 482.5 |
| I-238 | benzyl 8-(3-methoxy-3-oxopropyl)-4,7-dioxo-6-phenethylhexahydropyrazino[2,1-c][1,2,4]oxadiazine-1(6H)-carboxylate | I-1 | II-238 | A | 4.72 | 496.5 |
| I-239 | benzyl 6-(benzyloxymethyl)-8-(3-methoxy-3-oxopropyl)-4,7-dioxohexahydropyrazino[2,1-c][1,2,4]oxadiazine-1(6H)-carboxylate | I-1 | II-239 | A | 4.67 | 512.5 |
| I-240 | benzyl 8-(3-methoxy-3-oxopropyl)-6-(naphthalen-1-ylmethyl)-4,7-dioxohexahydropyrazino[2,1-c][1,2,4]oxadiazine-1(6H)-carboxylate | I-1 | II-240 | A | 4.49 | 532.6 |
| I-241 | benzyl 8-(3-methoxy-3-oxopropyl)-6-(naphthalen-2-ylmethyl)-4,7-dioxohexahydropyrazino[2,1-c][1,2,4]oxadiazine-1(6H)-carboxylate | I-1 | II-241 | A | 4.51 | 532.6 |
| I-242 | 1-(benzylsulfonyl)-8-isopentyl-6-methyltetrahydropyrazino[2,1-c][1,2,4]oxadiazine-4,7(1H,3H)-dione | I-1 | II-242 | A | 4.57 | 410.5 |
| I-243 | 1-(benzylsulfonyl)-6-(4-hydroxybenzyl)-8-isopentyltetrahydropyrazino[2,1-c][1,2,4]oxadiazine-4,7(1H,3H)-dione | I-1 | II-243 | A | 4.65 | 502.6 |
| I-244 | 6-(4-aminobutyl)-1-(benzylsulfonyl)-8-isopentyltetrahydropyrazino[2,1-c][1,2,4]oxadiazine-4,7(1H,3H)-dione | I-1 | II-244 | A | 3.26 | 467.6 |
| I-245 | 2-(1-(benzylsulfonyl)-8-isopentyl-4,7-dioxooctahydropyrazino[2,1-c][1,2,4]oxadiazin-6-yl)acetic acid | I-1 | II-245 | A | 4.29 | 454.5 |
| I-246 | 2-(1-(benzylsulfonyl)-8-isopentyl-4,7-dioxooctahydropyrazino[2,1-c][1,2,4]oxadiazin-6-yl)acetamide | I-1 | II-246 | A | 4.07 | 453.5 |

TABLE C1-continued

| Ex. No. | chemical name | Syn. | Int | method | RT | Mass |
|---|---|---|---|---|---|---|
| I-247 | 1-(benzylsulfonyl)-6-(hydroxymethyl)-8-isopentyltetrahydropyrazino[2,1-c][1,2,4]oxadiazine-4,7(1H,3H)-dione | I-1 | II-247 | A | 4.29 | 426.5 |
| I-248 | 1-(benzylsulfonyl)-6-isobutyl-8-isopentyltetrahydropyrazino[2,1-c][1,2,4]oxadiazine-4,7(1H,3H)-dione | I-1 | II-248 | A | 5.16 | 452.6 |
| I-249 | 1-(benzylsulfonyl)-8-isopentyl-6-phenyltetrahydropyrazino[2,1-c][1,2,4]oxadiazine-4,7(1H,3H)-dione | I-1 | II-249 | A | 5.06 | 472.6 |
| I-250 | 6-benzyl-1-(benzylsulfonyl)-8-isopentyltetrahydropyrazino[2,1-c][1,2,4]oxadiazine-4,7(1H,3H)-dione | I-1 | II-250 | A | 5.18 | 486.6 |
| I-251 | 1-(benzylsulfonyl)-8-isopentyl-6-phenethyltetrahydropyrazino[2,1-c][1,2,4]oxadiazine-4,7(1H,3H)-dione | I-1 | II-251 | A | 5.32 | 500.6 |
| I-252 | 6-(benzyloxymethyl)-1-(benzylsulfonyl)-8-isopentyltetrahydropyrazino[2,1-c][1,2,4]oxadiazine-4,7(1H,3H)-dione | I-1 | II-252 | A | 5.28 | 516.6 |
| I-253 | 1-(benzylsulfonyl)-8-isopentyl-6-(naphthalen-1-ylmethyl)tetrahydropyrazino[2,1-c][1,2,4]oxadiazine-4,7(1H,3H)-dione | I-1 | II-253 | A | 5.08 | 536.7 |
| I-254 | 1-(benzylsulfonyl)-8-isopentyl-6-(naphthalen-2-ylmethyl)tetrahydropyrazino[2,1-c][1,2,4]oxadiazine-4,7(1H,3H)-dione | I-1 | II-254 | A | 5.10 | 536.7 |
| I-255 | 1-(benzylsulfonyl)-6-methyl-8-phenethyltetrahydropyrazino[2,1-c][1,2,4]oxadiazine-4,7(1H,3H)-dione | I-1 | II-255 | A | 4.55 | 444.5 |
| I-256 | 1-(benzylsulfonyl)-6-(4-hydroxybenzyl)-8-phenethyltetrahydropyrazino[2,1-c][1,2,4]oxadiazine-4,7(1H,3H)-dione | I-1 | II-256 | A | 4.59 | 536.6 |
| I-257 | 6-(4-aminobutyl)-1-(benzylsulfonyl)-8-phenethyltetrahydropyrazino[2,1-c][1,2,4]oxadiazine-4,7(1H,3H)-dione | I-1 | II-257 | A | 3.24 | 501.6 |
| I-258 | 2-(1-(benzylsulfonyl)-4,7-dioxo-8-phenethyloctahydropyrazino[2,1-c][1,2,4]oxadiazin-6-yl)acetic acid | I-1 | II-258 | A | 4.29 | 488.5 |
| I-259 | 2-(1-(benzylsulfonyl)-4,7-dioxo-8-phenethyloctahydropyrazino[2,1-c][1,2,4]oxadiazin-6-yl)acetamide | I-1 | II-259 | A | 4.09 | 487.5 |
| I-260 | 1-(benzylsulfonyl)-6-(hydroxymethyl)-8-phenethyltetrahydropyrazino[2,1-c][1,2,4]oxadiazine-4,7(1H,3H)-dione | I-1 | II-260 | A | 4.25 | 460.5 |
| I-261 | 1-(benzylsulfonyl)-6-isobutyl-8-phenethyltetrahydropyrazino[2,1-c][1,2,4]oxadiazine-4,7(1H,3H)-dione | I-1 | II-261 | A | 5.12 | 486.6 |
| I-262 | 1-(benzylsulfonyl)-8-phenethyl-6-phenyltetrahydropyrazino[2,1-c][1,2,4]oxadiazine-4,7(1H,3H)-dione | I-1 | II-262 | A | 5.02 | 506.6 |
| I-263 | 6-benzyl-1-(benzylsulfonyl)-8-phenethyltetrahydropyrazino[2,1-c][1,2,4]oxadiazine-4,7(1H,3H)-dione | I-1 | II-263 | A | 5.12 | 520.6 |
| I-264 | 1-(benzylsulfonyl)-6,8-diphenethyltetrahydropyrazino[2,1-c][1,2,4]oxadiazine-4,7(1H,3H)-dione | I-1 | II-264 | A | 5.28 | 534.6 |
| I-265 | 6-(benzyloxymethyl)-1-(benzylsulfonyl)-8-phenethyltetrahydropyrazino[2,1-c][1,2,4]oxadiazine-4,7(1H,3H)-dione | I-1 | II-265 | A | 5.24 | 550.6 |
| I-266 | 1-(benzylsulfonyl)-6-(naphthalen-1-ylmethyl)-8-phenethyltetrahydropyrazino[2,1-c][1,2,4]oxadiazine-4,7(1H,3H)-dione | I-1 | II-266 | A | 5.04 | 570.7 |
| I-267 | 1-(benzylsulfonyl)-6-(naphthalen-2-ylmethyl)-8-phenethyltetrahydropyrazino[2,1-c][1,2,4]oxadiazine-4,7(1H,3H)-dione | I-1 | II-267 | A | 5.08 | 570.7 |
| I-268 | 1-(benzylsulfonyl)-6-methyl-8-(3-phenylpropyl)tetrahydropyrazino[2,1-c][1,2,4]oxadiazine-4,7(1H,3H)-dione | I-1 | II-268 | A | 4.73 | 458.5 |
| I-269 | 1-(benzylsulfonyl)-6-(4-hydroxybenzyl)-8-(3-phenylpropyl)tetrahydropyrazino[2,1-c][1,2,4]oxadiazine-4,7(1H,3H)-dione | I-1 | II-269 | A | 4.75 | 550.6 |
| I-270 | 6-(4-aminobutyl)-1-(benzylsulfonyl)-8-(3-phenylpropyl)tetrahydropyrazino[2,1-c][1,2,4]oxadiazine-4,7(1H,3H)-dione | I-1 | II-270 | A | 3.38 | 515.6 |
| I-271 | 2-(1-(benzylsulfonyl)-4,7-dioxo-8-(3-phenylpropyl)octahydropyrazino[2,1-c][1,2,4]oxadiazin-6-yl)acetic acid | I-1 | II-271 | A | 4.47 | 502.6 |
| I-272 | 2-(1-(benzylsulfonyl)-4,7-dioxo-8-(3-phenylpropyl)octahydropyrazino[2,1-c][1,2,4]oxadiazin-6-yl)acetamide | I-1 | II-272 | A | 4.27 | 501.6 |
| I-273 | 1-(benzylsulfonyl)-6-(hydroxymethyl)-8-(3-phenylpropyl)tetrahydropyrazino[2,1-c][1,2,4]oxadiazine-4,7(1H,3H)-dione | I-1 | II-273 | A | 4.45 | 474.5 |
| I-274 | 1-(benzylsulfonyl)-6-isobutyl-8-(3-phenylpropyl)tetrahydropyrazino[2,1-c][1,2,4]oxadiazine-4,7(1H,3H)-dione | I-1 | II-274 | A | 5.26 | 500.6 |

TABLE C1-continued

| Ex. No. | chemical name | Syn. | Int | method | RT | Mass |
|---|---|---|---|---|---|---|
| I-275 | 1-(benzylsulfonyl)-6-phenyl-8-(3-phenylpropyl)tetrahydropyrazino[2,1-c][1,2,4]oxadiazine-4,7(1H,3H)-dione | I-1 | II-275 | A | 5.20 | 520.6 |
| I-276 | 6-benzyl-1-(benzylsulfonyl)-8-(3-phenylpropyl)tetrahydropyrazino[2,1-c][1,2,4]oxadiazine-4,7(1H,3H)-dione | I-1 | II-276 | A | 5.26 | 534.6 |
| I-277 | 1-(benzylsulfonyl)-6-phenethyl-8-(3-phenylpropyl)tetrahydropyrazino[2,1-c][1,2,4]oxadiazine-4,7(1H,3H)-dione | I-1 | II-277 | A | 5.40 | 548.7 |
| I-278 | 6-(benzyloxymethyl)-1-(benzylsulfonyl)-8-(3-phenylpropyl)tetrahydropyrazino[2,1-c][1,2,4]oxadiazine-4,7(1H,3H)-dione | I-1 | II-278 | A | 5.36 | 564.7 |
| I-279 | 1-(benzylsulfonyl)-6-(naphthalen-1-ylmethyl)-8-(3-phenylpropyl)tetrahydropyrazino[2,1-c][1,2,4]oxadiazine-4,7(1H,3H)-dione | I-1 | II-279 | A | 5.14 | 584.7 |
| I-280 | 1-(benzylsulfonyl)-6-(naphthalen-2-ylmethyl)-8-(3-phenylpropyl)tetrahydropyrazino[2,1-c][1,2,4]oxadiazine-4,7(1H,3H)-dione | I-1 | II-280 | A | 5.16 | 584.7 |
| I-281 | 1-(benzylsulfonyl)-8-(3,3-diphenylpropyl)-6-methyltetrahydropyrazino[2,1-c][1,2,4]oxadiazine-4,7(1H,3H)-dione | I-1 | II-281 | A | 5.12 | 534.6 |
| I-282 | 1-(benzylsulfonyl)-8-(3,3-diphenylpropyl)-6-(4-hydroxybenzyl)tetrahydropyrazino[2,1-c][1,2,4]oxadiazine-4,7(1H,3H)-dione | I-1 | II-282 | A | 5.18 | 626.7 |
| I-283 | 6-(4-aminobutyl)-1-(benzylsulfonyl)-8-(3,3-diphenylpropyl)tetrahydropyrazino[2,1-c][1,2,4]oxadiazine-4,7(1H,3H)-dione | I-1 | II-283 | A | 3.62 | 591.7 |
| I-284 | 2-(1-(benzylsulfonyl)-8-(3,3-diphenylpropyl)-4,7-dioxooctahydropyrazino[2,1-c][1,2,4]oxadiazin-6-yl)acetic acid | I-1 | II-284 | A | 4.87 | 578.6 |
| I-285 | 2-(1-(benzylsulfonyl)-8-(3,3-diphenylpropyl)-4,7-dioxooctahydropyrazino[2,1-c][1,2,4]oxadiazin-6-yl)acetamide | I-1 | II-285 | A | 4.71 | 577.7 |
| I-286 | 1-(benzylsulfonyl)-8-(3,3-diphenylpropyl)-6-(hydroxymethyl)tetrahydropyrazino[2,1-c][1,2,4]oxadiazine-4,7(1H,3H)-dione | I-1 | II-286 | A | 4.87 | 550.6 |
| I-287 | 1-(benzylsulfonyl)-8-(3,3-diphenylpropyl)-6-isobutyltetrahydropyrazino[2,1-c][1,2,4]oxadiazine-4,7(1H,3H)-dione | I-1 | II-287 | A | 5.60 | 576.7 |
| I-288 | 1-(benzylsulfonyl)-8-(3,3-diphenylpropyl)-6-phenyltetrahydropyrazino[2,1-c][1,2,4]oxadiazine-4,7(1H,3H)-dione | I-1 | II-288 | A | 5.54 | 596.7 |
| I-289 | 6-benzyl-1-(benzylsulfonyl)-8-(3,3-diphenylpropyl)tetrahydropyrazino[2,1-c][1,2,4]oxadiazine-4,7(1H,3H)-dione | I-1 | II-289 | A | 5.60 | 610.7 |
| I-290 | 1-(benzylsulfonyl)-8-(3,3-diphenylpropyl)-6-phenethyltetrahydropyrazino[2,1-c][1,2,4]oxadiazine-4,7(1H,3H)-dione | I-1 | II-290 | A | 5.72 | 624.8 |
| I-291 | 6-(benzyloxymethyl)-1-(benzylsulfonyl)-8-(3,3-diphenylpropyl)tetrahydropyrazino[2,1-c][1,2,4]oxadiazine-4,7(1H,3H)-dione | I-1 | II-291 | A | 5.70 | 640.8 |
| I-292 | 1-(benzylsulfonyl)-8-(3,3-diphenylpropyl)-6-(naphthalen-1-ylmethyl)tetrahydropyrazino[2,1-c][1,2,4]oxadiazine-4,7(1H,3H)-dione | I-1 | II-292 | A | 5.46 | 660.8 |
| I-293 | 1-(benzylsulfonyl)-8-(3,3-diphenylpropyl)-6-(naphthalen-2-ylmethyl)tetrahydropyrazino[2,1-c][1,2,4]oxadiazine-4,7(1H,3H)-dione | I-1 | II-293 | A | 5.48 | 660.8 |
| I-294 | 1-(benzylsulfonyl)-6-methyl-8-(naphthalen-2-ylmethyl)tetrahydropyrazino[2,1-c][1,2,4]oxadiazine-4,7(1H,3H)-dione | I-1 | II-294 | A | 4.87 | 480.5 |
| I-295 | 1-(benzylsulfonyl)-6-(4-hydroxybenzyl)-8-(naphthalen-2-ylmethyl)tetrahydropyrazino[2,1-c][1,2,4]oxadiazine-4,7(1H,3H)-dione | I-1 | II-295 | A | 4.89 | 572.6 |
| I-296 | 6-(4-aminobutyl)-1-(benzylsulfonyl)-8-(naphthalen-2-ylmethyl)tetrahydropyrazino[2,1-c][1,2,4]oxadiazine-4,7(1H,3H)-dione | I-1 | II-296 | A | 3.42 | 537.6 |
| I-297 | 2-(1-(benzylsulfonyl)-8-(naphthalen-2-ylmethyl)-4,7-dioxooctahydropyrazino[2,1-c][1,2,4]oxadiazin-6-yl)acetic acid | I-1 | II-297 | A | 4.57 | 524.6 |
| I-298 | 2-(1-(benzylsulfonyl)-8-(naphthalen-2-ylmethyl)-4,7-dioxooctahydropyrazino[2,1-c][1,2,4]oxadiazin-6-yl)acetamide | I-1 | II-298 | A | 4.39 | 523.6 |
| I-299 | 1-(benzylsulfonyl)-6-(hydroxymethyl)-8-(naphthalen-2-ylmethyl)tetrahydropyrazino[2,1-c][1,2,4]oxadiazine-4,7(1H,3H)-dione | I-1 | II-299 | A | 4.55 | 496.5 |
| I-300 | 1-(benzylsulfonyl)-6-isobutyl-8-(naphthalen-2-ylmethyl)tetrahydropyrazino[2,1-c][1,2,4]oxadiazine-4,7(1H,3H)-dione | I-1 | II-300 | A | 5.42 | 522.6 |
| I-301 | 1-(benzylsulfonyl)-8-(naphthalen-2-ylmethyl)-6-phenyltetrahydropyrazino[2,1-c][1,2,4]oxadiazine-4,7(1H,3H)-dione | I-1 | II-301 | A | 5.34 | 542.6 |

TABLE C1-continued

| Ex. No. | chemical name | Syn. | Int | method | RT | Mass |
|---|---|---|---|---|---|---|
| I-302 | 6-benzyl-1-(benzylsulfonyl)-8-(naphthalen-2-ylmethyl)tetrahydropyrazino[2,1-c][1,2,4]oxadiazine-4,7(1H,3H)-dione | I-1 | II-302 | A | 5.42 | 556.6 |
| I-303 | 1-(benzylsulfonyl)-8-(naphthalen-2-ylmethyl)-6-phenethyltetrahydropyrazino[2,1-c][1,2,4]oxadiazine-4,7(1H,3H)-dione | I-1 | II-303 | A | 5.56 | 570.7 |
| I-304 | 6-(benzyloxymethyl)-1-(benzylsulfonyl)-8-(naphthalen-2-ylmethyl)tetrahydropyrazino[2,1-c][1,2,4]oxadiazine-4,7(1H,3H)-dione | I-1 | II-304 | A | 5.50 | 586.7 |
| I-305 | 1-(benzylsulfonyl)-6-(naphthalen-1-ylmethyl)-8-(naphthalen-2-ylmethyl)tetrahydropyrazino[2,1-c][1,2,4]oxadiazine-4,7(1H,3H)-dione | I-1 | II-305 | A | 5.30 | 606.7 |
| I-306 | 1-(benzylsulfonyl)-6,8-bis(naphthalen-2-ylmethyl)tetrahydropyrazino[2,1-c][1,2,4]oxadiazine-4,7(1H,3H)-dione | I-1 | II-306 | A | 5.30 | 606.7 |
| I-307 | 1-(benzylsulfonyl)-6-methyl-8-(pyridin-4-ylmethyl)tetrahydropyrazino[2,1-c][1,2,4]oxadiazine-4,7(1H,3H)-dione | I-1 | II-307 | A | 2.71 | 431.5 |
| I-308 | 1-(benzylsulfonyl)-6-(4-hydroxybenzyl)-8-(pyridin-4-ylmethyl)tetrahydropyrazino[2,1-c][1,2,4]oxadiazine-4,7(1H,3H)-dione | I-1 | II-308 | A | 2.98 | 523.6 |
| I-309 | 6-(4-aminobutyl)-1-(benzylsulfonyl)-8-(pyridin-4-ylmethyl)tetrahydropyrazino[2,1-c][1,2,4]oxadiazine-4,7(1H,3H)-dione | I-1 | II-309 | A | 2.17 | 488.6 |
| I-310 | 2-(1-(benzylsulfonyl)-4,7-dioxo-8-(pyridin-4-ylmethyl)octahydropyrazino[2,1-c][1,2,4]oxadiazin-6-yl)acetic acid | I-1 | II-310 | A | 2.57 | 475.5 |
| I-311 | 2-(1-(benzylsulfonyl)-4,7-dioxo-8-(pyridin-4-ylmethyl)octahydropyrazino[2,1-c][1,2,4]oxadiazin-6-yl)acetamide | I-1 | II-311 | A | 2.45 | 474.5 |
| I-312 | 1-(benzylsulfonyl)-6-(hydroxymethyl)-8-(pyridin-4-ylmethyl)tetrahydropyrazino[2,1-c][1,2,4]oxadiazine-4,7(1H,3H)-dione | I-1 | II-312 | A | 2.75 | 447.5 |
| I-313 | 1-(benzylsulfonyl)-6-isobutyl-8-(pyridin-4-ylmethyl)tetrahydropyrazino[2,1-c][1,2,4]oxadiazine-4,7(1H,3H)-dione | I-1 | II-313 | A | 3.30 | 473.6 |
| I-314 | 1-(benzylsulfonyl)-6-phenyl-8-(pyridin-4-ylmethyl)tetrahydropyrazino[2,1-c][1,2,4]oxadiazine-4,7(1H,3H)-dione | I-1 | II-314 | A | 3.24 | 493.5 |
| I-315 | 6-benzyl-1-(benzylsulfonyl)-8-(pyridin-4-ylmethyl)tetrahydropyrazino[2,1-c][1,2,4]oxadiazine-4,7(1H,3H)-dione | I-1 | II-315 | A | 3.34 | 507.6 |
| I-316 | 1-(benzylsulfonyl)-6-phenethyl-8-(pyridin-4-ylmethyl)tetrahydropyrazino[2,1-c][1,2,4]oxadiazine-4,7(1H,3H)-dione | I-1 | II-316 | A | 3.52 | 521.6 |
| I-317 | 6-(benzyloxymethyl)-1-(benzylsulfonyl)-8-(pyridin-4-ylmethyl)tetrahydropyrazino[2,1-c][1,2,4]oxadiazine-4,7(1H,3H)-dione | I-1 | II-317 | A | 3.40 | 537.6 |
| I-318 | 1-(benzylsulfonyl)-6-(naphthalen-1-ylmethyl)-8-(pyridin-4-ylmethyl)tetrahydropyrazino[2,1-c][1,2,4]oxadiazine-4,7(1H,3H)-dione | I-1 | II-318 | A | 3.33 | 557.6 |
| I-319 | 1-(benzylsulfonyl)-6-(naphthalen-2-ylmethyl)-8-(pyridin-4-ylmethyl)tetrahydropyrazino[2,1-c][1,2,4]oxadiazine-4,7(1H,3H)-dione | I-1 | II-319 | A | 3.28 | 557.6 |
| I-320 | 1-(benzylsulfonyl)-8-(cyclohexylmethyl)-6-methyltetrahydropyrazino[2,1-c][1,2,4]oxadiazine-4,7(1H,3H)-dione | I-1 | II-320 | A | 4.87 | 436.5 |
| I-321 | 1-(benzylsulfonyl)-8-(cyclohexylmethyl)-6-(4-hydroxybenzyl)tetrahydropyrazino[2,1-c][1,2,4]oxadiazine-4,7(1H,3H)-dione | I-1 | II-321 | A | 4.83 | 528.6 |
| I-322 | 6-(4-aminobutyl)-1-(benzylsulfonyl)-8-(cyclohexylmethyl)tetrahydropyrazino[2,1-c][1,2,4]oxadiazine-4,7(1H,3H)-dione | I-1 | II-322 | A | 3.40 | 493.6 |
| I-323 | 2-(1-(benzylsulfonyl)-8-(cyclohexylmethyl)-4,7-dioxooctahydropyrazino[2,1-c][1,2,4]oxadiazin-6-yl)acetic acid | I-1 | II-323 | A | 4.53 | 480.5 |
| I-324 | 2-(1-(benzylsulfonyl)-8-(cyclohexylmethyl)-4,7-dioxooctahydropyrazino[2,1-c][1,2,4]oxadiazin-6-yl)acetamide | I-1 | II-324 | A | 4.33 | 479.6 |
| I-325 | 1-(benzylsulfonyl)-8-(cyclohexylmethyl)-6-(hydroxymethyl)tetrahydropyrazino[2,1-c][1,2,4]oxadiazine-4,7(1H,3H)-dione | I-1 | II-325 | A | 4.53 | 452.5 |
| I-326 | 1-(benzylsulfonyl)-8-(cyclohexylmethyl)-6-isobutyltetrahydropyrazino[2,1-c][1,2,4]oxadiazine-4,7(1H,3H)-dione | I-1 | II-326 | A | 5.42 | 478.6 |
| I-327 | 1-(benzylsulfonyl)-8-(cyclohexylmethyl)-6-phenyltetrahydropyrazino[2,1-c][1,2,4]oxadiazine-4,7(1H,3H)-dione | I-1 | II-327 | A | 5.34 | 498.6 |

TABLE C1-continued

| Ex. No. | chemical name | Syn. | Int | method | RT | Mass |
|---|---|---|---|---|---|---|
| I-328 | 6-benzyl-1-(benzylsulfonyl)-8-(cyclohexylmethyl)tetrahydropyrazino[2,1-c][1,2,4]oxadiazine-4,7(1H,3H)-dione | I-1 | II-328 | A | 5.42 | 512.6 |
| I-329 | 1-(benzylsulfonyl)-8-(cyclohexylmethyl)-6-phenethyltetrahydropyrazino[2,1-c][1,2,4]oxadiazine-4,7(1H,3H)-dione | I-1 | II-329 | A | 5.58 | 526.7 |
| I-330 | 6-(benzyloxymethyl)-1-(benzylsulfonyl)-8-(cyclohexylmethyl)tetrahydropyrazino[2,1-c][1,2,4]oxadiazine-4,7(1H,3H)-dione | I-1 | II-330 | A | 5.54 | 542.7 |
| I-331 | 1-(benzylsulfonyl)-8-(cyclohexylmethyl)-6-(naphthalen-1-ylmethyl)tetrahydropyrazino[2,1-c][1,2,4]oxadiazine-4,7(1H,3H)-dione | I-1 | II-331 | A | 5.32 | 562.7 |
| I-332 | 1-(benzylsulfonyl)-8-(cyclohexylmethyl)-6-(naphthalen-2-ylmethyl)tetrahydropyrazino[2,1-c][1,2,4]oxadiazine-4,7(1H,3H)-dione | I-1 | II-332 | A | 5.36 | 562.7 |
| I-333 | 1-(benzylsulfonyl)-8-(2-hydroxyethyl)-6-methyltetrahydropyrazino[2,1-c][1,2,4]oxadiazine-4,7(1H,3H)-dione | I-1 | II-333 | A | 3.64 | 384.4 |
| I-334 | 1-(benzylsulfonyl)-6-(4-hydroxybenzyl)-8-(2-hydroxyethyl)tetrahydropyrazino[2,1-c][1,2,4]oxadiazine-4,7(1H,3H)-dione | I-1 | II-334 | A | 3.84 | 476.5 |
| I-335 | 6-(4-aminobutyl)-1-(benzylsulfonyl)-8-(2-hydroxyethyl)tetrahydropyrazino[2,1-c][1,2,4]oxadiazine-4,7(1H,3H)-dione | I-1 | II-335 | A | 2.64 | 441.5 |
| I-336 | 2-(1-(benzylsulfonyl)-8-(2-hydroxyethyl)-4,7-dioxooctahydropyrazino[2,1-c][1,2,4]oxadiazin-6-yl)acetic acid | I-1 | II-336 | A | 3.54 | 428.4 |
| I-337 | 2-(1-(benzylsulfonyl)-8-(2-hydroxyethyl)-4,7-dioxooctahydropyrazino[2,1-c][1,2,4]oxadiazin-6-yl)acetamide | I-1 | II-337 | A | 3.18 | 427.4 |
| I-338 | 1-(benzylsulfonyl)-8-(2-hydroxyethyl)-6-(hydroxymethyl)tetrahydropyrazino[2,1-c][1,2,4]oxadiazine-4,7(1H,3H)-dione | I-1 | II-338 | A | 3.15 | 400.4 |
| I-339 | 1-(benzylsulfonyl)-8-(2-hydroxyethyl)-6-isobutyltetrahydropyrazino[2,1-c][1,2,4]oxadiazine-4,7(1H,3H)-dione | I-1 | II-339 | A | 4.33 | 426.5 |
| I-340 | 1-(benzylsulfonyl)-8-(2-hydroxyethyl)-6-phenyltetrahydropyrazino[2,1-c][1,2,4]oxadiazine-4,7(1H,3H)-dione | I-1 | II-340 | A | 4.25 | 446.5 |
| I-341 | 6-benzyl-1-(benzylsulfonyl)-8-(2-hydroxyethyl)tetrahydropyrazino[2,1-c][1,2,4]oxadiazine-4,7(1H,3H)-dione | I-1 | II-341 | A | 4.37 | 460.5 |
| I-342 | 1-(benzylsulfonyl)-8-(2-hydroxyethyl)-6-phenethyltetrahydropyrazino[2,1-c][1,2,4]oxadiazine-4,7(1H,3H)-dione | I-1 | II-342 | A | 4.53 | 474.5 |
| I-343 | 6-(benzyloxymethyl)-1-(benzylsulfonyl)-8-(2-hydroxyethyl)tetrahydropyrazino[2,1-c][1,2,4]oxadiazine-4,7(1H,3H)-dione | I-1 | II-343 | A | 4.47 | 490.5 |
| I-344 | 1-(benzylsulfonyl)-8-(2-hydroxyethyl)-6-(naphthalen-1-ylmethyl)tetrahydropyrazino[2,1-c][1,2,4]oxadiazine-4,7(1H,3H)-dione | I-1 | II-344 | A | 4.77 | 510.6 |
| I-345 | 1-(benzylsulfonyl)-8-(2-hydroxyethyl)-6-(naphthalen-2-ylmethyl)tetrahydropyrazino[2,1-c][1,2,4]oxadiazine-4,7(1H,3H)-dione | I-1 | II-345 | A | 4.79 | 510.6 |
| I-346 | 3-(1-(benzylsulfonyl)-6-methyl-4,7-dioxohexahydropyrazino[2,1-c][1,2,4]oxadiazin-8(1H)-yl)propanoic acid | I-1 | II-346 | A | 3.44 | 412.4 |
| I-347 | 3-(1-(benzylsulfonyl)-6-(4-hydroxybenzyl)-4,7-dioxohexahydropyrazino[2,1-c][1,2,4]oxadiazin-8(1H)-yl)propanoic acid | I-1 | II-347 | A | 3.56 | 504.5 |
| I-348 | 3-(6-(4-aminobutyl)-1-(benzylsulfonyl)-4,7-dioxohexahydropyrazino[2,1-c][1,2,4]oxadiazin-8(1H)-yl)propanoic acid | I-1 | II-348 | A | 2.57 | 469.5 |
| I-349 | 3-(1-(benzylsulfonyl)-6-(carboxymethyl)-4,7-dioxohexahydropyrazino[2,1-c][1,2,4]oxadiazin-8(1H)-yl)propanoic acid | I-1 | II-349 | A | 3.24 | 456.4 |
| I-350 | 3-(6-(2-amino-2-oxoethyl)-1-(benzylsulfonyl)-4,7-dioxohexahydropyrazino[2,1-c][1,2,4]oxadiazin-8(1H)-yl)propanoic acid | I-1 | II-350 | A | 3.08 | 455.5 |
| I-351 | 3-(1-(benzylsulfonyl)-6-(hydroxymethyl)-4,7-dioxohexahydropyrazino[2,1-c][1,2,4]oxadiazin-8(1H)-yl)propanoic acid | I-1 | II-351 | A | 3.20 | 428.4 |
| I-352 | 3-(1-(benzylsulfonyl)-6-isobutyl-4,7-dioxohexahydropyrazino[2,1-c][1,2,4]oxadiazin-8(1H)-yl)propanoic acid | I-1 | II-352 | A | 4.07 | 454.5 |
| I-353 | 3-(1-(benzylsulfonyl)-4,7-dioxo-6-phenylhexahydropyrazino[2,1-c][1,2,4]oxadiazin-8(1H)-yl)propanoic acid | I-1 | II-353 | A | 3.99 | 474.5 |
| I-354 | 3-(6-benzyl-1-(benzylsulfonyl)-4,7-dioxohexahydropyrazino[2,1-c][1,2,4]oxadiazin-8(1H)-yl)propanoic acid | I-1 | II-354 | A | 4.07 | 488.5 |

TABLE C1-continued

| Ex. No. | chemical name | Syn. | Int | method | RT | Mass |
|---|---|---|---|---|---|---|
| I-355 | 3-(1-(benzylsulfonyl)-4,7-dioxo-6-phenethylhexahydropyrazino[2,1-c][1,2,4]oxadiazin-8(1H)-yl)propanoic acid | I-1 | II-355 | A | 4.31 | 502.6 |
| I-356 | 3-(6-(benzyloxymethyl)-1-(benzylsulfonyl)-4,7-dioxohexahydropyrazino[2,1-c][1,2,4]oxadiazin-8(1H)-yl)propanoic acid | I-1 | II-356 | A | 4.21 | 518.6 |
| I-357 | 3-(1-(benzylsulfonyl)-6-(naphthalen-1-ylmethyl)-4,7-dioxohexahydropyrazino[2,1-c][1,2,4]oxadiazin-8(1H)-yl)propanoic acid | I-1 | II-357 | A | 4.05 | 538.6 |
| I-358 | 3-(1-(benzylsulfonyl)-6-(naphthalen-2-ylmethyl)-4,7-dioxohexahydropyrazino[2,1-c][1,2,4]oxadiazin-8(1H)-yl)propanoic acid | I-1 | II-358 | A | 4.07 | 538.6 |
| I-359 | methyl 3-(1-(benzylsulfonyl)-6-methyl-4,7-dioxohexahydropyrazino[2,1-c][1,2,4]oxadiazin-8(1H)-yl)propanoate | I-1 | II-359 | A | 3.84 | 426.5 |
| I-360 | methyl 3-(1-(benzylsulfonyl)-6-(4-hydroxybenzyl)-4,7-dioxohexahydropyrazino[2,1-c][1,2,4]oxadiazin-8(1H)-yl)propanoate | I-1 | II-360 | A | 3.97 | 518.6 |
| I-361 | 2-(1-(benzylsulfonyl)-8-(3-methoxy-3-oxopropyl)-4,7-dioxooctahydropyrazino[2,1-c][1,2,4]oxadiazin-6-yl)acetic acid | I-1 | II-361 | A | 3.60 | 470.5 |
| I-362 | methyl 3-(6-(2-amino-2-oxoethyl)-1-(benzylsulfonyl)-4,7-dioxohexahydropyrazino[2,1-c][1,2,4]oxadiazin-8(1H)-yl)propanoate | I-1 | II-362 | A | 3.42 | 469.5 |
| I-363 | methyl 3-(1-(benzylsulfonyl)-6-isobutyl-4,7-dioxohexahydropyrazino[2,1-c][1,2,4]oxadiazin-8(1H)-yl)propanoate | I-1 | II-363 | A | 4.47 | 468.5 |
| I-364 | methyl 3-(1-(benzylsulfonyl)-4,7-dioxo-6-phenylhexahydropyrazino[2,1-c][1,2,4]oxadiazin-8(1H)-yl)propanoate | I-1 | II-364 | A | 4.37 | 488.5 |
| I-365 | methyl 3-(6-benzyl-1-(benzylsulfonyl)-4,7-dioxohexahydropyrazino[2,1-c][1,2,4]oxadiazin-8(1H)-yl)propanoate | I-1 | II-365 | A | 4.47 | 502.6 |
| I-366 | methyl 3-(1-(benzylsulfonyl)-4,7-dioxo-6-phenethylhexahydropyrazino[2,1-c][1,2,4]oxadiazin-8(1H)-yl)propanoate | I-1 | II-366 | A | 4.67 | 516.6 |
| I-367 | methyl 3-(6-(benzyloxymethyl)-1-(benzylsulfonyl)-4,7-dioxohexahydropyrazino[2,1-c][1,2,4]oxadiazin-8(1H)-yl)propanoate | I-1 | II-367 | A | 4.61 | 532.6 |
| I-368 | methyl 3-(1-(benzylsulfonyl)-6-(naphthalen-1-ylmethyl)-4,7-dioxohexahydropyrazino[2,1-c][1,2,4]oxadiazin-8(1H)-yl)propanoate | I-1 | II-368 | A | 4.39 | 552.6 |
| I-369 | methyl 3-(1-(benzylsulfonyl)-6-(naphthalen-2-ylmethyl)-4,7-dioxohexahydropyrazino[2,1-c][1,2,4]oxadiazin-8(1H)-yl)propanoate | I-1 | II-369 | A | 4.41 | 552.6 |

In the table A, the compounds having inhibitory activity more than 50% at the concentration of 10 microM (μM) determined by reporter gene assay are shown below.

Reporter Gene Assay

Screening for inhibitoty action of the Wnt signaling pathway was carried out according to the following procedure using the stably transfected cell line Hek-293, STF1.1

Growth Medium: DMEM, 10% FBS, Pen-Strep, supplemented with 400 μg/ml G418 to maintain selection of SuperTOPFLASH driven Luciferase gene 1. On the day prior to assay, split cells into a white opaque 96-well plate at 20,000 cells per well in 200 microliters of complete growth medium
2. Incubate the plate overnight at 37° C., 5% CO2 and allow the cells to attach
3. Next day, prepare the inhibitors to be tested in complete growth medium, without G418, at 2× the desired final concentration (all conditions are done in duplicates)
4. Carefully remove the old medium from each well using a multiple pipettor
5. Add 50 microliters of fresh growth medium (without G148) containing the inhibitor to each well
6. Be sure to include 2 wells containing medium only, 2 wells for stimulation control, 2 wells for DMSO control, and wells for the positive control ICG-001 (2, 5, and 10 micromolar)
7. Once all inhibitors and controls are added, incubate the plate for 1 hour at 37° C., 5% CO2
8. While plate is incubating, prepare fresh 20 mM LiCl in complete growth medium (without G418)
9. After 1 hour, remove plate from incubator and add 50 microliters of the medium containing 20 mM LiCl to each well, except for the two wells of the unstimulated control (add 50 microliters of just complete medium)
10. Incubate the plate for 24 hours at 37° C., 5% CO2
11. After 24 hours, add 100 microliters of BrightGlo (Promega, Cat. #: G7573) to each well
12. Shake plate for 5 minutes to ensure complete lysis
13. Read plate on the Packard TopCount

TABLE A

| Compound No. | chemical name |
|---|---|
| I-3 | N-benzyl-6'-(4-hydroxybenzyl)-4',7'-dioxo-8'-(quinolin-8-ylmethyl)hexahydrospiro[cyclopropane-1,3'-pyrazino[1,2-a]pyrimidine]-1'(2'H)-carboxamide |
| I-8 | N-benzyl-6-(4-hydroxybenzyl)-3,3-dimethyl-8-(naphthalen-1-ylmethyl)-4,7-dioxooctahydro-1H-pyrimido[1,2-a]pyrazine-1-carboxamide |

TABLE A-continued

| Compound No. | chemical name |
|---|---|
| I-9 | 8-((2-aminobenzo[d]thiazol-4-yl)methyl)-N-benzyl-6-(4-hydroxybenzyl)-3,3-dimethyl-4,7-dioxooctahydro-1H-pyrimido[1,2-a]pyrazine-1-carboxamide |
| I-10 | 2-allyl-N-benzyl-6-(4-hydroxybenzyl)-3,3-dimethyl-8-(naphthalen-1-ylmethyl)-4,7-dioxooctahydro-1H-pyrazino[2,1-c][1,2,4]triazine-1-carboxamide |
| I-11 | N-benzyl-6-(4-hydroxybenzyl)-8-(naphthalen-1-ylmethyl)-4,7-dioxohexahydropyrazino[2,1-c][1,2,4]oxadiazine-1(6H)-carboxamide |
| I-12 | 8-((2-aminobenzo[d]thiazol-4-yl)methyl)-N-benzyl-6-(4-hydroxybenzyl)-4,7-dioxohexahydropyrazino[2,1-c][1,2,4]oxadiazine-1(6H)-carboxamide |
| I-13 | N-benzyl-6-(4-hydroxybenzyl)-2,3,3-trimethyl-8-(naphthalen-1-ylmethyl)-4,7-dioxooctahydro-1H-pyrazino[2,1-c][1,2,4]triazine-1-carboxamide |

INDUSTRIAL APPLICABILITY

The compound of the formula (I) in the present invention blocks TCF4/β-catenin transcriptional pathway by inhibiting CBP, and therefore can be used for treatment of cancer, especially colorectal cancer, and fibrotic diseases.

This application is based on provisional application No. 61/105,088 filed in U.S.A., the contents of which are hereby incorporated by reference.

Although only some exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention.

The invention claimed is:

1. A compound having the following general formula (I):

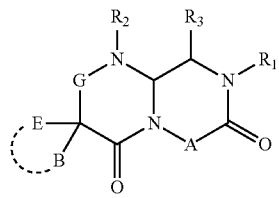

wherein
A is —(CHR$^7$)—;
  wherein
  R$^7$ is hydrogen, optionally substituted alkyl, optionally substituted alkenyl, optionally substituted alkynyl, optionally substituted aryl, optionally substituted heteroaryl, optionally substituted cycloalkyl, optionally substituted heterocycloalkyl, optionally substituted arylalkyl, optionally substituted heteroarylalkyl, optionally substituted cycloalkylalkyl, or optionally substituted heterocycloalkylalkyl;
B and E are the same or different and independently selected from hydrogen, optionally substituted alkyl, optionally substituted alkenyl, and optionally substituted alkynyl, and wherein B and E do not form an optionally substituted spiro ring indicated by dashed lines;
G is —NH—, —NR$^6$—, —O—, —CH$_2$—, —CHR$^6$— or —C(R$^6$)$_2$—;

wherein
each R$^6$ is the same or different and independently selected from optionally substituted alkyl, optionally substituted alkenyl, and optionally substituted alkynyl;
R$^1$ is optionally substituted alkyl, optionally substituted alkenyl, optionally substituted alkynyl, optionally substituted arylalkyl, optionally substituted heteroarylalkyl, optionally substituted cycloalkylalkyl, or optionally substituted heterocycloalkylalkyl;
R$^2$ is —W$^{21}$—W$^{22}$—Rb—R$^{20}$;
  wherein
  W$^{21}$ is —(CO)— or —(SO$_2$)—;
  W$^{22}$ is bond, —O—, —NH— or optionally substituted lower alkylene;
  Rb is bond or optionally substituted lower alkylene; and
  R$^{20}$ is optionally substituted alkyl, optionally substituted alkenyl, optionally substituted alkynyl, optionally substituted aryl, optionally substituted heteroaryl, optionally substituted cycloalkyl, or optionally substituted heterocycloalkyl; and
R$^3$ is hydrogen, optionally substituted alkyl, optionally substituted alkenyl, or optionally substituted alkynyl;
with the proviso that
1) when Rb is optionally substituted lower alkylene, then W$^{22}$ should be —O— or —NH—,
2) when E and B are hydrogen, then R$^3$ should be hydrogen,
3) when G is —NH—, —CH$_2$—, —CHR$^6$— or —NR$^6$—, then neither B nor E should be hydrogen, and
4) when G is —O—, B and E are hydrogen and R$^3$ is hydrogen, then R$^1$ should not be 8-quinolylmethyl;
or a pharmaceutically acceptable salt thereof.

2. The compound of claim 1,
wherein
B and E are the same or different and independently selected from hydrogen, and optionally substituted alkyl.

3. The compound of claim 1
wherein
G is —NR$^6$—, —O—, —CH$_2$— or —C(R$^6$)$_2$—;
  wherein
  each R$^6$ is the same or different and independently selected from optionally substituted alkyl, optionally substituted alkenyl, and optionally substituted alkynyl.

4. The compound of claim 1
wherein
A is —(CHR$^7$)—;
  wherein
  R$^7$ is optionally substituted alkyl, optionally substituted aryl, or optionally substituted arylalkyl.

5. The compound of claim 1
wherein
R$^1$ is optionally substituted alkyl, optionally substituted arylalkyl, optionally substituted heteroarylalkyl, or optionally substituted cycloalkylalkyl.

6. The compound of claim 1
wherein
R$^2$ is —W$^{21}$—W$^{22}$—Rb—R$^{20}$;
  wherein
  W$^{21}$ is —(CO)— or —(SO$_2$)—;
  W$^{22}$ is bond, —O—, —NH— or optionally substituted lower alkylene;
  Rb is bond or optionally substituted lower alkylene; and
  R$^{20}$ is optionally substituted alkyl, optionally substituted aryl, or optionally substituted heteroaryl.

7. The compound of claim 1, wherein

R¹ is —Ra—R¹⁰;
wherein
Ra is optionally substituted lower alkylene and
R¹⁰ is optionally substituted aryl or optionally substituted heteroaryl.

8. The compound of claim 7,
wherein
R¹⁰ is optionally substituted biphenyl, optionally substituted phenyl, optionally substituted pyridyl, optionally substituted pyrimidyl, optionally substituted pyridazinyl, optionally substituted pyrazinyl, optionally substituted triazinyl, optionally substituted pyrrolyl, optionally substituted thienyl, optionally substituted furyl, optionally substituted thiazolyl, optionally substituted oxazolyl, optionally substituted imidazolyl, optionally substituted naphthyl, optionally substituted tetrahydronaphthyl, optionally substituted quinolinyl, optionally substituted isoquinolinyl, optionally substituted quinazolinyl, optionally substituted quinoxalinyl, optionally substituted cinnolinyl, optionally substituted naphthyridinyl, optionally substituted benzotriazinyl, optionally substituted pyridopyrimidinyl, optionally substituted pyridopyrazinyl, optionally substituted pyridopyridazinyl, optionally substituted pyridotriazinyl, optionally substituted indenyl, optionally substituted benzofuryl, optionally substituted benzothienyl, optionally substituted indolyl, optionally substituted indazolyl, optionally substituted benzoxazolyl, optionally substituted benzimidazolyl, optionally substituted benzothiazolyl, optionally substituted benzothiadiazolyl, optionally substituted furopyridinyl, optionally substituted thienopyridinyl, optionally substituted pyrrolopyridinyl, optionally substituted oxazolopyridinyl, optionally substituted thiazolopyridinyl or optionally substituted imidazopyridinyl.

9. The compound of claim 1,
wherein
R² is —W²¹—W²²—Rb—R²⁰;
wherein
W²¹ is —(CO)— or —(SO₂)—;
W²² is bond, —O—, —NH— or optionally substituted lower alkylene;
Rb is bond or optionally substituted lower alkylene; and
R²⁰ is optionally substituted aryl or optionally substituted heteroaryl.

10. The compound of claim 9,
wherein
R²⁰ is optionally substituted biphenyl, optionally substituted phenyl, optionally substituted pyridyl, optionally substituted pyrimidyl, optionally substituted pyridazinyl, optionally substituted pyrazinyl, optionally substituted triazinyl, optionally substituted pyrrolyl, optionally substituted thienyl, optionally substituted furyl, optionally substituted thiazolyl, optionally substituted oxazolyl, optionally substituted imidazolyl, optionally substituted naphthyl, optionally substituted tetrahydronaphthyl, optionally substituted quinolinyl, optionally substituted isoquinolinyl, optionally substituted quinazolinyl, optionally substituted quinoxalinyl, optionally substituted cinnolinyl, optionally substituted naphthyridinyl, optionally substituted benzotriazinyl, optionally substituted pyridopyrimidinyl, optionally substituted pyridopyrazinyl, optionally substituted pyridopyridazinyl, optionally substituted pyridotriazinyl, optionally substituted indenyl, optionally substituted benzofuryl, optionally substituted benzothienyl, optionally substituted indolyl, optionally substituted indazolyl, optionally substituted benzoxazolyl, optionally substituted benzimidazolyl, optionally substituted benzothiazolyl, optionally substituted benzothiadiazolyl, optionally substituted furopyridinyl, optionally substituted thienopyridinyl, optionally substituted pyrrolopyridinyl, optionally substituted oxazolopyridinyl, optionally substituted thiazolopyridinyl or optionally substituted imidazopyridinyl.

11. The compound of claim 1,
wherein
R³ is selected from hydrogen and $C_{1-4}$ lower alkyl group.

12. The compound of claim 1,
wherein
R⁷ of A is -Rc-R⁷⁰
wherein
Rc is bond or optionally substituted lower alkylene, and
R⁷⁰ is optionally substituted aryl or optionally substituted heteroaryl.

13. The compound of claim 12,
wherein
R⁷⁰ is optionally substituted biphenyl, optionally substituted phenyl, optionally substituted pyridyl, optionally substituted pyrimidyl, optionally substituted pyridazinyl, optionally substituted pyrazinyl, optionally substituted triazinyl, optionally substituted pyrrolyl, optionally substituted thienyl, optionally substituted furyl, optionally substituted thiazolyl, optionally substituted oxazolyl, optionally substituted imidazolyl, optionally substituted naphthyl, optionally substituted tetrahydronaphthyl, optionally substituted quinolinyl, optionally substituted isoquinolinyl, optionally substituted quinazolinyl, optionally substituted quinoxalinyl, optionally substituted cinnolinyl, optionally substituted naphthyridinyl, optionally substituted benzotriazinyl, optionally substituted pyridopyrimidinyl, optionally substituted pyridopyrazinyl, optionally substituted pyridopyridazinyl, optionally substituted pyridotriazinyl, optionally substituted indenyl, optionally substituted benzofuryl, optionally substituted benzothienyl, optionally substituted indolyl, optionally substituted indazolyl, optionally substituted benzoxazolyl, optionally substituted benzimidazolyl, optionally substituted benzothiazolyl, optionally substituted benzothiadiazolyl, optionally substituted furopyridinyl, optionally substituted thienopyridinyl, optionally substituted pyrrolopyridinyl, optionally substituted oxazolopyridinyl, optionally substituted thiazolopyridinyl or optionally substituted imidazopyridinyl.

14. The compound of claim 1,
wherein
R¹ is —Ra—R¹⁰;
wherein
Ra is optionally substituted lower alkylene, and
R¹⁰ is optionally substituted aryl, or optionally substituted heteroaryl, and
R³ is selected from hydrogen and $C_{1-4}$ lower alkyl group.

15. The compound of claim 1,
wherein
R² is —W²¹—W²²—Rb—R²⁰;
wherein
W²¹ is —(CO)— or —(SO₂)—;
W²² is bond, —O—, —NH— or optionally substituted lower alkylene;
Rb is bond or optionally substituted lower alkylene; and
R²⁰ is optionally substituted aryl or optionally substituted heteroaryl; and
R³ is selected from hydrogen and $C_{1-4}$ lower alkyl group.

16. The compound of claim 1,
wherein
$R^7$ of A is -Rc-$R^{70}$
   wherein
   Rc is bond or optionally substituted lower alkylene, and
   $R^{70}$ is optionally substituted aryl or optionally substituted heteroaryl; and
$R^3$ is selected from hydrogen and $C_{1-4}$ lower alkyl group.

17. The compound of claim 2,
wherein
$R^1$ is —Ra—$R^{10}$;
   wherein
   Ra is optionally substituted lower alkylene, and
   $R^{10}$ is optionally substituted allyl and
$R^3$ is selected from hydrogen or $C_{1-4}$ lower alkyl group.

18. The compound of claim 2,
wherein
$R^2$ is —$W^{21}$—$W^{22}$—Rb—$R^{20}$;
   wherein
   $W^{21}$ is —(CO)— or —(SO$_2$)—;
   $W^{22}$ is bond, —O—, —NH— or optionally substituted lower alkylene;
   Rb is bond or optionally substituted lower alkylene; and
   $R^{20}$ is optionally substituted aryl or optionally substituted heteroaryl, and
$R^3$ is selected from hydrogen and $C_{1-4}$ lower alkyl group.

19. The compound of claim 2,
wherein
$R^7$ of A is -Rc-$R^{70}$
   wherein
   Rc is bond or optionally substituted lower alkylene, and
   $R^{70}$ is optionally substituted aryl or optionally substituted heteroaryl; and
$R^3$ is selected from hydrogen and $C_{1-4}$ lower alkyl group.

20. The compound of claim 1,
wherein
$R^1$ is —Ra—$R^{10}$;
   wherein
   Ra is optionally substituted lower alkylene, and
   $R^{10}$ is optionally substituted aryl, or optionally substituted heteroaryl,
$R^2$ is —$W^{21}$—$W^{22}$—Rb—$R^{20}$;
   wherein
   $W^{21}$ is —(CO)— or —(SO$_2$)—;
   $W^{22}$ is bond, —O—, —NH— or optionally substituted lower alkylene;
   Rb is bond or optionally substituted lower alkylene;
   $R^{20}$ is optionally substituted aryl or optionally substituted heteroaryl;
$R^3$ is selected from hydrogen and $C_{1-4}$ lower alkyl group;
$R^7$ of A is -Rc-$R^{70}$
   wherein
   Rc is bond or optionally substituted lower alkylene, and
   $R^{70}$ is optionally substituted aryl or optionally substituted heteroaryl.

21. The compound of claim 14,
wherein
$R^{10}$ is optionally substituted biphenyl, optionally substituted phenyl, optionally substituted pyridyl, optionally substituted pyrimidyl, optionally substituted pyridazinyl, optionally substituted pyrazinyl, optionally substituted triazinyl, optionally substituted pyrrolyl, optionally substituted thienyl, optionally substituted furyl, optionally substituted thiazolyl, optionally substituted oxazolyl, optionally substituted imidazolyl, optionally substituted naphthyl, optionally substituted tetrahydronaphthyl, optionally substituted quinolinyl, optionally substituted isoquinolinyl, optionally substituted quinazolinyl, optionally substituted quinoxalinyl, optionally substituted cinnolinyl, optionally substituted naphthyridinyl, optionally substituted benzotriazinyl, optionally substituted pyridopyrimidinyl, optionally substituted pyridopyrazinyl, optionally substituted pyridopyridazinyl, optionally substituted pyridotriazinyl, optionally substituted indenyl, optionally substituted benzofuryl, optionally substituted benzothienyl, optionally substituted indolyl, optionally substituted indazolyl, optionally substituted benzoxazolyl, optionally substituted benzimidazolyl, optionally substituted benzothiazolyl, optionally substituted benzothiadiazolyl, optionally substituted furopyridinyl, optionally substituted thienopyridinyl, optionally substituted pyrrolopyridinyl, optionally substituted oxazolopyridinyl, optionally substituted thiazolopyridinyl or optionally substituted imidazopyridinyl.

22. The compound of claim 15,
wherein
$R^{20}$ is optionally substituted biphenyl, optionally substituted phenyl, optionally substituted pyridyl, optionally substituted pyrimidyl, optionally substituted pyridazinyl, optionally substituted pyrazinyl, optionally substituted triazinyl, optionally substituted pyrrolyl, optionally substituted thienyl, optionally substituted furyl, optionally substituted thiazolyl, optionally substituted oxazolyl, optionally substituted imidazolyl, optionally substituted naphthyl, optionally substituted tetrahydronaphthyl, optionally substituted quinolinyl, optionally substituted isoquinolinyl, optionally substituted quinazolinyl, optionally substituted quinoxalinyl, optionally substituted cinnolinyl, optionally substituted naphthyridinyl, optionally substituted benzotriazinyl, optionally substituted pyridopyrimidinyl, optionally substituted pyridopyrazinyl, optionally substituted pyridopyridazinyl, optionally substituted pyridotriazinyl, optionally substituted indenyl, optionally substituted benzofuryl, optionally substituted benzothienyl, optionally substituted indolyl, optionally substituted indazolyl, optionally substituted benzoxazolyl, optionally substituted benzimidazolyl, optionally substituted benzothiazolyl, optionally substituted benzothiadiazolyl, optionally substituted furopyridinyl, optionally substituted thienopyridinyl, optionally substituted pyrrolopyridinyl, optionally substituted oxazolopyridinyl, optionally substituted thiazolopyridinyl or optionally substituted imidazopyridinyl.

23. The compound of claim 16,
wherein
$R^{70}$ is optionally substituted biphenyl, optionally substituted phenyl, optionally substituted pyridyl, optionally substituted pyrimidyl, optionally substituted pyridazinyl, optionally substituted pyrazinyl, optionally substituted triazinyl, optionally substituted pyrrolyl, optionally substituted thienyl, optionally substituted furyl, optionally substituted thiazolyl, optionally substituted oxazolyl, optionally substituted imidazolyl, optionally substituted naphthyl, optionally substituted tetrahydronaphthyl, optionally substituted quinolinyl, optionally substituted isoquinolinyl, optionally substituted quinazolinyl, optionally substituted quinoxalinyl, optionally substituted cinnolinyl, optionally substituted naphthyridinyl, optionally substituted benzotriazinyl, optionally substituted pyridopyrimidinyl, optionally substituted pyridopyrazinyl, optionally substituted pyridopyridazinyl, optionally substituted pyridotriazinyl, optionally substituted indenyl, optionally substituted benzofuryl, optionally substituted benzothienyl, optionally substituted indolyl, optionally substituted indazolyl, optionally substituted benzoxazolyl, optionally substituted benzimidazolyl, optionally substituted benzothiazolyl, optionally substituted benzothiadiazolyl, optionally substituted furopyridinyl, optionally substituted thienopyridinyl, optionally substituted pyrrolopyridinyl, optionally substituted oxazolopyridinyl, optionally substituted thiazolopyridinyl or optionally substituted imidazopyridinyl.

24. A pharmaceutical composition comprising a compound according to claim 1 or a pharmaceutically acceptable salt thereof, and optionally a pharmaceutically acceptable carrier or diluent.

25. A library of compounds, comprising at least one compound according to claim 1.

26. A process for preparing a compound having the following general formula (I):

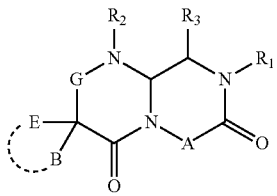

wherein
A is —(CHR$^7$)—;
wherein
R$^7$ is hydrogen, optionally substituted alkyl, optionally substituted alkenyl, optionally substituted alkynyl, optionally substituted aryl, optionally substituted heteroaryl, optionally substituted cycloalkyl, optionally substituted heterocycloalkyl, optionally substituted arylalkyl, optionally substituted heteroarylalkyl, optionally substituted cycloalkylalkyl, or optionally substituted heterocycloalkylalkyl;
B and E are the same or different and independently selected from hydrogen, optionally substituted alkyl, optionally substituted alkenyl, and optionally substituted alkynyl, and wherein B and E do not form an optionally substituted spiro ring indicated by dashed lines;
G is —NH—, —NR$^6$—, —O—, —CH$_2$—, —CHR$^6$— or —C(R$^6$)$_2$—;
wherein
each R$^6$ is the same or different and independently selected from optionally substituted alkyl, optionally substituted alkenyl, and optionally substituted alkynyl;

R$^1$ is optionally substituted alkyl, optionally substituted alkenyl, optionally substituted alkynyl, optionally substituted arylalkyl, optionally substituted heteroarylalkyl, optionally substituted cycloalkylalkyl, or optionally substituted heterocycloalkylalkyl;
R$^2$ is —W$^{21}$—W$^{22}$—Rb—R$^{20}$;
wherein
W$^{21}$ is —(CO)— or —(SO$_2$)—;
W$^{22}$ is bond, —O—, —NH— or optionally substituted lower alkylene;
Rb is bond or optionally substituted lower alkylene; and
R$^{20}$ is optionally substituted alkyl, optionally substituted alkenyl, optionally substituted alkynyl, optionally substituted aryl, optionally substituted heteroaryl, optionally substituted cycloalkyl, or optionally substituted heterocycloalkyl; and
R$^3$ is hydrogen, optionally substituted alkyl, optionally substituted alkenyl, or optionally substituted alkynyl;
with the proviso that
1) when Rb is optionally substituted lower alkylene, then W$^{22}$ should be —O— or —NH—,
2) when E and B are hydrogen, then R$^3$ should be hydrogen,
3) when G is —NH—, —CH$_2$—, —CHR$^6$— or —NR$^6$—, then neither B nor E should be hydrogen, and
4) when G is —O—, B and E are hydrogen and R$^3$ is hydrogen, then R$^1$ should not be 8-quinolylmethyl;
or a salt thereof, which comprises reacting a compound having the following general formula (II):

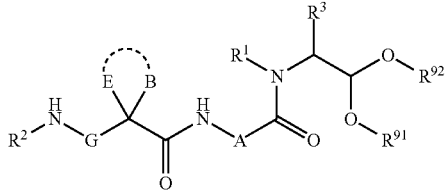

wherein
R$^{91}$ is selected from optionally substituted alkyl, linker and solid support;
R$^{92}$ is selected from optionally substituted alkyl, linker and solid support; and
the other symbols are as defined above, or a salt thereof, with an acid.

* * * * *

UNITED STATES PATENT AND TRADEMARK OFFICE
CERTIFICATE OF CORRECTION

PATENT NO. : 8,691,819 B2  Page 1 of 1
APPLICATION NO. : 13/124104
DATED : April 8, 2014
INVENTOR(S) : Kouji et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 54 days.

Signed and Sealed this
Twenty-ninth Day of September, 2015

Michelle K. Lee
*Director of the United States Patent and Trademark Office*